(12) United States Patent
Merino

(10) Patent No.: US 9,006,409 B2
(45) Date of Patent: Apr. 14, 2015

(54) METHODS OF INCREASING SECRETION OF POLYPEPTIDES HAVING BIOLOGICAL ACTIVITY

(71) Applicant: Novozymes, Inc., Davis, CA (US)

(72) Inventor: Sandra Merino, West Sacramento, CA (US)

(73) Assignee: Novozymes, Inc., Davis, CA (US)

( * ) Notice: Subject to any disclaimer, the term of this patent is extended or adjusted under 35 U.S.C. 154(b) by 0 days.

(21) Appl. No.: 14/524,793

(22) Filed: Oct. 27, 2014

(65) Prior Publication Data

US 2015/0044756 A1    Feb. 12, 2015

Related U.S. Application Data

(62) Division of application No. 14/279,624, filed on May 16, 2004, now Pat. No. 8,871,486, and a division of application No. 14/024,292, filed on Sep. 11, 2013, now Pat. No. 8,735,549, which is a division of application No. 11/781,151, filed on Jul. 20, 2007, now Pat. No. 8,546,106.

(60) Provisional application No. 60/832,511, filed on Jul. 21, 2006.

(51) Int. Cl.
| | |
|---|---|
| *C07H 21/04* | (2006.01) |
| *C12N 1/00* | (2006.01) |
| *C12N 15/00* | (2006.01) |
| *C12N 9/42* | (2006.01) |
| *C12N 15/80* | (2006.01) |

(52) U.S. Cl.
CPC ............ *C12N 9/2437* (2013.01); *C12N 9/2445* (2013.01); *C12N 15/80* (2013.01); *C07K 2319/00* (2013.01)

(58) Field of Classification Search
None
See application file for complete search history.

(56) References Cited

U.S. PATENT DOCUMENTS

| | | |
|---|---|---|
| 7,393,664 B2 | 7/2008 | Maiyuran et al. |
| 2003/0162218 A1 | 8/2003 | Emalfarb et al. |
| 2004/0018573 A1 | 1/2004 | Power et al. |
| 2005/0164355 A1 | 7/2005 | Vlasenko et al. |
| 2006/0019301 A1 | 1/2006 | Hansen et al. |
| 2007/0244020 A1 | 10/2007 | Alapuranen et al. |

FOREIGN PATENT DOCUMENTS

| | | |
|---|---|---|
| EP | 0 953 644 A1 | 7/1997 |
| WO | 91/17244 A1 | 11/1991 |
| WO | 95/02675 A1 | 1/1995 |
| WO | 96/29397 A1 | 9/1996 |
| WO | 98/16633 A1 | 4/1998 |
| WO | 99/57260 A1 | 11/1999 |
| WO | 2004099228 A2 | 11/2004 |
| WO | 2005/093050 A1 | 10/2005 |
| WO | 2008/151043 A1 | 12/2008 |

OTHER PUBLICATIONS

Foreman et al, 2003, J Biol Chem 278(34), 31988-31997.
Archer et al, 1994, Antonie Van Leeuwenhoek 65, 245-250.
Bushell et al, 2003, Biotechnol Bioeng 82(6), 678-683.
Machida et al, 2005, Nature 438, 1157-1161.

*Primary Examiner* — Suzanne M Noakes
*Assistant Examiner* — Jae W Lee
(74) *Attorney, Agent, or Firm* — Eric J. Fechter

(57) ABSTRACT

The present invention relates to methods for producing a secreted polypeptide having biological activity, comprising: (a) transforming a fungal host cell with a fusion protein construct encoding a fusion protein, which comprises: (i) a first polynucleotide encoding a signal peptide; (ii) a second polynucleotide encoding at least a catalytic domain of an endoglucanase or a portion thereof; and (iii) a third polynucleotide encoding at least a catalytic domain of a polypeptide having biological activity; wherein the signal peptide and at least the catalytic domain of the endoglucanase increases secretion of the polypeptide having biological activity compared to the absence of at least the catalytic domain of the endoglucanase; (b) cultivating the transformed fungal host cell under conditions suitable for production of the fusion protein; and (c) recovering the fusion protein, a component thereof, or a combination thereof, having biological activity, from the cultivation medium.

19 Claims, 21 Drawing Sheets

ATG AAG CTT GGT TGG ATC GAG GTG GCC GCA TTG GCG GCT GCC TCA GTA GTC AGT GCC
M   K   L   G   W   I   E   V   A   A   L   A   A   A   S   V   V   S   A

Fig. 7

ATG CGT TCC TCC CCC CTC CTC CGC TCC GCC GTT GTG GCC GCC CTG CCG GTG TTG GCC CTT GCC
M   R   S   S   P   L   L   R   S   A   V   V   A   A   L   P   V   L   A   L   A

Fig. 8

```
                           M  R  S  S  P  L  L  R  S  ·
1201                       ATGCGTTCCTCCCCCCTCCTCCGCTC
                           TACGCAAGGAGGGGGGAGGAGGCGAG
       · A  V  V  A  A  L  P  V  L  A  L  A  A  D  G  R  S  T  R  Y ·
1261   CGCCGTTGTGGCCGCCCTGCCGGTGTTGGCCCTTGCCGCTGATGGCAGGTCCACCCGCTA
       GCGGCAACACCGGCGGGACGGCCACAACCGGGAACGGCGACTACCGTCCAGGTGGGCGAT
       · W  D  C  C  K  P  S  C  G  W  A  K  K  A  P  V  N  Q  P  V ·
1321   CTGGGACTGCTGCAAGCCTTCGTGCGGCTGGGCCAAGAAGGCTCCCGTGAACCAGCCTGT
       GACCCTGACGACGTTCGGAAGCACGCCGACCCGGTTCTTCCGAGGGCACTTGGTCGGACA
       · F  S  C  N  A  N  F  Q  R  I  T  D  F  D  A  K  S  G  C  E ·
1381   CTTTTCCTGCAACGCCAACTTCCAGCGTATCACGGACTTCGACGCCAAGTCCGGCTGCGA
       GAAAAGGACGTTGCGGTTGAAGGTCGCATAGTGCCTGAAGCTGCGGTTCAGGCCGACGCT
       · P  G  G  V  A  Y  S  C  A  D  Q  T  P  W  A  V  N  D  D  F ·
1441   GCCGGGCGGTGTCGCCTACTCGTGCGCCGACCAGACCCCATGGGCTGTGAACGACGACTT
       CGGCCCGCCACAGCGGATGAGCACGCGGCTGGTCTGGGGTACCCGACACTTGCTGCTGAA
       · A  L  G  F  A  A  T  S  I  A  G  S  N  E  A  G  W  C  C  A ·
1501   CGCGCTCGGTTTTGCTGCCACCTCTATTGCCGGCAGCAATGAGGCGGGCTGGTGCTGCGC
       GCGCGAGCCAAAACGACGGTGGAGATAACGGCCGTCGTTACTCCGCCCGACCACGACGCG
       · C  Y  E  L  T  F  T  S  G  P  V  A  G  K  K  M  V  V  Q  S ·
1561   CTGCTACGAGCTCACCTTCACATCCGGTCCTGTTGCTGGCAAGAAGATGGTCGTCCAGTC
       GACGATGCTCGAGTGGAAGTGTAGGCCAGGACAACGACCGTTCTTCTACCAGCAGGTCAG
       · T  S  T  G  G  D  L  G  S  N  H  F  D  L  N  I  P  G  G  G ·
1621   CACCAGCACTGGCGGTGATCTTGGCAGCAACCACTTCGATCTCAACATCCCCGGCGGCGG
       GTGGTCGTGACCGCCACTAGAACCGTCGTTGGTGAAGCTAGAGTTGTAGGGGCCGCCGCC
       · V  G  I  F  D  G  C  T  P  Q  F  G  G  L  P  G  Q  R  Y  G ·
1681   CGTCGGCATCTTCGACGGATGCACTCCCCAGTTCGGTGGTCTGCCCGGCCAGCGCTACGG
       GCAGCCGTAGAAGCTGCCTACGTGAGGGGTCAAGCCACCAGACGGGCCGGTCGCGATGCC
       · G  I  S  S  R  N  E  C  D  R  F  P  D  A  L  K  P  G  C  Y ·
1741   CGGCATCTCGTCCCGCAACGAGTGCGATCGGTTCCCCGACGCCCTCAAGCCCGGCTGCTA
       GCCGTAGAGCAGGGCGTTGCTCACGCTAGCCAAGGGGCTGCGGGAGTTCGGGCCGACGAT
       · W  R  F  D  W  F  K  N  A  D  N  P  S  F  S  F  R  Q  V  Q ·
1801   CTGGCGCTTCGACTGGTTCAAGAACGCCGACAATCCGAGCTTCAGCTTCCGTCAGGTCCA
       GACCGCGAAGCTGACCAAGTTCTTGCGGCTGTTAGGCTCGAAGTCGAAGGCAGTCCAGGT
       · C  P  A  E  L  V  A  R  T  G  C  R  R  N  D  D  G  N  F  P ·
1861   GTGCCCAGCCGAGCTCGTCGCTCGCACCGGATGCCGCCGCAACGACGACGGCAACTTCCC
       CACGGGTCGGCTCGAGCAGCGAGCGTGGCCTACGGCGGCGTTGCTGCTGCCGTTGAAGGG
       · A  V  Q  I  P  M  R  S  S  P  L  L  R  S  A  V  V  A  A  L ·
1921   TGCCGTCCAGATCCCCATGCGTTCCTCCCCCCTCCTCCGCTCCGCCGTTGTGGCCGCCCT
       ACGGCAGGTCTAGGGGTACGCAAGGAGGGGGGAGGAGGCGAGGCGGCAACACCGGCGGGA
       · P  V  L  A  L  A  K  D  D  L  A  Y  S  P  P  F  Y  P  S  P ·
1981   GCCGGTGTTGGCCCTTGCCAAGGATGATCTCGCGTACTCCCCTCCTTTCTACCCTTCCCC
       CGGCCACAACCGGGAACGGTTCCTACTAGAGCGCATGAGGGGAGGAAAGATGGGAAGGGG
       · W  A  D  G  Q  G  E  W  A  E  V  Y  K  R  A  V  D  I  V  S ·
2041   ATGGGCAGATGGTCAGGGTGAATGGGCGGAAGTATACAAACGCGCTGTAGACATAGTTTC
       TACCCGTCTACCAGTCCCACTTACCCGCCTTCATATGTTTGCGCGACATCTGTATCAAAG
       · Q  M  T  L  T  E  K  V  N  L  T  T  G  T  W  Q  L  E  R ·
2101   CCAGATGACGTTGACAGAGAAAGTCAACTTAACGACTGGAACAGGATGGCAACTAGAGAG
       GGTCTACTGCAACTGTCTCTTTCAGTTGAATTGCTGACCTTGTCCTACCGTTGATCTCTC
       · C  V  G  Q  T  G  S  V  P  R  L  N  I  P  S  L  C  L  Q  D ·
```

Fig. 14A

```
2161 GTGTGTTGGACAAACTGGCAGTGTTCCCAGACTCAACATCCCCAGCTTGTGTTTGCAGGA
     CACACAACCTGTTTGACCGTCACAAGGGTCTGAGTTGTAGGGGTCGAACACAAACGTCCT
      · S  P  L  G  I  R  F  S  D  Y  N  S  A  F  P  A  G  V  N  V ·
2221 TAGTCCTCTTGGTATTCGTTTCTCGGACTACAATTCAGCTTTCCCTGCGGGTGTTAATGT
     ATCAGGAGAACCATAAGCAAAGAGCCTGATGTTAAGTCGAAAGGGACGCCCACAATTACA
      · A  A  T  W  D  K  T  L  A  Y  L  R  G  Q  A  M  G  E  E  F ·
2281 CGCTGCCACCTGGGACAAGACGCTCGCCTACCTTCGTGGTCAGGCAATGGGTGAGGAGTT
     GCGACGGTGGACCCTGTTCTGCGAGCGGATGGAAGCACCAGTCCGTTACCCACTCCTCAA
      · S  D  K  G  I  D  V  Q  L  G  P  A  A  G  P  L  G  A  H  P ·
2341 CAGTGATAAGGGTATTGACGTTCAGCTGGGTCCTGCTGCTGGCCCTCTCGGTGCTCATCC
     GTCACTATTCCCATAACTGCAAGTCGACCCAGGACGACGACCGGGAGAGCCACGAGTAGG
      · D  G  G  R  N  W  E  S  F  S  P  D  P  A  L  T  G  V  L  F ·
2401 GGATGGCGGTAGAAACTGGGAAAGTTTCTCACCAGATCCAGCCCTCACCGGTGTACTTTT
     CCTACCGCCATCTTTGACCCTTTCAAAGAGTGGTCTAGGTCGGGAGTGGCCACATGAAAA
      · A  E  T  I  K  G  I  Q  D  A  G  V  I  A  T  A  K  H  Y  I ·
2461 TGCGGAGACGATTAAGGGTATTCAAGATGCTGGTGTCATTGCGACAGCTAAGCATTATAT
     ACGCCTCTGCTAATTCCCATAAGTTCTACGACCACAGTAACGCTGTCGATTCGTAATATA
      · M  N  E  Q  H  F  R  Q  Q  P  E  A  A  G  Y  G  F  N  V ·
2521 CATGAACGAACAAGAGCATTTCCGCCAACAACCCGAGGCTGCGGGTTACGGATTCAACGT
     GTACTTGCTTGTTCTCGTAAAGGCGGTTGTTGGGCTCCGACGCCCAATGCCTAAGTTGCA
      · S  D  S  L  S  S  N  V  D  D  K  T  M  H  E  L  Y  W  P ·
2581 AAGCGACAGTTTGAGTTCCAACGTTGATGACAAGACTATGCATGAATTGTACCTCTGGCC
     TTCGCTGTCAAACTCAAGGTTGCAACTACTGTTCTGATACGTACTTAACATGGAGACCGG
      · F  A  D  A  V  R  A  G  V  G  A  V  M  C  S  Y  N  Q  I  N ·
2641 CTTCGCGGATGCAGTACGCGCTGGAGTCGGTGCTGTTATGTGCTCTTACAACCAAATCAA
     GAAGCGCCTACGTCATGCGCGACCTCAGCCACGACAATACACGAGAATGTTGGTTTAGTT
      · N  S  Y  G  C  E  N  S  E  T  L  N  K  L  L  K  A  E  L  G ·
2701 CAACAGCTACGGTTGCGAGAATAGCGAAACTCTGAACAAGCTTTTGAAGGCGGAGCTTGG
     GTTGTCGATGCCAACGCTCTTATCGCTTTGAGACTTGTTCGAAAACTTCCGCCTCGAACC
      · F  Q  G  F  V  M  S  D  W  T  A  Q  H  S  G  V  G  A  A  L ·
2761 TTTCCAAGGCTTCGTCATGAGTGATTGGACCGCTCAACACAGCGGCGTAGGCGCTGCTTT
     AAAGGTTCCGAAGCAGTACTCACTAACCTGGCGAGTTGTGTCGCCGCATCCGCGACGAAA
      · A  G  L  D  M  S  M  P  G  D  V  T  F  D  S  G  T  S  F  W ·
2821 AGCAGGTCTGGATATGTCGATGCCCGGTGATGTTACCTTCGATAGTGGTACGTCTTTCTG
     TCGTCCAGACCTATACAGCTACGGGCCACTACAATGGAAGCTATCACCATGCAGAAAGAC
      · G  A  N  L  T  V  G  V  L  N  G  T  I  P  Q  W  R  V  D  D ·
2881 GGGTGCAAACTTGACGGTCGGTGTCCTTAACGGTACAATCCCCCAATGGCGTGTTGATGA
     CCCACGTTTGAACTGCCAGCCACAGGAATTGCCATGTTAGGGGGTTACCGCACAACTACT
      · M  A  V  R  I  M  A  A  Y  Y  K  V  G  R  D  T  K  Y  T  P ·
2941 CATGGCTGTCCGTATCATGGCCGCTTATTACAAGGTTGGCCGCGACACCAAATACACCCC
     GTACCGACAGGCATAGTACCGGCGAATAATGTTCCAACCGGCGCTGTGGTTTATGTGGGG
      · P  N  F  S  S  W  T  R  D  E  Y  G  F  A  H  N  H  V  S  E ·
3001 TCCCAACTTCAGCTCGTGGACCAGGGACGAATATGGTTTCGCGCATAACCATGTTTCGGA
     AGGGTTGAAGTCGAGCACCTGGTCCCTGCTTATACCAAAGCGCGTATTGGTACAAAGCCT
      · G  A  Y  E  R  V  N  E  F  V  D  V  Q  R  D  H  A  D  L  I ·
3061 AGGTGCTTACGAGAGGGTCAACGAATTCGTGGACGTGCAACGCGATCATGCCGACCTAAT
     TCCACGAATGCTCTCCCAGTTGCTTAAGCACCTGCACGTTGCGCTAGTACGGCTGGATTA
      · R  R  I  G  A  Q  S  T  V  L  L  K  N  K  G  A  L  P  L  S ·
3121 CCGTCGCATCGGCGCGCAGAGCACTGTTCTGCTGAAGAACAAGGGTGCCTTGCCCTTGAG
     GGCAGCGTAGCCGCGCGTCTCGTGACAAGACGACTTCTTGTTCCCACGGAACGGGAACTC
      · R  K  E  K  L  V  A  L  L  G  E  D  A  G  S  N  S  W  G  A ·
```

Fig. 14B

```
3181 CCGCAAGGAAAAGCTGGTCGCCCTTCTGGGAGAGGATGCGGGTTCCAACTCGTGGGGCGC
     GGCGTTCCTTTTCGACCAGCGGGAAGACCCTCTCCTACGCCCAAGGTTGAGCACCCCGCG
     · N  G  C  D  D  R  G  C  D  N  G  T  L  A  M  A  W  G  S  G ·
3241 TAACGGCTGTGATGACCGTGGTTGCGATAACGGTACCCTTGCCATGGCCTGGGGTAGCGG
     ATTGCCGACACTACTGGCACCAACGCTATTGCCATGGGAACGGTACCGGACCCCATCGCC
     · T  A  N  F  P  Y  L  V  T  P  E  Q  A  I  Q  N  E  V  L  Q ·
3301 TACTGCGAATTTCCCATACCTCGTGACACCAGAGCAGGCGATTCAGAACGAAGTTCTTCA
     ATGACGCTTAAAGGGTATGGAGCACTGTGGTCTCGTCCGCTAAGTCTTGCTTCAAGAAGT
     · G  R  G  N  V  F  A  V  T  D  S  W  A  L  D  K  I  A  A  A ·
3361 GGGCCGTGGTAATGTCTTCGCCGTGACCGACAGTTGGGCGCTCGACAAGATCGCTGCGGC
     CCCGGCACCATTACAGAAGCGGCACTGGCTGTCAACCCGCGAGCTGTTCTAGCGACGCCG
     · A  R  Q  A  S  V  S  L  V  F  V  N  S  D  S  G  E  G  Y  L ·
3421 TGCCCGCCAGGCCAGCGTATCTCTCGTGTTCGTCAACTCCGACTCAGGAGAAGGCTATCT
     ACGGGCGGTCCGGTCGCATAGAGAGCACAAGCAGTTGAGGCTGAGTCCTCTTCCGATAGA
     · S  V  D  G  N  E  G  D  R  N  N  I  T  L  W  K  N  G  D  N ·
3481 TAGTGTGGATGGAAATGAGGGCGATCGTAACAACATCACTCTGTGGAAGAACGGCGACAA
     ATCACACCTACCTTTACTCCCGCTAGCATTGTTGTAGTGAGACACCTTCTTGCCGCTGTT
     · V  V  K  T  A  A  N  N  C  N  N  T  V  V  I  I  H  S  V  G ·
3541 TGTGGTCAAGACCGCAGCGAATAACTGTAACAACACCGTTGTCATCATCCACTCCGTCGG
     ACACCAGTTCTGGCGTCGCTTATTGACATTGTTGTGGCAACAGTAGTAGGTGAGGCAGCC
     · P  V  L  I  D  E  W  Y  D  H  P  N  V  T  G  I  L  W  A  G ·
3601 ACCAGTTTTGATCGATGAATGGTATGACCACCCCAATGTCACTGGTATTCTCTGGGCTGG
     TGGTCAAAACTAGCTACTTACCATACTGGTGGGGTTACAGTGACCATAAGAGACCCGACC
     · L  P  G  Q  E  S  G  N  S  I  A  D  V  L  Y  G  R  V  N  P ·
3661 TCTGCCAGGCCAGGAGTCTGGTAACTCCATTGCCGATGTGCTGTACGGTCGTGTCAACCC
     AGACGGTCCGGTCCTCAGACCATTGAGGTAACGGCTACACGACATGCCAGCACAGTTGGG
     · G  A  K  S  P  F  T  W  G  K  T  R  E  S  Y  G  S  P  L  V ·
3721 TGGCGCCAAGTCTCCTTTCACTTGGGGCAAGACCCGGGAGTCGTATGGTTCTCCCTTGGT
     ACCGCGGTTCAGAGGAAAGTGAACCCCGTTCTGGGCCCTCAGCATACCAAGAGGGAACCA
     · K  D  A  N  N  G  N  G  A  P  Q  S  D  F  T  Q  G  V  F  I ·
3781 CAAGGATGCCAACAATGGCAACGGAGCGCCCCAGTCTGATTTCACCCAGGGTGTTTTCAT
     GTTCCTACGGTTGTTACCGTTGCCTCGCGGGGTCAGACTAAAGTGGGTCCCACAAAAGTA
     · D  Y  R  H  F  D  K  F  N  E  T  P  I  Y  E  F  G  Y  G  L ·
3841 CGATTACCGCCATTTCGATAAGTTCAATGAGACCCCTATCTACGAGTTTGGCTACGGCTT
     GCTAATGGCGGTAAAGCTATTCAAGTTACTCTGGGGATAGATGCTCAAACCGATGCCGAA
     · S  Y  T  T  T  F  E  L  S  D  L  H  V  Q  P  L  N  A  S  R  Y ·
3901 GAGCTACACCACCTTCGAGCTCTCCGACCTCCATGTTCAGCCCCTGAACGCGTCCCGATA
     CTCGATGTGGTGGAAGCTCGAGAGGCTGGAGGTACAAGTCGGGGACTTGCGCAGGGCTAT
     · T  P  T  S  G  M  T  E  A  A  K  N  F  G  E  I  G  D  A  S ·
3961 CACTCCCACCAGTGGCATGACTGAAGCTGCAAAGAACTTTGGTGAAATTGGCGATGCGTC
     GTGAGGGTGGTCACCGTACTGACTTCGACGTTTCTTGAAACCACTTTAACCGCTACGCAG
     · E  Y  V  Y  P  E  G  L  E  R  I  H  E  F  I  Y  P  W  I  N ·
4021 GGAGTACGTGTATCCGGAGGGGCTGGAAAGGATCCATGAGTTTATCTATCCCTGGATCAA
     CCTCATGCACATAGGCCTCCCCGACCTTTCCTAGGTACTCAAATAGATAGGGACCTAGTT
     · S  T  D  L  K  A  S  S  D  D  S  N  Y  G  W  E  D  S  K  Y ·
4081 CTCTACCGACCTGAAGGCATCGTCTGACGATTCTAACTACGGCTGGGAAGACTCCAAGTA
     GAGATGGCTGGACTTCCGTAGCAGACTGCTAAGATTGATGCCGACCCTTCTGAGGTTCAT
     · I  P  E  G  A  T  D  G  S  A  Q  P  R  L  P  A  S  G  G  A ·
```

Fig. 14C

```
4141 TATTCCCGAAGGCGCCACGGATGGGTCTGCCCAGCCCCGTTTGCCCGCTAGTGGTGGTGC
     ATAAGGGCTTCCGCGGTGCCTACCCAGACGGGTCGGGGCAAACGGGCGATCACCACCACG
       · G  G  N  P  G  L  Y  E  D  L  F  R  V  S  V  K  V  K  N  T ·
4201 CGGAGGAAACCCCGGTCTGTACGAGGATCTTTTCCGCGTCTCTGTGAAGGTCAAGAACAC
     GCCTCCTTTGGGGCCAGACATGCTCCTAGAAAAGGCGCAGAGACACTTCCAGTTCTTGTG
       · G  N  V  A  G  D  E  V  P  Q  L  Y  V  S  L  G  G  P  N  E ·
4261 GGGCAATGTCGCCGGTGATGAAGTTCCTCAGCTGTACGTTTCCCTAGGCGGCCCGAATGA
     CCCGTTACAGCGGCCACTACTTCAAGGAGTCGACATGCAAAGGGATCCGCCGGGCTTACT
       · P  K  V  V  L  R  K  F  E  R  I  H  L  A  P  S  Q  E  A  V ·
4321 GCCCAAGGTGGTACTGCGCAAGTTTGAGCGTATTCACTTGGCCCCTTCGCAGGAGGCCGT
     CGGGTTCCACCATGACGCGTTCAAACTCGCATAAGTGAACCGGGGAAGCGTCCTCCGGCA
       · W  T  T  T  L  T  R  R  D  L  A  N  W  D  V  S  A  Q  D  W ·
4381 GTGGACAACGACCCTTACCCGTCGTGACCTTGCAAACTGGGACGTTTCGGCTCAGGACTG
     CACCTGTTGCTGGGAATGGGCAGCACTGGAACGTTTGACCCTGCAAAGCCGAGTCCTGAC
       · T  V  T  P  Y  P  K  T  I  Y  V  G  N  S  S  R  K  L  P  L ·
4441 GACCGTCACTCCTTACCCCAAGACGATCTACGTTGGAAACTCCTCACGGAAACTGCCGCT
     CTGGCAGTGAGGAATGGGGTTCTGCTAGATGCAACCTTTGAGGAGTGCCTTTGACGGCGA
       · Q  A  S  L  P  K  A  Q  *
4501 CCAGGCCTCGCTGCCTAAGGCCCAGTAA
     GGTCCGGAGCGACGGATTCCGGGTCATT
```

Fig. 14D

```
                        M   R   S   S   P   L   L   R   S  ·
1201                    ATGCGTTCCTCCCCCCTCCTCCGCTC
                        TACGCAAGGAGGGGGAGGAGGCGAG
      · A   V   V   A   A   L   P   V   L   A   L   A   A   D   G   R   S   T   R   Y  ·
1261  CGCCGTTGTGGCCGCCCTGCCGGTGTTGGCCCTTGCCGCTGATGGCAGGTCCACCCGCTA
      GCGGCAACACCGGCGGGACGGCCACAACCGGGAACGGCGACTACCGTCCAGGTGGGCGAT
      · W   D   C   C   K   P   S   C   G   W   A   K   K   A   P   V   N   Q   P   V  ·
1321  CTGGGACTGCTGCAAGCCTTCGTGCGGCTGGGCCAAGAAGGCTCCCGTGAACCAGCCTGT
      GACCCTGACGACGTTCGGAAGCACGCCGACCCGGTTCTTCCGAGGGCACTTGGTCGGACA
      · F   S   C   N   A   N   F   Q   R   I   T   D   F   D   A   K   S   G   C   E  ·
1381  CTTTTCCTGCAACGCCAACTTCCAGCGTATCACGGACTTCGACGCCAAGTCCGGCTGCGA
      GAAAAGGACGTTGCGGTTGAAGGTCGCATAGTGCCTGAAGCTGCGGTTCAGGCCGACGCT
      · P   G   G   V   A   Y   S   C   A   D   Q   T   P   W   A   V   N   D   D   F  ·
1441  GCCGGGCGGTGTCGCCTACTCGTGCGCCGACCAGACCCCATGGGCTGTGAACGACGACTT
      CGGCCCGCCACAGCGGATGAGCACGCGGCTGGTCTGGGGTACCCGACACTTGCTGCTGAA
      · A   L   G   F   A   A   T   S   I   A   G   S   N   E   A   G   W   C   C   A  ·
1501  CGCGCTCGGTTTTGCTGCCACCTCTATTGCCGGCAGCAATGAGGCGGGCTGGTGCTGCGC
      GCGCGAGCCAAAACGACGGTGGAGATAACGGCCGTCGTTACTCCGCCCGACCACGACGCG
      · C   Y   E   L   T   F   T   S   G   P   V   A   G   K   K   M   V   V   Q   S  ·
1561  CTGCTACGAGCTCACCTTCACATCCGGTCCTGTTGCTGGCAAGAAGATGGTCGTCCAGTC
      GACGATGCTCGAGTGGAAGTGTAGGCCAGGACAACGACCGTTCTTCTACCAGCAGGTCAG
      · T   S   T   G   G   D   L   G   S   N   H   F   D   L   N   I   P   G   G   G  ·
1621  CACCAGCACTGGCGGTGATCTTGGCAGCAACCACTTCGATCTCAACATCCCCGGCGGCGG
      GTGGTCGTGACCGCCACTAGAACCGTCGTTGGTGAAGCTAGAGTTGTAGGGGCCGCCGCC
      · V   G   I   F   D   G   C   T   P   Q   F   G   G   L   P   G   Q   R   Y   G  ·
1681  CGTCGGCATCTTCGACGGATGCACTCCCCAGTTCGGTGGTCTGCCCGGCCAGCGCTACGG
      GCAGCCGTAGAAGCTGCCTACGTGAGGGGTCAAGCCACCAGACGGGCCGGTCGCGATGCC
      · G   I   S   S   R   N   E   C   D   R   F   P   D   A   L   K   P   G   C   Y  ·
1741  CGGCATCTCGTCCCGCAACGAGTGCGATCGGTTCCCCGACGCCCTCAAGCCCGGCTGCTA
      GCCGTAGAGCAGGGCGTTGCTCACGCTAGCCAAGGGGCTGCGGGAGTTCGGGCCGACGAT
      · W   R   F   D   W   F   K   N   A   D   N   P   S   F   S   F   R   Q   V   Q  ·
1801  CTGGCGCTTCGACTGGTTCAAGAACGCCGACAATCCGAGCTTCAGCTTCCGTCAGGTCCA
      GACCGCGAAGCTGACCAAGTTCTTGCGGCTGTTAGGCTCGAAGTCGAAGGCAGTCCAGGT
      · C   P   A   E   L   V   A   R   T   G   C   R   R   N   D   D   G   N   F   P  ·
1861  GTGCCCAGCCGAGCTCGTCGCTCGCACCGGATGCCGCCGCAACGACGACGGCAACTTCCC
      CACGGGTCGGCTCGAGCAGCGAGCGTGGCCTACGGCGGCGTTGCTGCTGCCGTTGAAGGG
      · A   V   Q   I   P   M   R   S   S   P   L   L   R   S   A   V   V   A   A   L  ·
1921  TGCCGTCCAGATCCCCATGCGTTCCTCCCCCCTCCTCCGCTCCGCCGTTGTGGCCGCCCT
      ACGGCAGGTCTAGGGGTACGCAAGGAGGGGGAGGAGGCGAGGCGGCAACACCGGCGGGA
      · P   V   L   A   L   A   K   D   D   L   A   Y   S   P   P   F   Y   P   S   P  ·
1981  GCCGGTGTTGGCCCTTGCCAAGGATGATCTCGCGTACTCCCCTCCTTTCTACCCTTCCCC
      CGGCCACAACCGGGAACGGTTCCTACTAGAGCGCATGAGGGGAGGAAAGATGGGAAGGGG
      · W   A   D   G   Q   G   E   W   A   E   V   Y   K   R   A   V   D   I   V   S  ·
2041  ATGGGCAGATGGTCAGGGTGAATGGGCGGAAGTATACAAACGCGCTGTAGACATAGTTTC
      TACCCGTCTACCAGTCCCACTTACCCGCCTTCATATGTTTGCGCGACATCTGTATCAAAG
      · Q   M   T   L   T   E   K   V   N   L   T   T   G   T   G   W   Q   L   E   R  ·
2101  CCAGATGACGTTGACAGAGAAAGTCAACTTAACGACTGGAACAGGATGGCAACTAGAGAG
      GGTCTACTGCAACTGTCTCTTTCAGTTGAATTGCTGACCTTGTCCTACCGTTGATCTCTC
      · C   V   G   Q   T   G   S   V   P   R   L   N   I   P   S   L   C   L   Q   D  ·
```

Fig. 15A

```
2161 GTGTGTTGGACAAACTGGCAGTGTTCCCAGACTCAACATCCCCAGCTTGTGTTTGCAGGA
     CACACAACCTGTTTGACCGTCACAAGGGTCTGAGTTGTAGGGGTCGAACACAAACGTCCT
      · S  P  L  G  I  R  F  S  D  Y  N  S  A  F  P  A  G  V  N  V ·
2221 TAGTCCTCTTGGTATTCGTTTCTCGGACTACAATTCAGCTTTCCCTGCGGGTGTTAATGT
     ATCAGGAGAACCATAAGCAAAGAGCCTGATGTTAAGTCGAAAGGGACGCCCACAATTACA
      · A  A  T  W  D  K  T  L  A  Y  L  R  G  Q  A  M  G  E  E  F ·
2281 CGCTGCCACCTGGGACAAGACGCTCGCCTACCTTCGTGGTCAGGCAATGGGTGAGGAGTT
     GCGACGGTGGACCCTGTTCTGCGAGCGGATGGAAGCACCAGTCCGTTACCCACTCCTCAA
      · S  D  K  G  I  D  V  Q  L  G  P  A  A  G  P  L  G  A  H  P ·
2341 CAGTGATAAGGGTATTGACGTCAGCTGGGTCCTGCTGCTGGCCCTCTCGGTGCTCATCC
     GTCACTATTCCCATAACTGCAAGTCGACCCAGGACGACGACCGGGAGAGCCACGAGTAGG
      · D  G  G  R  N  W  E  G  F  S  P  D  P  A  L  T  G  V  L  F ·
2401 GGATGGCGGTAGAAACTGGGAAGGTTTCTCACCAGATCCAGCCCTCACCGGTGTACTTTT
     CCTACCGCCATCTTTGACCCTTCCAAAGAGTGGTCTAGGTCGGGAGTGGCCACATGAAAA
      · A  E  T  I  K  G  I  Q  D  A  G  V  I  A  T  A  K  H  Y  I ·
2461 TGCGGAGACGATTAAGGGTATTCAAGATGCTGGTGTCATTGCGACAGCTAAGCATTATAT
     ACGCCTCTGCTAATTCCCATAAGTTCTACGACCACAGTAACGCTGTCGATTCGTAATATA
      · M  N  E  Q  H  F  R  Q  Q  P  E  A  A  G  Y  G  F  N  V ·
2521 CATGAACGAACAAGAGCATTTCCGCCAACAACCCGAGGCTGCGGGTTACGGATTCAACGT
     GTACTTGCTTGTTCTCGTAAAGGCGGTTGTTGGGCTCCGACGCCCAATGCCTAAGTTGCA
      · S  D  S  L  S  S  N  V  D  D  K  T  M  H  E  L  Y  L  W  P ·
2581 AAGCGACAGTTTGAGTTCCAACGTTGATGACAAGACTATGCATGAATTGTACCTCTGGCC
     TTCGCTGTCAAACTCAAGGTTGCAACTACTGTTCTGATACGTACTTAACATGGAGACCGG
      · F  A  D  A  V  R  A  G  V  G  A  V  M  C  S  Y  N  Q  I  N ·
2641 CTTCGCGGATGCAGTACGCGCTGGAGTCGGTGCTGTCATGTGCTCTTACAACCAAATCAA
     GAAGCGCCTACGTCATGCGCGACCTCAGCCACGACAGTACACGAGAATGTTGGTTTAGTT
      · N  S  Y  G  C  E  N  S  E  T  L  N  K  L  L  K  A  E  L  G ·
2701 CAACAGCTACGGTTGCGAGAATAGCGAAACTCTGAACAAGCTTTTGAAGGCGGAGCTTGG
     GTTGTCGATGCCAACGCTCTTATCGCTTTGAGACTTGTTCGAAAACTTCCGCCTCGAACC
      · F  Q  G  F  V  M  S  D  W  T  A  H  H  S  G  V  G  A  A  L ·
2761 TTTTCCAAGGCTTCGTCATGAGTGATTGGACCGCTCATCACAGCGGCGTAGGCGCTGCTTT
     AAAGGTTCCGAAGCAGTACTCACTAACCTGGCGAGTAGTGTCGCCGCATCCGCGACGAAA
      · A  G  L  D  M  S  M  P  G  D  V  T  F  D  S  G  T  S  F  W ·
2821 AGCAGGTCTGGATATGTCGATGCCCGGTGATGTTACCTTCGATAGTGGTACGTCTTTCTG
     TCGTCCAGACCTATACAGCTACGGGCCACTACAATGGAAGCTATCACCATGCAGAAAGAC
      · G  A  N  L  T  V  G  V  L  N  G  T  I  P  Q  W  R  V  D  D ·
2881 GGGTGCAAACTTGACGGTCGGTGTCCTTAACGGTACAATCCCCCAATGGCGTGTTGATGA
     CCCACGTTTGAACTGCCAGCCACAGGAATTGCCATGTTAGGGGGTTACCGCACAACTACT
      · M  A  V  R  I  M  A  A  Y  Y  K  V  G  R  D  T  K  Y  T  P ·
2941 CATGGCTGTCCGTATCATGGCCGCTTATTACAAGGTTGGCCGCGACACCAAATACACCCC
     GTACCGACAGGCATAGTACCGGCGAATAATGTTCCAACCGGCGCTGTGGTTTATGTGGGG
      · P  N  F  S  S  W  T  R  D  E  Y  G  F  A  H  N  H  V  S  E ·
3001 TCCCAACTTCAGCTCGTGGACCAGGGACGAATATGGTTTCGCGCATAACCATGTTTCGGA
     AGGGTTGAAGTCGAGCACCTGGTCCCTGCTTATACCAAAGCGCGTATTGGTACAAAGCCT
      · G  A  Y  E  R  V  N  E  F  V  D  V  Q  R  D  H  A  D  L  I ·
3061 AGGTGCTTACGAGAGGGTCAACGAATTCGTGGACGTGCAACGCGATCATGCCGACCTAAT
     TCCACGAATGCTCTCCCAGTTGCTTAAGCACCTGCACGTTGCGCTAGTACGGCTGGATTA
      · R  R  I  G  A  Q  S  T  V  L  L  K  N  K  G  A  L  P  L  S ·
```

Fig. 15B

```
3121 CCGTCGCATCGGCGCGCAGAGCACTGTTCTGCTGAAGAACAAGGGTGCCTTGCCCTTGAG
     GGCAGCGTAGCCGCGCGTCTCGTGACAAGACGACTTCTTGTTCCCACGGAACGGGAACTC
      · R  K  E  K  L  V  A  L  L  G  E  D  A  G  S  N  S  W  G  A ·
3181 CCGCAAGGAAAAGCTGGTCGCCCTTCTGGGAGAGGATGCGGGTTCCAACTCGTGGGGCGC
     GGCGTTCCTTTTCGACCAGCGGGAAGACCCTCTCCTACGCCCAAGGTTGAGCACCCCGCG
      · N  G  C  D  D  R  G  C  D  N  G  T  L  A  M  A  W  G  S  G ·
3241 TAACGGCTGTGATGACCGTGGTTGCGATAACGGTACCCTTGCCATGGCCTGGGGTAGCGG
     ATTGCCGACACTACTGGCACCAACGCTATTGCCATGGGAACGGTACCGGACCCCATCGCC
      · T  A  N  F  P  Y  L  V  T  P  E  Q  A  I  Q  N  E  V  L  Q ·
3301 TACTGCGAATTTCCCATACCTCGTGACACCAGAGCAGGCGATTCAGAACGAAGTTCTTCA
     ATGACGCTTAAAGGGTATGGAGCACTGTGGTCTCGTCCGCTAAGTCTTGCTTCAAGAAGT
      · G  R  G  N  V  F  A  V  T  D  S  W  A  L  D  K  I  A  A  A ·
3361 GGGCCGTGGTAATGTCTTCGCCGTGACCGACAGTTGGGCGCTCGACAAGATCGCTGCGGC
     CCCGGCACCATTACAGAAGCGGCACTGGCTGTCAACCCGCGAGCTGTTCTAGCGACGCCG
      · A  R  Q  A  S  V  S  L  V  F  V  N  S  D  S  G  E  G  Y  L ·
3421 TGCCCGCCAGGCCAGCGTATCTCTCGTGTTCGTCAACTCCGACTCAGGAGAAGGCTATCT
     ACGGGCGGTCCGGTCGCATAGAGAGCACAAGCAGTTGAGCCTGAGTCCTCTTCCGATAGA
      · S  V  D  G  N  E  G  D  R  N  N  I  T  L  W  K  N  G  D  N ·
3481 TAGTGTGGATGGAAATGAGGGCGATCGTAACAACATCACTCTGTGGAAGAACGGCGACAA
     ATCACACCTACCTTTACTCCCGCTAGCATTGTTGTAGTGAGACACCTTCTTGCCGCTGTT
      · V  V  K  T  A  A  N  N  C  N  N  T  V  V  I  I  H  S  V  G ·
3541 TGTGGTCAAGACCGCAGCGAATAACTGTAACAACACCGTTGTCATCATCCACTCCGTCGG
     ACACCAGTTCTGGCGTCGCTTATTGACATTGTTGTGGCAACAGTAGTAGGTGAGGCAGCC
      · P  V  L  I  D  E  W  Y  D  H  P  N  V  T  G  I  L  W  A  G ·
3601 ACCAGTTTTGATCGATGAATGGTATGACCACCCCAATGTCACTGGTATTCTCTGGGCTGG
     TGGTCAAAACTAGCTACTTACCATACTGGTGGGGTTACAGTGACCATAAGAGACCCGACC
      · L  P  G  Q  E  S  G  N  S  I  A  D  V  L  Y  G  R  V  N  P ·
3661 TCTGCCAGGCCAGGAGTCTGGTAACTCCATTGCCGATGTGCTGTACGGTCGTGTCAACCC
     AGACGGTCCGGTCCTCAGACCATTGAGGTAACGGCTACACGACATGCCAGCACAGTTGGG
      · G  A  K  S  P  F  T  W  G  K  T  R  E  S  Y  G  S  P  L  V ·
3721 TGGCGCCAAGTCTCCTTTCACTTGGGGCAAGACCCGGGAGTCGTATGGTTCTCCCTTGGT
     ACCGCGGTTCAGAGGAAAGTGAACCCCGTTCTGGGCCCTCAGCATACCAAGAGGGAACCA
      · K  D  A  N  N  G  N  G  A  P  Q  S  D  F  T  Q  G  V  F  I ·
3781 CAAGGATGCCAACAATGGCAACGGAGCGCCCAGTCTGATTTCACCCAGGGTGTTTTCAT
     GTTCCTACGGTTGTTACCGTTGCCTCGCGGGGTCAGACTAAAGTGGGTCCCACAAAAGTA
      · D  Y  R  H  F  D  K  F  N  E  T  P  I  Y  E  F  G  Y  G  L ·
3841 CGATTACCGCCATTTCGATAAGTTCAATGAGACCCCTATCTACGAGTTTGGCTACGGCTT
     GCTAATGGCGGTAAAGCTATTCAAGTTACTCTGGGGATAGATGCTCAAACCGATGCCGAA
      · S  Y  T  T  T  F  E  L  S  D  L  H  V  Q  P  L  N  A  S  R  Y ·
3901 GAGCTACACCACCTTCGAGCTCTCCGACCTCCATGTTCAGCCCCTGAACGCGTCCCGATA
     CTCGATGTGGTGGAAGCTCGAGAGGCTGGAGGTACAAGTCGGGGACTTGCGCAGGGCTAT
      · T  P  T  S  G  M  T  E  A  A  K  N  F  G  E  I  G  D  A  S ·
3961 CACTCCCACCAGTGGCATGACTGAAGCTGCAAAGAACTTTGGTGAAATTGGCGATGCGTC
     GTGAGGGTGGTCACCGTACTGACTTCGACGTTTCTTGAAACCACTTTAACCGCTACGCAG
      · E  Y  V  V  Y  P  E  G  L  E  R  I  H  E  F  I  Y  P  W  I  N ·
4021 GGAGTACGTGTATCCGGAGGGGCTGGAAAGGATCCATGAGTTTATCTATCCCTGGATCAA
     CCTCATGCACATAGGCCTCCCCGACCTTTCCTAGGTACTCAAATAGATAGGGACCTAGTT
      · S  T  D  L  K  A  S  S  D  D  S  N  Y  G  W  E  D  S  K  Y ·
```

Fig. 15C

```
4081  CTCTACCGACCTGAAGGCATCGTCTGACGATTCTAACTACGGCTGGGAAGACTCCAAGTA
      GAGATGGCTGGACTTCCGTAGCAGACTGCTAAGATTGATGCCGACCCTTCTGAGGTTCAT
       · I   P   E   G   A   T   D   G   S   A   Q   P   R   L   P   A   S   G   G   A ·
4141  TATTCCCGAAGGCGCCACGGATGGGTCTGCCCAGCCCGTTTGCCCGCTAGTGGTGGTGC
      ATAAGGGCTTCCGCGGTGCCTACCCAGACGGGTCGGGGCAAACGGGCGATCACCACCACG
       · G   G   N   P   G   L   Y   E   D   L   F   R   V   S   V   K   V   K   N   T ·
4201  CGGAGGAAACCCCGGTCTGTACGAGGATCTTTTCCGCGTCTCTGTGAAGGTCAAGAACAC
      GCCTCCTTTGGGGCCAGACATGCTCCTAGAAAAGGCGCAGAGACACTTCCAGTTCTTGTG
       · G   N   V   A   G   D   E   V   P   Q   L   Y   V   S   L   G   G   P   N   E ·
4261  GGGCAATGTCGCCGGTGATGAAGTTCCTCAGCTGTACGTTTCCCTAGGCGGCCCGAATGA
      CCCGTTACAGCGGCCACTACTTCAAGGAGTCGACATGCAAAGGGATCCGCCGGGCTTACT
       · P   K   V   V   L   R   K   F   E   R   I   H   L   A   P   S   Q   E   A   V ·
4321  GCCCAAGGTGGTACTGCGCAAGTTTGAGCGTATTCACTTGGCCCCTTCGCAGGAGGCCGT
      CGGGTTCCACCATGACGCGTTCAAACTCGCATAAGTGAACCGGGGAAGCGTCCTCCGGCA
       · W   T   T   T   L   T   R   R   D   L   A   N   W   D   V   S   A   Q   D   W ·
4381  GTGGACAACGACCCTTACCCGTCGTGACCTTGCAAACTGGGACGTTTCGGCTCAGGACTG
      CACCTGTTGCTGGGAATGGGCAGCACTGGAACGTTTGACCCTGCAAAGCCGAGTCCTGAC
       · T   V   T   P   Y   P   K   T   I   Y   V   G   N   S   R   K   L   P   L ·
4441  GACCGTCACTCCTTACCCCAAGACGATCTACGTTGGAAACTCCTCACGGAAACTGCCGCT
      CTGGCAGTGAGGAATGGGGTTCTGCTAGATGCAACCTTTGAGGAGTGCCTTTGACGGCGA
       · Q   A   S   L   P   K   A   Q   *
4501  CCAGGCCTCGCTGCCTAAGGCCCAGTAA
      GGTCCGGAGCGACGGATTCCGGGTCATT
```

Fig. 15D

METHODS OF INCREASING SECRETION OF POLYPEPTIDES HAVING BIOLOGICAL ACTIVITY

CROSS-REFERENCE TO RELATED APPLICATION

This application is a divisional of U.S. patent application Ser. No. 14/279,624, filed May 16, 2014, which is a divisional of U.S. patent application Ser. No. 14/024,292, filed Sep. 11, 2013, now U.S. Pat. No. 8,735,549, which is a divisional of U.S. patent application Ser. No. 11/781,151, filed Jul. 20, 2007, now U.S. Pat. No. 8,546,106, which claims the benefit of U.S. Provisional Application No. 60/832,511, filed Jul. 21, 2006, which applications are incorporated herein by reference.

STATEMENT AS TO RIGHTS TO INVENTIONS MADE UNDER FEDERALLY SPONSORED RESEARCH AND DEVELOPMENT

This invention was made with Government support under NREL Subcontract No. ZCO-30017-02, Prime Contract DE-AC36-98GO10337 awarded by the Department of Energy. The government has certain rights in this invention.

BACKGROUND OF THE INVENTION

1. Field of the Invention

The present invention relates to methods of producing secreted polypeptides having biological activity and to fusion proteins and polynucleotides thereof.

2. Description of the Related Art

The recombinant production of a heterologous polypeptide in a fungal host cell, particularly a filamentous fungal cell such as *Aspergillus* or *Trichoderma* or a yeast cell such *Saccharomyces*, may provide for a more desirable vehicle for producing the polypeptide in commercially relevant quantities.

Recombinant production of a secreted heterologous polypeptide is generally accomplished by constructing an expression cassette in which the DNA coding for the polypeptide is operably linked to a promoter suitable for the host cell and a signal peptide coding region that codes for an amino acid sequence linked in frame to the amino terminus of the polypeptide and directs the encoded polypeptide into the cell's secretory pathway. The expression cassette is introduced into the host cell, usually by plasmid-mediated transformation. Production of the secreted heterologous protein is then achieved by culturing the transformed host cell under inducing conditions necessary for the proper functioning of the promoter contained on the expression cassette.

While expression of a heterologous polypeptide in a host cell may be improved, an obstacle often encountered is that the polypeptide is poorly secreted into the culture medium. One method of improving secretion of the polypeptide is to replace the native signal peptide coding sequence with a foreign signal peptide coding region to enhance secretion of the polypeptide. However, in some cases, such a replacement does not provide a sufficient improvement for producing the polypeptide in commercially relevant quantities. Another method is to fuse the polypeptide to another polypeptide that is highly secreted by a host cell. The highly secreted polypeptide functions as a carrier to transport the poorly secreted or non-secreted polypeptide as a fusion protein through the cell's secretory pathway.

WO 05/093050 discloses a fusion protein composed of an exo-cellobiohydrolase catalytic domain and a cellulase catalytic domain to increase the yield of a cellulase enzyme. Gouka et al., 1997, *Applied and Environmental Microbiology* February 1997, p. 488-497, discloses glucoamylase gene fusions that alleviate limitations for protein production in *Aspergillus awamori*. Nyyssonen and Keranen, 1995, *Current Genetics* 28: 71-79, discloses multiple roles of the cellobiohydrolase I in enhancing production of fusion antibodies by *Trichoderma reesei*.

It is an object of the present invention to provide methods for increasing the secretion of polypeptides having biological activity.

SUMMARY OF THE INVENTION

The present invention relates to methods for producing a secreted polypeptide having biological activity, comprising:

(a) transforming a fungal host cell with a fusion protein construct encoding a fusion protein, wherein the fusion protein construct comprises:
 (i) a first polynucleotide comprising a nucleotide sequence encoding a signal peptide;
 (ii) a second polynucleotide comprising a nucleotide sequence encoding at least a catalytic domain of an endoglucanase or a portion thereof; and
 (iii) a third polynucleotide comprising a nucleotide sequence encoding at least a catalytic domain of a polypeptide having biological activity or a portion thereof; wherein the signal peptide and at least the catalytic domain of the endoglucanase or the portion thereof increases secretion of the polypeptide having biological activity or the portion thereof compared to the absence of at least the catalytic domain of the endoglucanase or the portion thereof;

(b) cultivating the transformed fungal host cell under conditions suitable for production of the fusion protein; and (c) recovering the fusion protein, a component thereof, or a combination thereof, from the cultivation medium, wherein the fusion protein or the component thereof has biological activity.

In one aspect, the 3' end of the first polynucleotide is operably linked to the 5' end of the second polynucleotide and the 3' end of the second polynucleotide is operably linked to the 5' end of the third polynucleotide or the 3' end of the first polynucleotide is operably linked to the 5' end of the third polynucleotide and the 3' end of the third polynucleotide is operably linked to the 5' end of the second polynucleotide to encode a fusion protein.

The present invention also relates to isolated fusion proteins, comprising:

(a) a first amino acid sequence comprising a signal peptide;
(b) a second amino acid sequence comprising at least a catalytic domain of an endoglucanase or a portion thereof; and
(c) a third amino acid sequence comprising at least a catalytic domain of a polypeptide having biological activity or a portion thereof.

The present invention also relates to polynucleotides encoding the fusion proteins, and fusion protein constructs, expression vectors, and recombinant host cells comprising such polynucleotides.

In another aspect, the C-terminal end of the first amino acid sequence is linked in frame to the N-terminal end of the second amino acid sequence and the C-terminal end of the second amino acid sequence is linked in frame to the N-terminal end of the third amino acid sequence or the C-terminal end of the first amino acid sequence is linked in frame to the N-terminal end of the third amino acid sequence and the C-terminal end of the third amino acid sequence is linked in frame to the N-terminal end of the second amino acid sequence.

The present invention further relates to methods of using the fusion proteins or components thereof.

BRIEF DESCRIPTION OF THE FIGURES

FIG. 7 shows the DNA sequence and amino acid sequence of an *Aspergillus oryzae* beta-glucosidase native signal sequence (SEQ ID NOs: 59 and 60).
FIG. 8 shows the DNA sequence and amino acid sequence of a *Humicola insolens* endoglucanase V signal sequence (SEQ ID NOs: 63 and 64).
FIGS. 14A, 14B, 14C, and 14D show the DNA sequence and deduced amino acid sequence of the *Aspergillus oryzae* beta-glucosidase variant fusion protein (SEQ ID NOs: 73 and 74, respectively).
FIGS. 15A, 15B, 15C, and 15D show the DNA sequence and deduced amino acid sequence of the *Aspergillus oryzae* beta-glucosidase fusion protein (SEQ ID NOs: 75 and 76, respectively).

DEFINITIONS

Figure 1:
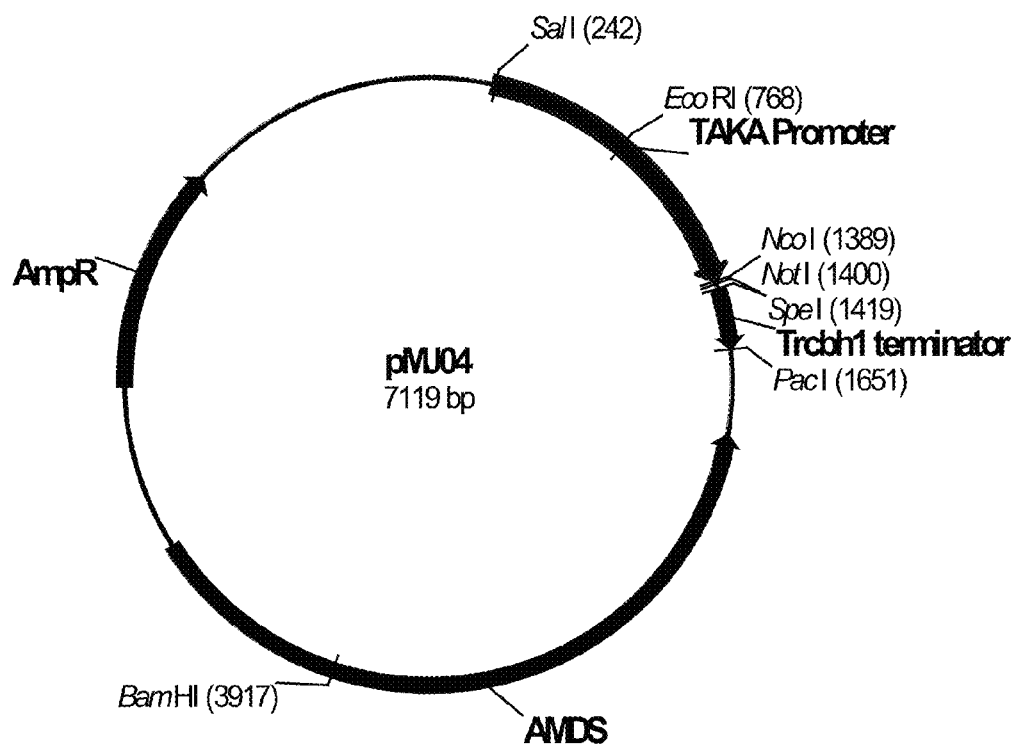
FIG. 1 shows a restriction map of pMJ04.

Endoglucanase activity: The term "endoglucanase activity" is defined herein as an endo-1,4-beta-D-glucan 4-glucanohydrolase (E.C. 3.2.1.4), which catalyses endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. For purposes of the present invention, endoglucanase activity is determined using carboxymethyl cellulose (CMC) hydrolysis according to the procedure of Ghose, 1987, Pure and Appl. Chem. 59: 257-268. One unit of endoglucanase activity is defined as 1.0 urnole of reducing sugars produced per minute at 50° C., pH 4.8.

Beta-glucosidase activity: The term "beta-glucosidase" is defined herein as a beta-D-glucoside glucohydrolase (E.C. 3.2.1.21), which catalyzes the hydrolysis of terminal non-reducing beta-D-glucose residues with the release of beta-D-glucose. For purposes of the present invention, beta-glucosidase activity is determined according to the procedure described by Venturi et al., 2002, *J. Basic Microbiol.* 42: 55-66, except different conditions are employed as described herein. One unit of beta-glucosidase activity is defined as 1.0 μmole of p-nitrophenol produced per minute at 50° C., pH 5 from 4 mM p-nitrophenyl-beta-D-glucopyranoside as substrate in 100 mM sodium citrate, 0.01% TWEEN® 20.

Full-length polypeptide: The term "full-length polypeptide" is defined herein as a precursor form of a polypeptide having biological activity, wherein the precursor contains a signal peptide region and alternatively also a propeptide region, wherein upon secretion from a cell, the signal peptide is cleaved and alternatively also the propeptide is cleaved yielding a polypeptide with biological activity.

Signal peptide: The term "signal peptide" is defined herein as a peptide linked in frame to the amino terminus of a polypeptide and directs the encoded polypeptide into a cell's secretory pathway.

Signal peptide coding sequence: The term "signal peptide coding sequence" is defined herein as a peptide coding region that codes for an amino acid sequence linked in frame to the amino terminus of an encoded polypeptide and directs the encoded polypeptide into a cell's secretory pathway.

Propeptide: The term "propeptide" is defined herein as a peptide linked in frame to the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. Where both signal peptide and propeptide regions are present at the amino terminus of a polypeptide, the propeptide region is linked in frame to the amino terminus of a polypeptide and the signal peptide region is linked in frame to the amino terminus of the propeptide region.

Propeptide coding sequence: The term "propeptide coding sequence" is defined herein as a peptide coding region that codes for an amino acid sequence linked in frame to the amino terminus of a polypeptide forming a proenzyme or propolypeptide (or a zymogen in some cases).

Mature polypeptide: The term "mature polypeptide" is defined herein as a polypeptide having biological activity that is in its final form following translation and any post-translational modifications, such as N-terminal processing, C-terminal truncation, glycosylation, phosphorylation, etc.

Catalytic domain: The term "catalytic domain" is defined herein as a structural portion or region of the amino acid sequence of an endoglucanase or a polypeptide having biological activity (e.g., beta-glucosidase activity), which possesses the catalytic activity of the endoglucanase or the polypeptide having biological activity (e.g., beta-glucosidase). The catalytic domain is also referred to as the "core" region herein.

Fusion protein: The term "fusion protein" is defined herein as a polypeptide that exhibits biological activity and that comprises at least both an endoglucanase catalytic domain and a catalytic domain of a polypeptide having biological activity (e.g., beta-glucosidase).

Beta-glucosidase fusion protein: The term "beta-glucosidase fusion protein" is defined herein as a polypeptide that exhibits beta-glucosidase activity and that comprises at least both a beta-glucosidase catalytic domain and an endoglucanase catalytic domain.

Components of a fusion protein: The term "components of a fusion protein" is defined herein as individual (cleaved) fragments of the fusion protein, wherein each fragment has biological activity and includes either at least the catalytic domain of a endoglucanase and at least the catalytic domain of a polypeptide having biological activity or at least the catalytic domain of a polypeptide having biological activity. For example, the presence of a cleavage site, e.g., Kex2 site, between the components of at least the catalytic domain of a endoglucanase and at least the catalytic domain of a polypeptide having biological activity of the fusion protein can result in the production of a polypeptide having endoglucanase activity and another polypeptide having biological activity.

Components of a beta-glucosidase fusion protein: The term "components of a beta-glucosidase fusion protein" is defined herein as individual (cleaved) fragments of the beta-glucosidase fusion protein, wherein each fragment has beta-glucosidase activity and is either at least the catalytic domain of the endoglucanase and at least the beta-glucosidase catalytic domain or at least the beta-glucosidase catalytic domain. For example, the presence of a cleavage site, e.g., Kex2 site, between the endoglucanase and beta-glucosidase components of the fusion protein can result in the production of a polypeptide having endoglucanase activity and another polypeptide having beta-glucosidase activity.

Carbohydrate binding module: The term "carbohydrate binding module (CBM)" is defined herein as a portion of the amino acid sequence of an endoglucanase (cellulase) that is involved in the binding of the endoglucanase to cellulose (lignocellulose). Carbohydrate binding modules generally function by non-covalently binding the endoglucanase to cellulose, a cellulose derivative, or a polysaccharide equivalent thereof. CBMs typically function independent of the catalytic domain.

Fusion protein construct: The term "fusion protein construct" refers to a nucleic acid construct that is composed of different genes or portions thereof in operable linkage. The components include from the 5' end a DNA molecule encoding at least an endoglucanase catalytic domain and a DNA molecule encoding at least a catalytic domain of a polypeptide having biological activity.

Beta-glucosidase fusion construct: The term "beta-glucosidase fusion construct" refers to a nucleic acid construct that is composed of different genes or portions thereof in operable linkage. The components include from the 5' end a DNA molecule encoding at least an endoglucanase catalytic domain and a DNA molecule encoding at least a beta-glucosidase catalytic domain.

Isolated polypeptide: The term "isolated polypeptide" as used herein refers to a polypeptide that is at least 20% pure, preferably at least 40% pure, more preferably at least 60% pure, even more preferably at least 80% pure, most preferably at least 90% pure, and even most preferably at least 95% pure, as determined by SDS-PAGE.

Substantially pure polypeptide: The term "substantially pure polypeptide" denotes herein a polypeptide preparation that contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively or recombinantly associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation. The polypeptides of the present invention are preferably in a substantially pure form, i.e., that the polypeptide preparation is essentially free of other polypeptide material with which it is natively or recombinantly associated. This can be accomplished, for example, by preparing the polypeptide by means of well-known recombinant methods or by classical purification methods.

Identity: The relatedness between two amino acid sequences or between two nucleotide sequences is described by the parameter "identity".

For purposes of the present invention, the degree of identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, Trends in Genetics 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment)

For purposes of the present invention, the degree of identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Polypeptide fragment: The term "polypeptide fragment" is defined herein as a polypeptide having one or more amino acids deleted from the amino and/or carboxyl terminus of a fusion protein (e.g., beta-glucosidase fusion protein) or components thereof, wherein the fragment has biological activity (e.g., beta-glucosidase activity).

Subsequence: The term "subsequence" is defined herein as a nucleotide sequence having one or more nucleotides deleted from the 5' and/or 3' end of a polynucleotide, wherein the subsequence encodes a polypeptide fragment having biological activity, e.g., beta-glucosidase activity or endoglucanase activity.

Isolated polynucleotide: The term "isolated polynucleotide" as used herein refers to a polynucleotide that is at least 20% pure, preferably at least 40% pure, more preferably at least 60% pure, even more preferably at least 80% pure, most preferably at least 90% pure, and even most preferably at least 95% pure, as determined by agarose electrophoresis.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively or recombinantly associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99%, and even most preferably at least 99.5% pure by weight. The polynucleotides are preferably in a substantially pure form, i.e., that the polynucleotide preparation is essentially free of other polynucleotide material with which it is natively or recombinantly associated. The polynucleotides may be of genomic, cDNA, RNA, semisynthetic, synthetic origin, or any combinations thereof.

cDNA: The term "cDNA" is defined herein as a DNA molecule that can be prepared by reverse transcription from a mature, spliced, mRNA molecule obtained from a eukaryotic cell. cDNA lacks intron sequences that are usually present in the corresponding genomic DNA. The initial, primary RNA transcript is a precursor to mRNA that is processed through a series of steps before appearing as mature spliced mRNA. These steps include the removal of intron sequences by a process called splicing. cDNA derived from mRNA lacks, therefore, any intron sequences.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature. The term nucleic acid construct is synonymous with the term "expression cassette" when the nucleic acid construct contains the control sequences required for expression of a coding sequence.

Control sequence: The term "control sequences" is defined herein to include all components, which are necessary or advantageous for the expression of a polynucleotide encoding a polypeptide. Each control sequence may be native or foreign to the nucleotide sequence encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of a polynucleotide sequence such that the control sequence directs the expression of the coding sequence of a polypeptide. In addition, the term "operably linked" also relates to two polynucleotides that are linked or fused, which are expressed together as a fused or fusion protein.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TAA, TAG and TGA. The coding sequence may be a DNA, cDNA, or recombinant nucleotide sequence.

Expression: The term "expression" includes any step involved in the production of the polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the invention and is operably linked to additional nucleotides that provide for its expression.

Host cell: The term "host cell", as used herein, includes any cell type that is susceptible to transformation, transfection, transduction, and the like with a nucleic acid construct or expression vector comprising a polynucleotide.

Variant: When used herein, the term "variant" means a polypeptide having biological activity produced by an organism expressing a modified nucleotide sequence, e.g., SEQ ID NO: 25 or a homologous sequence thereof, or the mature coding region thereof. The modified nucleotide sequence is obtained through human intervention by modification of a nucleotide sequence, e.g., SEQ ID NO: 23 or a homologous sequence thereof, or the mature coding region thereof. The modification can be a substitution, a deletion, and/or an insertion of one or more amino acids as well as a replacement of one or more amino acid side chains.

DETAILED DESCRIPTION OF THE INVENTION

The present invention relates to methods for producing a secreted polypeptide having biological activity, comprising: (a) transforming a fungal host cell with a fusion protein construct encoding a fusion protein, wherein the fusion protein construct comprises: (i) a first polynucleotide comprising a nucleotide sequence encoding a signal peptide; (ii) a second polynucleotide comprising a nucleotide sequence encoding at least a catalytic domain of an endoglucanase or a portion thereof; and (iii) a third polynucleotide comprising a nucleotide sequence encoding at least a catalytic domain of a polypeptide having biological activity or a portion thereof; wherein the signal peptide and at least the catalytic domain of the endoglucanase or the portion thereof increases secretion of the polypeptide having biological activity or the portion thereof compared to the absence of at least the catalytic domain of the endoglucanase or the portion thereof; (b) cultivating the transformed fungal host cell under conditions suitable for production of the fusion protein; and (c) recovering the fusion protein, a component thereof, or a combination thereof, from the cultivation medium, wherein the fusion protein or the component thereof has biological activity.

In a preferred aspect, the 3' end of the first polynucleotide is operably linked to the 5' end of the second polynucleotide and the 3' end of the second polynucleotide is operably linked to the 5' end of the third polynucleotide. In another preferred aspect, the 3' end of the first polynucleotide is operably linked to the 5' end of the third polynucleotide and the 3' end of the third polynucleotide is operably linked to the 5' end of the second polynucleotide to encode a fusion protein.

A fusion protein is produced by fusing a nucleotide sequence encoding a polypeptide having biological activity or a portion thereof to a nucleotide sequence encoding a polypeptide having endoglucanase activity or a portion thereof and a nucleotide sequence encoding a signal peptide operably linked to the nucleotide sequence encoding the polypeptide having endoglucanase activity or a portion thereof. Techniques for producing fusion proteins are known in the art, and include, for example, ligating the coding sequences encoding the polypeptides so that they are in frame and expression of the fused polypeptide is under control of the same promoter(s) and terminator. Fusion proteins may also be constructed using intein technology in which fusions are created post-translationally (Cooper et al., 1993, *EMBO J.* 12: 2575-2583; Dawson et al., 1994, *Science* 266: 776-779).

A fusion protein having biological activity comprising a signal peptide, at least the catalytic domain of an endoglucanase or a portion thereof, and at least the catalytic domain of a polypeptide having biological activity or a portion thereof, increases secretion of the fusion protein compared to the absence of at least the catalytic domain of the endoglucanase or a portion thereof. The increase in secretion of the fusion protein having biological activity is at least 5%, preferably at least 10%, more preferably at least 25%, even more preferably at least 50%, more preferably at least 100%, even more preferably at least 150%, even more preferably at least 200%, most preferably at least 500%, and even most preferably at least 1000% compared to the absence of at least the catalytic domain of the endoglucanase.

In each of the preferred aspects below, the components of a fusion protein construct (nucleic acid construct) are operably linked from the 5' end to the 3' end of the construct.

In a preferred aspect, the fusion protein construct comprises a polynucleotide comprising a nucleotide sequence encoding a signal peptide; a polynucleotide comprising a nucleotide sequence encoding a catalytic domain of an endoglucanase; and a polynucleotide comprising a nucleotide sequence encoding a catalytic domain of a polypeptide having biological activity.

In another preferred aspect, the fusion protein construct comprises a polynucleotide comprising a nucleotide sequence encoding a signal peptide; a polynucleotide comprising a nucleotide sequence encoding a catalytic domain of a polypeptide having biological activity; and a polynucleotide comprising a nucleotide sequence encoding a catalytic domain of an endoglucanase.

In another preferred aspect, the fusion protein construct comprises a polynucleotide comprising a nucleotide sequence encoding a signal peptide; a polynucleotide comprising a nucleotide sequence encoding a mature polypeptide of an endoglucanase; and a polynucleotide comprising a nucleotide sequence encoding a catalytic domain of a polypeptide having biological activity.

In another preferred aspect, the fusion protein construct comprises a polynucleotide comprising a nucleotide sequence encoding a signal peptide; a polynucleotide comprising a nucleotide sequence encoding a catalytic domain of a polypeptide having biological activity; and a polynucleotide comprising a nucleotide sequence encoding a mature polypeptide of an endoglucanase.

In another preferred aspect, the fusion protein construct comprises a polynucleotide comprising a nucleotide sequence encoding a signal peptide; a polynucleotide comprising a nucleotide sequence encoding a catalytic domain of an endoglucanase; and a polynucleotide comprising a nucleotide sequence encoding a mature polypeptide of a polypeptide having biological activity.

In another preferred aspect, the fusion protein construct comprises a polynucleotide comprising a nucleotide sequence encoding a signal peptide; a polynucleotide comprising a nucleotide sequence encoding a mature polypeptide of a polypeptide having biological activity; and a polynucleotide comprising a nucleotide sequence encoding a catalytic domain of an endoglucanase.

In another preferred aspect, the fusion protein construct comprises a polynucleotide comprising a nucleotide sequence encoding a signal peptide; a polynucleotide comprising a nucleotide sequence encoding a mature polypeptide of an endoglucanase; and a polynucleotide comprising a nucleotide sequence encoding a mature polypeptide of a polypeptide having biological activity.

In another preferred aspect, the fusion protein construct comprises a polynucleotide comprising a nucleotide sequence encoding a signal peptide; a polynucleotide comprising a nucleotide sequence encoding a mature polypeptide of a polypeptide having biological activity; and a polynucleotide comprising a nucleotide sequence encoding a mature polypeptide of an endoglucanase.

In another preferred aspect, the fusion protein construct comprises a polynucleotide comprising a nucleotide sequence encoding a signal peptide; a polynucleotide comprising a nucleotide sequence encoding a catalytic domain of an endoglucanase; and a polynucleotide comprising a nucleotide sequence encoding a full-length polypeptide of a polypeptide having biological activity.

In another preferred aspect, the fusion protein construct comprises a polynucleotide comprising a nucleotide sequence encoding a signal peptide; a polynucleotide comprising a nucleotide sequence encoding a full-length polypeptide of a polypeptide having biological activity; and a polynucleotide comprising a nucleotide sequence encoding a catalytic domain of an endoglucanase.

In another preferred aspect, the fusion protein construct comprises a polynucleotide comprising a nucleotide sequence encoding a signal peptide; a polynucleotide comprising a nucleotide sequence encoding a mature polypeptide of an endoglucanase; and a polynucleotide comprising a nucleotide sequence encoding a full-length polypeptide of a polypeptide having biological activity.

In another preferred aspect, the fusion protein construct comprises a polynucleotide comprising a nucleotide sequence encoding a signal peptide; a polynucleotide comprising a nucleotide sequence encoding a full-length polypeptide of a polypeptide having biological activity; and a polynucleotide comprising a nucleotide sequence encoding a mature polypeptide of an endoglucanase.

In another preferred aspect, the fusion protein construct comprises a polynucleotide comprising a nucleotide sequence encoding a full-length polypeptide of an endoglucanase (signal peptide and mature polypeptide); and a polynucleotide comprising a nucleotide sequence encoding a full-length polypeptide of a polypeptide having biological activity.

In another preferred aspect, the fusion protein construct comprises a polynucleotide comprising a nucleotide sequence encoding a full-length polypeptide of a polypeptide having biological activity and a polynucleotide comprising a nucleotide sequence encoding a full-length polypeptide of an endoglucanase (signal peptide and mature polypeptide).

In another preferred aspect, the fusion protein construct comprises a polynucleotide comprising a nucleotide sequence encoding a signal peptide; a polynucleotide comprising a nucleotide sequence encoding a catalytic domain of an endoglucanase, and a polynucleotide encoding a linker and/or a polynucleotide encoding a carbohydrate binding module; and a polynucleotide comprising a nucleotide sequence encoding a catalytic domain of a polypeptide having biological activity.

In another preferred aspect, the fusion protein construct comprises a polynucleotide comprising a nucleotide sequence encoding a signal peptide; a polynucleotide comprising a nucleotide sequence encoding a catalytic domain of a polypeptide having biological activity, and a polynucleotide encoding a linker and/or a polynucleotide encoding a carbohydrate binding module; and a polynucleotide comprising a nucleotide sequence encoding a catalytic domain of an endoglucanase.

In another preferred aspect, the fusion protein construct comprises a polynucleotide comprising a nucleotide sequence encoding a signal peptide; a polynucleotide comprising a nucleotide sequence encoding a mature polypeptide of an endoglucanase, and a polynucleotide encoding a linker and/or a polynucleotide encoding a carbohydrate binding module; and a polynucleotide comprising a nucleotide sequence encoding a catalytic domain of a polypeptide having biological activity.

In another preferred aspect, the fusion protein construct comprises a polynucleotide comprising a nucleotide sequence encoding a signal peptide; a polynucleotide comprising a nucleotide sequence encoding a catalytic domain of a polypeptide having biological activity, and a polynucleotide encoding a linker and/or a polynucleotide encoding a carbohydrate binding module; and a polynucleotide comprising a nucleotide sequence encoding a mature polypeptide of an endoglucanase.

In another preferred aspect, the fusion protein construct comprises a polynucleotide comprising a nucleotide sequence encoding a signal peptide; a polynucleotide comprising a nucleotide sequence encoding a catalytic domain of an endoglucanase, and a polynucleotide encoding a linker and/or a polynucleotide encoding a carbohydrate binding module; and a polynucleotide comprising a nucleotide sequence encoding a mature polypeptide of a polypeptide having biological activity.

In another preferred aspect, the fusion protein construct comprises a polynucleotide comprising a nucleotide sequence encoding a signal peptide; a polynucleotide comprising a nucleotide sequence encoding a mature polypeptide of a polypeptide having biological activity, and a polynucleotide encoding a linker and/or a polynucleotide encoding a carbohydrate binding module; and a polynucleotide comprising a nucleotide sequence encoding a catalytic domain of an endoglucanase.

In another preferred aspect, the fusion protein construct comprises a polynucleotide comprising a nucleotide sequence encoding a signal peptide; a polynucleotide comprising a nucleotide sequence encoding a mature polypeptide of an endoglucanase, and a polynucleotide encoding a linker and/or a polynucleotide encoding a carbohydrate binding module; and a polynucleotide comprising a nucleotide sequence encoding a mature polypeptide of a polypeptide having biological activity.

In another preferred aspect, the fusion protein construct comprises a polynucleotide comprising a nucleotide sequence encoding a signal peptide; a polynucleotide comprising a nucleotide sequence encoding a mature polypeptide of a polypeptide having biological activity, and a polynucleotide encoding a linker and/or a polynucleotide encoding a carbohydrate binding module; and a polynucleotide comprising a nucleotide sequence encoding a mature polypeptide of an endoglucanase.

In another preferred aspect, the fusion protein construct comprises a polynucleotide comprising a nucleotide sequence encoding a signal peptide; a polynucleotide comprising a nucleotide sequence encoding a catalytic domain of an endoglucanase, and a polynucleotide encoding a linker and/or a polynucleotide encoding a carbohydrate binding module; and a polynucleotide comprising a nucleotide sequence encoding a full-length polypeptide of a polypeptide having biological activity.

In another preferred aspect, the fusion protein construct comprises a polynucleotide comprising a nucleotide sequence encoding a signal peptide; a polynucleotide comprising a nucleotide sequence encoding a full-length polypeptide of a polypeptide having biological activity, and a polynucleotide encoding a linker and/or a polynucleotide encoding a carbohydrate binding module; and a polynucleotide comprising a nucleotide sequence encoding a catalytic domain of an endoglucanase.

In another preferred aspect, the fusion protein construct comprises a polynucleotide comprising a nucleotide sequence encoding a signal peptide; a polynucleotide comprising a nucleotide sequence encoding a mature polypeptide of an endoglucanase, and a polynucleotide encoding a linker and/or a polynucleotide encoding a carbohydrate binding module; and a polynucleotide comprising a nucleotide sequence encoding a full-length polypeptide of a polypeptide having biological activity.

In another preferred aspect, the fusion protein construct comprises a polynucleotide comprising a nucleotide sequence encoding a signal peptide; a polynucleotide comprising a nucleotide sequence encoding a full-length polypeptide of a polypeptide having biological activity, and a polynucleotide encoding a linker and/or a polynucleotide encoding a carbohydrate binding module; and a polynucleotide comprising a nucleotide sequence encoding a mature polypeptide of an endoglucanase.

In another preferred aspect, the fusion protein construct comprises a polynucleotide comprising a nucleotide sequence encoding a signal peptide; a polynucleotide comprising a nucleotide sequence encoding a catalytic domain of an endoglucanase; a polynucleotide comprising a nucleotide sequence encoding another signal peptide; and a polynucleotide comprising a nucleotide sequence encoding a catalytic domain of a polypeptide having biological activity.

In another preferred aspect, the fusion protein construct comprises a polynucleotide comprising a nucleotide sequence encoding a signal peptide; a polynucleotide comprising a nucleotide sequence encoding a catalytic domain of a polypeptide having biological activity; a polynucleotide comprising a nucleotide sequence encoding another signal peptide; and a polynucleotide comprising a nucleotide sequence encoding a catalytic domain of an endoglucanase.

In another preferred aspect, the fusion protein construct comprises a polynucleotide comprising a nucleotide sequence encoding a signal peptide; a polynucleotide comprising a nucleotide sequence encoding a mature polypeptide of an endoglucanase; a polynucleotide comprising a nucleotide sequence encoding another signal peptide; and a polynucleotide comprising a nucleotide sequence encoding a catalytic domain of a polypeptide having biological activity.

In another preferred aspect, the fusion protein construct comprises a polynucleotide comprising a nucleotide sequence encoding a signal peptide; a polynucleotide comprising a nucleotide sequence encoding a catalytic domain of a polypeptide having biological activity; a polynucleotide comprising a nucleotide sequence encoding another signal peptide; and a polynucleotide comprising a nucleotide sequence encoding a mature polypeptide of an endoglucanase.

In another preferred aspect, the fusion protein construct comprises a polynucleotide comprising a nucleotide sequence encoding a signal peptide; a polynucleotide comprising a nucleotide sequence encoding a catalytic domain of an endoglucanase; a polynucleotide comprising a nucleotide sequence encoding another signal peptide; and a polynucleotide comprising a nucleotide sequence encoding a mature polypeptide of a polypeptide having biological activity.

In another preferred aspect, the fusion protein construct comprises a polynucleotide comprising a nucleotide sequence encoding a signal peptide; a polynucleotide comprising a nucleotide sequence encoding a mature polypeptide of a polypeptide having biological activity; a polynucleotide comprising a nucleotide sequence encoding another signal peptide; and a polynucleotide comprising a nucleotide sequence encoding a catalytic domain of an endoglucanase.

In another preferred aspect, the fusion protein construct comprises a polynucleotide comprising a nucleotide sequence encoding a signal peptide; a polynucleotide comprising a nucleotide sequence encoding a mature polypeptide of an endoglucanase; a polynucleotide comprising a nucleotide sequence encoding another signal peptide; and a polynucleotide comprising a nucleotide sequence encoding a mature polypeptide of a polypeptide having biological activity.

In another preferred aspect, the fusion protein construct comprises a polynucleotide comprising a nucleotide sequence encoding a signal peptide; a polynucleotide comprising a nucleotide sequence encoding a mature polypeptide of a polypeptide having biological activity; a polynucleotide comprising a nucleotide sequence encoding another signal peptide; and a polynucleotide comprising a nucleotide sequence encoding a mature polypeptide of an endoglucanase.

In another preferred aspect, the fusion protein construct comprises a polynucleotide comprising a nucleotide sequence encoding a signal peptide; a polynucleotide comprising a nucleotide sequence encoding a catalytic domain of an endoglucanase, and a polynucleotide encoding a linker and/or a polynucleotide encoding a carbohydrate binding module; a polynucleotide comprising a nucleotide sequence encoding another signal peptide; and a polynucleotide comprising a nucleotide sequence encoding a catalytic domain of a polypeptide having biological activity.

In another preferred aspect, the fusion protein construct comprises a polynucleotide comprising a nucleotide sequence encoding a signal peptide; polynucleotide comprising a nucleotide sequence encoding a catalytic domain of a polypeptide having biological activity, and a polynucleotide encoding a linker and/or a polynucleotide encoding a carbohydrate binding module; a polynucleotide comprising a nucleotide sequence encoding another signal peptide; and a polynucleotide comprising a nucleotide sequence encoding a catalytic domain of an endoglucanase.

In another preferred aspect, the fusion protein construct comprises a polynucleotide comprising a nucleotide sequence encoding a signal peptide; a polynucleotide comprising a nucleotide sequence encoding a mature polypeptide of an endoglucanase, and a polynucleotide encoding a linker and/or a polynucleotide encoding a carbohydrate binding module; a polynucleotide comprising a nucleotide sequence encoding another signal peptide; and a polynucleotide comprising a nucleotide sequence encoding a catalytic domain of a polypeptide having biological activity.

In another preferred aspect, the fusion protein construct comprises a polynucleotide comprising a nucleotide sequence encoding a signal peptide; a polynucleotide comprising a nucleotide sequence encoding a catalytic domain of a polypeptide having biological activity, and a polynucleotide encoding a linker and/or a polynucleotide encoding a carbohydrate binding module; a polynucleotide comprising a nucleotide sequence encoding another signal peptide; and a polynucleotide comprising a nucleotide sequence encoding a mature polypeptide of an endoglucanase.

In another preferred aspect, the fusion protein construct comprises a polynucleotide comprising a nucleotide sequence encoding a signal peptide; a polynucleotide comprising a nucleotide sequence encoding a catalytic domain of an endoglucanase, and a polynucleotide encoding a linker and/or a polynucleotide encoding a carbohydrate binding module; a polynucleotide comprising a nucleotide sequence encoding another signal peptide; and a polynucleotide comprising a nucleotide sequence encoding a mature polypeptide of a polypeptide having biological activity.

In another preferred aspect, the fusion protein construct comprises a polynucleotide comprising a nucleotide sequence encoding a signal peptide; a polynucleotide comprising a nucleotide sequence encoding a mature polypeptide of a polypeptide having biological activity, and a polynucleotide encoding a linker and/or a polynucleotide encoding a carbohydrate binding module; a polynucleotide comprising a nucleotide sequence encoding another signal peptide; and a polynucleotide comprising a nucleotide sequence encoding a catalytic domain of an endoglucanase.

In another preferred aspect, the fusion protein construct comprises a polynucleotide comprising a nucleotide sequence encoding a signal peptide; a polynucleotide comprising a nucleotide sequence encoding a mature polypeptide of an endoglucanase, and a polynucleotide encoding a linker and/or a polynucleotide encoding a carbohydrate binding module; a polynucleotide comprising a nucleotide sequence encoding another signal peptide; and a polynucleotide comprising a nucleotide sequence encoding a mature polypeptide of a polypeptide having biological activity.

In another preferred aspect, the fusion protein construct comprises a polynucleotide comprising a nucleotide sequence encoding a signal peptide; and a polynucleotide comprising a nucleotide sequence encoding a mature polypeptide of a polypeptide having biological activity, and a polynucleotide encoding a linker and/or a polynucleotide encoding a carbohydrate binding module; a polynucleotide comprising a nucleotide sequence encoding another signal peptide; and a polynucleotide comprising a nucleotide sequence encoding a mature polypeptide of an endoglucanase.

In another preferred aspect, for each of the preferred aspects above, the polynucleotides may encode a portion of the catalytic domain, the mature polypeptide, or the full-length polypeptide of an endoglucanase or a polypeptide having biological activity. The portion of the endoglucanase may or may not have endoglucanase activity. In a more preferred aspect, the portion of the endoglucanase has endoglucanase activity.

In each of the preferred aspects above, the components of the fusion protein constructs further comprise a promoter region and/or a terminator region.

Endoglucanases and Polynucleotides Thereof

A polynucleotide encoding a catalytic domain, mature polypeptide, or full-length polypeptide of an endoglucanase, or portions thereof, may be obtained from any organism. For purposes of the present invention, the term "polypeptide" will be understood to include a full-length polypeptide, mature polypeptide, or catalytic domain; or portions or fragments thereof that have activity. The term "obtained from" as used herein in connection with a given source shall mean that the polypeptide encoded by a nucleotide sequence is produced by the source or by a strain in which the nucleotide sequence from the source has been inserted.

Many endoglucanases have a multidomain structure consisting of a catalytic domain separated from a carbohydrate binding domain (CBM) by a linker peptide (Suurnakki et al., 2000, *Cellulose* 7: 189-209). The catalytic domain contains the active site whereas the CBM interacts with cellulose by binding the enzyme to it (van Tilbeurgh et al., 1986, FEBS Letters 204: 223-227; Tomme et al., 1988, *European Journal of Biochemistry* 170: 575-581)

A polynucleotide encoding a polypeptide having endoglucanase activity may be obtained from a gene encoding a bacterial polypeptide. For example, the polypeptide may be a Gram positive bacterial polypeptide including, but not limited to, a *Bacillus, Streptococcus, Streptomyces, Staphylococcus, Enterococcus, Lactobacillus, Lactococcus, Clostridium, Geobacillus,* or *Oceanobacillus* polypeptide, e.g., a *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis, Bacillus thuringiensis, Streptococcus equisimilis, Streptococcus pyogenes, Streptococcus uberis,* and *Streptococcus equi* subsp. *Zooepidemicus, Streptomyces lividans,* or *Streptomyces murinus* polypeptide; or a Gram negative bacterial polypeptide including, but not limited to, an *E. coli, Pseudomonas, Salmonella, Campylobacter, Helicobacter, Flavobacterium, Fusobacterium, Ilyobacter, Neisseria,* or *Ureaplasma* polypeptide.

Examples of bacterial endoglucanases that can be used as sources for the polynucleotides in the methods of the present invention, include, but are not limited to, an *Acidothermus cellulolyticus* endoglucanase (WO 91/05039; WO 93/15186; U.S. Pat. No. 5,275,944; WO 96/02551; U.S. Pat. No. 5,536, 655, WO 00/70031, WO 05/093050); *Thermobifida fusca* endoglucanase III (WO 05/093050); and *Thermobifida fusca* endoglucanase V (WO 05/093050).

A polynucleotide encoding a polypeptide having endoglucanase activity may be obtained from a gene encoding a fungal polypeptide, and more preferably a yeast polypeptide such as a *Candida, Kluyveromyces, Pichia, Saccharomyces, Schizosaccharomyces,* or *Yarrowia* polypeptide; or more preferably a filamentous fungal polypeptide such as an *Acremonium, Aspergillus, Aureobasidium, Cladorrhinum, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium,* or *Trichoderma* polypeptide.

In a preferred aspect, a polynucleotide encoding a polypeptide having endoglucanase activity may be obtained from a gene encoding a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* polypeptide.

In another preferred aspect, a polynucleotide encoding a polypeptide having endoglucanase activity may be obtained from a gene encoding an *Aspergillus aculeatus, Aspergillus awamori, Aspergillus fumigatus, Aspergillus foetidus, Aspergillus japonicus, Aspergillus nidulans, Aspergillus niger, Aspergillus oryzae, Cladorrhinum foecundissimum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Thielavia terricola, Thielavia thermophila, Thielavia variospora, Thielavia wareingii, Trichoderma harzianum, Trichoderma koningii, Trichoderma longibrachiatum, Trichoderma reesei,* or *Trichoderma viride* polypeptide.

Examples of fungal endoglucanases that can be used as sources for the polynucleotides in the methods of the present invention, include, but are not limited to, a *Trichoderma reesei* EG1 (Penttila et al., 1986, *Gene* 45: 253-263; GENBANK™ accession no. M15665); *Trichoderma reesei* EG2 (Saloheimo, et al., 1988, *Gene* 63:11-22; GENBANK™ accession no. M19373); *Trichoderma reesei* EG3 (Okada et al., 1988, *Appl. Environ. Microbiol.* 64: 555-563; GENBANK™ accession no. AB003694); *Trichoderma reesei* EG4 (Saloheimo et al., 1997, *Eur. J. Biochem.* 249: 584-591; GENBANK™ accession no. Y11113); and *Trichoderma reesei* EG5 (Saloheimo et al., 1994, *Molecular Microbiology* 13: 219-228; GENBANK™ accession no. Z33381); *Aspergillus aculeatus* endoglucanase (Ooi et al., 1990, *Nucleic Acids Research* 18: 5884); *Aspergillus kawachii* (Sakamoto et al., 1995, *Current Genetics* 27: 435-439); *Erwinia carotovara* endoglucanase (Saarilahti et al., 1990, *Gene* 90: 9-14); *Fusarium oxysporum* (GENBANK™ accession no. L29381); *Humicola grisea* var. *thermoidea* (GENBANK™ accession no. AB003107); *Melanocarpus albomyces* (GENBANK™ accession no. MAL515703); and *Neurospora crassa* (GENBANK™ accession no. XM_324477).

Other endoglucanases are disclosed in numerous Glycosyl Hydrolase families using the classification according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696.

The techniques used to isolate or clone a polynucleotide encoding a polypeptide having endoglucanase activity are known in the art and include isolation from genomic DNA, preparation from cDNA, or a combination thereof. The cloning of the polynucleotides from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application,* Academic Press, New York. Other nucleic acid amplification procedures such as ligase chain reaction (LCR), ligated activated transcription (LAT) and nucleotide sequence-based amplification (NASBA) may be used.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

In a preferred aspect, the full-length polypeptide, mature polypeptide, or catalytic domain of the endoglucanase, or a portion thereof, is encoded by a polynucleotide obtained from an endoglucanase I gene.

In another preferred aspect, the full-length polypeptide, mature polypeptide, or catalytic domain of the endoglucanase, or a portion thereof, is encoded by a polynucleotide obtained from an endoglucanase II gene.

In another preferred aspect, the full-length polypeptide, mature polypeptide, or catalytic domain of the endoglucanase, or a portion thereof, is encoded by a polynucleotide obtained from an endoglucanase III gene.

In another preferred aspect, the full-length polypeptide, mature polypeptide, or catalytic domain of the endoglucanase, or a portion thereof, is encoded by a polynucleotide obtained from an endoglucanase IV gene.

In another preferred aspect, the full-length polypeptide, mature polypeptide, or catalytic domain of the endoglucanase, or a portion thereof, is encoded by a polynucleotide obtained from an endoglucanase V gene. In a more preferred aspect, the full-length polypeptide, mature polypeptide, or catalytic domain of the endoglucanase, or a portion thereof, is encoded by a polynucleotide obtained from a *Humicola insolens* endoglucanase V gene. In a most preferred aspect, the full-length polypeptide, mature polypeptide, or catalytic domain of the endoglucanase, or a portion thereof, is encoded by a polynucleotide obtained from a *Humicola insolens* endoglucanase V gene that encodes the polypeptide of SEQ ID NO: 2. In another most preferred aspect, the full-length polypeptide of the endoglucanase, or a portion thereof, is encoded by a polynucleotide obtained from a *Humicola insolens* endoglucanase V gene that encodes the full-length polypeptide of SEQ ID NO: 2. In another most preferred aspect, the mature polypeptide of the endoglucanase, or a portion thereof, is encoded by a polynucleotide obtained from a *Humicola insolens* endoglucanase V gene that encodes the mature polypeptide of SEQ ID NO: 2. In another most preferred aspect, the catalytic domain of the endoglucanase, or a portion thereof, is encoded by a polynucleotide obtained from a *Humicola insolens* endoglucanase V gene that encodes the catalytic domain of SEQ ID NO: 2. In another most preferred aspect, the full-length polypeptide, mature polypeptide, or catalytic domain of the endoglucanase, or a portion thereof, is encoded by a polynucleotide obtained from a *Humicola insolens* endoglucanase V gene comprising SEQ ID NO: 1. In another most preferred aspect, the full-length polypeptide of the endoglucanase, or a portion thereof, is encoded by a polynucleotide obtained from a *Humicola insolens* endoglucanase V gene comprising SEQ ID NO: 1. In another most preferred aspect, the mature polypeptide of the endoglucanase, or a portion thereof, is encoded by a polynucleotide obtained from a *Humicola insolens* endoglucanase V gene comprising the mature polypeptide coding sequence of SEQ ID NO: 1. In another most preferred aspect, the catalytic domain of the endoglucanase, or a portion thereof, is encoded by a polynucleotide obtained from a *Humicola insolens* endoglucanase V gene comprising the catalytic domain coding sequence of SEQ ID NO: 1.

In another preferred aspect, the full-length polypeptide, mature polypeptide, or catalytic domain of the endoglucanase, or a portion thereof, is encoded by a polynucleotide obtained from an endoglucanase VI gene.

In another preferred aspect, the full-length polypeptide, mature polypeptide, or catalytic domain of the endoglucanase, or a portion thereof, is encoded by a polynucleotide obtained from a Family 5 endoglucanase gene. In a more preferred aspect, the full-length polypeptide, mature polypeptide, or catalytic domain of the endoglucanase, or a portion thereof, is encoded by a polynucleotide obtained from a *Myceliophthora thermophila* CBS 117.65 endoglucanase gene. In a most preferred aspect, the full-length polypeptide, mature polypeptide, or catalytic domain of the endoglucanase, or a portion thereof, is encoded by a polynucleotide obtained from a *Myceliophthora thermophila* CBS 117.65 endoglucanase gene that encodes the polypeptide of SEQ ID NO: 4. In another most preferred aspect, the full-length polypeptide, mature polypeptide, or catalytic domain of the endoglucanase, or a portion thereof, is encoded by a polynucleotide obtained from a *Myceliophthora thermophila* CBS 117.65 endoglucanase gene comprising SEQ ID NO: 3. In another more preferred aspect, the full-length polypeptide, mature polypeptide, or catalytic domain of the endoglucanase, or a portion thereof, is encoded by a polynucleotide obtained from a basidiomycete CBS 495.95 endoglucanase gene. In another most preferred aspect, the full-length polypeptide, mature polypeptide, or catalytic domain of the endoglucanase, or a portion thereof, is encoded by a polynucleotide obtained from a basidiomycete CBS 495.95 endoglucanase gene that encodes the polypeptide of SEQ ID NO: 6. In another most preferred aspect, the full-length polypeptide, mature polypeptide, or catalytic domain of the endoglucanase, or a portion thereof, is encoded by a polynucleotide obtained from a basidiomycete CBS 495.95 endoglucanase gene comprising SEQ ID NO: 5. In another more preferred aspect, the full-length polypeptide, mature polypeptide, or catalytic domain of the endoglucanase, or a portion thereof, is encoded by a polynucleotide obtained from a basidiomycete CBS 494.95 endoglucanase gene. In another most preferred aspect, the full-length polypeptide, mature polypeptide, or catalytic domain of the endoglucanase, or a portion thereof, is encoded by a polynucleotide obtained from a basidiomycete CBS 494.95 endoglucanase gene that encodes the polypeptide of SEQ ID NO: 8. In another most preferred aspect, the full-length polypeptide, mature polypeptide, or catalytic domain of the endoglucanase, or a portion thereof, is encoded by a polynucleotide obtained from a basidiomycete CBS 494.95 endoglucanase gene comprising SEQ ID NO: 7.

In another preferred aspect, the full-length polypeptide, mature polypeptide, or catalytic domain of the endoglucanase, or a portion thereof, is encoded by a polynucleotide obtained from a Family 6 endoglucanase gene. In another more preferred aspect, the full-length polypeptide, mature polypeptide, or catalytic domain of the endoglucanase, or a portion thereof, is encoded by a polynucleotide obtained from a *Thielavia terrestris* NRRL 8126 CEL6B endoglucanase gene. In another most preferred aspect, the full-length polypeptide, mature polypeptide, or catalytic domain of the endoglucanase, or a portion thereof, is encoded by a polynucleotide obtained from a *Thielavia terrestris* NRRL 8126 CEL6B endoglucanase gene that encodes the polypeptide of SEQ ID NO: 10. In another most preferred aspect, the full-length polypeptide, mature polypeptide, or catalytic domain of the endoglucanase, or a portion thereof, is encoded by a polynucleotide obtained from a *Thielavia terrestris* NRRL 8126 CEL6B endoglucanase gene comprising SEQ ID NO: 9. In another more preferred aspect, the full-length polypeptide, mature polypeptide, or catalytic domain of the endoglucanase, or a portion thereof, is encoded by a polynucleotide obtained from a *Thielavia terrestris* NRRL 8126 CEL6C endoglucanase gene. In another most preferred aspect, the full-length polypeptide, mature polypeptide, or catalytic domain of the endoglucanase, or a portion thereof, is encoded by a polynucleotide obtained from a *Thielavia terrestris* NRRL 8126 CEL6C endoglucanase gene that encodes the polypeptide of SEQ ID NO: 12. In another most preferred aspect, the full-length polypeptide, mature polypeptide, or catalytic domain of the endoglucanase, or a portion thereof, is encoded by a polynucleotide obtained from a *Thielavia terrestris* NRRL 8126 CEL6C endoglucanase gene comprising SEQ ID NO: 11.

In another preferred aspect, the full-length polypeptide, mature polypeptide, or catalytic domain of the endoglucanase, or a portion thereof, is encoded by a polynucleotide obtained from a Family 7 endoglucanase gene. In another more preferred aspect, the full-length polypeptide, mature polypeptide, or catalytic domain of the endoglucanase, or a portion thereof, is encoded by a polynucleotide obtained from a *Thielavia terrestris* NRRL 8126 CEL7C endoglucanase gene. In another most preferred aspect, the full-length polypeptide, mature polypeptide, or catalytic domain of the endoglucanase, or a portion thereof, is encoded by a polynucleotide obtained from a *Thielavia terrestris* NRRL 8126 CEL7C endoglucanase gene that encodes the polypeptide of SEQ ID NO: 14. In another most preferred aspect, the full-length polypeptide, mature polypeptide, or catalytic domain of the endoglucanase, or a portion thereof, is encoded by a polynucleotide obtained from a *Thielavia terrestris* NRRL 8126 CEL7C endoglucanase gene comprising SEQ ID NO: 13. In another more preferred aspect, the full-length polypeptide, mature polypeptide, or catalytic domain of the endoglucanase, or a portion thereof, is encoded by a polynucleotide obtained from a *Thielavia terrestris* NRRL 8126 CEL7E endoglucanase gene. In another most preferred aspect, the full-length polypeptide, mature polypeptide, or catalytic domain of the endoglucanase, or a portion thereof, is encoded by a polynucleotide obtained from a *Thielavia terrestris* NRRL 8126 CEL7E endoglucanase gene that encodes the polypeptide of SEQ ID NO: 16. In another most preferred aspect, the full-length polypeptide, mature polypeptide, or catalytic domain of the endoglucanase, or a portion thereof, is encoded by a polynucleotide obtained from a *Thielavia terrestris* NRRL 8126 CEL7E endoglucanase gene comprising SEQ ID NO: 15. In another more preferred aspect, the full-length polypeptide, mature polypeptide, or catalytic domain of the endoglucanase, or a portion thereof, is encoded by a polynucleotide obtained from a *Thielavia terrestris* NRRL 8126 CEL7F endoglucanase gene. In another most preferred aspect, the full-length polypeptide, mature polypeptide, or catalytic domain of the endoglucanase, or a portion thereof, is encoded by a polynucleotide obtained from a *Thielavia terrestris* NRRL 8126 CEL7F endoglucanase gene that encodes the polypeptide of SEQ ID NO: 18. In another most preferred aspect, the full-length polypeptide, mature polypeptide, or catalytic domain of the endoglucanase, or a portion thereof, is encoded by a polynucleotide obtained from a *Thielavia terrestris* NRRL 8126 CEL7F endoglucanase gene comprising SEQ ID NO: 17. In another more preferred aspect, the full-length polypeptide, mature polypeptide, or catalytic domain of the endoglucanase, or a portion thereof, is encoded by a polynucleotide obtained from a *Cladorrhinum foecundissimum* ATCC 62373 CEL7A endoglucanase gene. In another most preferred aspect, the full-length polypeptide, mature polypeptide, or catalytic domain of the endoglucanase, or a portion thereof, is encoded by a polynucleotide obtained from a *Cladorrhinum foecundissimum* ATCC 62373 CEL7A endoglucanase gene that encodes the polypeptide of SEQ ID NO: 20. In another most preferred aspect, the full-length polypeptide, mature polypeptide, or catalytic domain of the endoglucanase, or a portion thereof, is encoded by a polynucleotide obtained from a *Cladorrhinum foecundissimum* ATCC 62373 CEL7A endoglucanase gene comprising SEQ ID NO: 19.

In another most preferred aspect, the full-length polypeptide, mature polypeptide, or catalytic domain of the endoglucanase, or a portion thereof, is encoded by a polynucleotide obtained from a *Trichoderma reesei* strain No. VTT-D-80133 endoglucanase gene that encodes the polypeptide of SEQ ID NO: 22 (GENBANK™ accession no. M15665). In another most preferred aspect, the full-length polypeptide, mature polypeptide, or catalytic domain of the endoglucanase, or a portion thereof, is encoded by a polynucleotide obtained from a *Trichoderma reesei* strain No. VTT-D-80133 endoglucanase gene comprising SEQ ID NO: 21 (GENBANK™ accession no. M15665).

In another preferred aspect, the full-length polypeptide, mature polypeptide, or catalytic domain of the endoglucanase, or a portion thereof, is encoded by a polynucleotide obtained from a Family 9 endoglucanase gene.

In another preferred aspect, the full-length polypeptide, mature polypeptide, or catalytic domain of the endoglucanase, or a portion thereof, is encoded by a polynucleotide obtained from a Family 12 endoglucanase gene.

In another preferred aspect, the full-length polypeptide, mature polypeptide, or catalytic domain of the endoglucanase, or a portion thereof, is encoded by a polynucleotide obtained from a Family 45 endoglucanase gene.

In another preferred aspect, the full-length polypeptide, mature polypeptide, or catalytic domain of the endoglucanase, or a portion thereof, is encoded by a polynucleotide obtained from a Family 74 endoglucanase gene.

In another preferred aspect, the full-length polypeptide, mature polypeptide, or catalytic domain of the endoglucanase, or a portion thereof, is encoded by a polynucleotide obtained from a gene encoding a homologous polypeptide comprising an amino acid sequence that has a degree of identity to the amino acid sequences of the full-length polypeptide, mature polypeptide, or catalytic domain of SEQ ID NO: 2, SEQ ID NO: 4, SEQ ID NO: 6, or SEQ ID NO: 8, SEQ ID NO: 10, SEQ ID NO: 12, SEQ ID NO: 14, SEQ ID NO: 16, SEQ ID NO: 18, SEQ ID NO: 20, or SEQ ID NO: 22 of at least 60%, preferably at least 65%, more preferably at least 70%, more preferably at least 75%, more preferably at least 80%, more preferably at least 85%, even more preferably at least 90%, most preferably at least 95%, and even most preferably 96%, 97%, 98%, to or 99%, which have endoglucanase activity. In a preferred aspect, the homologous polypeptide has an amino acid sequence that differs by ten amino acids, preferably by five amino acids, more preferably by four amino acids, even more preferably by three amino acids, most preferably by two amino acids, and even most preferably by one amino acid from the full-length polypeptide, mature polypeptide, or catalytic domain of SEQ ID NO: 2, SEQ ID NO: 4, SEQ ID NO: 6, or SEQ ID NO: 8, SEQ ID NO: 10, SEQ ID NO: 12, SEQ ID NO: 14, SEQ ID NO: 16, SEQ ID NO: 18, SEQ ID NO: 20, or SEQ ID NO: 22.

In another preferred aspect, the full-length polypeptide, mature polypeptide, or catalytic domain of the endoglucanase, or a portion thereof, is encoded by a polynucleotide comprising a nucleotide sequence that hybridizes under very low stringency conditions, preferably low stringency conditions, more preferably medium stringency conditions, more preferably medium-high stringency conditions, even more preferably high stringency conditions, and most preferably very high stringency conditions with (i) SEQ ID NO: 1, SEQ ID NO: 3, SEQ ID NO: 5, or SEQ ID NO: 7, SEQ ID NO: 9, SEQ ID NO: 11, SEQ ID NO: 13, SEQ ID NO: 15, SEQ ID NO: 17, SEQ ID NO: 19, or SEQ ID NO: 21, (ii) the cDNA sequence contained in SEQ ID NO: 1, SEQ ID NO: 3, SEQ ID NO: 5, or SEQ ID NO: 7, SEQ ID NO: 9, SEQ ID NO: 11, SEQ ID NO: 13, SEQ ID NO: 15, SEQ ID NO: 17, SEQ ID NO: 19, or SEQ ID NO: 21, (iii) a subsequence of (i) or (ii), or (iv) a complementary strand of (i), (ii), or (iii) (J. Sambrook, E. F. Fritsch, and T. Maniatis, 1989, *Molecular Cloning, A Laboratory Manual*, 2d edition, Cold Spring Harbor, N.Y.). A subsequence of SEQ ID NO: 1, SEQ ID NO: 3, SEQ ID NO: 5, or SEQ ID NO: 7, SEQ ID NO: 9, SEQ ID NO: 11, SEQ ID NO: 13, SEQ ID NO: 15, SEQ ID NO: 17, SEQ ID NO: 19, or SEQ ID NO: 21 contains at least 100 contiguous nucleotides or preferably at least 200 contiguous nucleotides.

The nucleotide sequence of SEQ ID NO: 1, SEQ ID NO: 3, SEQ ID NO: 5, or SEQ ID NO: 7, SEQ ID NO: 9, SEQ ID NO: 11, SEQ ID NO: 13, SEQ ID NO: 15, SEQ ID NO: 17, SEQ ID NO: 19, or SEQ ID NO: 21, or a subsequence thereof, as well as the amino acid sequence of SEQ ID NO: 2, SEQ ID NO: 4, SEQ ID NO: 6, or SEQ ID NO: 8, SEQ ID NO: 10, SEQ ID NO: 12, SEQ ID NO: 14, SEQ ID NO: 16, SEQ ID NO: 18, SEQ ID NO: 20, or SEQ ID NO: 22, or a fragment thereof, may be used to design a nucleic acid probe to identify and clone DNA encoding polypeptides having endoglucanase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes that are at least 600 nucleotides, at least preferably at least 700 nucleotides, more preferably at least 800 nucleotides, or most preferably at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other organisms may, therefore, be screened for DNA that hybridizes with the probes described above and encodes a polypeptide having endoglucanase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with the sequences described above, the carrier material is used in a Southern blot.

For purposes of the present invention, hybridization indicates that the nucleotide sequence hybridizes to a labeled nucleic acid probe corresponding to one of the nucleotide sequences described above under very low to very high stringency conditions. Molecules to that the nucleic acid probe hybridizes under these conditions can be detected using X-ray film.

For long probes of at least 100 nucleotides in length, very low to very high stringency conditions are defined as prehybridization and hybridization at 42° C. in 5×SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at 45° C. (very low stringency), more preferably at 50° C. (low stringency), more preferably at 55° C. (medium stringency), more preferably at 60° C. (medium-high stringency), even more preferably at 65° C. (high stringency), and most preferably at 70° C. (very high stringency).

For short probes that are about 15 nucleotides to about 70 nucleotides in length, stringency conditions are defined as prehybridization, hybridization, and washing post-hybridization at about 5° C. to about 10° C. below the calculated $T_n$, using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally.

For short probes that are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

Polypeptides Having Biological Activity and Polynucleotides Thereof

Any polypeptide that is poorly secreted or not secreted at all may be used in the methods of the present invention. The polypeptide may be any polypeptide having a biological activity of interest. The polypeptide having biological activity may be native or heterologous (foreign) to the fungal host cell of interest. The term "heterologous polypeptide" is defined herein as a polypeptide that is not native to the host cell; or a native polypeptide in which structural modifications have been made to alter the native polypeptide.

In a preferred aspect, the polypeptide is an antibody, antigen, antimicrobial peptide, enzyme, growth factor, hormone, immunodilator, neurotransmitter, receptor, reporter protein, or structural protein.

In another preferred aspect, the polypeptide is an albumin, collagen, tropoelastin, elastin, or gelatin.

In a more preferred aspect, the polypeptide is an oxidoreductase, transferase, hydrolase, lyase, isomerase, or ligase.

In an even more preferred aspect, the polypeptide is an alpha-amylase, alpha-1,3-glucanase, alpha-galactosidase, alpha-glucosidase, alpha-1,6-mannosidase, aminopeptidase, amylase, arabinase, beta-agarase beta-amylase, beta-1,3-glucanase, beta-1,6-glucanase, beta-galactosidase, beta-glucosidase, beta-mannosidase, carbohydrase, carboxypeptidase, catalase, cellulase, chitinase, chitosanase, cutinase, cyclodextrin glycosyltransferase, deoxyribonuclease, dextranase, endo-1,4-beta-galactanase, endo-1,6-beta-galactanase, esterase, fucosidase, glucoamylase, glucocerebrosidase, hyaluronidase, inulinase, invertase, laccase, levanase, licheninase, lipase, lysozyme, mannosidase, mutanase, oxidase, pectinolytic enzyme, peroxidase, phospholipase, phytase, polygalacturonase, polyphenoloxidase, proteolytic enzyme, rhamnogalacturonase, rhamnosidase, ribonuclease, trehalase, transglutaminase, transglycosylase, urokinase, or xylanase.

In another even more preferred aspect, the polypeptide is a cellulolytic enzyme or cellulase. Examples of cellulolytic enzymes include, but are not limited to, endoglucanases, cellobiohydrolases, and beta-glucosidases. Other proteins that assist cellulolytic enzyme action are polypeptides having cellulolytic enhancing activity (see, for example, WO 2005/074647, WO 2005/074656, and U.S. Published Application 2007/0077630).

In a most preferred aspect, the polypeptide is an endoglucanase. In another most preferred aspect, the polypeptide is a cellobiohydrolase. In another most preferred aspect, the polypeptide is a beta-glucosidase. In another most preferred aspect, the polypeptide is a polypeptide having cellulolytic enhancing activity.

In another more preferred aspect, the polypeptide is a hemicellulase. Hemicellulases can be placed into three general categories: the endo-acting enzymes that attack internal bonds within the polysaccharide chain, the exo-acting enzymes that act processively from either the reducing or nonreducing end of polysaccharide chain, and the accessory enzymes, acetylesterases and esterases that hydrolyze lignin glycoside bonds, such as coumaric acid esterase and ferulic acid esterase (Wong, K. K. Y., Tan, L. U. L., and Saddler, J. N., 1988, Multiplicity of β-1,4-xylanase in microorganisms: Functions and applications, *Microbiol. Rev.* 52: 305-317; Tenkanen, M., and Poutanen, K., 1992, Significance of esterases in the degradation of xylans, in *Xylans and Xylanases*, Visser, J., Beldman, G., Kuster-van Someren, M. A., and Voragen, A. G. J., eds., Elsevier, New York, N.Y., 203-212; Coughlan, M. P., and Hazlewood, G. P., 1993, *Hemicellulose and hemicellulases*, Portland, London, UK; Brigham, J. S., Adney, W. S., and Himmel, M. E., 1996, Hemicellulases: Diversity and applications, in *Handbook on Bioethanol: Production and Utilization*, Wyman, C. E., ed., Taylor & Francis, Washington, D.C., 119-141).

Hemicellulases include, but are not limited to, xylanases, arabinofuranosidases, acetyl xylan esterase, glucuronidases, endo-galactanase, mannanases, endo- or exo-arabinases, exo-galactanases, and mixtures thereof. Examples of endo-acting hemicellulases and ancillary enzymes include, but are not limited to, endoarabinanase, endoarabinogalactanase, endoglucanase, endomannanase, endoxylanase, and feraxan endoxylanase. Examples of exo-acting hemicellulases and ancillary enzymes include, but are not limited to, alpha-L-arabinosidase, beta-L-arabinosidase, alpha-1,2-L-fucosidase, alpha-D-galactosidase, beta-D-galactosidase, beta-D-glucosidase, beta-D-glucuronidase, beta-D-mannosidase, beta-D-xylosidase, exoglucosidase, exocellobiohydrolase, exomannobiohydrolase, exomannanase, exoxylanase, xylan alpha-glucuronidase, and coniferin beta-glucosidase. Examples of esterases include, but are not limited to, acetyl esterases (acetylgalactan esterase, acetylmannan esterase, and acetylxylan esterase) and aryl esterases (coumaric acid esterase and ferulic acid esterase).

In another most preferred aspect, the polypeptide is a xylanase. In another most preferred aspect, the polypeptide is a xyloglucanase. In another most preferred aspect, the polypeptide is an arabinofuranosidase. In another most preferred aspect, the polypeptide is a glucuronidase, e.g., alpha-glucuronidase. In another most preferred aspect, the polypeptide is an endo-galactanase. In another most preferred aspect, the polypeptide is a mannanase. In another most preferred aspect, the polypeptide is an endo-arabinase. In another most preferred aspect, the polypeptide is an exo-arabinase. In another most preferred aspect, the polypeptide is an endoarabinanase. In another most preferred aspect, the polypeptide is an endoarabinogalactanase. In another most preferred aspect, the polypeptide is an endoglucanase. In another most preferred aspect, the polypeptide is an endomannanase. In another most preferred aspect, the polypeptide is an endoxylanase. In another most preferred aspect, the polypeptide is an feraxan endoxylanase. In another most preferred aspect, the polypeptide is an alpha-L-arabinosidase. In another most preferred aspect, the polypeptide is an beta-L-arabinosidase. In another most preferred aspect, the polypeptide is an beta-glucanase. In another most preferred aspect, the polypeptide is an alpha-1,2-L-fucosidase. In another most preferred aspect, the polypeptide is an alpha-D-galactosidase. In another most preferred aspect, the polypeptide is a beta-D-galactosidase. In another most preferred aspect, the polypeptide is a beta-D-glucosidase. In another most preferred aspect, the polypeptide is a beta-D-glucuronidase. In another most preferred aspect, the polypeptide is a beta-D-mannosidase. In another most preferred aspect, the polypeptide is a beta-D-xylosidase. In another most preferred aspect, the polypeptide is a exoglucosidase. In another most preferred aspect, the polypeptide is a exomannobiohydrolase. In another most preferred aspect, the polypeptide is a exomannanase. In another most preferred aspect, the polypeptide is a exoxylanase. In another most preferred aspect, the polypeptide is a xylan alpha-glucuronidase. In another most preferred aspect, the polypeptide is a coniferin beta-glucosidase.

In another more preferred aspect, the polypeptide is an esterase. As used herein, an "esterase" also known as a carboxylic ester hydrolase, refers to enzymes acting on ester bonds, and includes enzymes classified in EC 3.1.1 Carboxylic Ester Hydrolases according to Enzyme Nomenclature (*Enzyme Nomenclature*, 1992, Academic Press, San Diego, Calif., with Supplement 1 (1993), Supplement 2 (1994), Supplement 3 (1995), Supplement 4 (1997) and Supplement 5, in *Eur. J. Biochem.* 223: 1-5, 1994; *Eur. J. Biochem.* 232: 1-6, 1995; *Eur. J. Biochem.* 237: 1-5, 1996; *Eur. J. Biochem.* 250: 1-6, 1997, and *Eur. J. Biochem.* 264: 610-650, 1999; respectively). Non-limiting examples of esterases include arylesterase, triacylglycerol lipase, acetylesterase, acetylcholinesterase, cholinesterase, tropinesterase, pectinesterase, sterol esterase, chlorophyllase, L-arabinonolactonase, gluconolactonase, uronolactonase, tannase, retinyl-palmitate esterase, hydroxybutyrate-dimer hydrolase, acylglycerol lipase, 3-oxoadipate enol-lactonase, 1,4-lactonase, galactolipase, 4-pyridoxolactonase, acylcarnitine hydrolase, aminoacyl-tRNA hydrolase, D-arabinonolactonase, 6-phosphogluconolactonase, phospholipase A1, 6-acetylglucose deacetylase, lipoprotein lipase, dihydrocoumarin lipase, limonin-D-ring-lactonase, steroid-lactonase, triacetate-lactonase, actinomycin lactonase, orsellinate-depside hydrolase, cephalosporin-C deacetylase, chlorogenate hydrolase, alpha-amino-acid esterase, 4-methyloxaloacetate esterase, carboxymethylenebutenolidase, deoxylimonate A-ring-lactonase, 2-acetyl-1-alkylglycerophosphocholine esterase, fusarinine-C ornithinesterase, sinapine esterase, wax-ester hydrolase, phorbol-diester hydrolase, phosphatidylinositol deacylase, sialate 0-acetylesterase, acetoxybutynyl-bithiophene deacetylase, acetylsalicylate deacetylase, methylumbelliferyl-acetate deacetylase, 2-pyrone-4,6-dicarboxylate lactonase, N-acetylgalactosaminoglycan deacetylase, juvenile-hormone esterase, bis(2-ethylhexyl)phthalate esterase, protein-glutamate methylesterase, 11-cis-retinyl-palmitate hydrolase, all-trans-retinyl-palmitate hydrolase, L-rhamnono-1,4-lactonase, 5-(3,4-diacetoxybut-1-ynyl)-2, 2'-bithiophene deacetylase, fatty-acyl-ethyl-ester synthase, xylono-1,4-lactonase, N-acetylglucosaminylphosphatidylinositol deacetylase, cetraxate benzylesterase, and acetylalkylglycerol acetylhydrolase. Esterases that can be used for bioconversion of cellulose include acetyl esterases such as acetylgalactan esterase, acetylmannan esterase, and acetylxylan esterase, and esterases that hydrolyze lignin glycoside bonds, such as coumaric acid esterase and ferulic acid esterase.

In another most preferred aspect, the polypeptide is an acetyl esterase. In another most preferred aspect, the polypeptide is an acetylgalactan esterase. In another most preferred aspect, the polypeptide is an acetylmannan esterase. In another most preferred aspect, the polypeptide is an acetyl xylan esterase. In another most preferred aspect, the polypeptide is an aryl esterase. In another most preferred aspect, the polypeptide is a coumaric acid esterase. In another most preferred aspect, the polypeptide is a ferulic acid esterase.

In another more preferred aspect, the polypeptide is a lipase. In another more preferred aspect, the polypeptide is a phospholipase, e.g., phospholipase A1, phospholipase A2, phospholipase C, phospholipase C, or phospholipase D.

In another more preferred aspect, the polypeptide is a cutinase.

In another most preferred aspect, the polypeptide is a glucose isomerase. In another most preferred aspect, the polypeptide is a xylose isomerase.

In another more preferred aspect, the polypeptide is a proteolytic enzyme. Proteases are well known in the art and refer to enzymes that catalyze the cleavage of peptide bonds.

In another most preferred aspect, the polypeptide is a serine protease. In another most preferred aspect, the polypeptide is a metalloprotease. In another most preferred aspect, the polypeptide is a thiol protease.

In another more preferred aspect, the polypeptide is a peptidase. In another most preferred aspect, the polypeptide is an aminopeptidase, e.g., dipeptidylaminopeptidase or tripeptidylaminopeptidase. In another most preferred aspect, the polypeptide is a carboxypeptidase.

In another more preferred aspect, the polypeptide is a laccase.

In another more preferred aspect, the polypeptide is a peroxidase.

In another more preferred aspect, the polypeptide is a starch degrading enzyme. In another most preferred aspect, the polypeptide is an alpha-amylase. In another most preferred aspect, the polypeptide is an amyloglucosidase. In another most preferred aspect, the polypeptide is pullulanase. In another most preferred aspect, the polypeptide is a debranching enzyme. In another most preferred aspect, the polypeptide is a cylcodextrin glycosyltransferase.

A polynucleotide encoding a catalytic domain, mature polypeptide, or full-length polypeptide of a polypeptide having biological activity, or a portion thereof, may be obtained from any organism.

A polynucleotide encoding a polypeptide having biological activity may be obtained from a gene encoding a bacterial polypeptide. For example, the polypeptide may be a Gram positive bacterial polypeptide including, but not limited to, a *Bacillus, Streptococcus, Streptomyces, Staphylococcus, Enterococcus, Lactobacillus, Lactococcus, Clostridium, Geobacillus,* or *Oceanobacillus* polypeptide; or a Gram negative bacterial polypeptide including, but not limited to, an *E. coli, Pseudomonas, Salmonella, Campylobacter, Helicobacter, Flavobacterium, Fusobacterium, Ilyobacter, Neisseria,* or *Ureaplasma* polypeptide.

In a preferred aspect, a polynucleotide encoding a polypeptide having biological activity may be obtained from a gene encoding a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* polypeptide.

In another preferred aspect, a polynucleotide encoding a polypeptide having biological activity may be obtained from a gene encoding a *Streptococcus equisimilis, Streptococcus pyogenes, Streptococcus uberis,* or *Streptococcus equi* subsp. *Zooepidemicus* polypeptide.

In another preferred aspect, a polynucleotide encoding a polypeptide having biological activity may be obtained from a gene encoding a *Streptomyces achromogenes, Streptomyces avermitilis, Streptomyces coelicolor, Streptomyces griseus,* or *Streptomyces lividans* polypeptide.

A polynucleotide encoding a polypeptide having biological activity may also be obtained from a gene encoding a fungal polypeptide, and more preferably a yeast polypeptide such as a *Candida, Kluyveromyces, Pichia, Saccharomyces, Schizosaccharomyces,* or *Yarrowia* polypeptide; or more preferably a filamentous fungal polypeptide such as an *Acremonium, Agaricus, Alternaria, Aspergillus, Aureobasidium, Botryosphaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella,* or *Xylaria* polypeptide.

In a preferred aspect, a polynucleotide encoding a polypeptide having biological activity may be obtained from a gene encoding a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* polypeptide.

In another preferred aspect, a polynucleotide encoding a polypeptide having endoglucanase activity may be obtained from a gene encoding an *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Cladorrhinum foecundissimum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Thielavia variospora, Thielavia wareingii, Trichoderma harzianum, Trichoderma koningii, Trichoderma longibrachiatum, Trichoderma reesei,* or *Trichoderma viride*

In a particularly preferred aspect, the polypeptide having biological activity is a beta-glucosidase. Examples of beta-glucosidases that can be used as sources for the polynucleotides in the methods of the present invention, include, but are not limited to, an *Aspergillus oryzae* beta-glucosidase (WO 02/095014; WO 04/099228); *Aspergillus aculeatus* beta-glucosidase (Kawaguchi et al., 1996, *Gene* 173: 287-288); *Aspergillus avenaceus* (GENBANK™ accession no. AY943971); *Aspergillus fumigatus* (GENBANK™ accession no. XM745234); *Aspergillus kawachii* (GENBANK™ accession no. AB003470); *Aspergillus niger* (GENBANK™ AJ132386); *Magnaporthe grisea* (GENBANK™ accession no. AY849670); *Phanerochaete chrysosporium* (GENBANK™ accession no. AB253327); *Talaromyces emersonii* (GENBANK™ accession no. AY072918), and *Trichoderma reesei* (GENBANK™ accession nos. U09580, AB003110, AY281374, AY281375, AY281377, AY281378, and AY281379). Variants of beta-glucosidases may also be used as sources for the polynucleotides such as those described in WO 04/099228.

In a preferred aspect, the full-length polypeptide, mature polypeptide, or catalytic domain of the beta-glucosidase, or a portion thereof, is encoded by a polynucleotide obtained from a Family 1 beta-glucosidase gene.

In another preferred aspect, the full-length polypeptide, mature polypeptide, or catalytic domain of the beta-glucosidase, or a portion thereof, is encoded by a polynucleotide obtained from a Family 3 beta-glucosidase gene.

In another preferred aspect, the full-length polypeptide, mature polypeptide, or catalytic domain of the beta-glucosidase, or a portion thereof, is encoded by a polynucleotide obtained from an *Aspergillus oryzae* beta-glucosidase gene. In a most preferred aspect, the full-length polypeptide, mature polypeptide, or catalytic domain of the beta-glucosidase, or a portion thereof, is encoded by a polynucleotide obtained from an *Aspergillus oryzae* beta-glucosidase gene comprising SEQ ID NO: 23 that encodes the polypeptide of SEQ ID NO: 24 or an *Aspergillus oryzae* beta-glucosidase mutant gene comprising SEQ ID NO: 25 that encodes the polypeptide of SEQ ID NO: 26.

In another preferred aspect, the full-length polypeptide, mature polypeptide, or catalytic domain of the beta-glucosidase, or a portion thereof, is encoded by a polynucleotide obtained from an *Aspergillus fumigatus* beta-glucosidase gene. In a most preferred aspect, the full-length polypeptide, mature polypeptide, or catalytic domain of the beta-glucosidase, or a portion thereof, is encoded by a polynucleotide obtained from an *Aspergillus fumigatus* beta-glucosidase gene comprising SEQ ID NO: 27 that encodes the polypeptide of SEQ ID NO: 28.

In another preferred aspect, the full-length polypeptide, mature polypeptide, or catalytic domain of the beta-glucosidase, or a portion thereof, is encoded by a polynucleotide obtained from a *Penicillium brasilianum* strain IBT 20888 beta-glucosidase gene. In a most preferred aspect, the full-length polypeptide, mature polypeptide, or catalytic domain of the beta-glucosidase, or a portion thereof, is encoded by a polynucleotide obtained from a *Penicillium brasilianum* strain IBT 20888 beta-glucosidase gene comprising SEQ ID NO: 29 that encodes the polypeptide of SEQ ID NO: 30.

In another preferred aspect, the full-length polypeptide, mature polypeptide, or catalytic domain of the beta-glucosidase, or a portion thereof, is encoded by a polynucleotide obtained from a *Trichoderma reesei* strain No. QM9414 beta-glucosidase gene. In another most preferred aspect, the full-length polypeptide, mature polypeptide, or catalytic domain of the beta-glucosidase, or a portion thereof, is encoded by a polynucleotide obtained from a *Trichoderma reesei* strain No. QM9414 beta-glucosidase gene comprising SEQ ID NO: 31 that encodes the polypeptide of SEQ ID NO: 32 (GENBANK™ accession no. U09580).

In another preferred aspect, the beta-glucosidase is naturally secreted. In another preferred aspect, the beta-glucosidase is not naturally secreted.

In another preferred aspect, the full-length polypeptide, mature polypeptide, or catalytic domain of the beta-glucosidase, or a portion thereof, is encoded by a polynucleotide obtained from a gene encoding a homologous polypeptide comprising an amino acid sequence that has a degree of identity to the amino acid sequences of the full-length polypeptide, mature polypeptide, or catalytic domain of SEQ ID NO: 24, SEQ ID NO: 26, SEQ ID NO: 28, SEQ ID NO: 30, or SEQ ID NO: 32 of at least 60%, preferably at least 65%, more preferably at least 70%, more preferably at least 75%, more preferably at least 80%, more preferably at least 85%, even more preferably at least 90%, most preferably at least 95%, and even most preferably 96%, 97%, 98%, or 99%, which have endoglucanase activity. In a preferred aspect, the homologous polypeptide has an amino acid sequence that differs by ten amino acids, preferably by five amino acids, more preferably by four amino acids, even more preferably by three amino acids, most preferably by two amino acids, and even most preferably by one amino acid from the full-length polypeptide, mature polypeptide, or catalytic domain of SEQ ID NO: 24, SEQ ID NO: 26, SEQ ID NO: 28, SEQ ID NO: 30, or SEQ ID NO: 32.

In another preferred aspect, the full-length polypeptide, mature polypeptide, or catalytic domain of the beta-glucosidase, or a portion thereof, is encoded by a polynucleotide that hybridizes under very low stringency conditions, preferably low stringency conditions, more preferably medium stringency conditions, more preferably medium-high stringency conditions, even more preferably high stringency conditions, and most preferably very high stringency conditions with (i) SEQ ID NO: 23, SEQ ID NO: 25, SEQ ID NO: 27, SEQ ID NO: 29, or SEQ ID NO: 31, (ii) the cDNA sequence contained in SEQ ID NO: 23, SEQ ID NO: 25, SEQ ID NO: 27, SEQ ID NO: 29, or SEQ ID NO: 31, (iii) a subsequence of (i) or (ii), or (iv) a complementary strand of (i), (ii), or (iii) (J. Sambrook, E. F. Fritsch, and T. Maniatis, 1989, *Molecular Cloning, A Laboratory Manual*, 2d edition, Cold Spring Harbor, N.Y.). A subsequence of SEQ ID NO: 23, SEQ ID NO: 25, SEQ ID NO: 27, SEQ ID NO: 29, or SEQ ID NO: 31 contains at least 100 contiguous nucleotides or preferably at least 200 contiguous nucleotides.

The nucleotide sequence of SEQ ID NO: 23, SEQ ID NO: 25, SEQ ID NO: 27, SEQ ID NO: 29, or SEQ ID NO: 31, or a subsequence thereof, as well as the amino acid sequence of SEQ ID NO: 24, SEQ ID NO: 26, SEQ ID NO: 28, SEQ ID NO: 30, or SEQ ID NO: 32, or a fragment thereof, may be used to design a nucleic acid probe to identify and clone DNA encoding polypeptides having beta-glucosidase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes that are at least 600 nucleotides, at least preferably at least 700 nucleotides, more preferably at least 800 nucleotides, or most preferably at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

Signal Peptides

The signal peptide can be any appropriate signal peptide recognized by a host cell for extracellular secretion of a fusion protein of the present invention. The signal sequence is preferably that which is naturally associated with the endoglucanase component of the fusion protein to be expressed.

The 5' end of the coding sequence of the nucleotide sequence encoding a polypeptide may inherently contain a signal peptide coding region naturally linked in translation reading frame with the segment of the coding region that encodes the secreted polypeptide. Alternatively, the 5' end of the coding sequence may contain a signal peptide coding region that is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region that directs the expressed fusion protein into the secretory pathway of a host cell of choice, i.e., secreted into a culture medium, may be used in the present invention.

Effective signal peptide coding sequences for filamentous fungal host cells are the signal peptide coding sequence obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola insolens* endoglucanase V, and *Humicola lanuginosa* lipase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, and *Trichoderma reesei* beta-xylosidase.

Useful signal peptide coding sequences for yeast host cells are obtained from the genes for *Saccharomyces cerevisiae* alpha-factor and *Saccharomyces cerevisiae* invertase. Other useful signal peptide coding sequence are described by Romanos et al., 1992, supra.

In a preferred aspect, the signal peptide coding sequence is obtained from a gene that encodes an endoglucanase. In a more preferred aspect, the signal peptide coding sequence is obtained from a gene that encodes an endoglucanase V. In an even more preferred aspect, the signal peptide coding sequence is obtained from a *Humicola insolens* gene that encodes an endoglucanase V. In a most preferred aspect, the signal peptide coding sequence encodes amino acids 1 to 21 of SEQ ID NO: 2. In another most preferred aspect, the signal peptide coding sequence is nucleotides 1 to 63 of SEQ ID NO: 1.

The fusion protein may further comprise a second signal peptide that is associated with the beta-glucosidase component of the fusion protein. The signal peptide coding sequence may be the signal peptide coding sequence that is naturally associated with the coding sequence of the polypeptide having biological activity or may be a different signal peptide coding sequence such as one of those described above.

In a preferred aspect, the signal peptide coding sequence is a sequence naturally associated with a beta-glucosidase coding sequence.

Linkers

As mentioned supra, many endoglucanases have a multi-domain structure consisting of a catalytic domain separated from one or more carbohydrate binding modules by a linker peptide(s). In the methods of the present invention, the fusion protein constructs can further comprise a linker coding sequence located 3' to the sequence comprising the endoglucanase catalytic domain and 5' to the sequence comprising the catalytic domain of the polypeptide having biological activity.

The linker can be obtained from the same gene as the catalytic domain of the endoglucanase or from a different endoglucanase gene. On the other hand, the linker can be synthetic in origin.

Examples of linkers that can be used in the methods of the present invention include, but are not limited to, linkers obtained from the genes for the *Trichoderma reesei* cellobiohydrolase I (Srisodsuk et al., 1993, *Journal of Biological Chemistry* 268: 20765-20761); *Hypocrea jecorina* (formerly *Trichoderma reesei*) Cel7A cellobiohydrolase (Mulakala et al., 2005, *Proteins* 60: 598-605); *Humicola insolens* endoglucanase V; and *Thielavia terrestris* NRRL 8126 CEL7C endoglucanase.

In a preferred aspect, the linker is obtained from a *Humicola insolens* endoglucanase gene. In another preferred aspect, the linker is obtained from a *Trichoderma reesei* endoglucanase gene. In a more preferred aspect, the linker is obtained from a *Humicola insolens* endoglucanase V (eg5) gene.

In another preferred aspect, the linker is obtained from a *Thielavia terrestris* endoglucanase gene. In another more preferred aspect, the linker is obtained from a *Thielavia terrestris* NRRL 8126 CEL7C endoglucanase gene.

In a preferred aspect, the linker is at least 5 amino acid residues. In a more preferred aspect, the linker is at least 15 amino acid residues. In a most preferred aspect, the linker is at least 25 amino acid residues.

In a preferred aspect, the linker is between about 5 to about 60 amino acid residues. In a more preferred aspect, the linker is between about 15 to about 50 amino acid residues. In a most preferred aspect, the linker is between about 25 to about 45 amino acid residues.

Carbohydrate Binding Modules

Carbohydrate binding modules (CBMs) are defined as contiguous amino acid sequences with a discrete fold having carbohydrate binding activity, and are commonly found within carbohydrate-active enzymes. A number of types of CBMs have been described, and a majority thereof bind to insoluble polysaccharides (see Boraston et al, 2004, *Biochem J.* 382: 769-781). Carbohydrate binding modules have been characterized which mediate interaction with, for example, crystalline cellulose, non-crystalline cellulose, chitin, beta-1,3-glucans and beta-1,3-1,4-mixed linkage glucans, xylan, mannan, galactan and starch. Carbohydrate binding modules, occur in frequently in multi-domain cellulases. While some CBMS confer specific binding to a subset of carbohydrate structures, others are more general in their ability to associate with various polysaccharides. CBMs which confer binding to cellulose are sometimes referred to as cellulose binding domains, or CBDs (Boraston et al, 2004, *Biochem J.* 382: 769-781). CBMs are grouped by amino acid similarity; currently, 48 CBM families are described.

Glycoside hydrolases can comprise more than one catalytic domain and one, two, three, or more CBMs, and optionally further comprise one or more polypeptide amino acid sequence regions linking the CBM(s) with the catalytic domain(s), a region of the latter type usually being denoted a "linker". Examples of hydrolytic enzymes comprising a CBM are cellulases, xylanases, mannanases, arabinofuranosidases, acetylesterases and chitinases (See P. Tomme et al., *Cellulose-Binding Domains—Classification and Proper-* ties in *Enzymatic Degradation of Insoluble Carbohydrates*, John N. Saddler and Michael H. Penner (Eds.), ACS Symposium Series, No. 618, 1996).

A CBM may be located at the N or C terminus or at an internal position of a protein or polypeptide. The region of a polypeptide or protein that constitutes a CBM typically consists of more than about 30 and less than about 250 amino acid residues. For example: those CBMs listed and classified in Family I consist of 33-37 amino acid residues, those listed and classified in Family 2a consist of 95-108 amino acid residues, and those listed and classified in Family 6 consist of 85-92 amino acid residues. Accordingly, the molecular weight of an amino acid sequence constituting a CBM will typically be in the range of from about 4 kDa to about 40 kDa, and usually below about 35 kDa.

In the methods of the present invention, any CBM may be used. The CBM may be naturally associated with the endoglucanase or may be foreign to the endoglucanase.

In a preferred aspect, a CBM is obtained from a *Trichoderma reesei* endoglucanase (EG) gene. In a more preferred aspect, a CBM is obtained from a *Trichoderma reesei* endoglucanase EGI gene. In another more preferred aspect, a CBM is obtained from a *Trichoderma reesei* endoglucanase EGII gene. In another more preferred aspect, a CBM is obtained from a *Trichoderma reesei* endoglucanase EGV.

In another preferred aspect, a CBM is obtained from a *Trichoderma reesei* cellobiohydrolase (CBH) gene. In another preferred aspect, a CBM is obtained from a *Trichoderma reesei* CBHI gene (Terri et al., 1987, *Gene* 51: 42-52; Linder and Teeri, 1996, *Biochemistry* 93: 12251-12255). In another preferred aspect, a CBM is obtained from a *Trichoderma reesei* CBHII gene.

In another preferred aspect, a CBM is obtained from a *Thielavia terrestris* endoglucanase gene. In another more preferred aspect, a CBM is obtained from a *Thielavia terrestris* NRRL 8126 CEL7C endoglucanase gene.

Cleavage Site

In the methods of the present invention, the fusion protein constructs can further comprise a nucleotide sequence encoding a cleavage site. The cleavage site is preferably located between the sequence comprising at least the endoglucanase catalytic domain and the sequence comprising at least the catalytic domain of the polypeptide having biological activity. Upon secretion of the fusion protein, the site is cleaved releasing the polypeptide having biological activity from the fusion protein.

Examples of cleavage sites include, but are not limited to, a Kex2 site that encodes the dipeptide Lys-Arg (Martin et al., 2003, *J. Ind. Microbiol. Biotechnol.* 3: 568-76; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381), an Ile-(Glu or Asp)-Gly-Arg site, which is cleaved by a Factor Xa protease after the arginine residue (Eaton et al., 1986, *Biochem.* 25: 505-512); a Asp-Asp-Asp-Asp-Lys site, which is cleaved by an enterokinase after the lysine (Collins-Racie et al., 1995, *Biotechnology* 13: 982-987); a His-Tyr-Glu site or His-Tyr-Asp site, which is cleaved by Genenase I (Carter et al., 1989, *Proteins: Structure, Function, and Genetics* 6: 240-248); a Leu-Val-Pro-Arg-Gly-Ser site, which is cleaved by thrombin after the Arg (Stevens, 2003, *Drug Discovery World* 4: 35-48); a Glu-Asn-Leu-Tyr-Phe-Gln-Gly site, which is cleaved by TEV protease after the Gln (Stevens, 2003, supra); and a Leu-Glu-Val-Leu-Phe-Gln-Gly-Pro site, which is cleaved by a genetically engineered form of human rhinovirus 3C protease after the Gln (Stevens, 2003, supra).

Fusion Proteins

A fusion protein having biological activity of the present invention comprising a signal peptide, at least the catalytic domain of an endoglucanase or a portion thereof, and at least the catalytic domain of a polypeptide having biological activity or a portion thereof, increases secretion of the fusion protein compared to the absence of at least the catalytic domain of the endoglucanase or a portion thereof. In each of the preferred aspects below, the components of a fusion protein are linked in frame from the N terminus to the C terminus of the protein.

In a preferred aspect, the fusion protein comprises a signal peptide; a catalytic domain of an endoglucanase; and a catalytic domain of a polypeptide having biological activity.

In another preferred aspect, the fusion protein comprises a signal peptide; a catalytic domain of a polypeptide having biological activity; and a catalytic domain of an endoglucanase.

In another preferred aspect, the fusion protein comprises a signal peptide; a mature polypeptide of an endoglucanase; and a catalytic domain of a polypeptide having biological activity.

In another preferred aspect, the fusion protein comprises a signal peptide; a catalytic domain of a polypeptide having biological activity; and a mature polypeptide of an endoglucanase.

In another preferred aspect, the fusion protein comprises a signal peptide; a catalytic domain of an endoglucanase; and a mature polypeptide of a polypeptide having biological activity.

In another preferred aspect, the fusion protein comprises a signal peptide; a mature polypeptide of a polypeptide having biological activity; and a catalytic domain of an endoglucanase.

In another preferred aspect, the fusion protein comprises a signal peptide; a mature polypeptide of an endoglucanase; and a mature polypeptide of a polypeptide having biological activity.

In another preferred aspect, the fusion protein comprises a signal peptide; a mature polypeptide of a polypeptide having biological activity; and a mature polypeptide of an endoglucanase.

In another preferred aspect, the fusion protein comprises a signal peptide; a catalytic domain of an endoglucanase; and a full-length polypeptide of a polypeptide having biological activity.

In another preferred aspect, the fusion protein comprises a signal peptide; a full-length polypeptide of a polypeptide having biological activity; and a catalytic domain of an endoglucanase.

In another preferred aspect, the fusion protein comprises a signal peptide; a mature polypeptide of an endoglucanase; and a full-length polypeptide of a polypeptide having biological activity.

In another preferred aspect, the fusion protein comprises a signal peptide; a full-length polypeptide of a polypeptide having biological activity; and a mature polypeptide of an endoglucanase.

In another preferred aspect, the fusion protein comprises a full-length polypeptide of an endoglucanase (signal peptide and mature polypeptide); and a full-length polypeptide of a polypeptide having biological activity.

In another preferred aspect, the fusion protein comprises a full-length polypeptide of a polypeptide having biological activity and a full-length polypeptide of an endoglucanase (signal peptide and mature polypeptide).

In another preferred aspect, the fusion protein comprises a signal peptide; a catalytic domain of an endoglucanase, a linker and/or a carbohydrate binding module; and a catalytic domain of a polypeptide having biological activity.

In another preferred aspect, the fusion protein comprises a signal peptide; a catalytic domain of a polypeptide having biological activity, a linker and/or a carbohydrate binding module; and a catalytic domain of an endoglucanase.

In another preferred aspect, the fusion protein comprises a signal peptide; a mature polypeptide of an endoglucanase, a linker and/or a carbohydrate binding module; and a catalytic domain of a polypeptide having biological activity.

In another preferred aspect, the fusion protein comprises a signal peptide; a catalytic domain of a polypeptide having biological activity, a linker and/or a carbohydrate binding module; and a mature polypeptide of an endoglucanase.

In another preferred aspect, the fusion protein comprises a signal peptide; a catalytic domain of an endoglucanase, a linker and/or a carbohydrate binding module; and a mature polypeptide of a polypeptide having biological activity.

In another preferred aspect, the fusion protein comprises a signal peptide; a mature polypeptide of a polypeptide having biological activity, a linker and/or a carbohydrate binding module; and a catalytic domain of an endoglucanase.

In another preferred aspect, the fusion protein comprises a signal peptide; a mature polypeptide of an endoglucanase, a linker and/or a carbohydrate binding module; and a mature polypeptide of a polypeptide having biological activity.

In another preferred aspect, the fusion protein comprises a signal peptide; a mature polypeptide of a polypeptide having biological activity, a linker and/or a carbohydrate binding module; and a mature polypeptide of an endoglucanase.

In another preferred aspect, the fusion protein comprises a signal peptide; a catalytic domain of an endoglucanase, a linker and/or a carbohydrate binding module; and a full-length polypeptide of a polypeptide having biological activity.

In another preferred aspect, the fusion protein comprises a signal peptide; a full-length polypeptide of a polypeptide having biological activity, a linker and/or a carbohydrate binding module; and a catalytic domain of an endoglucanase.

In another preferred aspect, the fusion protein comprises a signal peptide; a mature polypeptide of an endoglucanase, a linker and/or a carbohydrate binding module; and a full-length polypeptide of a polypeptide having biological activity.

In another preferred aspect, the fusion protein comprises a signal peptide; a full-length polypeptide of a polypeptide having biological activity, a linker and/or a carbohydrate binding module; and a mature polypeptide of an endoglucanase.

In another preferred aspect, the fusion protein comprises a signal peptide; a catalytic domain of an endoglucanase; a second signal peptide; and a catalytic domain of a polypeptide having biological activity.

In another preferred aspect, the fusion protein comprises a signal peptide; a catalytic domain of a polypeptide having biological activity; a second signal peptide; and a catalytic domain of an endoglucanase.

In another preferred aspect, the fusion protein comprises a signal peptide; a mature polypeptide of an endoglucanase; a second signal peptide; and a catalytic domain of a polypeptide having biological activity.

In another preferred aspect, the fusion protein comprises a signal peptide; a catalytic domain of a polypeptide having biological activity; a second signal peptide; and a mature polypeptide of an endoglucanase.

In another preferred aspect, the fusion protein comprises a signal peptide; a catalytic domain of an endoglucanase; a second signal peptide; and a mature polypeptide of a polypeptide having biological activity.

In another preferred aspect, the fusion protein comprises a signal peptide; a mature polypeptide of a polypeptide having biological activity; a second signal peptide; and a catalytic domain of an endoglucanase.

In another preferred aspect, the fusion protein comprises a signal peptide; a mature polypeptide of an endoglucanase; a second signal peptide; and a mature polypeptide of a polypeptide having biological activity.

In another preferred aspect, the fusion protein comprises a signal peptide; a mature polypeptide of a polypeptide having biological activity; a second signal peptide; and a mature polypeptide of an endoglucanase.

In another preferred aspect, the fusion protein comprises a signal peptide; a catalytic domain of an endoglucanase, a linker and/or a carbohydrate binding module; a second signal peptide; and a catalytic domain of a polypeptide having biological activity.

In another preferred aspect, the fusion protein comprises a signal peptide; a catalytic domain of a polypeptide having biological activity, a linker and/or a carbohydrate binding module; a second signal peptide; and a catalytic domain of an endoglucanase.

In another preferred aspect, the fusion protein comprises a signal peptide; a mature polypeptide of an endoglucanase, a linker and/or a carbohydrate binding module; a second signal peptide; and a catalytic domain of a polypeptide having biological activity.

In another preferred aspect, the fusion protein comprises a signal peptide; a catalytic domain of a polypeptide having biological activity, a linker and/or a carbohydrate binding module; a second signal peptide; and a mature polypeptide of an endoglucanase.

In another preferred aspect, the fusion protein comprises a signal peptide; a catalytic domain of an endoglucanase, a linker and/or a carbohydrate binding module; a second signal peptide; and a mature polypeptide of a polypeptide having biological activity.

In another preferred aspect, the fusion protein comprises a signal peptide; a mature polypeptide of a polypeptide having biological activity, a linker and/or a carbohydrate binding module; a second signal peptide; and a catalytic domain of an endoglucanase.

In another preferred aspect, the fusion protein comprises a signal peptide; a mature polypeptide of an endoglucanase, a linker and/or a carbohydrate binding module; a second signal peptide; and a mature polypeptide of a polypeptide having biological activity.

In another preferred aspect, the fusion protein comprises a signal peptide; and a mature polypeptide of a polypeptide having biological activity, a linker and/or a carbohydrate binding module; a second signal peptide; and a mature polypeptide of an endoglucanase.

In another preferred aspect, for each of the preferred aspects above, the fusion protein may alternatively comprise a portion of the catalytic domain, the mature polypeptide, or the full-length polypeptide of an endoglucanase or a polypeptide having biological activity. The a portion of the endoglucanase may or may not have endoglucanase activity. In a more preferred aspect, the portion of the endoglucanase has endoglucanase activity.

Promoters

The promoter region can be any appropriate promoter sequence recognized by a host cell for expression of a fusion protein. The promoter sequence contains transcriptional control sequences that mediate the expression of the polypeptide. The promoter may be any nucleotide sequence that shows transcriptional activity in the host cell of choice including mutant, truncated, tandem, and hybrid promoters, and may be obtained from genes encoding extracellular or intracellular polypeptides either native or foreign (heterologous) to the host cell. Exemplary promoters include both constitutive promoters and inducible promoters.

Examples of suitable promoters for directing transcription of the fusion protein constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American*, 1980, 242: 74-94; and in Sambrook et al., 1989, supra.

Examples of suitable promoters for directing transcription of the fusion protein constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Dania (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, *Coprinus cinereus* beta-tubulin, and *Trichoderma reesei* swollenin, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionine (CUP1), and *Saccharomyces cerevisiae* 3-phosphoglycerate kinase. Other useful promoters for yeast host cells are described by Romanos et al., 1992, *Yeast* 8: 423-488.

In a preferred aspect, the promoter is a cellobiohydrolase promoter. In a more preferred aspect, the promoter is a cellobiohydrolase I (cbh1) promoter. In an even more preferred aspect, the promoter is a *Trichoderma reesei* cellobiohydrolase I gene (cbh1) promoter. In a most preferred aspect, the promoter is the *Trichoderma reesei* cbh1 promoter of nucleotides 505 to 1501 of SEQ ID NO: 29 (GENBANK™ accession no. D86235). In another more preferred aspect, the promoter is a cellobiohydrolase II (cbh2) promoter. In another even more preferred aspect, the promoter is a *Trichoderma reesei* cellobiohydrolase II gene (cbh2) promoter. In another most preferred aspect, the promoter is the *Trichoderma reesei* cbh2 promoter of nucleotides 1 to 582 of SEQ ID NO: 30 (GENBANK™ accession no. M55080).

In another preferred aspect, the promoter is the NA2-tpi promoter. In another preferred aspect, the promoter is a TAKA amylase promoter. In another preferred aspect, the promoter is a *Fusarium venenatum* amyloglucosidase promoter. In another preferred aspect, the promoter is a *Fusarium oxysporum* trypsin-like protease promoter. In another preferred aspect, the promoter is an *Aspergillus niger* or *Aspergillus awamori* glucoamylase (glaA) promoter.

In a preferred aspect, the promoter region drives expression of the first, second, and third polynucleotides, and alternatively also the fourth polynucleotide.

Terminators

The terminator can be any suitable transcription terminator sequence recognized by a host cell to terminate transcription. The terminator sequence is operably linked to the 3' terminus of the nucleotide sequence encoding the polypeptide. Any terminator that is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

In a preferred aspect, the terminator is a cellobiohydrolase gene terminator. In a more preferred aspect, the terminator is a cellobiohydrolase I gene (cbh1) terminator. In an even more preferred aspect, the terminator is a *Trichoderma reesei* cellobiohydrolase I gene (cbh1) terminator. In a most preferred aspect, the terminator is the *Trichoderma reesei* cbh1 terminator of SEQ ID NO: 31. In another more preferred aspect, the terminator is a cellobiohydrolase II gene (cbh2) terminator. In another even more preferred aspect, the terminator is a *Trichoderma reesei* cellobiohydrolase II gene (cbh2) terminator. In another most preferred aspect, the terminator is the *Trichoderma reesei* cbh2 terminator of SEQ ID NO: 32.

In another preferred aspect, the terminator is a TAKA amylase terminator. In another preferred aspect, the promoter is a *Fusarium oxysporum* trypsin-like protease terminator. In another preferred aspect, the promoter is an *Aspergillus niger* or *Aspergillus awamori* glucoamylase (glaA) terminator.

Other Regulatory Sequences

The fusion protein constructs can further comprise other regulatory elements such as a leader, polyadenylation sequence, and other elements.

The regulatory sequence may also be a suitable leader sequence, a nontranslated region of an mRNA that is important for translation by the host cell. The leader sequence is operably linked to the 5' terminus of the nucleotide sequence encoding a fusion protein. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The regulatory sequence may also be a polyadenylation sequence, a sequence operably linked to the 3' terminus of the nucleotide sequence and, when transcribed, is recognized by the host cell as a signal to add polyadenosine residues to transcribed mRNA. Any polyadenylation sequence that is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those that allow for gene amplification. In eukaryotic systems, these include the dihydrofolate reductase gene, which is amplified in the presence of methotrexate, and the metallothionein genes, which are amplified with heavy metals. In these cases, the nucleotide sequence encoding the polypeptide would be operably linked with the regulatory sequence.

The fusion protein constructs preferably contain one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers that confer antibiotic resistance such as ampicillin, kanamycin, chloramphenicol, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

Expression Vectors

The present invention also relates to recombinant expression vectors comprising a polynucleotide encoding a fusion protein, a promoter, and transcriptional and translational stop signals. The various nucleic acids and control sequences described herein may be joined together to produce a recombinant expression vector that may include one or more convenient restriction sites to allow for insertion or substitution of the nucleotide sequence encoding the polypeptide at such sites. Alternatively, a polynucleotide encoding a fusion protein may be expressed by inserting the nucleotide sequence or a fusion protein construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon may be used.

The vectors of the present invention preferably contain one or more selectable markers that permit easy selection of transformed, transfected, transduced, or the like cells. Examples of bacterial, yeast, filamentous fungal selectable markers are described herein.

A vector of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMR1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, Gene 98: 61-67; Cullen et al., 1987, Nucleic Acids Research 15: 9163-9175; WO 00/24883). Isolation of the AMA1 gene and construction of plasmids or vectors comprising the gene can be accomplished according to the methods disclosed in WO 00/24883.

More than one copy of a polynucleotide encoding a fusion protein may be inserted into the host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant fungal host cells, comprising a polynucleotide encoding a fusion protein of the present invention, which are advantageously used in the recombinant production of the protein. A vector comprising a polynucleotide of the present invention is introduced into a fungal host cell so that the vector is maintained as a chromosomal integrant or as a self-replicating extra-chromosomal vector as described earlier. The term "host cell" encompasses any progeny of a parent cell that is not identical to the parent cell due to mutations that occur during replication.

The fungal host cell may be any fungal cell useful in the recombinant production of a polypeptide of the present invention.

"Fungi" as used herein includes the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

In a more preferred aspect, the yeast host cell is a *Candida*, *Hansenula*, *Kluyveromyces*, *Pichia*, *Saccharomyces*, *Schizosaccharomyces*, or *Yarrowia* cell.

In a most preferred aspect, the yeast host cell is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In a more preferred aspect, the filamentous fungal host cell is an *Acremonium*, *Aspergillus*, *Aureobasidium*, *Bjerkandera*, *Ceriporiopsis*, *Chrysosporium*, *Coprinus*, *Coriolus*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Phanerochaete*, *Phlebia*, *Piromyces*, *Pleurotus*, *Schizophyllum*, *Talaromyces*, *Thermoascus*, *Thielavia*, *Tolypocladium*, *Trametes*, or *Trichoderma* cell.

In a most preferred aspect, the filamentous fungal host cell is an *Aspergillus awamori*, *Aspergillus fumigatus*, *Aspergillus foetidus*, *Aspergillus japonicus*, *Aspergillus nidulans*, *Aspergillus niger* or *Aspergillus oryzae* cell. In another most preferred aspect, the filamentous fungal host cell is a *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, or *Fusarium venenatum* cell. In another most preferred aspect, the filamentous fungal host cell is a *Bjerkandera adusta*, *Ceriporiopsis aneirina*, *Ceriporiopsis aneirina*, *Ceriporiopsis caregiea*, *Ceriporiopsis gilvescens*, *Ceriporiopsis pannocinta*, *Ceriporiopsis rivulosa*, *Ceriporiopsis subrufa*, *Ceriporiopsis subvermispora*, *Chrysosporium keratinophilum*, *Chrysosporium lucknowense*, *Chrysosporium tropicum*, *Chrysosporium merdarium*, *Chrysosporium inops*, *Chrysosporium pannicola*, *Chrysosporium queenslandicum*, *Chrysosporium zonatum*, *Coprinus cinereus*, *Coriolus hirsutus*, *Humicola insolens*, *Humicola lanuginosa*, *Mucor miehei*, *Myceliophthora thermophila*, *Neurospora crassa*, *Penicillium purpurogenum*, *Phanerochaete chrysosporium*, *Phlebia radiata*, *Pleurotus eryngii*, *Thielavia terrestris*, *Trametes villosa*, *Trametes versicolor*, *Trichoderma harzianum*, *Trichoderma koningii*, *Trichoderma longibrachiatum*, *Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Production and Recovery

In the methods of the present invention, the fungal host cell is cultivated in a nutrient medium suitable for production of a polypeptide having biological activity using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection).

In the methods of the present invention, the polypeptide having biological activity is selected from the group consisting of a fusion protein, components of the fusion protein, and a combination of the fusion protein and the components thereof.

In a preferred aspect, the polypeptide having biological activity is a fusion protein.

In another preferred aspect, the polypeptide having biological activity is a component(s) of a fusion protein.

In another preferred aspect, the polypeptide having biological activity is a combination of a fusion protein and components thereof.

The polypeptides having biological activity may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide, as described herein, which can include both endoglucanase activity and a specific biological activity.

The resulting polypeptide having biological activity, e.g., beta-glucosidase fusion protein or a component thereof, may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure polypeptides.

Compositions

The present invention also relates to compositions comprising a polypeptide having biological activity of the present invention. Preferably, the compositions are enriched in such a polypeptide. The term "enriched" indicates that the biological activity of the composition has been increased, e.g., with an enrichment factor of at least 1.1.

The composition may comprise a polypeptide of the present invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by a microorganism belonging to the genus *Aspergillus*, preferably *Aspergillus aculeatus*, *Aspergillus awamori*, *Aspergillus fumigatus*, *Aspergillus foetidus*, *Aspergillus japonicus*, *Aspergillus nidulans*, *Aspergillus niger*, or *Aspergillus oryzae*; *Fusarium*, preferably *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sulphureum*, *Fusarium toruloseum*, *Fusarium trichothecioides*, or *Fusarium venenatum*; *Humicola*, preferably *Humicola insolens* or *Humicola lanuginosa*; or *Trichoderma*, preferably *Trichoderma harzianum*, *Trichoderma koningii*, *Trichoderma longibrachiatum*, *Trichoderma reesei*, or *Trichoderma viride*.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Uses

The present invention is also directed to methods for using the fusion proteins or components thereof, or compositions thereof.

Methods of Processing Cellulosic Material

The methods of the present invention are particularly useful for improving the secretion of polypeptides having cellulolytic or hemicellulolytic activity in commercially important quantities, which can be used to degrade or convert lignocellulosic material. Such polypeptides include, but are not limited to endoglucanases, cellobiohydrolases, beta-glucosidases, xylanases, beta-xylosidases, arabinofuranosidases, acetyl xylan esterases, and ferulic acid esterases. Consequently, the present invention also relates to methods for degrading or converting a cellulosic material, comprising: treating the cellulosic material with an effective amount of a cellulolytic enzyme composition in the presence of an effective amount of a fusion protein or a component thereof having cellulolytic activity or hemicellulolytic activity obtained according to the instant methods. For purposes of illustration, a polypeptide having beta-glucosidase activity obtained according to the methods of the present invention, e.g., a beta-glucosidase fusion protein or a component thereof, is used for illustrative purposes.

Cellulosic biomass can include, but is not limited to, wood resources, municipal solid waste, wastepaper, crops, and crop residues (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York).

The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix. It will be understood herein that the term "cellulosic material" or "cellulose" also encompasses lignocellulose.

In the methods of the present invention, the cellulolytic enzyme composition may comprise any protein involved in the processing of cellulosic material to glucose, or hemicellulose to xylose, mannose, galactose, and arabinose, their polymers, or products derived from them as described below. The cellulolytic enzyme composition may be a monocomponent preparation, e.g., an endoglucanase, a multicomponent preparation, e.g., endoglucanase, cellobiohydrolase, beta-glucosidase, or a combination of multicomponent and monocomponent protein preparations. The cellulolytic proteins may have activity, i.e., hydrolyze cellulose, either in the acid, neutral, or alkaline pH-range. The cellulolytic enzyme composition can further comprise a polypeptide having cellulolytic enhancing activity according to WO 2005/074647, WO 2005/074656, and U.S. Published Application 2007/0077630.

The cellulolytic protein may be of fungal or bacterial origin, which may be obtainable or isolated and purified from microorganisms that are known capable of producing cellulolytic enzymes, e.g., species of *Bacillus, Pseudomonas, Humicola, Coprinus, Thielavia, Fusarium, Myceliophthora, Acremonium, Cephalosporium, Scytalidium, Penicillium* or *Aspergillus* (see, for example, EP 458162), especially those produced by a strain selected from *Humicola insolens* (reclassified as *Scytalidium thermophilum*, see for example, U.S. Pat. No. 4,435,307), *Coprinus cinereus, Fusarium oxysporum, Myceliophthora thermophila, Meripilus giganteus, Thielavia terrestris, Acremonium* sp., *Acremonium persicinum, Acremonium acremonium, Acremonium brachypenium, Acremonium dichromosporum, Acremonium obclavatum, Acremonium pinkertoniae, Acremonium roseogriseum, Acremonium incoloratum*, and *Acremonium furatum*; preferably from *Humicola insolens* DSM 1800, *Fusarium oxysporum* DSM 2672, *Myceliophthora thermophila* CBS 117.65, *Cephalosporium* sp. RYM-202, *Acremonium* sp. CBS 478.94, *Acremonium* sp. CBS 265.95, *Acremonium persicinum* CBS 169.65, *Acremonium acremonium* AHU 9519, *Cephalosporium* sp. CBS 535.71, *Acremonium brachypenium* CBS 866.73, *Acremonium dichromosporum* CBS 683.73, *Acremonium obclavatum* CBS 311.74, *Acremonium pinkertoniae* CBS 157.70, *Acremonium roseogriseum* CBS 134.56, *Acremonium incoloratum* CBS 146.62, and *Acremonium furatum* CBS 299.70H. Cellulolytic proteins may also be obtained from *Trichoderma* (particularly *Trichoderma viride, Trichoderma reesei*, and *Trichoderma koningii*), alkalophilic *Bacillus* (see, for example, U.S. Pat. No. 3,844,890 and EP 458162), and *Streptomyces* (see, for example, EP 458162). Chemically modified or protein engineered mutants of cellulolytic proteins may also be used.

Especially suitable cellulolytic proteins are the cellulases described in EP 495,257, EP 531,372, WO 96/11262, WO 96/29397, WO 98/08940. Other examples are cellulase variants such as those described in WO 94/07998, EP 531,315, U.S. Pat. No. 4,435,307, U.S. Pat. No. 5,457,046, U.S. Pat. No. 5,648,263, U.S. Pat. No. 5,686,593, U.S. Pat. No. 5,691,178, U.S. Pat. No. 5,763,254, U.S. Pat. No. 5,776,757, WO 89/09259, WO 95/24471, WO 98/12307, and PCT/DK98/00299.

As mentioned above, the cellulolytic proteins used in the methods of the present invention may be monocomponent preparations, i.e., a component essentially free of other cellulolytic components. The single component may be a recombinant component, i.e., produced by cloning of a DNA sequence encoding the single component and subsequent cell transformed with the DNA sequence and expressed in a host (see, for example, WO 91/17243 and WO 91/17244). The host is preferably a heterologous host (enzyme is foreign to host), but the host may under certain conditions also be a homologous host (enzyme is native to host). Monocomponent cellulolytic proteins may also be prepared by purifying such a protein from a fermentation broth.

The cellulolytic proteins used in the methods of the present invention may be produced by fermentation of the above-noted microbial strains on a nutrient medium containing suitable carbon and nitrogen sources and inorganic salts, using procedures known in the art (see, e.g., Bennett, J. W. and LaSure, L. (eds.), *More Gene Manipulations in Fungi*, Academic Press, CA, 1991). Suitable media are available from commercial suppliers or may be prepared according to published compositions (e.g., in catalogues of the American Type Culture Collection). Temperature ranges and other conditions suitable for growth and cellulolytic protein production are known in the art (see, e.g., Bailey, J. E., and Ollis, D. F., *Biochemical Engineering Fundamentals*, McGraw-Hill Book Company, NY, 1986).

The fermentation can be any method of cultivation of a cell resulting in the expression or isolation of a cellulolytic protein. Fermentation may, therefore, be understood as comprising shake flask cultivation, or small- or large-scale fermentation (including continuous, batch, fed-batch, or solid state fermentations) in laboratory or industrial fermentors performed in a suitable medium and under conditions allowing the cellulolytic protein to be expressed or isolated. The resulting cellulolytic proteins produced by the methods described above may be recovered from the fermentation medium and purified by conventional procedures as described herein.

Examples of commercial cellulolytic enzyme preparations suitable for use in the present invention include, for example, CELLUCLAST™ (available from Novozymes NS) and NOVOZYM™ 188 (available from Novozymes NS). Other commercially available preparations comprising cellulase that may be used include CELLUZYME™, CEREFLO™ and ULTRAFLO™ (Novozymes NS), LAMINEX™ and SPEZYME™ CP (Genencor Int.), ROHAMENT™ 7069 W (Röhm GmbH), and FIBREZYME® LDI, FIBREZYME® LBR, or VISCOSTAR® 150 L (Dyadic International, Inc., Jupiter, Fla., USA). The cellulase enzymes are added in amounts effective from about 0.001% to about 5.0% wt. of solids, more preferably from about 0.025% to about 4.0% wt. of solids, and most preferably from about 0.005% to about 2.0% wt. of solids.

The resulting cellulolytic proteins or beta-glucosidase proteins produced by the methods described above may be recovered from the fermentation medium by conventional procedures including, but not limited to, centrifugation, filtration, spray-drying, evaporation, or precipitation. The recovered protein may then be further purified by a variety of chromatographic procedures, e.g., ion exchange chromatography, gel filtration chromatography, affinity chromatography, or the like.

The activity of a cellulolytic protein can be determined using any method known in the art.

Examples of cellulolytic preparations suitable for use in the present invention include, for example, CELLUCLAST™ (available from Novozymes NS) and NOVOZYM™ 188 (available from Novozymes NS). Other commercially available preparations comprising cellulase that may be used include CELLUZYME™, CEREFLO™ and ULTRAFLO™ (Novozymes NS), LAMINEX™ and SPEZYME™ CP (Genencor Int.), and ROHAMENT™ 7069 W (Röhm GmbH). The cellulase enzymes are added in amounts effective from about 0.001% to about 5.0% wt. of solids, more preferably from about 0.025% to about 4.0% wt. of solids, and most preferably from about 0.005% to about 2.0% wt. of solids.

As mentioned above, the cellulolytic proteins used in the methods of the present invention may be monocomponent preparations, i.e., a component essentially free of other cellulolytic components. The single component may be a recombinant component, i.e., produced by cloning of a DNA sequence encoding the single component and subsequent cell transformed with the DNA sequence and expressed in a host (see, for example, WO 91/17243 and WO 91/17244). Other examples of monocomponent cellulolytic proteins include, but are not limited to, those disclosed in JP-07203960-A and WO-9206209. The host is preferably a heterologous host (enzyme is foreign to host), but the host may under certain conditions also be a homologous host (enzyme is native to host). Monocomponent cellulolytic proteins may also be prepared by purifying such a protein from a fermentation broth.

Examples of monocomponent cellulolytic proteins useful in practicing the methods of the present invention include, but are not limited to, endoglucanase, cellobiohydrolase, and other enzymes useful in degrading cellulosic biomass.

The term "endoglucanase" is already defined herein. The term "cellobiohydrolase" is defined herein as a 1,4-beta-D-glucan cellobiohydrolase (E.C. 3.2.1.91), which catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain. For purposes of the present invention, cellobiohydrolase activity can be determined according to the procedures described by Lever et al., 1972, *Anal. Biochem.* 47: 273-279 and by van Tilbeurgh et al., 1982, *FEBS Letters* 149: 152-156; van Tilbeurgh and Claeyssens, 1985, *FEBS Letters* 187: 283-288. In the present invention, the Lever et al. method was employed to assess hydrolysis of cellulose in corn stover.

The polypeptides of the present invention are used in conjunction with cellulolytic proteins to degrade the cellulosic component of the biomass substrate, (see, for example, Brigham et al., 1995, in *Handbook on Bioethanol* (Charles E. Wyman, editor), pp. 119-141, Taylor & Francis, Washington D.C.; Lee, 1997, *Journal of Biotechnology* 56: 1-24).

The optimum amounts of a polypeptide having beta-glucosidase activity and of cellulolytic proteins depends on several factors including, but not limited to, the mixture of component cellulolytic proteins, the cellulosic substrate, the concentration of cellulosic substrate, the pretreatment(s) of the cellulosic substrate, temperature, time, pH, and inclusion of fermenting organism (e.g., yeast for Simultaneous Saccharification and Fermentation). The term "cellulolytic proteins" is defined herein as those proteins or mixtures of proteins shown as being capable of hydrolyzing or converting or degrading cellulose under the conditions tested. Their amounts are usually measured by a common assay such as BCA (bicinchoninic acid, P. K. Smith et al., 1985, *Anal. Biochem.* 150: 76), and the preferred amount added in proportion to the amount of biomass being hydrolyzed.

In a preferred aspect, the amount of polypeptide having beta-glucosidase activity per g of cellulosic material is about 0.01 to about 2.0 mg, preferably about 0.025 to about 1.5 mg, more preferably about 0.05 to about 1.25 mg, more preferably about 0.075 to about 1.25 mg, more preferably about 0.1 to about 1.25 mg, even more preferably about 0.15 to about 1.25 mg, and most preferably about 0.25 to about 1.0 mg per g of cellulosic material.

In another preferred aspect, the amount of cellulolytic proteins per g of cellulosic material is about 0.5 to about 50 mg, preferably about 0.5 to about 40 mg, more preferably about 0.5 to about 25 mg, more preferably about 0.75 to about 20 mg, more preferably about 0.75 to about 15 mg, even more preferably about 0.5 to about 10 mg, and most preferably about 2.5 to about 10 mg per g of cellulosic material.

The methods of the present invention can be used to degrade or convert a cellulosic material, e.g., lignocellulose, to many useful substances, e.g., chemicals and fuels. In addition to ethanol, some commodity and specialty chemicals that can be produced from cellulose include xylose, acetone, acetate, glycine, lysine, organic acids (e.g., lactic acid), 1,3-propanediol, butanediol, glycerol, ethylene glycol, furfural, polyhydroxyalkanoates, and cis,cis-muconic acid (Lynd, L. R., Wyman, C. E., and Gerngross, T. U., 1999, *Biocommodity Engineering, Biotechnol. Prog.*, 15: 777-793; Philippidis, G. P., 1996, Cellulose bioconversion technology, in *Handbook on Bioethanol: Production and Utilization*, Wyman, C. E., ed., Taylor & Francis, Washington, D.C., 179-212; and Ryu, D. D. Y., and Mandels, M., 1980, Cellulases: biosynthesis and applications, *Enz. Microb. Technol.*, 2: 91-102). Potential coproduction benefits extend beyond the synthesis of multiple organic products from fermentable carbohydrate. Lignin-rich residues remaining after biological processing can be converted to lignin-derived chemicals, or used for power production.

Conventional methods used to process the cellulosic material in accordance with the methods of the present invention are well understood to those skilled in the art. The methods of the present invention may be implemented using any conventional biomass processing apparatus configured to operate in accordance with the invention.

Such an apparatus may include a fed-batch stirred reactor, a batch-stirred reactor, a continuous flow stirred reactor with ultrafiltration, a continuous plug-flow column reactor (Fernanda de Castilhos Corazza, Flávio Faria de Moraes, Gisella Maria Zanin and Ivo Neitzel, 2003, Optimal control in fed-batch reactor for the cellobiose hydrolysis, *Acta Scientiarum. Technology* 25(1): 33-38; Gusakov, A. V., and Sinitsyn, A. P., 1985, Kinetics of the enzymatic hydrolysis of cellulose: 1. A mathematical model for a batch reactor process, *Enz. Microb. Technol.* 7: 346-352), an attrition reactor (Ryu, S. K., and Lee, J. M., 1983, Bioconversion of waste cellulose by using an attrition bioreactor, *Biotechnol. Bioeng.* 25: 53-65), or a reactor with intensive stirring induced by an electromagnetic field (Gusakov, A. V., Sinitsyn, A. P., Davydkin, I. Y., Davydkin, V. Y., Protas, O. V., 1996, Enhancement of enzymatic cellulose hydrolysis using a novel type of bioreactor with intensive stirring induced by electromagnetic field, *Appl. Biochem. Biotechnol.* 56: 141-153).

The conventional methods include, but are not limited to, saccharification, fermentation, separate hydrolysis and fermentation (SHF), simultaneous saccharification and fermentation (SSF), simultaneous saccharification and cofermentation (SSCF), hybrid hydrolysis and fermentation (HHF), and direct microbial conversion (DMC).

SHF uses separate process steps to first enzymatically hydrolyze cellulose to fermentable sugars and then, in a subsequent step, ferments sugars to ethanol. In SSF, the enzymatic hydrolysis of cellulose and the fermentation of fermentable sugar to ethanol are combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF includes the cofermentation of multiple sugars (Sheehan, J., and Himmel, M., 1999, Enzymes, energy and the environment: A strategic perspective on the U.S. Department of Energy's research and development activities for bioethanol, *Biotechnol. Prog.* 15: 817-827). HHF includes two separate steps carried out in the same reactor but at different temperatures, i.e., high temperature enzymatic saccharification followed by SSF at a lower temperature that the fermentation strain can tolerate. DMC combines all three processes (cellulase production, cellulose hydrolysis, and fermentation) in one step (Lynd, L. R., Weimer, P. J., van Zyl, W. H., and Pretorius, I. S., 2002, Microbial cellulose utilization: Fundamentals and biotechnology, *Microbiol. Mol. Biol. Reviews* 66: 506-577).

"Fermentation" or "fermentation process" refers to any fermentation process or any process comprising a fermentation step. A fermentation process includes, without limitation, fermentation processes used to produce fermentation products including alcohols (e.g., arabinitol, butanol, ethanol, glycerol, methanol, 1,3-propanediol, sorbitol, and xylitol); organic acids (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, propionic acid, succinic acid, and xylonic acid); ketones (e.g., acetone); amino acids (e.g., aspartic acid, glutamic acid, glycine, lysine, serine, and threonine); gases (e.g., methane, hydrogen ($H_2$), carbon dioxide ($CO_2$), and carbon monoxide (CO)). Fermentation processes also include fermentation processes used in the consumable alcohol industry (e.g., beer and wine), dairy industry (e.g., fermented dairy products), leather industry, and tobacco industry.

A fusion protein or a component thereof having cellulolytic activity or hemicellulolytic activity obtained according to the methods of the present invention, e.g., a beta-glucosidase fusion protein or a component thereof, and host cells thereof, can be used in the production of monosaccharides, disaccharides, and polysaccharides as chemical or fermentation feedstocks from biomass for the production of ethanol, plastics, other products or intermediates. In particular, the polypeptides and host cells may be used to increase the value of processing residues (dried distillers grain, spent grains from brewing, sugarcane bagasse, etc.) by partial or complete solubilization of cellulose or hemicellulose. In boosting the processing of cellulosic material by the cellulolytic enzyme preparation to glucose, xylose, mannose, galactose, and arabinose, their polymers, or products derived from them as described below, the polypeptides may be in the form of a crude fermentation broth with or without the cells or in the form of a semi-purified or purified enzyme preparation. The polypeptide may be a monocomponent preparation, a multicomponent protein preparation, or a combination of multicomponent and monocomponent protein preparations. Alternatively, a host cell may be used as a source of such a polypeptide in a fermentation process with the biomass. The host cell may also contain native or heterologous genes that encode cellulolytic protein as well as other enzymes useful in the processing of biomass.

The present invention further relates to methods for producing an organic substance, comprising: (a) saccharifying a cellulosic material with an effective amount of a cellulolytic enzyme composition i in the presence of an effective amount of a fusion protein or a component thereof having cellulolytic activity or hemicellulolytic activity obtained according to the instant methods; (b) fermenting the saccharified cellulosic material of step (a) with one or more fermenting microorganisms; and (c) recovering the organic substance from the fermentation. As indicated earlier, for purposes of illustration, a polypeptide having beta-glucosidase activity obtained according to the methods of the present invention, e.g., a beta-glucosidase fusion protein or a component thereof, is used for illustrative purposes. The polypeptide having beta-glucosidase activity may be in the form of a crude fermentation broth with or without the cells or in the form of a semi-purified or purified enzyme preparation. The beta-glucosidase protein may be a monocomponent preparation, a multicomponent protein preparation, or a combination of multicomponent and monocomponent protein preparations.

The substance can be any substance derived from the fermentation. In a preferred aspect, the substance is an alcohol. It will be understood that the term "alcohol" encompasses a substance that contains one or more hydroxyl moieties. In a more preferred aspect, the alcohol is arabinitol. In another more preferred aspect, the alcohol is butanol. In another more preferred aspect, the alcohol is ethanol. In another more preferred aspect, the alcohol is glycerol. In another more preferred aspect, the alcohol is methanol. In another more preferred aspect, the alcohol is 1,3-propanediol. In another more preferred aspect, the alcohol is sorbitol. In another more preferred aspect, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002, The biotechnological production of sorbitol, *Appl. Microbiol. Biotechnol.* 59: 400-408; Nigam, P., and Singh, D., 1995, Processes for fermentative production of xylitol—a sugar substitute, *Process Biochemistry* 30 (2): 117-124; Ezeji, T. C., Qureshi, N. and Blaschek, H. P., 2003, Production of acetone, butanol and ethanol by *Clostridium beijerinckii* BA101 and in situ recovery by gas stripping, *World Journal of Microbiology and Biotechnology* 19 (6): 595-603.

In another preferred aspect, the substance is an organic acid. In another more preferred aspect, the organic acid is acetic acid. In another more preferred aspect, the organic acid is acetonic acid. In another more preferred aspect, the organic acid is adipic acid. In another more preferred aspect, the organic acid is ascorbic acid. In another more preferred aspect, the organic acid is citric acid. In another more preferred aspect, the organic acid is 2,5-diketo-D-gluconic acid. In another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another preferred aspect, the organic acid is 3-hydroxypropionic acid. In another more preferred aspect, the organic acid is itaconic acid. In another more preferred aspect, the organic acid is lactic acid. In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen, R., and Lee, Y. Y., 1997, Membrane-mediated extractive fermentation for lactic acid production from cellulosic biomass, *Appl. Biochem. Biotechnol.* 63-65: 435-448.

In another preferred aspect, the substance is a ketone. It will be understood that the term "ketone" encompasses a substance that contains one or more ketone moieties. In another more preferred aspect, the ketone is acetone. See, for example, Qureshi and Blaschek, 2003, supra.

In another preferred aspect, the substance is an amino acid. In another more preferred aspect, the organic acid is aspartic acid. In another more preferred aspect, the amino acid is glutamic acid. In another more preferred aspect, the amino acid is glycine. In another more preferred aspect, the amino acid is lysine. In another more preferred aspect, the amino acid is serine. In another more preferred aspect, the amino acid is threonine. See, for example, Richard, A., and Margaritis, A., 2004, Empirical modeling of batch fermentation kinetics for poly(glutamic acid) production and other microbial biopolymers, *Biotechnology and Bioengineering* 87 (4): 501-515.

In another preferred aspect, the substance is a gas. In another more preferred aspect, the gas is methane. In another more preferred aspect, the gas is $H_2$. In another more preferred aspect, the gas is $CO_2$. In another more preferred aspect, the gas is CO. See, for example, Kataoka, N., A. Miya, and K. Kiriyama, 1997, Studies on hydrogen production by continuous culture system of hydrogen-producing anaerobic bacteria, *Water Science and Technology* 36 (6-7): 41-47; and Gunaseelan V. N. in *Biomass and Bioenergy*, Vol. 13 (1-2), pp. 83-114, 1997, Anaerobic digestion of biomass for methane production: A review.

Production of a substance from cellulosic material typically requires four major steps.

These four steps are pretreatment, enzymatic hydrolysis, fermentation, and recovery. Exemplified below is a process for producing ethanol, but it will be understood that similar processes can be used to produce other substances, for example, the substances described above.

Pretreatment.

In the pretreatment or pre-hydrolysis step, the cellulosic material is heated to break down the lignin and carbohydrate structure, solubilize most of the hemicellulose, and make the cellulose fraction accessible to cellulolytic enzymes. The heating is performed either directly with steam or in slurry where a catalyst may also be added to the material to speed up the reactions. Catalysts include strong acids, such as sulfuric acid and $SO_2$, or alkali, such as sodium hydroxide. The purpose of the pre-treatment stage is to facilitate the penetration of the enzymes and microorganisms. Cellulosic biomass may also be subject to a hydrothermal steam explosion pre-treatment (See U.S. Patent Application No. 20020164730). However, it is understood that in practicing the methods of the present invention, any pretreatment can be used employing thermal, chemical, and/or mechanical pretreatment.

Saccharification.

In the enzymatic hydrolysis step, also known as saccharification, enzymes as described herein are added to the pretreated material to convert the cellulose fraction to glucose and/or other sugars. The saccharification is generally performed in stirred-tank reactors or fermentors under controlled pH, temperature, and mixing conditions. A saccharification step may last up to 200 hours. Saccharification may be carried out at temperatures from about 30° C. to about 65° C., in particular around 50° C., and at a pH in the range between about 4 to about 5, especially around pH 4.5. To produce glucose that can be metabolized by yeast, the hydrolysis is typically performed in the presence of a beta-glucosidase.

Fermentation.

In the fermentation step, sugars, released from the cellulosic material as a result of the pretreatment and enzymatic hydrolysis steps, are fermented to ethanol by a fermenting organism, such as yeast. The fermentation can also be carried out simultaneously with the enzymatic hydrolysis in the same vessel, again under controlled pH, temperature, and mixing conditions. When saccharification and fermentation are performed simultaneously in the same vessel, the process is generally termed simultaneous saccharification and fermentation or SSF.

Any suitable cellulosic material or raw material may be used in the fermentation step in practicing the present invention. The material is generally selected based on the desired fermentation product, i.e., the substance to be obtained from the fermentation, and the process employed, as is well known in the art. Examples of substrates suitable for use in the methods of present invention, include cellulose-containing materials, such as wood or plant residues or low molecular sugars DP1-3 obtained from processed cellulosic material that can be metabolized by the fermenting microorganism, and which may be supplied by direct addition to the fermentation medium.

The term "fermentation medium" will be understood to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism suitable for use in a desired fermentation process. Suitable fermenting microorganisms are able to ferment, i.e., convert, sugars, such as glucose, xylose, arabinose, mannose, galactose, or oligosaccharides directly or indirectly into the desired fermentation product. Examples of fermenting microorganisms include fungal organisms, such as yeast. Preferred yeast includes strains of the *Saccharomyces* spp., and in particular, *Saccharomyces cerevisiae*. Commercially available yeast include, e.g., RED STAR®/Lesaffre Ethanol Red (available from RED STAR®/Lesaffre, USA) FALI (available from Fleischmann's Yeast, a division of Burns Philp Food Inc., USA), SUPERSTART (available from Alltech), GERT STRAND (available from Gert Strand AB, Sweden) and FERMIOL (available from DSM Specialties).

In a preferred aspect, the yeast is a *Saccharomyces* spp. In a more preferred aspect, the yeast is *Saccharomyces cerevisiae*. In another more preferred aspect, the yeast is *Saccharomyces distaticus*. In another more preferred aspect, the yeast is *Saccharomyces uvarum*. In another preferred aspect, the yeast is a *Kluyveromyces*. In another more preferred aspect, the yeast is *Kluyveromyces marxianus*. In another more preferred aspect, the yeast is *Kluyveromyces fragilis*. In another preferred aspect, the yeast is a *Candida*. In another more preferred aspect, the yeast is *Candida pseudotropicalis*. In another more preferred aspect, the yeast is *Candida brassicae*. In another preferred aspect, the yeast is a *Clavispora*. In another more preferred aspect, the yeast is *Clavispora lusitaniae*. In another more preferred aspect, the yeast is *Clavispora opuntiae*. In another preferred aspect, the yeast is a *Pachysolen*. In another more preferred aspect, the yeast is *Pachysolen tannophilus*. In another preferred aspect, the yeast is a *Bretannomyces*. In another more preferred aspect, the yeast is *Bretannomyces clausenii* (Philippidis, G. P., 1996, Cellulose bioconversion technology, in *Handbook on Bioethanol: Production and Utilization*, Wyman, C. E., ed., Taylor & Francis, Washington, D.C., 179-212).

Bacteria that can efficiently ferment glucose to ethanol include, for example, *Zymomonas mobilis* and *Clostridium thermocellum* (Philippidis, 1996, supra).

It is well known in the art that the organisms described above can also be used to produce other substances, as described herein.

The cloning of heterologous genes in *Saccharomyces cerevisiae* (Chen, Z., Ho, N. W. Y., 1993, Cloning and improving the expression of *Pichia stipitis* xylose reductase gene in *Saccharomyces cerevisiae*, *Appl. Biochem. Biotechnol.* 39-40: 135-147; Ho, N. W. Y., Chen, Z, Brainard, A. P., 1998, Genetically engineered *Saccharomyces* yeast capable of effectively cofermenting glucose and xylose, *Appl. Environ. Microbiol.* 64: 1852-1859), or in bacteria such as *Escherichia coli* (Beall, D. S., Ohta, K., Ingram, L. O., 1991, Parametric studies of ethanol production from xylose and other sugars by recombinant *Escherichia coli*, *Biotech. Bioeng.* 38: 296-303), *Klebsiella oxytoca* (Ingram, L. O., Gomes, P. F., Lai, X., Moniruzzaman, M., Wood, B. E., Yomano, L. P., York, S. W., 1998, Metabolic engineering of bacteria for ethanol production, *Biotechnol. Bioeng.* 58: 204-214), and *Zymomonas mobilis* (Zhang, M., Eddy, C., Deanda, K., Finkelstein, M., and Picataggio, S., 1995, Metabolic engineering of a pentose metabolism pathway in ethanologenic *Zymomonas mobilis*, *Science* 267: 240-243; Deanda, K., Zhang, M., Eddy, C., and Picataggio, S., 1996, Development of an arabinose-fermenting *Zymomonas mobilis* strain by metabolic pathway engineering, *Appl. Environ. Microbiol.* 62: 4465-4470) has led to the construction of organisms capable of converting hexoses and pentoses to ethanol (cofermentation).

Yeast or another microorganism typically is added to the degraded cellulose or hydrolysate and the fermentation is performed for about 24 to about 96 hours, such as about 35 to about 60 hours. The temperature is typically between about 26° C. to about 40° C., in particular at about 32° C., and at about pH 3 to about pH 6, in particular around pH 4-5.

In a preferred aspect, yeast or another microorganism is applied to the degraded cellulose or hydrolysate and the fermentation is performed for about 24 to about 96 hours, such as typically 35-60 hours. In a preferred aspect, the temperature is generally between about 26 to about 40° C., in particular about 32° C., and the pH is generally from about pH 3 to about pH 6, preferably around pH 4-5. Yeast or another microorganism is preferably applied in amounts of approximately $10^5$ to $10^{12}$, preferably from approximately $10^7$ to $10^{10}$, especially approximately $5\times10^7$ viable cell count per ml of fermentation broth. During an ethanol producing phase the yeast cell count should preferably be in the range from approximately $10^7$ to $10^{10}$, especially around approximately $2\times10^8$. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

The most widely used process in the art is the simultaneous saccharification and fermentation (SSF) process where there is no holding stage for the saccharification, meaning that yeast and enzyme are added together.

For ethanol production, following the fermentation the mash is distilled to extract the ethanol. The ethanol obtained according to the process of the invention may be used as, e.g., fuel ethanol, drinking ethanol, i.e., potable neutral spirits, or industrial ethanol.

A fermentation stimulator may be used in combination with any of the enzymatic processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Recovery.

The alcohol is separated from the fermented cellulosic material and purified by conventional methods of distillation. Ethanol with a purity of up to about 96 vol.% can be obtained, which can be used as, for example, fuel ethanol, drinking ethanol, i.e., potable neutral spirits, or industrial ethanol.

For other substances, any method known in the art can be used including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, distillation, or extraction.

In the methods of the present invention, besides beta-glucosidase, the cellulolytic enzyme preparation and cellulolytic enhancing polypeptide(s) may be supplemented by one or more additional enzyme activities to improve the degradation of the cellulosic material. Preferred additional enzymes are hemicellulases, esterases (e.g., lipases, phospholipases, and/or cutinases), proteases, laccases, peroxidases, or mixtures thereof.

In the methods of the present invention, the additional enzyme(s) may be added prior to or during fermentation, including during or after the propagation of the fermenting microorganism(s).

The enzymes referenced herein may be derived or obtained from any suitable origin, including, bacterial, fungal, yeast or mammalian origin. The term "obtained" means herein that the enzyme may have been isolated from an organism that naturally produces the enzyme as a native enzyme. The term "obtained" also means herein that the enzyme may have been produced recombinantly in a host organism, wherein the recombinantly produced enzyme is either native or foreign to the host organism or has a modified amino acid sequence, e.g., having one or more amino acids that are deleted, inserted and/or substituted, i.e., a recombinantly produced enzyme that is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained recombinantly, such as by site-directed mutagenesis or shuffling.

The enzymes may also be purified. The term "purified" as used herein covers enzymes free from other components from the organism from which it is derived. The term "purified" also covers enzymes free from components from the native organism from which it is obtained. The enzymes may be purified, with only minor amounts of other proteins being present. The expression "other proteins" relate in particular to other enzymes. The term "purified" as used herein also refers to removal of other components, particularly other proteins and most particularly other enzymes present in the cell of origin of the enzyme of the invention. The enzyme may be "substantially pure polypeptide," that is, free from other components from the organism in which it is produced, that is, for example, a host organism for recombinantly produced enzymes.

The enzymes used in the present invention may be in any form suitable for use in the processes described herein, such as, for example, a crude fermentation broth with or without cells, a dry powder or granulate, a non-dusting granulate, a liquid, a stabilized liquid, or a protected enzyme. Granulates may be produced, e.g., as disclosed in U.S. Pat. Nos. 4,106,991 and 4,661,452, and may optionally be coated by process known in the art. Liquid enzyme preparations may, for instance, be stabilized by adding stabilizers such as a sugar, a sugar alcohol or another polyol, and/or lactic acid or another organic acid according to established process. Protected enzymes may be prepared according to the process disclosed in EP 238,216.

Detergent Compositions

The methods of the present invention are particularly useful for improving the secretion of polypeptides in commercially important quantities for use in detergent compositions. Such polypeptides include, but are not limited to proteases, cellulolytic enzymes, amylases, and peroxidases, or any other enzyme or biological protein useful to the detergent industry.

The detergent composition of the present invention may be, for example, formulated as a hand or machine laundry detergent composition including a laundry additive composition suitable for pre-treatment of stained fabrics and a rinse added fabric softener composition, or formulated as a detergent composition for use in general household hard surface cleaning operations, or formulated for hand or machine dishwashing operations.

In a specific aspect, the present invention provides a detergent additive comprising a polypeptide having biological activity (e.g., fusion protein, a component thereof, or combinations thereof) obtained according to the present invention. The detergent additive as well as the detergent composition may comprise one or more other enzymes such as a protease, lipase, cutinase, an amylase, carbohydrase, cellulase, pectinase, mannanase, arabinase, galactanase, xylanase, oxidase, e.g., a laccase, and/or peroxidase.

In general the properties of the enzymatic components should be compatible with the selected detergent, (i.e., pH optimum, compatibility with other enzymatic and non-enzymatic ingredients, etc.), and the enzymatic components should be present in effective amounts.

Proteases:

Suitable proteases include those of animal, vegetable or microbial origin. Microbial origin is preferred. Chemically modified or protein engineered mutants are included. The protease may be a serine protease or a metalloprotease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g., of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274.

Preferred commercially available protease enzymes include ALCALASE™ SAVINASE™, PRIMASE™, DURALASE™, ESPERASE™, AND KANNASE™ (NOVOZYMES NS), MAXATASE™, MAXACAL™, MAXAPEM™, PROPERASE™, PURAFECT™, PURAFECT OXP™, FN2™, and FN3™ (Genencor International Inc.).

Lipases:

Suitable lipases include those of bacterial or fungal origin. Chemically modified or protein engineered mutants are included. Examples of useful lipases include lipases from *Humicola* (synonym *Thermomyces*), e.g., from *H. lanuginosa* (*T. lanuginosus*) as described in EP 258 068 and EP 305 216 or from *H. insolens* as described in WO 96/13580, a *Pseudomonas* lipase, e.g., from *P. alcaligenes* or *P. pseudoalcaligenes* (EP 218 272), *P. cepacia* (EP 331 376), *P. stutzeri* (GB 1,372,034), *P. fluorescens*, *Pseudomonas* sp. strain SD 705 (WO 95/06720 and WO 96/27002), *P. wisconsinensis* (WO 96/12012), a *Bacillus* lipase, e.g., from *B. subtilis* (Dartois et al., 1993, *Biochemica et Biophysica Acta*, 1131, 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipases include LIPOLASE™, LIPEX™, and Lipolase ULTRA™ (Novozymes NS).

Amylases:

Suitable amylases ($\alpha$ and/or $\beta$) include those of bacterial or fungal origin. Chemically modified or protein engineered mutants are included. Amylases include, for example, $\alpha$-amylases obtained from *Bacillus*, e.g., a special strain of *Bacillus licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are DURAMYL™, TERMAMYL™, FUNGAMYL™ and BAN™ (Novozymes NS), Rapidase™ and Purastar™ (from Genencor International Inc.).

Cellulases:

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, or *Trichoderma* e.g., the fungal cellulases produced from *Humicola insolens, Myceliophthora thermophila* and *Fusarium oxysporum* disclosed in U.S. Pat. No.

4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and PCT/DK98/00299.

Commercially available cellulases include CELLUCLAST®, CELLUZYME™, and CAREZYME™ (Novozymes NS), Clazinase™, and Puradax HA™ (Genencor International Inc.), and KAC-500(B)™ (Kao Corporation).

Peroxidases/Oxidases:

Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257.

Commercially available peroxidases include GUARDZYME™ (Novozymes NS).

The enzymatic component(s) may be included in a detergent composition by adding separate additives containing one or more enzymes, or by adding a combined additive comprising all of these enzymes. A detergent additive of the present invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the present invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g., SKS-6 from Hoechst).

The detergent may comprise one or more polymers. Examples are carboxymethylcellulose, poly(vinylpyrrolidone), poly(ethylene glycol), poly(vinyl alcohol), poly(vinylpyridine-N-oxide), poly(vinylimidazole), polycarboxylates such as polyacrylates, maleic/acrylic acid copolymers, and lauryl methacrylate/acrylic acid copolymers.

The detergent may contain a bleaching system that may comprise a $H_2O_2$ source such as perborate or percarbonate that may be combined with a peracid-forming bleach activator such as tetraacetylethylenediamine or nonanoyloxybenzenesulfonate. Alternatively, the bleaching system may comprise peroxyacids of, for example, the amide, imide, or sulfone type.

The enzymatic component(s) of the detergent composition of the present invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, for example, WO 92/19709 and WO 92/19708.

The detergent may also contain other conventional detergent ingredients such as fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

In the detergent compositions any enzymatic component, in particular the polypeptides having biological activity of the present invention, may be added in an amount corresponding to 0.01-100 mg of enzyme protein per liter of wash liquor, preferably 0.05-5 mg of enzyme protein per liter of wash liquor, in particular 0.1-1 mg of enzyme protein per liter of wash liquor.

The polypeptides having biological activity of the present invention may additionally be incorporated in the detergent formulations disclosed in WO 97/07202, which is hereby incorporated as reference.

Other Uses

Polypeptides having biological activity (e.g., fusion protein, a component thereof, or combinations thereof) obtained according to the present invention o may also be used in combination with other glycohydrolases and related enzymes, as described herein, in the treatment of textiles as biopolishing agents and for reducing of fuzz, pilling, texture modification, and stonewashing (N. K. Lange, in P. Suominen, T. Reinikainen (Eds.), *Trichoderma reesei* Cellulases and Other Hydrolases, Foundation for Biotechnical and Industrial Fermentation Research, Helsinki, 1993, pp. 263-272). In addition, the described polypeptides may also be used in combination with other glycohydrolases and related enzymes, as described herein, in wood processing for biopulping or debarking, paper manufacturing for fiber modification, bleaching, and reduction of refining energy costs, whitewater treatment, important to wastewater recycling, lignocellulosic fiber recycling such as deinking and secondary fiber processing, and wood residue utilization (S. D, Mansfield and A. R. Esteghlalian in S. D, Mansfield and J. N. Saddler (Eds.), *Applications of Enzymes to Lignocellulosics*, ACS Symposium Series 855, Washington, D.C., 2003, pp. 2-29).

The present invention is further described by the following examples that should not be construed as limiting the scope of the invention.

EXAMPLES

Chemicals used as buffers and substrates were commercial products of at least reagent grade.

DNA Sequencing

DNA sequencing was performed using an Applied Biosystems Model 3130X Genetic Analyzer (Applied Biosystems, Foster City, Calif., USA) using dye terminator chemistry (Giesecke et al., 1992, *Journal of Virol. Methods* 38: 47-60). Sequences were assembled using phred/phrap/consed (University of Washington, Seattle, Wash., USA) with sequence specific primers.

Strain

*Trichoderma reesei* RutC30 (ATCC 56765; Montenecourt and Eveleigh, 1979, *Adv. Chem. Ser.* 181: 289-301) was derived from *Trichoderma reesei* Qm6A (ATCC 13631; Mandels and Reese, 1957, *J. Bacteriol.* 73: 269-278). *Trichoderma reesei* RutC30 and *Aspergillus oryzae* Ja1355 strain (WO 02/062973) were used for expression of the beta-glucosidase fusion protein.

Media and Solutions

YP medium was composed per liter of 10 g of yeast extract and 20 g of bacto tryptone.

Cellulase-inducing medium was composed per liter of 20 g of cellulose, 10 g of corn steep solids, 1.45 g of $(NH_4)_2SO_4$, 2.08 g of $KH_2PO_4$, 0.28 g of $CaCl_2$, 0.42 g of $MgSO_4.7H_2O$, and 0.42 ml of trace metals solution.

Trace metals solution was composed per liter of 216 g of $FeCl_3.6H_2O$, 58 g of $ZnSO_4.7H_2O$, 27 g of $MnSO_4.H_2O$, 10 g of $CuSO_4.5H_2O$, 2.4 g of $H_3BO_3$, and 336 g of citric acid.

STC was composed of 1 M sorbitol, 10 mM $CaCl_2$, and 10 mM Tris-HCl, pH 7.5.

COVE plates were composed per liter of 342 g of sucrose, 10 ml of COVE salts solution, 10 ml of 1 M acetamide, 10 ml of 1.5 M CsCl, and 25 g of Noble agar.

COVE salts solution was composed per liter of 26 g of KCl, 26 g of $MgSO_4$, 76 g of $KH_2PO_4$, and 50 ml of COVE trace metals solution.

COVE trace metals solution was composed per liter of 0.04 g of $Na_2B_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_2.H_2O$, and 10 g of $ZnSO_4.7H_2O$.

COVE2 plates were composed per liter of 30 g of sucrose, 20 ml of COVE salts solution, 25 g of Noble agar, and 10 ml of 1 M acetamide.

PDA plates were composed per liter of 39 grams of potato dextrose agar.

LB medium was composed per liter of 10 g of tryptone, 5 g of yeast extract, 5 g of sodium chloride.

2×YT plates were composed per liter of 10 g of tryptone, 5 g of yeast extract, 5 g of sodium chloride, and 15 g of Bacto Agar.

MDU2BP medium was composed per liter of 45 g of maltose, 1 g of $MgSO_4.7H_2O$, 1 g of NaCl, 2 g of $K_2HSO_4$, 12 g of $KH_2PO_4$, 2 g of urea, and 500 µl of AMG trace metals solution, the pH was adjusted to 5.0 and then filter sterilized with a 0.22 µm filtering unit.

AMG trace metals solution was composed per liter of 14.3 g of $ZnSO_4.7H_2O$, 2.5 g of $CuSO_4.5H_2O$, 0.5 g of $NiCl_2.6H_2O$, 13.8 g of $FeSO_4.7H_2O$, 8.5 g of $MnSO_4.7H_2O$, and 3 g of citric acid.

Minimal medium plates were composed per liter of 6 g of $NaNO_3$, 0.52 of KCl, 1.52 g of $KH_2PO_4$, 1 ml of COVE trace metals solution, 20 g of Noble agar, 20 ml of 50% glucose, 2.5 ml of 20% $MgSO_4.7H_2O$, and 20 ml of biotin stock solution.

Biotin stock solution was composed per liter of 0.2 g of biotin.

SOC medium was composed of 2% tryptone, 0.5% yeast extract, 10 mM NaCl, 2.5 mM KCl, 10 mM $MgCl_2$, and 10 mM $MgSO_4$, followed by addition of filter-sterilized glucose to 20 mM after autoclaving.

Example 1

Construction of pMJ04 Expression Vector

Expression vector pMJ04 was constructed by PCR amplifying the *Trichoderma reesei* cellobiohydrolase 1 gene (cbh1, CEL7A) terminator from *Trichoderma reesei* RutC30 genomic DNA using primers 993429 (antisense) and 993428 (sense) shown below. The antisense primer was engineered to have a PacI site at the 5'-end and a SpeI site at the 3'-end of the sense primer.

Primer 993429 (antisense):
5'-AACGTTAATTAAGGAATCGTTTTGTGTTT-3' (SEQ ID NO: 33)

Primer 993428 (sense):
5'-AGTACTAGTAGCTCCGTGGCGAAAGCCTG-3' (SEQ ID NO: 34)

*Trichoderma reesei* RutC30 genomic DNA was isolated using a DNEASY® Plant Maxi Kit (QIAGEN Inc., Valencia, Calif., USA).

The amplification reactions (50 µl) were composed of 1× ThermoPol Reaction Buffer (New England Biolabs, Beverly, Mass., USA), 0.3 mM dNTPs, 100 ng of *Trichoderma reesei* RutC30 genomic DNA, 0.3 µM primer 993429, 0.3 µM primer 993428, and 2 units of Vent DNA polymerase (New England Biolabs, Beverly, Mass., USA). The reactions were incubated in an EPPENDORF® MASTERCYCLER® 5333 (Eppendorf Scientific, Inc., Westbury, N.Y., USA) programmed for 5 cycles each for 30 seconds at 94° C., 30 seconds at 50° C., and 60 seconds at 72° C., followed by 25 cycles each for 30 seconds at 94° C., 30 seconds at 65° C., and 120 seconds at 72° C. (5 minute final extension). The reaction products were isolated on a 1.0% agarose gel using 40 mM Tris base-20 mM sodium acetate-1 mM disodium EDTA (TAE) buffer where a 229 bp product band was excised from the gel and purified using a QIAQUICK® Gel Extraction Kit (QIAGEN Inc., Valencia, Calif., USA) according to the manufacturer's instructions.

The resulting PCR fragment was digested with PacI and SpeI and ligated into pAlLo1 (WO 05/067531) digested with the same restriction enzymes using a Rapid Ligation Kit (Roche, Indianapolis, Ind., USA), to generate pMJ04 (FIG. 1).

Example 2

Construction of pCaHj568

Figure 2:
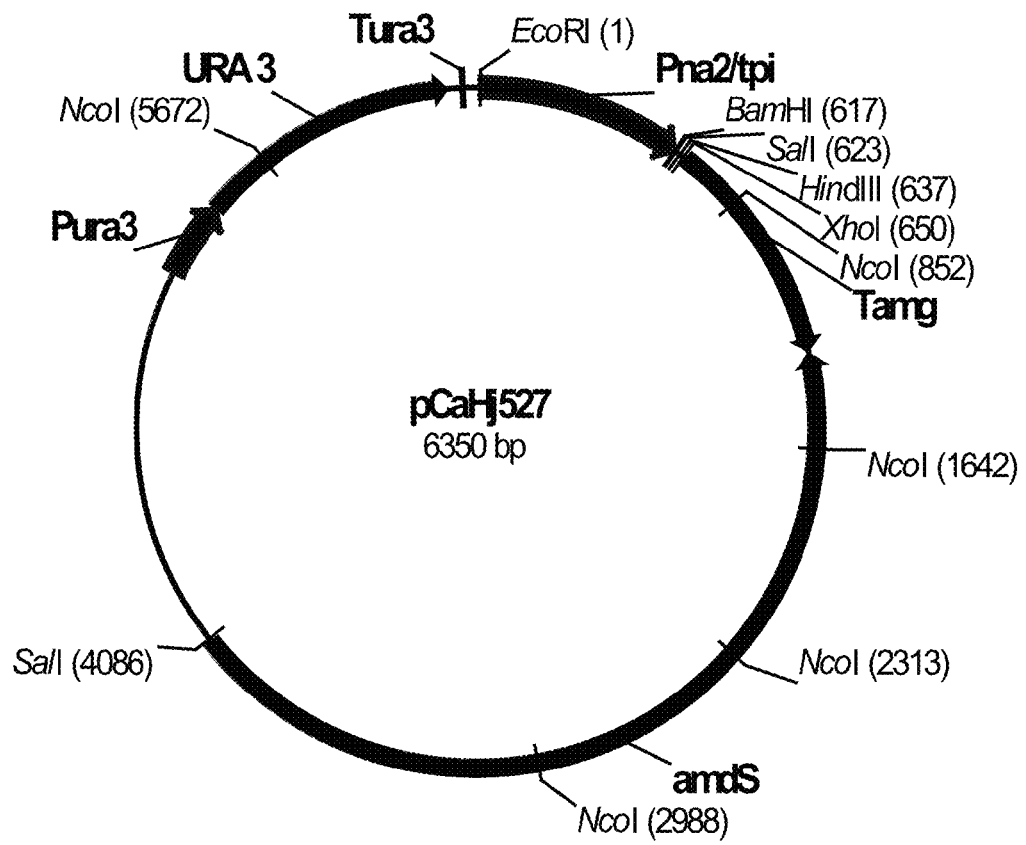
FIG. 2 shows a restriction map of pCaHj527.
Figure 3:
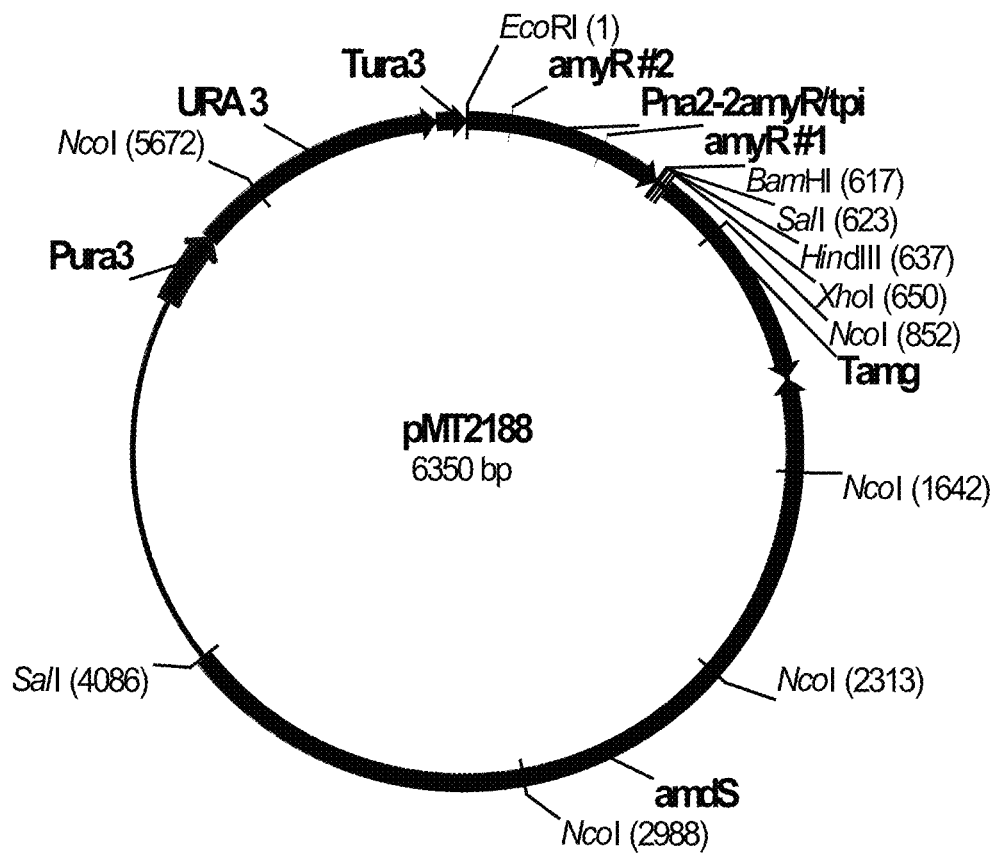
FIG. 3 shows a restriction map of pMT2188.
Figure 4:
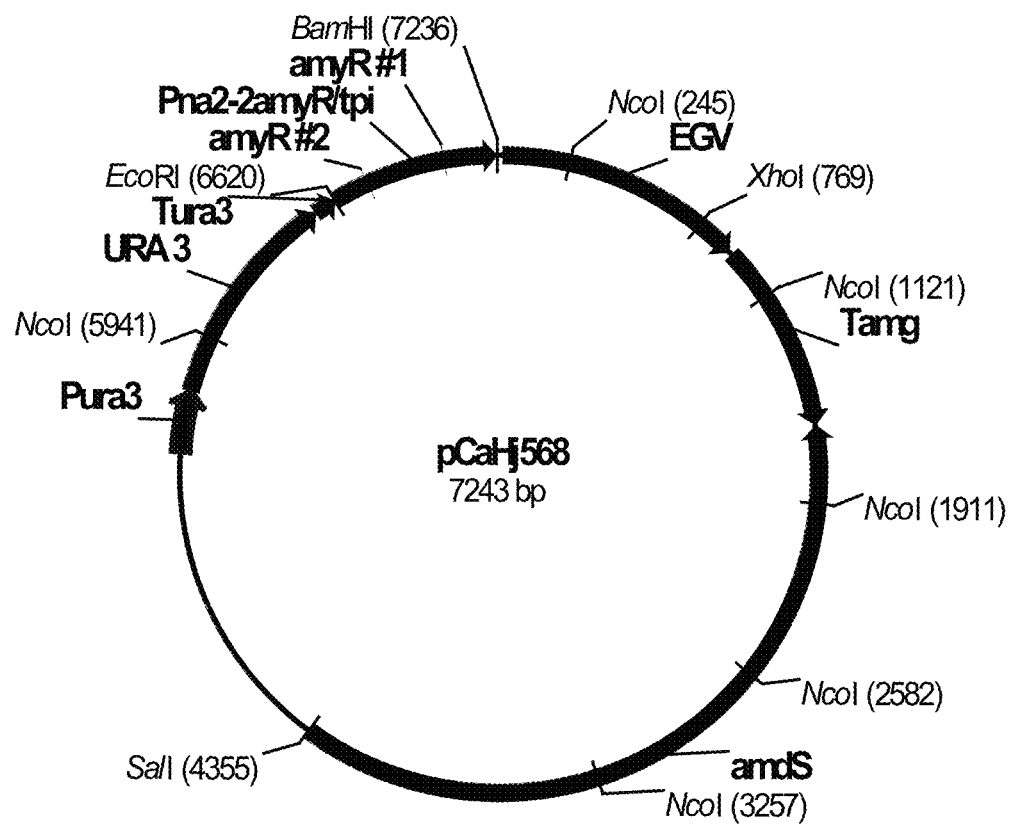
FIG. 4 shows a restriction map of pCaHj568.

Plasmid pCaHj568 was constructed from pCaHj170 (U.S. Pat. No. 5,763,254) and pMT2188. Plasmid pCaHj170 comprises the *Humicola insolens* endoglucanase V (CEL45A) full-length coding region (SEQ ID NO: 1, which encodes the amino acid sequence of SEQ ID NO: 2). Construction of pMT2188 was initiated by PCR amplifying the pUC19 origin of replication from pCaHj483 (WO 98/00529) using primers 142779 and 142780 shown below.
Primer 142780 introduces a BbuI site in the PCR fragment.
142779:
5'-TTGAATTGAAAATAGATTGATTTAAAACTTC-3' (SEQ ID NO: 35)
142780:
5'-TTGCATGCGTAATCATGGTCATAGC-3' (SEQ ID NO: 36)
An EXPAND® PCR System (Roche Molecular Biochemicals, Basel, Switzerland) was used following the manufacturer's instructions for this amplification. PCR products were separated on an agarose gel and an 1160 bp fragment was isolated and purified using a Jetquick Gel Extraction Spin Kit (Genomed, Wielandstr, Germany).
The URA3 gene was amplified from the general *Saccharomyces cerevisiae* cloning vector pYES2 (Invitrogen, Carlsbad, Calif., USA) using primers 140288 and 142778 shown below using an EXPAND® PCR System. Primer 140288 introduced an Eco RI site into the PCR fragment.
5'-TTGAATTCATGGGTAATAACTGATAT-3' (SEQ ID NO: 37)
142778:
5'-AAATCAATCTATTTTCAATTCAATTCATCATT-3' (SEQ ID NO: 38)
PCR products were separated on an agarose gel and an 1126 bp fragment was isolated and purified using a Jetquick Gel Extraction Spin Kit.
The two PCR fragments were fused by mixing and amplified using primers 142780 and 140288 shown above by the overlap splicing method (Horton et al., 1989, Gene 77: 61-68). PCR products were separated on an agarose gel and a 2263 bp fragment was isolated and purified using a Jetquick Gel Extraction Spin Kit.
The resulting fragment was digested with Eco RI and BbuI and ligated using standard protocols to the largest fragment of pCaHj483 digested with the same restriction enzymes. The ligation mixture was transformed into pyrF-negative *E. coli* strain DB6507 (ATCC 35673) made competent by the method of Mandel and Higa, 1970, *J. Mol. Biol.* 45: 154. Transformants were selected on solid M9 medium (Sambrook et al., 1989, *Molecular Cloning, A Laboratory Manual*, 2nd edition, Cold Spring Harbor Laboratory Press) supplemented per liter with 1 g of casamino acids, 500 µg of thiamine, and 10 mg of kanamycin. A plasmid from one transformant was isolated and designated pCaHj527 (FIG. 2).
The NA2-tpi promoter present on pCaHj527 was subjected to site-directed mutagenesis by a simple PCR approach using an EXPAND® PCR System according to the manufacturer's instructions. Nucleotides 134-144 were converted from GTACTAAAACC (SEQ ID NO: 39) to CCGTTAAATTT (SEQ ID NO: 40) using mutagenic primer 141223 shown below.
Primer 141223:
5'-GGATGCTGTTGACTCCGGAAATTTAACG-GTTTGGTCTTGCATCCC-3' (SEQ ID NO: 41) Nucleotides 423-436 were converted from ATGCAATTTAAACT (SEQ ID NO: 42) to CGGCAATTTAACGG (SEQ ID NO: 43) using mutagenic primer 141222 shown below.
Primer 141222:
5'-GGTATTGTCCTGCAGACGGCAATT-TAACGGCTTCTGCGAATCGC-3' (SEQ ID NO: 44) The resulting plasmid was designated pMT2188 (FIG. 3).
The *Humicola insolens* endoglucanase V coding region was transferred from pCaHj170 as a BamHI-SalI fragment into pMT2188 digested with BamHI and XhoI to generate pCaHj568 (FIG. 4). Plasmid pCaHj568 comprises a mutated NA2-tpi promoter operably linked to the *Humicola insolens* endoglucanase V full-length coding sequence.

Example 3

Construction of pMJ05

Plasmid pMJ05 was constructed by PCR amplifying the 915 bp *Humicola insolens* endoglucanase V full-length coding region from pCaHj568 using primers HiEGV-F and HiEGV-R shown below.
HiEGV-F (sense):
5'-AAGCTTAAGCATGCGTTCCTCCCCCCTCC-3' (SEQ ID NO: 45)
HiEGV-R (antisense):
5'-CTGCAGAATTCTACAGGCACTGATGGTACCAG-3' (SEQ ID NO: 46)
The amplification reactions (50 µl) were composed of 1× ThermoPol Reaction Buffer (New England Biolabs, Beverly, Mass., USA), 0.3 mM dNTPs, 10 ng/µl of pCaHj568, 0.3 µM HiEGV-F primer, 0.3 µM HiEGV-R primer, and 2 units of Vent DNA polymerase (New England Biolabs, Beverly, Mass., USA). The reactions were incubated in an EPPENDORF® MASTERCYCLER® 5333 programmed for 5 cycles each for 30 seconds at 94° C., 30 seconds at 50° C., and 60 seconds at 72° C., followed by 25 cycles each for 30 seconds at 94° C., 30 seconds at 65° C., and 120 seconds at 72° C. (5 minute final extension). The reaction products were isolated on a 1.0% agarose gel using TAE buffer where a 937 bp product band was excised from the gel and purified using a QIAQUICK® Gel Extraction Kit according to the manufacturer's instructions.
The 937 bp purified fragment was used as template DNA for subsequent amplifications using the following primers:
HiEGV-R (antisense):
5'-CTGCAGAATTCTACAGGCACTGATGGTACCAG-3' (SEQ ID NO: 47)
HiEGV-F-overlap (sense):
5'-ACCGCGGACTGCGCATC ATGCGTTCCTCCCCCCTCC-3' (SEQ ID NO: 48)
Primer sequences in italics are homologous to 17 bp of the *Trichoderma reesei* cellobiohydrolase I gene (cbh1) promoter and underlined primer sequences are homologous to 29 bp of the *Humicola insolens* endoglucanase V coding region. A 36 bp overlap between the promoter and the coding sequence allowed precise fusion of a 994 bp fragment comprising the *Trichoderma reesei* cbh1 promoter to the 918 bp fragment comprising the *Humicola insolens* endoglucanase V coding region.
The amplification reactions (50 µl) were composed of 1× ThermoPol Reaction Buffer, 0.3 mM dNTPs, 1 µl of the purified 937 bp PCR fragment, 0.3 µM HiEGV-F-overlap primer, 0.3 µM HiEGV-R primer, and 2 units of Vent DNA polymerase. The reactions were incubated in an EPPENDORF® MASTERCYCLER® 5333 programmed for 5 cycles each for 30 seconds at 94° C., 30 seconds at 50° C., and 60 seconds at 72° C., followed by 25 cycles each for 30 seconds at 94° C., 30 seconds at 65° C., and 120 seconds at 72° C. (5 minute final extension). The reaction products were isolated on a 1.0% agarose gel using TAE buffer where a 945 bp product band was excised from the gel and purified using a QIAQUICK® Gel Extraction Kit according to the manufacturer's instructions.
A separate PCR was performed to amplify the *Trichoderma reesei* cbh1 promoter sequence extending from 994 bp upstream of the ATG start codon of the gene from *Trichoderma reesei* RutC30 genomic DNA using the primers shown below (the sense primer was engineered to have a SalI restriction site at the 5'-end). *Trichoderma reesei* RutC30 genomic DNA was isolated using a DNEASY® Plant Maxi Kit.
TrCBHIpro-F (sense):
5'-AAACGTCGACCGAATGTAGGATTGTTATC-3' (SEQ ID NO: 49)
TrCBHIpro-R (antisense):
5'-GATGCGCAGTCCGCGGT-3' (SEQ ID NO: 50)

The amplification reactions (50 µl) were composed of 1× ThermoPol Reaction Buffer, 0.3 mM dNTPs, 100 ng/µl *Trichoderma reesei* RutC30 genomic DNA, 0.3 µM TrCBHIpro-F primer, 0.3 µM TrCBHIpro-R primer, and 2 units of Vent DNA polymerase. The reactions were incubated in an EPPENDORF® MASTERCYCLER® 5333 programmed for 30 cycles each for 30 seconds at 94° C., 30 seconds at 55° C., and 120 seconds at 72° C. (5 minute final extension). The reaction products were isolated on a 1.0% agarose gel using TAE buffer where a 998 bp product band was excised from the gel and purified using a QIAQUICK® Gel Extraction Kit according to the manufacturer's instructions.

The purified 998 bp PCR fragment was used as template DNA for subsequent amplifications using the primers shown below.
TrCBHIpro-F:
5'-AAACGTCGACCGAATGTAGGATTGTTATC-3' (SEQ ID NO: 51)
TrCBHIpro-R-overlap:
5'-GGAGGGGGGAGGAACGCAT*GATGCGCAGTCCGCGGT*-3' (SEQ ID NO: 52)

Sequences in italics are homologous to 17 bp of the *Trichoderma reesei* cbh1 promoter and underlined sequences are homologous to 29 bp of the *Humicola insolens* endoglucanase V coding region. A 36 bp overlap between the promoter and the coding sequence allowed precise fusion of the 994 bp fragment comprising the *Trichoderma reesei* cbh1 promoter to the 918 bp fragment comprising the *Humicola insolens* endoglucanase V full-length coding region.

The amplification reactions (50 µl) were composed of 1× ThermoPol Reaction Buffer, 0.3 mM dNTPs, 1 µl of the purified 998 bp PCR fragment, 0.3 µM TrCBHIpro-F primer, 0.3 µM TrCBH1pro-R-overlap primer, and 2 units of Vent DNA polymerase. The reactions were incubated in an EPPENDORF® MASTERCYCLER® 5333 programmed for 5 cycles each for 30 seconds at 94° C., 30 seconds at 50° C., and 60 seconds at 72° C., followed by 25 cycles each for 30 seconds at 94° C., 30 seconds at 65° C., and 120 seconds at 72° C. (5 minute final extension). The reaction products were isolated on a 1.0% agarose gel using TAE buffer where a 1017 bp product band was excised from the gel and purified using a QIAQUICK® Gel Extraction Kit according to the manufacturer's instructions.

The 1017 bp *Trichoderma reesei* cbh1 promoter PCR fragment and the 945 bp *Humicola insolens* endoglucanase V PCR fragment were used as template DNA for subsequent amplification using the following primers to precisely fuse the 994 bp cbh1 promoter to the 918 bp endoglucanase V full-length coding region using overlapping PCR.
TrCBHIpro-F:
5'-AAACGTCGACCGAATGTAGGATTGTTATC-3' (SEQ ID NO: 53)
HiEGV-R:
5'-CTGCAGAATTCTACAGGCACTGATGGTACCAG-3' (SEQ ID NO: 54)

The amplification reactions (50 µl) were composed of 1× ThermoPol Reaction Buffer, 0.3 mM dNTPs, 0.3 µM TrCBHIpro-F primer, 0.3 µM HiEGV-R primer, and 2 units of Vent DNA polymerase. The reactions were incubated in an EPPENDORF® MASTERCYCLER® 5333 programmed for 5 cycles each for 30 seconds at 94° C., 30 seconds at 50° C., and 60 seconds at 72° C., followed by 25 cycles each for 30 seconds at 94° C., 30 seconds at 65° C., and 120 seconds at 72° C. (5 minute final extension). The reaction products were isolated on a 1.0% agarose gel using TAE buffer where a 1926 bp product band was excised from the gel and purified using a QIAQUICK® Gel Extraction Kit according to the manufacturer's instructions.

Figure 5:
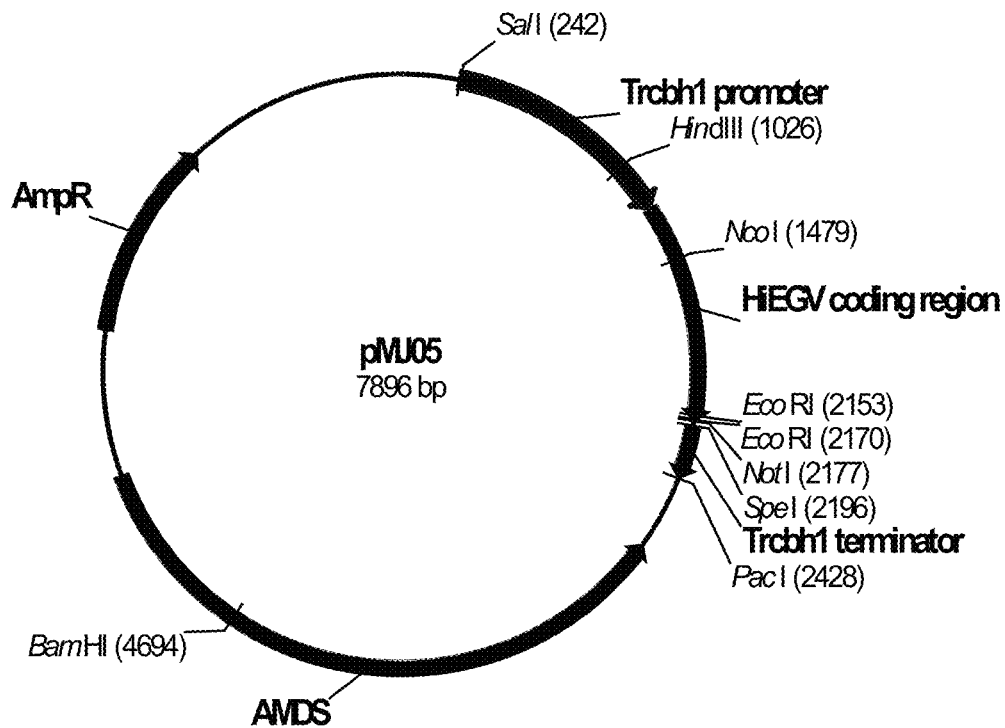
FIG. 5 shows a restriction map of pMJ05.

The resulting 1926 bp fragment was cloned into a pCR®-Blunt-II-TOPO® vector (Invitrogen, Carlsbad, Calif., USA) using a ZEROBLUNT® TOPO® PCR Cloning Kit (Invitrogen, Carlsbad, Calif., USA) following the manufacturer's protocol. The resulting plasmid was digested with NotI and SalI and the 1926 bp fragment was gel purified using a QIAQUICK® Gel Extraction Kit and ligated using T4 DNA ligase (Roche, Indianapolis, Ind., USA) into pMJ04, which was also digested with the same two restriction enzymes, to generate pMJ05 (FIG. 5). Plasmid pMJ05 comprises the *Trichoderma reesei* cellobiohydrolase I promoter and terminator operably linked to the *Humicola insolens* endoglucanase V full-length coding sequence.

Example 4

Construction of pSMai130 Expression Vector

A 2586 bp DNA fragment spanning from the ATG start codon to the TAA stop codon of the *Aspergillus oryzae* beta-glucosidase full-length coding sequence (SEQ ID NO: 21 for cDNA sequence and SEQ ID NO: 22 for the deduced amino acid sequence; *E. coli* DSM 14240) was amplified by PCR from pJaL660 (WO 2002/095014) as template with primers 993467 (sense) and 993456 (antisense) shown below. A SpeI site was engineered at the 5' end of the antisense primer to facilitate ligation. Primer sequences in italics are homologous to 24 bp of the *Trichoderma reesei* cbh1 promoter and underlined sequences are homologous to 22 bp of the *Aspergillus oryzae* beta-glucosidase coding region.
Primer 993467:
5'-ATAGTCAACCGCGGACTGCGCATC*ATGAAGCTTGGTTGGATCGAGG*-3' (SEQ ID NO: 55)
Primer 993456:
5'-ACTAGTTTACTGGGCCTTAGGCAGCG-3' (SEQ ID NO: 56)

The amplification reactions (50 µl) were composed of Pfx Amplification Buffer (Invitrogen, Carlsbad, Calif., USA), 0.25 mM dNTPs, 10 ng of pJaL660, 6.4 µM primer 993467, 3.2 µM primer 993456, 1 mM MgCl$_2$, and 2.5 units of Pfx DNA polymerase (Invitrogen, Carlsbad, Calif., USA). The reactions were incubated in an EPPENDORF® MASTERCYCLER® 5333 programmed for 30 cycles each for 1 minute at 94° C., 1 minute at 55° C., and 3 minutes at 72° C. (15 minute final extension). The reaction products were isolated on a 1.0% agarose gel using TAE buffer where a 2586 bp product band was excised from the gel and purified using a QIAQUICK® Gel Extraction Kit according to the manufacturer's instructions.

A separate PCR was performed to amplify the *Trichoderma reesei* cbh1 promoter sequence extending from 1000 bp upstream of the ATG start codon of the gene, using primer 993453 (sense) and primer 993463 (antisense) shown below to generate a 1000 bp PCR fragment.

Primer 993453:
5'-GTCGACTCGAAGCCCGAATGTAGGAT-3' (SEQ ID NO: 57)
Primer 993463:
5'-CCTCGATCCAACCAAGCTTCATGATGCGC-AGTCCGCGGTTGACTA-3' (SEQ ID NO: 58) Primer sequences in italics are homologous to 24 bp of the *Trichoderma reesei* cbh1 promoter and underlined primer sequences are homologous to 22 bp of the *Aspergillus oryzae* beta-glucosidase full-length coding region. The 46 bp overlap between the promoter and the coding sequence allowed precise fusion of the 1000 bp fragment comprising the *Trichoderma reesei* cbh1 promoter to the 2586 bp fragment comprising the *Aspergillus oryzae* beta-glucosidase coding region.

The amplification reactions (50 µl) were composed of Pfx Amplification Buffer, 0.25 mM dNTPs, 100 ng of *Trichoderma reesei* RutC30 genomic DNA, 6.4 µM primer 993453, 3.2 µM primer 993463, 1 mM MgCl$_2$, and 2.5 units of Pfx DNA polymerase. The reactions were incubated in an EPPENDORF® MASTERCYCLER® 5333 programmed for 30 cycles each for 1 minute at 94° C., 1 minute at 55° C., and 3 minutes at 72° C. (15 minute final extension). The reaction products were isolated on a 1.0% agarose gel using TAE buffer where a 1000 bp product band was excised from the gel and purified using a QIAQUICK® Gel Extraction Kit according to the manufacturer's instructions.

The purified fragments were used as template DNA for subsequent amplification by overlapping PCR using primer 993453 (sense) and primer 993456 (antisense) shown above to precisely fuse the 1000 bp fragment comprising the *Trichoderma reesei* cbh1 promoter to the 2586 bp fragment comprising the *Aspergillus oryzae* beta-glucosidase full-length coding region.

The amplification reactions (50 µl) were composed of Pfx Amplification Buffer, 0.25 mM dNTPs, 6.4 µM primer 99353, 3.2 µM primer 993456, 1 mM MgCl$_2$, and 2.5 units of Pfx DNA polymerase. The reactions were incubated in an EPPENDORF® MASTERCYCLER® 5333 programmed for 30 cycles each for 1 minute at 94° C., 1 minute at 60° C., and 4 minutes at 72° C. (15 minute final extension).

Figure 6:
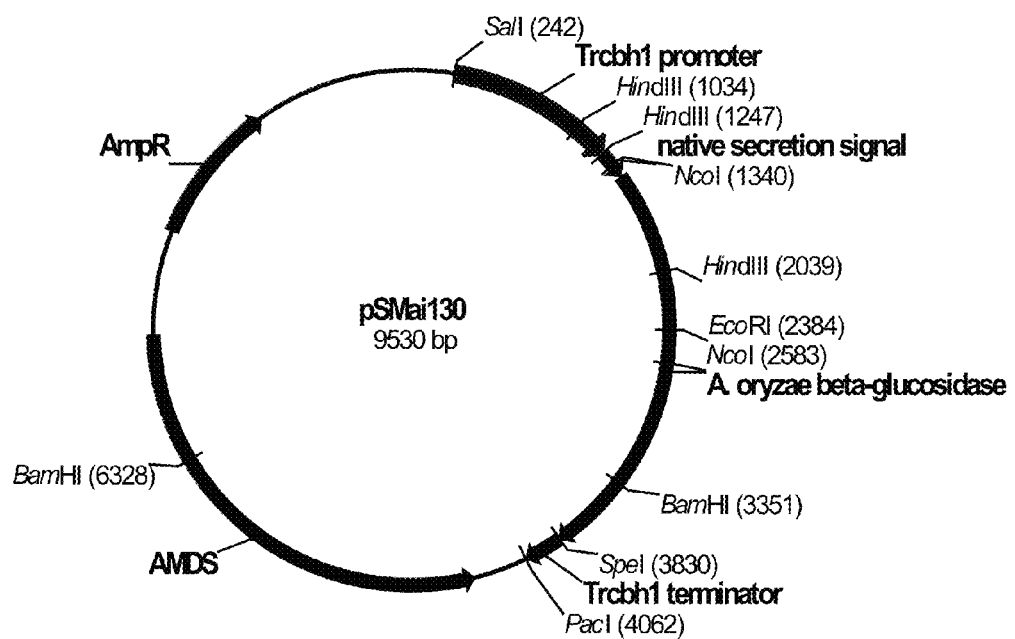
FIG. 6 shows a restriction map of pSMai130.

The resulting 3586 bp fragment was digested with SalI and SpeI and ligated into pMJ04, digested with the same two restriction enzymes, to generate pSMai130 (FIG. 6). Plasmid pSMai130 comprises the *Trichoderma reesei* cellobiohydrolase I gene promoter and terminator operably linked to the *Aspergillus oryzae* native beta-glucosidase signal sequence and coding sequence (i.e., full-length *Aspergillus oryzae* beta-glucosidase coding sequence).

Example 5

Construction of pSMai135

The *Aspergillus oryzae* beta-glucosidase mature coding region (minus the native signal sequence, see FIG. 7; SEQ ID NOs: 59 and 60) from Lys-20 to the TAA stop codon was PCR amplified from pJaL660 as template with primer 993728 (sense) and primer 993727 (antisense) shown below.
Primer 993728:
5'-TGCCGGTGTTGGCCCTTGCC AAGGATGATCTCGCGTACTCCC-3' (SEQ ID NO: 61)
Primer 993727:
5'-GACTAGTCTTACTGGGCCTTAGGCAGCG-3' (SEQ ID NO: 62)
Sequences in italics are homologous to 20 bp of the *Humicola insolens* endoglucanase V signal sequence and sequences underlined are homologous to 22 bp of the *Aspergillus oryzae* beta-glucosidase coding region. A SpeI site was engineered into the 5' end of the antisense primer.

The amplification reactions (50 µl) were composed of Pfx Amplification Buffer, 0.25 mM dNTPs, 10 ng/µl of pJaL660, 6.4 µM primer 993728, 3.2 µM primer 993727, 1 mM MgCl$_2$, and 2.5 units of Pfx DNA polymerase. The reactions were incubated in an EPPENDORF® MASTERCYCLER® 5333 programmed for 30 cycles each for 1 minute at 94° C., 1 minute at 55° C., and 3 minutes at 72° C. (15 minute final extension). The reaction products were isolated on a 1.0% agarose gel using TAE buffer where a 2523 bp product band was excised from the gel and purified using a QIAQUICK® Gel Extraction Kit according to the manufacturer's instructions.

A separate PCR amplification was performed to amplify 1000 bp of the *Trichoderma reesei* cbh1 promoter and 63 bp of the *Humicola insolens* endoglucanase V signal sequence (ATG start codon to Ala-21, FIG. 8, SEQ ID NOs: 63 and 64), using primer 993724 (sense) and primer 993729 (antisense) shown below.
Primer 993724:
5'-ACG CGTCGACCGAATGTAGGATTGTTATCC-3' (SEQ ID NO: 65)
Primer 993729:
5'-GGGAGTACGCGAGATCATCCTTGGCAAGG-GCCAACACCGGCA-3' (SEQ ID NO: 66)

Primer sequences in italics are homologous to 20 bp of the *Humicola insolens* endoglucanase V signal sequence and underlined primer sequences are homologous to the 22 by of the *Aspergillus oryzae* beta-glucosidase coding region.

Plasmid pMJ05, which comprises the *Humicola insolens* endoglucanase V coding region under the control of the cbh1 promoter, was used as template to generate a 1063 bp fragment comprising the *Trichoderma reesei* cbh1 promoter and *Humicola insolens* endoglucanase V signal sequence fragment. A 42 bp of overlap was shared between the *Trichoderma reesei* cbh1 promoter and *Humicola insolens* endoglucanase V signal sequence and the *Aspergillus oryzae* beta-glucosidase mature coding sequence to provide a perfect linkage between the promoter and the ATG start codon of the 2523 bp *Aspergillus oryzae* beta-glucosidase coding region.

The amplification reactions (50 µl) were composed of Pfx Amplification Buffer, 0.25 mM dNTPs, 10 ng/µl of pMJ05, 6.4 µM primer 993728, 3.2 µM primer 993727, 1 mM MgCl$_2$, and 2.5 units of Pfx DNA polymerase. The reactions were incubated in an EPPENDORF® MASTERCYCLER® 5333 programmed for 30 cycles each for 1 minute at 94° C., 1 minute at 60° C., and 4 minutes at 72° C. (15 minute final extension). The reaction products were isolated on a 1.0% agarose gel using TAE buffer where a 1063 bp product band was excised from the gel and purified using a QIAQUICK® Gel Extraction Kit according to the manufacturer's instructions.

The purified overlapping fragments were used as templates for amplification using primer 993724 (sense) and primer 993727 (antisense) described above to precisely fuse the 1063 bp fragment comprising the *Trichoderma reesei* cbh1 promoter and *Humicola insolens* endoglucanase V signal sequence to the 2523 bp fragment comprising the *Aspergillus oryzae* beta-glucosidase mature coding region frame by overlapping PCR.

The amplification reactions (50 µl) were composed of Pfx Amplification Buffer, 0.25 mM dNTPs, 6.4 µM primer 993724, 3.2 µM primer 993727, 1 mM MgCl$_2$, and 2.5 units of Pfx DNA polymerase. The reactions were incubated in an EPPENDORF® MASTERCYCLER® 5333 programmed for 30 cycles each for 1 minute at 94° C., 1 minute at 60° C., and 4 minutes at 72° C. (15 minute final extension). The reaction products were isolated on a 1.0% agarose gel using TAE buffer where a 3591 bp product band was excised from the gel and purified using a QIAQUICK® Gel Extraction Kit according to the manufacturer's instructions.

Figure 9:
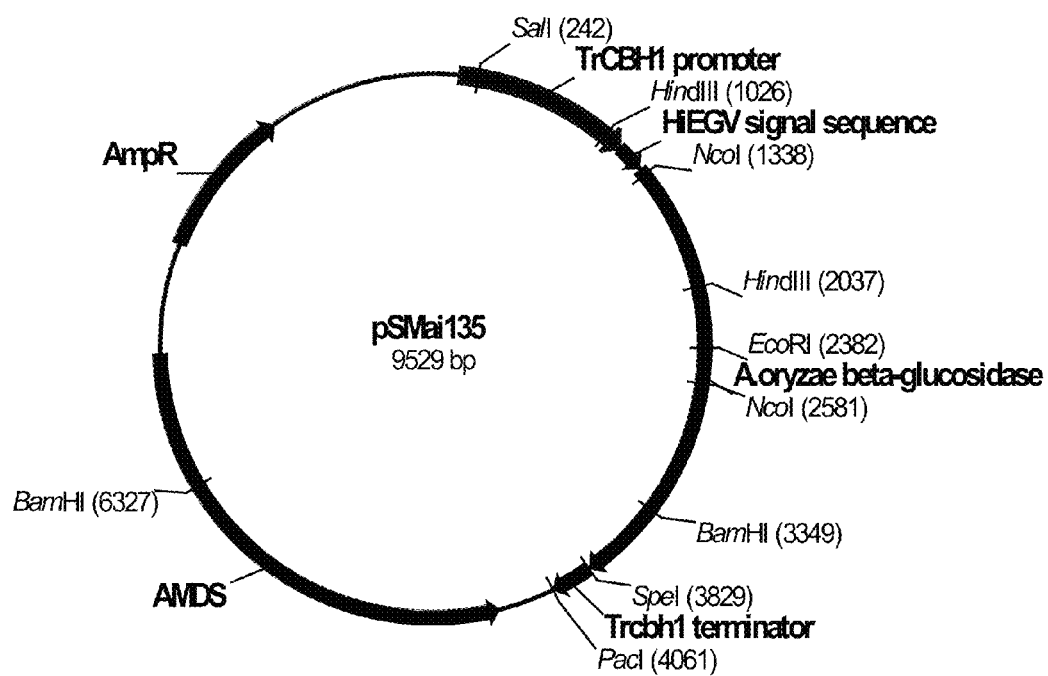
FIG. 9 shows a restriction map of pSMai135.

The resulting 3591 bp fragment was digested with SalI and SpeI and ligated into pMJ04 digested with the same restriction enzymes to generate pSMai135 (FIG. 9). Plasmid pSMai135 comprises the *Trichoderma reesei* cellobiohydrolase I gene promoter and terminator operably linked to the *Humicola insolens* endoglucanase V signal sequence and the *Aspergillus oryzae* beta-glucosidase mature coding sequence.

Example 6

Expression of *Aspergillus oryzae* Beta-Glucosidase with the *Humicola Insolens* Endoglucanase V Secretion Signal Plasmid pSMai135 encoding the mature *Aspergillus oryzae* beta-glucosidase linked to the *Humicola insolens* endoglucanase V secretion signal (FIG. 8) was introduced into *Trichoderma reesei* RutC30 bp PEG-mediated transformation (Penttila et al., 1987, *Gene* 61 155-164). The plasmid contained the *Aspergillus nidulans* amdS gene to enable transformants to grow on acetamide as the sole nitrogen source.

*Trichoderma reesei* RutC30 was cultivated at 27° C. and 90 rpm in 25 ml of YP medium supplemented with 2% (w/v) glucose and 10 mM uridine for 17 hours. Mycelia were collected by filtration using a Vacuum Driven Disposable Filtration System (Millipore, Bedford, Mass., USA) and washed twice with deionized water and twice with 1.2 M sorbitol. Protoplasts were generated by suspending the washed mycelia in 20 ml of 1.2 M sorbitol containing 15 mg of GLUCANEX® (Novozymes NS, Bagsvrd, Denmark) per ml and 0.36 units of chitinase (Sigma Chemical Co., St. Louis, Mo., USA) per ml and incubating for 15-25 minutes at 34° C. with gentle shaking at 90 rpm. Protoplasts were collected by centrifuging for 7 minutes at 400 x g and washed twice with cold 1.2 M sorbitol. The protoplasts were counted using a haemacytometer and re-suspended in STC to a final concentration of $1 \times 10^8$ protoplasts per ml. Excess protoplasts were stored in a Cryo 1° C. Freezing Container (Nalgene, Rochester, N.Y., USA) at −80° C.

Approximately 7 μg of pSMai135 digested with PmeI was added to 100 μl of protoplast solution and mixed gently, followed by 260 μl of PEG buffer, mixed, and incubated at room temperature for 30 minutes. STC (3 ml) was then added and mixed and the transformation solution was plated onto COVE plates using *Aspergillus nidulans* amdS selection. The plates were incubated at 28° C. for 5-7 days. Transformants were sub-cultured onto COVE2 plates and grown at 28° C.

Sixty-seven transformants designated SMA135 obtained with pSMai135 were subcultured onto fresh plates containing acetamide and allowed to sporulate for 7 days at 28° C.

The 67 SMA135 *Trichoderma reesei* transformants were cultivated in 125 ml baffled shake flasks containing 25 ml of cellulase-inducing media at pH 6.0 inoculated with spores of the transformants and incubated at 28° C. and 200 rpm for 7 days. *Trichoderma reesei* RutC30 was run as a control. Culture broth samples were removed at day 7. One ml of each culture broth was centrifuged at 15,700×g for 5 minutes in a micro-centrifuge and the supernatants transferred to new tubes. Samples were stored at 4° C. until enzyme assay. The supernatants were assayed for beta-glucosidase activity using p-nitrophenyl-beta-D-glucopyranoside as substrate, as described below.

Beta-glucosidase activity was determined at ambient temperature using 25 μl aliquots of culture supernatants, diluted 1:10 in 50 mM succinate pH 5.0, in 200 μl of 0.5 mg/ml p-nitrophenyl-beta-D-glucopyranoside as substrate in 50 mM succinate pH 5.0. After 15 minutes incubation the reaction was stopped by adding 100 μl of 1 M Tris-HCl pH 8.0 and the absorbance was read spectrophotometrically at 405 nm. One unit of beta-glucosidase activity corresponded to production of 1 μmol of p-nitrophenyl per minute per liter at pH 5.0, ambient temperature. *Aspergillus niger* beta-glucosidase (NOVOZYM™ 188, Novozymes NS, Bagsvrd, Denmark) was used as an enzyme standard.

A number of the SMA135 transformants showed beta-glucosidase activities several-fold higher than that secreted by *Trichoderma reesei* RutC30. Of the SMA135 transformants screened, transformant SMA135-04 produced the highest beta-glucosidase activity.

SDS-PAGE was carried out using CRITERION® Tris-HCl (5% resolving) gels (Bio-Rad, Hercules, Calif., USA) with the CRITERION® System (Bio-Rad, Hercules, Calif., USA). Five μl of day 7 supernatants (see above) were suspended in 2× concentration of Laemmli Sample Buffer (Bio-Rad, Hercules, Calif., USA) and boiled in the presence of 5% beta-mercaptoethanol for 3 minutes. The supernatant samples were loaded onto a polyacrylamide gel and subjected to electrophoresis with 1× Tris/Glycine/SDS as running buffer (Bio-Rad, Hercules, Calif., USA). The resulting gel was stained with BIO-SAFE® Coomassie Stain (Bio-Rad, Hercules, Calif., USA).

Of the 38 *Trichoderma reesei* SMA135 transformants analyzed by SDS-PAGE, 26 produced a protein of approximately 110 kDa that was not visible in *Trichoderma reesei* RutC30 as control. Transformant *Trichoderma reesei* SMA135-04 produced the highest level of beta-glucosidase as evidenced by abundance of the 110 kDa band seen by SDS-PAGE.

Example 7

Construction of Expression Vector pSMai140

Expression vector pSMai140 was constructed by digesting plasmid pSATe111BG41 (WO 04/099228), which carries the *Aspergillus oryzae* beta-glucosidase variant BG41 full-length coding region (SEQ ID NO: 23 that encodes the amino acid sequence of SEQ ID NO: 24), with NcoI. The resulting 1243 bp fragment was isolated on a 1.0% agarose gel using TAE buffer and purified using a QIAQUICK® Gel Extraction Kit according to the manufacturer's instructions.

Figure 10:
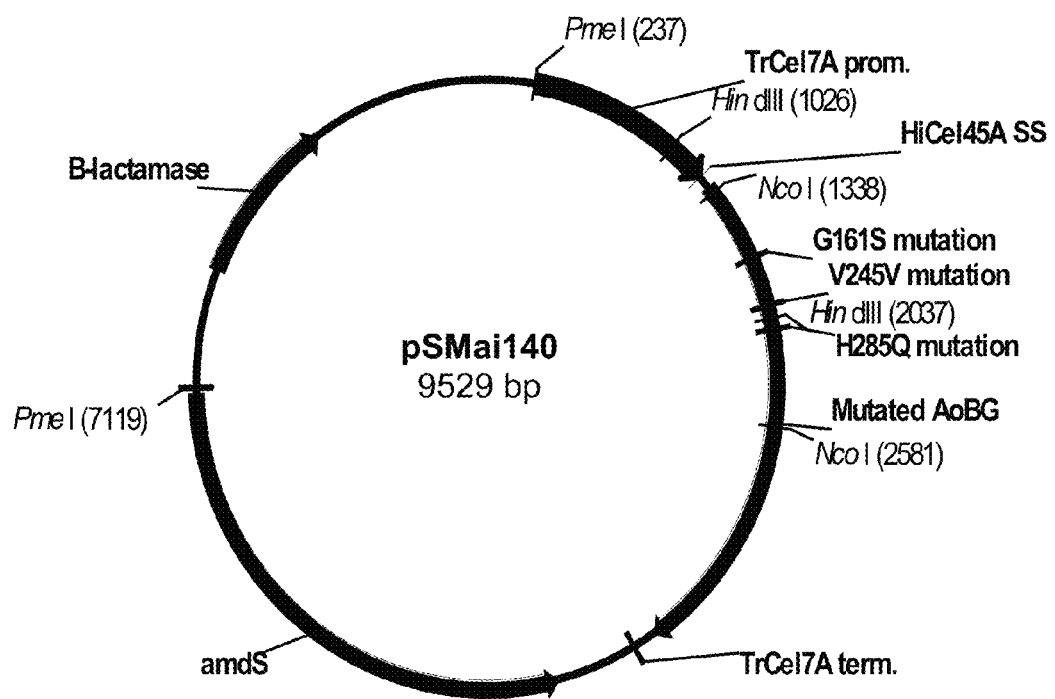
FIG. 10 shows a restriction map of pSMai140.

Expression vector pSMai135 was digested with NcoI and a 8286 bp fragment was isolated on a 1.0% agarose gel using TAE buffer and purified using a QIAQUICK® Gel Extraction Kit according to the manufacturer's instructions. The 1243 bp NcoI digested *Aspergillus oryzae* beta-glucosidase variant BG41 fragment was then ligated to the 8286 bp vector, using T4 DNA ligase (Roche, Indianapolis, Ind., USA) according to manufacturer's protocol, to create the expression vector pSMai140 (FIG. 10). Plasmid pSMai140 comprises the *Trichoderma reesei* cellobiohydrolase I (CEL7A) gene promoter and terminator operably linked to the *Humicola insolens* endoglucanase V signal sequence and the *Aspergillus oryzae* beta-glucosidase variant mature coding sequence.

Example 8

Transformation of *Trichoderma reesei* RutC30 with pSMai140

Plasmid pSMai140 was linearized with PmeI and transformed into the *Trichoderma reesei* RutC30 strain as described in Example 6. A total of 100 transformants were obtained from four independent transformation experiments, all of which were cultivated in shake flasks on cellulase-inducing medium, and the beta-glucosidase activity was measured from the culture medium of the transformants as described in Example 6. A number of *Trichoderma reesei* SMA140 transformants showed beta-glucosidase activities several fold higher than that of *Trichoderma reesei* RutC30.

The presence of the *Aspergillus oryzae* beta-glucosidase variant BG41 protein in the culture medium was detected by SDS-polyacrylamide gel electrophoresis as described in Example 6 and Coomassie staining from the same 13 culture supernatants from which enzyme activity were analyzed. All thirteen transformants that had high β-glucosidase activity, also expressed the approximately 110 KDa *Aspergillus oryzae* beta-glucosidase variant BG41, at varying yields.

The highest beta-glucosidase variant expressing transformant, as evaluated by beta-glucosidase activity assay and SDS-polyacrylamide gel electrophoresis, was designated *Trichoderma reesei* SMA140-43.

Example 9

Construction of Expression Vector pSaMe-F1

A DNA fragment containing 209 bp of the *Trichoderma reesei* cellobiohydrolase I gene promoter and the core region (nucleotides 1 to 702 of SEQ ID NO: 1 that encode amino acids 1 to 234 of SEQ ID NO: 2; WO 91/17243) of the *Humicola insolens* endoglucanase V gene was PCR amplified using pMJ05 as template using the primers shown below.
995103:
5'-cccaagcttagccaagaaca-3' (SEQ ID NO: 67)
995137:
5'-ggggaggaacgcatgggatcggacggc-3' (SEQ ID NO: 68)

The amplification reactions (50 µl) were composed of 1×Pfx Amplification Buffer, 10 mM dNTPs, 50 mM $MgSO_4$, 10 ng/µl of pMJ05, 50 picomoles of 995103 primer, 50 picomoles of 995137 primer, and 2 units of Pfx DNA polymerase. The reactions were incubated in an EPPENDORF® MASTERCYCLER® 5333 programmed for 30 cycles each for 30 seconds at 94° C., 30 seconds at 55° C., and 60 seconds at 72° C. (3 minute final extension).

The reaction products were isolated on a 1.0% agarose gel using TAE buffer where a 911 bp product band was excised from the gel and purified using a QIAQUICK® Gel Extraction Kit according to the manufacturer's instructions.

A DNA fragment containing 806 bp of the *Aspergillus oryzae* beta-glucosidase variant BG41 gene was PCR amplified using pSMai140 as template and the primers shown below.
995133:
5'-gccgtccagatccccatgcgttcctccccc-3' (SEQ ID NO: 69)
995111:
5'-ccaagcttgttcagagtttc-3' (SEQ ID NO: 70)

The amplification reactions (50 µl) were composed of 1×Pfx Amplification Buffer, 10 mM dNTPs, 50 mM $MgSO_4$, 100 ng of pSMai140, 50 picomoles of 995133 primer, 50 picomoles of 995111 primer, and 2 units of Pfx DNA polymerase. The reactions were incubated in an EPPENDORF® MASTERCYCLER® 5333 programmed for 30 cycles each for 30 seconds at 94° C., 30 seconds at 55° C., and 120 seconds at 72° C. (3 minute final extension).

The reaction products were isolated on a 1.0% agarose gel using TAE buffer where a 806 bp product band was excised from the gel and purified using a QIAQUICK® Gel Extraction Kit according to the manufacturer's instructions.

The two PCR fragments above were then subjected to overlapping PCR. The purified overlapping fragments were used as templates for amplification using primer 995103 (sense) and primer 995111 (antisense) described above to precisely fuse the 702 bp fragment comprising 209 bp of the *Trichoderma reesei* cellobiohydrolase I gene promoter and the *Humicola insolens* endoglucanase V core sequence to the 806 bp fragment comprising a portion of the *Aspergillus oryzae* beta-glucosidase variant BG41 coding region by overlapping PCR.

The amplification reactions (50 µl) were composed of 1×Pfx Amplification Buffer, 10 mM dNTPs, 50 mM $MgSO_4$, 2.5 µl of each fragment (20 ng/µl), 50 picomoles of 995103 primer, 50 picomoles of 995111 primer, and 2 units of high fidelity Pfx DNA polymerase. The reactions were incubated in an EPPENDORF® MASTERCYCLER® 5333 programmed for an initial denaturation of 3 minutes at 95° C. followed by 30 cycles each for 1 minute of denaturation, 1 minute annealing at 60° C., and a 3 minute extension at 72° C.

The reaction products were isolated on a 1.0% agarose gel using TAE buffer where a 1.7 kb product band was excised from the gel and purified using a QIAQUICK® Gel Extraction Kit according to the manufacturer's instructions.

The 1.7 kb fragment was ligated into a pCR®4 Blunt Vector (Invitrogen, Carlsbad, Calif., USA) according to the manufacturer's instructions. The construct was then transformed into ONE SHOT® TOP10 Chemically Competent *E. coli* cells (Invitrogen, Carlsbad, Calif., USA) according to the manufacturer's rapid chemical transformation procedure. Colonies were selected and analyzed by plasmid isolation and digestion with Hind III to release the 1.7 kb overlapping PCR fragment.

Figure 11:
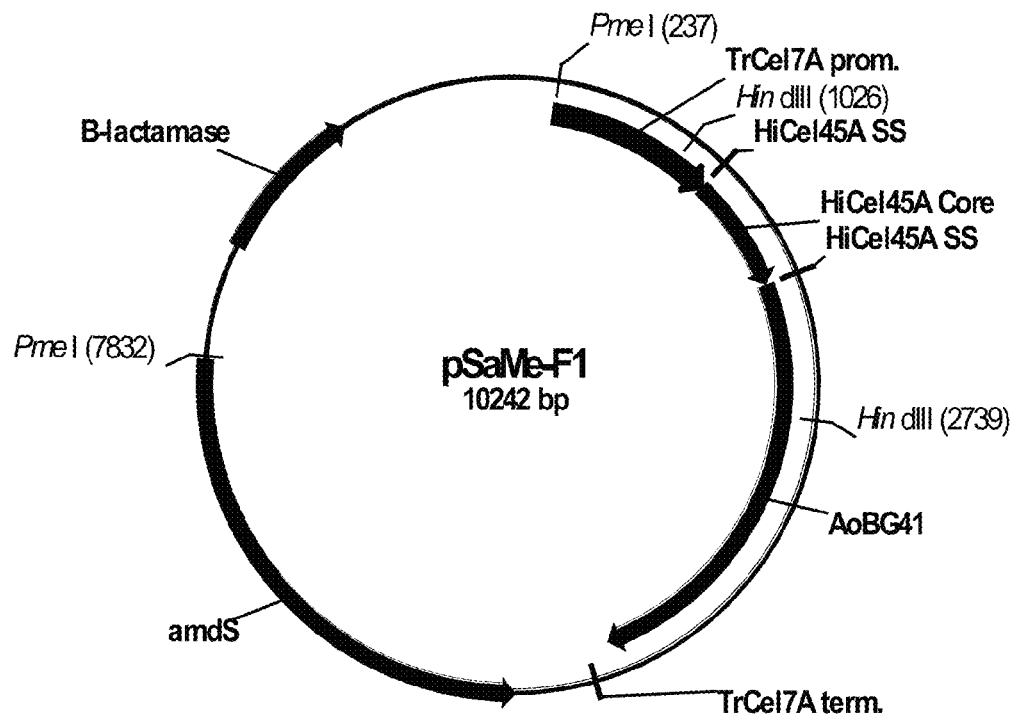
FIG. 11 shows a restriction map of pSaMe-F1.

Plasmid pSMai140 was also digested with Hind III to linearize the plasmid. Both digested fragments were combined in a ligation reaction using a Rapid DNA Ligation Kit following the manufacturer's instructions to produce pSaMe-F1 (FIG. 11).

*E. coli* XL1-Blue Subcloning-Grade Competent Cells (Stratagene, La Jolla, Calif., USA) were transformed with the ligation product. Identity of the construct was confirmed by DNA sequencing of the *Trichoderma reesei* cellobiohydrolase I gene promoter, *Humicola insolens* endoglucanase V signal sequence, *Humicola insolens* endoglucanase V core, *Humicola insolens* endoglucanase V signal sequence, *Aspergillus oryzae* beta-glucosidase variant BG41, and the *Trichoderma reesei* cellobiohydrolase I gene terminator sequence from plasmids purified from transformed *E. coli*. One clone containing the recombinant plasmid was designated pSaMe-F1. Plasmid pSaMe-F1 comprises the *Trichoderma reesei* cellobiohydrolase I gene promoter and terminator and the *Humicola insolens* endoglucanase V signal peptide sequence linked directly to the *Humicola insolens* endoglucanase V core polypeptide that are fused directly to the *Humicola insolens* endoglucanase V signal peptide that is linked directly to the *Aspergillus oryzae* beta-glucosidase variant BG41 mature coding sequence. The DNA sequence and deduced amino acid sequence of the *Aspergillus oryzae* beta-glucosidase variant BG fusion protein is shown in SEQ ID NOs: 73 and 74, respectively (see FIGS. 14A, 14B, 14C, and 14D).

Example 10

Transformation of *Trichoderma reesei* RutC30 with pSaMe-F1

Shake flasks containing 25 ml of YP medium supplemented with 2% glucose and 10 mM uridine were inoculated with $5 \times 10^7$ spores of *Trichoderma reesei* RutC30. Following incubation overnight for approximately 16 hours at 27° C., 90 rpm, the mycelia were collected using a Vacuum Driven Disposable Filtration System. The mycelia were washed twice in 100 ml of deionized water and twice in 1.2 M sorbitol. Protoplasts were generated as described in Example 6.

Two micrograms of pSaMe-F1 DNA linearized with PmeI, 100 µl of *Trichoderma reesei* RutC30 protoplasts, and 50% PEG (4000) were mixed and incubated for 30 minutes at room temperature. Then 3 ml of STC were added and the contents were poured onto a COVE plate supplemented with 10 mM uridine. The plate was then incubated at 28° C. Transformants began to appear by day 6 and were picked to COVE2 plates for growth at 28° C. and 6 days. Twenty-two *Trichoderma reesei* transformants were recovered.

Transformants were cultivated in shake flasks on cellulase-inducing medium, and beta-glucosidase activity was measured as described in Example 6. A number of pSaMe-F1 transformants produced beta-glucosidase activity. One transformant, designated *Trichoderma reesei* SaMeF1-9, produced the highest amount of beta-glucosidase, and had twice the activity of a strain expressing the *Aspergillus oryzae* beta-glucosidase variant (Example 9).

Endoglucanase activity was assayed using a carboxymethyl cellulose (CMC) overlay assay according to Beguin, 1983, *Analytical Biochem.* 131(2): 333-336. Five µg of total protein from five of the broth samples (those having the highest beta-glucosidase activity) were diluted in Native Sample Buffer (Bio-Rad, Hercules, Calif., USA) and run on a CRITERION® 8-16% Tris-HCl gel (Bio-Rad, Hercules, Calif., USA) using 10× Tris/glycine running buffer (Bio-Rad, Hercules, Calif., USA) and then the gel was laid on top of a plate containing 1% carboxymethylcellulose (CMC). After 1 hour incubation at 37° C., the gel was stained with 0.1% Congo Red for 20 minutes. The plate was then destained using 1 M NaCl in order to identify regions of clearing indicative of endoglucanase activity. Two clearing zones were visible, one upper zone at approximately 110 kDa and a lower zone at approximately 25 kDa. The predicted protein size of the *Humicola insolens* endoglucanase V and *Aspergillus oryzae* beta-glucosidase variant BG41 fusion is 118 kDa if the two proteins are not cleaved and remain as a single polypeptide; glycosylation of the individual endoglucanase V core domain and of the beta-glucosidase leads to migration of the individual proteins at higher mw than predicted from the primary sequence. If the two proteins are cleaved then the predicted sizes for the *Humicola insolens* endoglucanase V core domain is 24 kDa and 94 kDa for *Aspergillus oryzae* beta-glucosidase variant BG41. Since there was a clearing zone at approximately 110 kDa this result indicated that minimally a population of the endoglucanase and beta-glucosidase fusion protein remains intact as a single large protein. The lower clearing zone most likely represents an endogenous endoglucanase activity, and possibly additionally results from partial cleavage of the *Humicola insolens* endoglucanase V core domain from the *Aspergillus oryzae* β-glucosidase.

The results demonstrated the *Humicola insolens* endoglucanase V core was active even while fused to the *Aspergillus oryzae* beta-glucosidase. In addition, the increase in beta-glucosidase activity appeared to result from increased secretion of protein relative to the secretion efficiency of the non-fusion beta-glucosidase. By linking the *Aspergillus oryzae* beta-glucosidase variant BG41 sequence to the efficiently secreted *Humicola insolens* endoglucanase V core, more beta-glucosidase was secreted.

Example 11

Construction of Vector pSaMe-FX

Plasmid pSaMe-FX was constructed by modifying pSaMe-F1. Plasmid pSaMe-F1 was digested with Bst Z17 and Eco RI to generate a 1 kb fragment that contained the beta-glucosidase variant BG41 coding sequence and a 9.2 kb fragment containing the remainder of the plasmid. The fragments were separated on a 1.0% agarose gel using TAE buffer and the 9.2 kb fragment was excised and purified using a QIAQUICK® Gel Extraction Kit according to the manufacturer's instructions. Plasmid pSMai135 was also digested with Bst Z17 and Eco RI to generate a 1 kb fragment containing bases homologous to the *Aspergillus oryzae* beta-glucosidase variant BG41 coding sequence and a 8.5 kb fragment containing the remainder of the plasmid. The 1 kb fragment was isolated and purified as above.

The 9.2 kb and 1 kb fragments were combined in a ligation reaction using a Rapid DNA Ligation Kit following the manufacturer's instructions to produce pSaMe-FX, which is identical to pSaMe-F1 except that it contained the wild-type beta-glucosidase mature coding sequence rather than the variant mature coding sequence.

Figure 12:
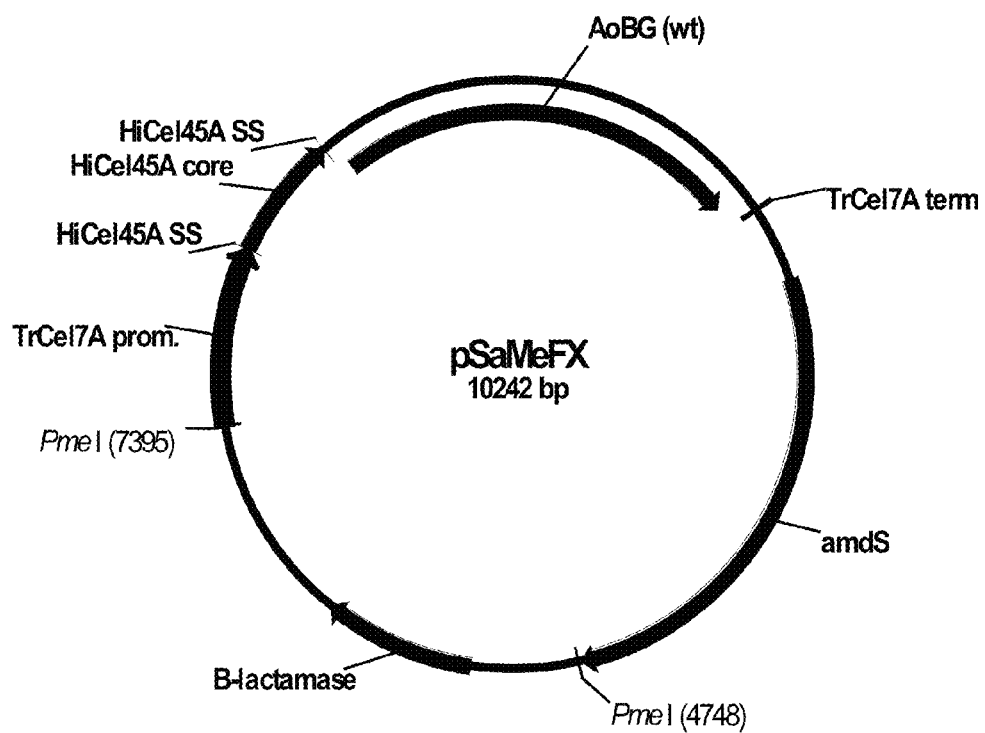
FIG. 12 shows a restriction map of pSaMe-FX.

*E. coli* SURE® Competent Cells (Stratagene, La Jolla, Calif., USA) were transformed with the ligation product. Identity of the construct was confirmed by DNA sequencing of the *Trichoderma reesei* cellobiohydrolase I gene promoter, *Humicola insolens* endoglucanase V signal sequence, *Humicola insolens* endoglucanase V core sequence, *Humicola insolens* endoglucanase V signal sequence, *Aspergillus oryzae* beta-glucosidase mature coding sequence, and the *Trichoderma reesei* cellobiohydrolase I gene terminator sequence from plasmids purified from transformed *E. coli*. One clone containing the recombinant plasmid was designated pSaMe-FX (FIG. 12). The DNA sequence and deduced amino acid sequence of the *Aspergillus oryzae* beta-glucosidase fusion protein is shown in SEQ ID NOs: 75 and 76, respectively (see FIGS. 15A, 15B, 15C, and 15D).

Example 12

Transformation and Expression of *Trichoderma* Transformants

The pSaMe-FX construct was linearized with PmeI and transformed into the *Trichoderma reesei* RutC30 strain as described in Example 10. A total of 63 transformants were obtained from a single transformation. Transformants were cultivated in shake flasks on cellulase-inducing medium, and beta-glucosidase activity was measured as described in Example 6. A number of pSaMe-FX transformants produced beta-glucosidase activity. One transformant designated SaMe-FX16 produced twice the amount of beta-glucosidase activity compared to *Trichoderma reesei* SaMeF1-9 (Example 10).

Example 13

Analysis of *Trichoderma reesei* Transformants

A fusion protein was constructed as described in Example 9 by fusing the *Humicola insolens* endoglucanase V core (containing its own native signal sequence) with the *Aspergillus oryzae* beta-glucosidase variant BG41 mature coding sequence linked to the *Humicola insolens* endoglucanase V signal sequence. This fusion construct resulted in a two-fold increase in secreted beta-glucosidase activity compared to the *Aspergillus oryzae* beta-glucosidase variant BG41 mature coding sequence linked to the *Humicola insolens* endoglucanase V signal sequence. A second fusion construct was made as described in Example 11 consisting of the *Humicola insolens* endoglucanase V core (containing its own signal sequence) fused with the *Aspergillus oryzae* wild-type beta-glucosidase coding sequence linked to the *Humicola insolens* endoglucanase V signal sequence, and this led to an even further improvement in beta-glucosidase activity. The strain transformed with the wild-type fusion had twice the secreted beta-glucosidase activity relative to the strain transformed with the beta-glucosidase variant BG41 fusion.

Example 14

Cloning of the Beta-Glucosidase Fusion Protein Encoding Sequence into an *Aspergillus oryzae* Expression Vector Two synthetic oligonucleotide primers, shown below, were designed to PCR amplify the full-length open reading frame from pSaMeFX encoding the beta-glucosidase fusion protein.
PCR Forward primer:
5'-GGACTGCGCAG̲CATGCGTTC-3' (SEQ ID NO: 71)
PCR Reverse primer:
5'-AGTTAATTAATTACTGGGCCTTAGGCAGCG-3' (SEQ ID NO: 72)
Bold letters represent coding sequence. The underlined "G" in the forward primer represents a base change introduced to create an Sph I restriction site. The remaining sequence contains sequence identity compared with the insertion sites of pSaMeFX. The underlined sequence in the reverse primer represents a PacI restriction site added to facilitate the cloning of this gene in the expression vector pAlLo2 (WO 04/099228).

Fifty picomoles of each of the primers above were used in a PCR reaction containing 50 ng of pSaMeFX DNA, 1×Pfx Amplification Buffer, 6 µl of 10 mM blend of dATP, dTTP, dGTP, and dCTP, 2.5 units of PLATINUM® Pfx DNA Polymerase, and 1 µl of 50 mM MgSO$_4$ in a final volume of 50 µl. An EPPENDORF® MASTERCYCLER® 5333 was used to amplify the fragment programmed for 1 cycle at 98° C. for 2 minutes; and 35 cycles each at 96° C. for 30 seconds, 61° C. for 30 seconds, and 68° C. for 3 minutes. After the 35 cycles, the reaction was incubated at 68° C. for 10 minutes and then cooled at 10° C. until further processed. A 3.3 kb PCR reaction product was isolated on a 0.8% GTG-agarose gel (Cambrex Bioproducts One Meadowlands Plaza East Rutherford, N.J., USA) using TAE buffer and 0.1 µg of ethidium bromide per ml. The DNA was visualized with the aid of a DARK READER™ (Clare Chemical Research, Dolores, Colo., USA) to avoid UV-induced mutations. A 3.3 kb DNA band was excised with a disposable razor blade and purified with an ULTRAFREE®-DA spin cup (Millipore, Billerica, Mass., USA) according to the manufacturer's instructions.

The purified 3.3 kb PCR product was cloned into a pCR®4Blunt-TOPO® vector (Invitrogen, Carlsbad, Calif., USA). Four microliters of the purified PCR product were mixed with 1 µl of a 2 M sodium chloride solution and 1 µl of the TOPO® vector. The reaction was incubated at room temperature for 15 minutes and then 2 µl of the reaction were used to transform One Shot® TOP10 Chemically Competent *E. coli* cells according to the manufacturer's instructions. Three aliquots of 83 µl each of the transformation reaction were spread onto three 150 mm 2×YT plates supplemented with 100 µg of ampicillin per ml and incubated overnight at 37° C.

Eight recombinant colonies were used to inoculate liquid cultures containing 3 ml of LB medium supplemented with 100 µg of ampicillin per ml. Plasmid DNA was prepared from these cultures using a BIOROBOT® 9600 (QIAGEN Inc., Valencia, Calif., USA). Clones were analyzed by restriction enzyme digestion with PacI. Plasmid DNA from each clone was digested with PacI and analyzed by 1.0% agarose gel electrophoresis using TAE buffer. All eight clones had the expected restriction digest pattern and clones 5, 6, 7, and 8 were selected to be sequenced to confirm that there were no mutations in the cloned insert. Sequence analysis of their 5' and 3' ends indicated that all 4 clones had the correct sequence. Clones 5 and 7 were selected for further sequencing. Both clones were sequenced to Phred Q values of greater than 40 to ensure that there were no PCR induced errors. Clones 5 and 7 were shown to have the expected sequence and clone 5 was selected for re-cloning into pAlLo2.

Plasmid DNA from clone 5 was linearized by digestion with Sph I. The linearized clone was then blunt-ended by adding 1.2 µl of a 10 mM blend of dATP, dTTP, dGTP, and dCTP and 6 units of T4 DNA polymerase (New England Bioloabs, Inc., Ipswich, Mass., USA). The mixture was incubated at 12° C. for 20 minutes and then the reaction was stopped by adding 1 µl of 0.5 M EDTA and heating at 75° C. for 20 minutes to inactivate the enzyme. A 3.3 kb fragment encoding the beta-glucosidase fusion protein was purified by gel electrophoresis and ultrafiltration as described above.

The vector pAlLo2 was linearized by digestion with NcoI. The linearized vector was then blunt-ended by adding 0.5 µl of a 10 mM blend of dATP, dTTP, dGTP, and dCTP and one unit of DNA polymerase I. The mixture was incubated at 25° C. for 15 minutes and then the reaction was stopped by adding 1 µl of 0.5M EDTA and heating at 75° C. for 15 minutes to inactivate the enzymes. Then the vector was digested with PacI. The blunt-ended vector was purified by gel electrophoresis and ultrafiltration as described above.

Figure 13:
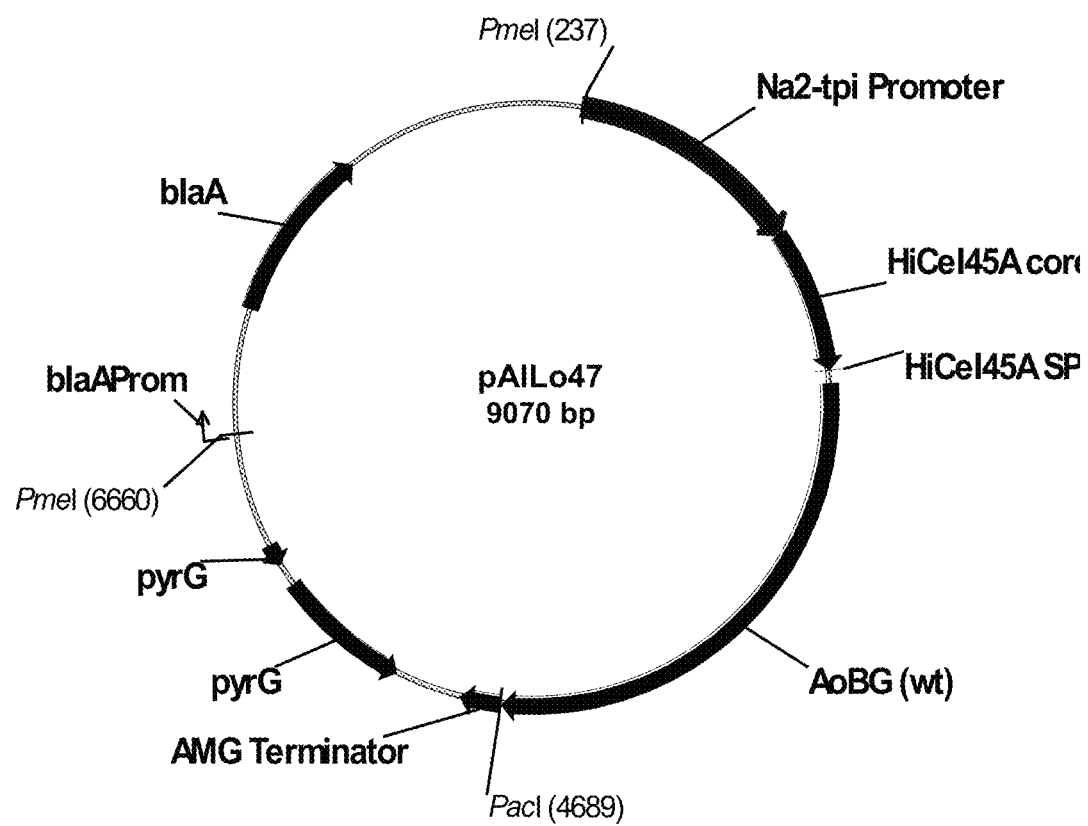
FIG. 13 shows a restriction map of pAILo47.

Cloning of the 3.3 kb fragment encoding the beta-glucosidase fusion protein into the linearized and purified pAlLo2 vector was performed with a Rapid Ligation Kit. A 1 µl sample of the reaction was used to transform *E. coli* XL10 SOLOPACK® Gold cells (Stratagene, La Jolla, Calif., USA) according to the manufacturer's instructions. After the recovery period, two 100 µl aliquots from the transformation reaction were plated onto two 150 mm 2×YT plates supplemented with 100 µg of ampicillin per ml and incubated overnight at 37° C. A set of eight putative recombinant clones was selected at random from the selection plates and plasmid DNA was prepared from each one using a BIOROBOT® 9600. Clones 1-4 were selected for sequencing with pAlLo2-specific primers to confirm that the junction vector/insert had the correct sequence. Clone 3 had a perfect vector/insert junction and was designated pAlLo47 (FIG. 13).

In order to create a marker-free expression strain, a restriction endonuclease digestion was performed to separate the blaA gene that confers resistance to the antibiotic ampicillin from the rest of the expression construct. Thirty micrograms of pAlLo47 were digested with PmeI. The digested DNA was then purified by agarose gel electrophoresis as described above. A 6.4 kb DNA band containing the expression construct but lacking the blaA gene was excised with a razor blade and purified with a QIAQUICK® Gel Extraction Kit.

Example 15

Expression of the Beta-Glucosidase Fusion Protein in *Aspergillus oryzae* JaL355

*Aspergillus oryzae* JaL355 (WO 00/240694) protoplasts were prepared according to the method of Christensen et al., 1988, *Bio/Technology* 6: 1419-1422. Ten microliters of the purified expression construct of Example 14 were used to transform *Aspergillus oryzae* JaL355 protoplasts. The transformation of *Aspergillus oryzae* JaL355 yielded approximately 90 transformants. Fifty transformants were isolated to individual PDA plates and incubated for five days at 34° C.

Forty-eight confluent spore plates were washed with 3 ml of 0.01% TWEEN® 80 and the spore suspension was used to inoculate 25 ml of MDU2BP medium in 125 ml glass shake flasks. Transformant cultures were incubated at 34° C. with constant shaking at 200 rpm. After 5 days, 1 ml aliquots of each culture was centrifuged at 12,000×g and their supernatants collected. Five μl of each supernatant were mixed with an equal volume of 2× loading buffer (10% beta-mercaptoethanol) and loaded onto a 1.5 mm 8%-16% Tris-Glycine SDS-PAGE gel and stained with BIO-SAFE® Coomassie Blue G250 protein stain (Bio-Rad, Hercules, Calif., USA). SDS-PAGE profiles of the culture broths showed that 33 out of 48 transformants were capable of expressing a new protein with an apparent molecular weight very close to the expected 118 kDa. Transformant 21 produced the best yield and was selected for further studies.

Example 16

Single Spore Isolation of *Aspergillus oryzae* JaL355 Transformant 21

*Aspergillus oryzae* JaL355 transformant 21 spores were spread onto a PDA plate and incubated for five days at 34° C. A small area of the confluent spore plate was washed with 0.5 ml of 0.01% TWEEN® 80 to resuspend the spores. A 100 μl aliquot of the spore suspension was diluted to a final volume of 5 ml with 0.01% TWEEN® 80. With the aid of a hemocytometer the spore concentration was determined and diluted to a final concentration of 0.1 spores per microliter. A 200 μl aliquot of the spore dilution was spread onto 150 mm Minimal medium plates and incubated for 2-3 days at 34° C. Emerging colonies were excised from the plates and transferred to PDA plates and incubated for 3 days at 34° C. Then the spores were spread across the plates and incubated again for 5 days at 34° C.

The confluent spore plates were washed with 3 ml of 0.01% TWEEN® 80 and the spore suspension was used to inoculate 25 ml of MDU2BP medium in 125 ml glass shake flasks. Single-spore cultures were incubated at 34° C. with constant shaking at 200 rpm. After 5 days, a 1 ml aliquot of each culture was centrifuged at 12,000×g and their supernatants collected. Five μl of each supernatant were mixed with an equal volume of 2× loading buffer (10% beta-mercaptoethanol) and loaded onto a 1.5 mm 8%-16% Tris-Glycine SDS-PAGE gel and stained with BIO-SAFE® Commassie Blue G250 protein stain. SDS-PAGE profiles of the culture broths showed that all eight transformants were capable of expressing the beta-glucosidase fusion protein at very high levels and one of the cultures designated *Aspergillus oryzae* JaL355AILo47 produced the best yield.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. A polynucleotide encoding a fusion protein comprising:
   (a) a first amino acid sequence comprising a signal peptide;
   (b) a second polynucleotide comprising a nucleotide sequence encoding at least a catalytic domain of a Cel45 endoglucanase or a portion thereof; and
   (c) a third amino acid sequence comprising at least a catalytic domain of a polypeptide having biological activity or a portion thereof; wherein said fusion protein comprises SEQ ID NO: 74 or SEQ ID NO: 76.

2. The polynucleotide of claim 1, wherein the fusion protein comprises a carbohydrate binding module.

3. The polynucleotide of claim 1, wherein the fusion protein comprises a linker located between the endoglucanase catalytic domain and the catalytic domain of the polypeptide having biological activity and/or the catalytic domain of a polypeptide having biological activity.

4. The polynucleotide of claim 1, wherein the fusion protein comprises a fourth amino acid sequence comprising a second signal peptide.

5. The polynucleotide of claim 4, wherein the second signal peptide is linked in frame to the N-terminus of the amino acid sequence comprising the catalytic domain of the polypeptide having biological activity or at least the catalytic domain of the endoglucanase.

6. The polynucleotide of claim 1, comprising SEQ ID NO: 73 or SEQ ID NO: 75.

7. The polynucleotide of claim 1, wherein the fusion protein has cellulolytic activity and/or hemicellulolytic activity.

8. A fusion protein construct, comprising the polynucleotide of claim 1 and a promoter.

9. The fusion protein construct of claim 8, wherein the promoter drives expression of the first, second, and third polynucleotides.

10. The fusion protein construct of claim 9, further comprising a terminator.

11. An expression vector, comprising the fusion protein construct of claim 10.

12. A host cell transformed with the polynucleotide of claim 1.

13. The host cell of claim 12, wherein the cell is a filamentous fungal host cell.

14. A host cell transformed with the expression vector of claim 11.

15. The host cell of claim 14, wherein the cell is a filamentous fungal host cell.

16. An isolated polynucleotide encoding a fusion protein, wherein said fusion protein comprises SEQ ID NO: 74 or SEQ ID NO: 76.

17. The isolated polynucleotide of claim 16, which further comprises a carbohydrate binding module.

18. The isolated polynucleotide of claim 16, comprising SEQ ID NO: 73 or SEQ ID NO: 75.

19. The isolated polynucleotide of claim 16, wherein the fusion protein has cellulolytic activity and/or hemicellulolytic activity.

* * * * *

SEQUENCE LISTING

<160> NUMBER OF SEQ ID NOS: 76

<210> SEQ ID NO 1
<211> LENGTH: 923
<212> TYPE: DNA
<213> ORGANISM: Humicola insolens

<400> SEQUENCE: 1

```
atgcgttcct cccccctcct ccgctccgcc gttgtggccg ccctgccggt gttggccctt      60
gccgctgatg gcaggtccac ccgctactgg gactgctgca agccttcgtg cggctgggcc     120
aagaaggctc ccgtgaacca gcctgtcttt tcctgcaacg ccaacttcca gcgtatcacg     180
gacttcgacg ccaagtccgg ctgcgagccg ggcggtgtcg cctactcgtg cgccgaccag     240
accccatggg ctgtgaacga cgacttcgcg ctcggttttg ctgccacctc tattgccggc     300
agcaatgagg cgggctggtg ctgcgcctgc tacgagctca ccttcacatc cggtcctgtt     360
gctggcaaga agatggtcgt ccagtccacc agcactggcg gtgatcttgg cagcaaccac     420
ttcgatctca acatccccgg cggcgcgtc ggcatcttcg acggatgcac tccccagttc     480
ggcggtctgc ccggccagcg ctacggcggc atctcgtccc gcaacgagtg cgatcggttc     540
```

```
cccgacgccc tcaagcccgg ctgctactgg cgcttcgact ggttcaagaa cgccgacaat    600
ccgagcttca gcttccgtca ggtccagtgc ccagccgagc tcgtcgctcg caccggatgc    660
cgccgcaacg acgacggcaa cttccctgcc gtccagatcc cctccagcag caccagctct    720
ccggtcaacc agcctaccag caccagcacc acgtccacct ccaccacctc gagcccgcca    780
gtccagccta cgactcccag cggctgcact gctgagaggt gggctcagtg cggcggcaat    840
ggctggagcg gctgcaccac ctgcgtcgct ggcagcactt gcacgaagat taatgactgg    900
taccatcagt gcctgtagaa ttc                                            923
```

```
<210> SEQ ID NO 2
<211> LENGTH: 305
<212> TYPE: PRT
<213> ORGANISM: Humicola insolens

<400> SEQUENCE: 2

Met Arg Ser Ser Pro Leu Leu Arg Ser Ala Val Ala Ala Leu Pro
1               5                   10                  15

Val Leu Ala Leu Ala Ala Asp Gly Arg Ser Thr Arg Tyr Trp Asp Cys
            20                  25                  30

Cys Lys Pro Ser Cys Gly Trp Ala Lys Lys Ala Pro Val Asn Gln Pro
        35                  40                  45

Val Phe Ser Cys Asn Ala Asn Phe Gln Arg Ile Thr Asp Phe Asp Ala
    50                  55                  60

Lys Ser Gly Cys Glu Pro Gly Gly Val Ala Tyr Ser Cys Ala Asp Gln
65              70                  75                  80

Thr Pro Trp Ala Val Asn Asp Asp Phe Ala Leu Gly Phe Ala Ala Thr
                85                  90                  95

Ser Ile Ala Gly Ser Asn Glu Ala Gly Trp Cys Cys Ala Cys Tyr Glu
            100                 105                 110

Leu Thr Phe Thr Ser Gly Pro Val Ala Gly Lys Lys Met Val Val Gln
        115                 120                 125

Ser Thr Ser Thr Gly Gly Asp Leu Gly Ser Asn His Phe Asp Leu Asn
    130                 135                 140

Ile Pro Gly Gly Gly Val Gly Ile Phe Asp Gly Cys Thr Pro Gln Phe
145             150                 155                 160

Gly Gly Leu Pro Gly Gln Arg Tyr Gly Gly Ile Ser Ser Arg Asn Glu
                165                 170                 175

Cys Asp Arg Phe Pro Asp Ala Leu Lys Pro Gly Cys Tyr Trp Arg Phe
            180                 185                 190

Asp Trp Phe Lys Asn Ala Asp Asn Pro Ser Phe Ser Phe Arg Gln Val
        195                 200                 205

Gln Cys Pro Ala Glu Leu Val Ala Arg Thr Gly Cys Arg Arg Asn Asp
    210                 215                 220

Asp Gly Asn Phe Pro Ala Val Gln Ile Pro Ser Ser Ser Thr Ser Ser
225             230                 235                 240

Pro Val Asn Gln Pro Thr Ser Thr Ser Thr Thr Ser Thr Ser Thr Thr
                245                 250                 255

Ser Ser Pro Pro Val Gln Pro Thr Thr Pro Ser Gly Cys Thr Ala Glu
            260                 265                 270

Arg Trp Ala Gln Cys Gly Gly Asn Gly Trp Ser Gly Cys Thr Thr Cys
        275                 280                 285

Val Ala Gly Ser Thr Cys Thr Lys Ile Asn Asp Trp Tyr His Gln Cys
    290                 295                 300
```

-continued

Leu
305

<210> SEQ ID NO 3
<211> LENGTH: 1188
<212> TYPE: DNA
<213> ORGANISM: Myceliophthora thermophila

<400> SEQUENCE: 3

| | | | | | |
|---|---|---|---|---|---|
| cgacttgaaa | cgccccaaat | gaagtcctcc | atcctcgcca | gcgtcttcgc | cacgggcgcc | 60 |
| gtggctcaaa | gtggtccgtg | gcagcaatgt | ggtggcatcg | gatggcaagg | atcgaccgac | 120 |
| tgtgtgtcgg | gctaccactg | cgtctaccag | aacgattggt | acagccagtg | cgtgcctggc | 180 |
| gcggcgtcga | caacgctgca | gacatcgacc | acgtccaggc | ccaccgccac | cagcaccgcc | 240 |
| cctccgtcgt | ccaccacctc | gcctagcaag | ggcaagctga | agtggctcgg | cagcaacgag | 300 |
| tcgggcgccg | agttcgggga | gggcaattac | cccggcctct | ggggcaagca | cttcatcttc | 360 |
| ccgtcgactt | cggcgattca | gacgctcatc | aatgatggat | acaacatctt | ccggatcgac | 420 |
| ttctcgatgg | agcgtctggt | gcccaaccag | ttgacgtcgt | ccttcgacca | gggttacctc | 480 |
| cgcaacctga | ccgaggtggt | caacttcgtg | acgaacgcgg | gcaagtacgc | cgtcctggac | 540 |
| ccgcacaact | acggccggta | ctacggcaac | atcatcacgg | acacgaacgc | gttccggacc | 600 |
| ttctggacca | acctggccaa | gcagttcgcc | tccaactcgc | tcgtcatctt | cgacaccaac | 660 |
| aacgagtaca | acacgatgga | ccagaccctg | gtgctcaacc | tcaaccaggc | cgccatcgac | 720 |
| ggcatccggg | ccgccggcgc | gacctcgcag | tacatcttcg | tcgagggcaa | cgcgtggagc | 780 |
| ggggcctgga | gctggaacac | gaccaacacc | aacatggccg | ccctgacgga | cccgcagaac | 840 |
| aagatcgtgt | acgagatgca | ccagtacctc | gactcggaca | gctcgggcac | ccacgccgag | 900 |
| tgcgtcagca | gcaccatcgg | cgcccagcgc | gtcgtcggag | ccacccagtg | gctccgcgcc | 960 |
| aacggcaagc | tcggcgtcct | cggcgagttc | gccggcggcg | ccaacgccgt | ctgccagcag | 1020 |
| gccgtcaccg | gcctcctcga | ccacctccag | gacaacagcg | acgtctggct | gggtgccctc | 1080 |
| tggtgggccg | ccggtccctg | gtggggcgac | tacatgtact | cgttcgagcc | tccttcgggc | 1140 |
| accggctatg | tcaactacaa | ctcgatcttg | aagaagtact | gccgtaa | | 1188 |

<210> SEQ ID NO 4
<211> LENGTH: 389
<212> TYPE: PRT
<213> ORGANISM: Myceliophthora thermophila

<400> SEQUENCE: 4

Met Lys Ser Ser Ile Leu Ala Ser Val Phe Ala Thr Gly Ala Val
1               5                   10                  15

Gln Ser Gly Pro Trp Gln Gln Cys Gly Gly Ile Gly Trp Gln Gly Ser
                20                  25                  30

Thr Asp Cys Val Ser Gly Tyr His Cys Val Tyr Gln Asn Asp Trp Tyr
            35                  40                  45

Ser Gln Cys Val Pro Gly Ala Ala Ser Thr Thr Leu Gln Thr Ser Thr
        50                  55                  60

Thr Ser Arg Pro Thr Ala Thr Ser Thr Ala Pro Pro Ser Ser Thr Thr
65                  70                  75                  80

Ser Pro Ser Lys Gly Lys Leu Lys Trp Leu Gly Ser Asn Glu Ser Gly
                85                  90                  95

Ala Glu Phe Gly Glu Gly Asn Tyr Pro Gly Leu Trp Gly Lys His Phe
            100                 105                 110

Ile Phe Pro Ser Thr Ser Ala Ile Gln Thr Leu Ile Asn Asp Gly Tyr
            115                 120                 125

Asn Ile Phe Arg Ile Asp Phe Ser Met Glu Arg Leu Val Pro Asn Gln
        130                 135                 140

Leu Thr Ser Ser Phe Asp Gln Gly Tyr Leu Arg Asn Leu Thr Glu Val
145                 150                 155                 160

Val Asn Phe Val Thr Asn Ala Gly Lys Tyr Ala Val Leu Asp Pro His
                165                 170                 175

Asn Tyr Gly Arg Tyr Gly Asn Ile Ile Thr Asp Thr Asn Ala Phe
            180                 185                 190

Arg Thr Phe Trp Thr Asn Leu Ala Lys Gln Phe Ala Ser Asn Ser Leu
        195                 200                 205

Val Ile Phe Asp Thr Asn Asn Glu Tyr Asn Thr Met Asp Gln Thr Leu
    210                 215                 220

Val Leu Asn Leu Asn Gln Ala Ala Ile Asp Gly Ile Arg Ala Ala Gly
225                 230                 235                 240

Ala Thr Ser Gln Tyr Ile Phe Val Glu Gly Asn Ala Trp Ser Gly Ala
                245                 250                 255

Trp Ser Trp Asn Thr Thr Asn Thr Asn Met Ala Ala Leu Thr Asp Pro
            260                 265                 270

Gln Asn Lys Ile Val Tyr Glu Met His Gln Tyr Leu Asp Ser Asp Ser
        275                 280                 285

Ser Gly Thr His Ala Glu Cys Val Ser Ser Thr Ile Gly Ala Gln Arg
    290                 295                 300

Val Val Gly Ala Thr Gln Trp Leu Arg Ala Asn Gly Lys Leu Gly Val
305                 310                 315                 320

Leu Gly Glu Phe Ala Gly Gly Ala Asn Ala Val Cys Gln Gln Ala Val
                325                 330                 335

Thr Gly Leu Leu Asp His Leu Gln Asp Asn Ser Asp Val Trp Leu Gly
            340                 345                 350

Ala Leu Trp Trp Ala Ala Gly Pro Trp Trp Gly Asp Tyr Met Tyr Ser
        355                 360                 365

Phe Glu Pro Pro Ser Gly Thr Gly Tyr Val Asn Tyr Asn Ser Ile Leu
    370                 375                 380

Lys Lys Tyr Leu Pro
385

<210> SEQ ID NO 5
<211> LENGTH: 1232
<212> TYPE: DNA
<213> ORGANISM: Myceliophthora thermophila

<400> SEQUENCE: 5
ggatccactt agtaacggcc gccagtgtgc tggaaagcat gaagtctctc ttcctgtcac     60
ttgtagcgac cgtcgcgctc agctcgccag tattctctgt cgcagtctgg ggcaatgcg    120 gcggcattgg cttcagcgga agcaccgtct gtgatgcagg cgccggctgt gtgaagctca   180
acgactatta ctctcaatgc caacccggcg ctcccactgc tacatccgcg gcgccaagta   240
gcaacgcacc gtccggcact tcgacggcct cggcccccctc ctccagcctt tgctctggca   300
gccgcacgcc gttccagttc ttcggtgtca cgaatccgg cgcggagttc ggcaacctga   360
acatccccgg tgttctgggc accgactaca cctggcgtc gccatccagc attgacttct    420
tcatgggcaa gggaatgaat accttccgta ttccgttcct catggagcgt cttgtccccc   480

-continued

```
ctgccactgg catcacagga cctctcgacc agacgtactt gggcggcctg cagacgattg    540
tcaactacat caccggcaaa ggcggctttg ctctcattga cccgcacaac tttatgatct    600
acaatggcca gacgatctcc agtaccagcg acttccagaa gttctggcag aacctcgcag    660
gagtgtttaa atcgaacagt cacgtcatct tcgatgttat gaacgagcct cacgatattc    720
ccgcccagac cgtgttccaa ctgaaccaag ccgctgtcaa tggcatccgt gcgagcggtg    780
cgacgtcgca gctcattctg gtcgagggca aagctggac tggagcctgg acctggacga    840
cctctggcaa cagcgatgca ttcggtgcca ttaaggatcc caacaacaac gtcgcgatcc    900
agatgcatca gtacctggat agcgatggct ctggcacttc gcagacctgc gtgtctccca    960
ccatcggtgc cgagcggttg caggctgcga ctcaatggtt gaagcagaac aacctcaagg   1020
gcttcctggg cgagatcggc gccggctcta actccgcttg catcagcgct gtgcagggtg   1080
cgttgtgttc gatgcagcaa tctggtgtgt ggctcggcgc tctctggtgg gctgcgggcc   1140
cgtggtgggg cgactactac cagtccatcg agccgccctc tggcccggcg gtgtccgcga   1200
tcctcccgca ggccctgctg ccgttcgcgt aa                                 1232
```

<210> SEQ ID NO 6
<211> LENGTH: 397
<212> TYPE: PRT
<213> ORGANISM: Myceliophthora thermophila

<400> SEQUENCE: 6

```
Met Lys Ser Leu Phe Leu Ser Leu Val Ala Thr Val Ala Leu Ser Ser
1               5                   10                  15

Pro Val Phe Ser Val Ala Val Trp Gly Gln Cys Gly Gly Ile Gly Phe
            20                  25                  30

Ser Gly Ser Thr Val Cys Asp Ala Gly Ala Gly Cys Val Lys Leu Asn
        35                  40                  45

Asp Tyr Tyr Ser Gln Cys Gln Pro Gly Ala Pro Thr Ala Thr Ser Ala
    50                  55                  60

Ala Pro Ser Ser Asn Ala Pro Ser Gly Thr Ser Thr Ala Ser Ala Pro
65                  70                  75                  80

Ser Ser Ser Leu Cys Ser Gly Ser Arg Thr Pro Phe Gln Phe Phe Gly
                85                  90                  95

Val Asn Glu Ser Gly Ala Glu Phe Gly Asn Leu Asn Ile Pro Gly Val
            100                 105                 110

Leu Gly Thr Asp Tyr Thr Trp Pro Ser Pro Ser Ser Ile Asp Phe Phe
        115                 120                 125

Met Gly Lys Gly Met Asn Thr Phe Arg Ile Pro Phe Leu Met Glu Arg
    130                 135                 140

Leu Val Pro Pro Ala Thr Gly Ile Thr Gly Pro Leu Asp Gln Thr Tyr
145                 150                 155                 160

Leu Gly Gly Leu Gln Thr Ile Val Asn Tyr Ile Thr Gly Lys Gly Gly
                165                 170                 175

Phe Ala Leu Ile Asp Pro His Asn Phe Met Ile Tyr Asn Gly Gln Thr
            180                 185                 190

Ile Ser Ser Thr Ser Asp Phe Gln Lys Phe Trp Gln Asn Leu Ala Gly
        195                 200                 205

Val Phe Lys Ser Asn Ser His Val Ile Phe Asp Val Met Asn Glu Pro
    210                 215                 220

His Asp Ile Pro Ala Gln Thr Val Phe Gln Leu Asn Gln Ala Ala Val
225                 230                 235                 240
```

```
Asn Gly Ile Arg Ala Ser Gly Ala Thr Ser Gln Leu Ile Leu Val Glu
                245                 250                 255
Gly Thr Ser Trp Thr Gly Ala Trp Thr Trp Thr Thr Ser Gly Asn Ser
            260                 265                 270
Asp Ala Phe Gly Ala Ile Lys Asp Pro Asn Asn Asn Val Ala Ile Gln
        275                 280                 285
Met His Gln Tyr Leu Asp Ser Asp Gly Ser Gly Thr Ser Gln Thr Cys
    290                 295                 300
Val Ser Pro Thr Ile Gly Ala Glu Arg Leu Gln Ala Ala Thr Gln Trp
305                 310                 315                 320
Leu Lys Gln Asn Asn Leu Lys Gly Phe Leu Gly Glu Ile Gly Ala Gly
                325                 330                 335
Ser Asn Ser Ala Cys Ile Ser Ala Val Gln Gly Ala Leu Cys Ser Met
            340                 345                 350
Gln Gln Ser Gly Val Trp Leu Gly Ala Leu Trp Trp Ala Ala Gly Pro
        355                 360                 365
Trp Trp Gly Asp Tyr Tyr Gln Ser Ile Glu Pro Pro Ser Gly Pro Ala
    370                 375                 380
Val Ser Ala Ile Leu Pro Gln Ala Leu Leu Pro Phe Ala
385                 390                 395

<210> SEQ ID NO 7
<211> LENGTH: 1303
<212> TYPE: DNA
<213> ORGANISM: BASIDIOMYCETE CBS 495.95

<400> SEQUENCE: 7
ggaaagcgtc agtatggtga aatttgcgct tgtggcaact gtcggcgcaa tcttgagcgc      60
ttctgcggcc aatgcggctt ctatctacca gcaatgtgga ggcattggat ggtctgggtc     120
cactgtttgc gacgccggtc tcgcttgcgt tatcctcaat gcgtactact ttcagtgctt     180
gacgcccgcc gcgggccaga caacgacggg ctcgggcgca ccggcgtcaa catcaacctc     240
tcactcaacg gtcactacgg ggagctcaca ctcaacaacc gggacgacgg cgacgaaaac     300
aactaccact ccgtcgacca ccacgaccct acccgccatc tctgtgtctg gtcgcgtctg     360
ctctggctcc aggacgaagt tcaagttctt cggtgtgaat gaaagcggcg ccgaattcgg     420
gaacactgct tggccagggc agctcgggaa agactataca tggccttcgc ctagcagcgt     480
ggactacttc atgggggctg gattcaatac attccgtatc accttcttga tggagcgtat     540
gagccctccg gctaccggac tcactggccc attcaaccag acgtacctgt cgggcctcac     600
caccattgtc gactacatca cgaacaaagg aggatacgct cttattgacc cccacaactt     660
catgcgttac aacaacggca taatcagcag cacatctgac ttcgcgactt ggtggagcaa     720
tttggccact gtattcaaat ccacgaagaa cgccatcttc gacatccaga acgagccgta     780
cggaatcgat gcgcagaccg tatacgaact gaatcaagct gccatcaatt cgatccgcgc     840
cgctggcgct acgtcacagt tgattctggt tgaaggaacg tcatacactg agcttggac      900 gtgggtctcg tccggaaacg gagctgcttt cgcggccgtt acggatcctt acaacaacac     960
ggcaattgaa atgcaccaat acctcgacag cgacggttct gggacaaacg aagactgtgt    1020
ctcctccacc attgggtcgc aacgtctcca agctgccact gcgtggctgc aacaaacagg    1080
actcaaggga ttcctcggag agacgggtgc tgggtcgaat tcccagtgca tcgacgccgt    1140
gttcgatgaa ctttgctata tgcaacagca aggcggctcc tggatcggtg cactctggtg    1200
ggctgcgggt ccctggtggg gcacgtacat ttactcgatt gaacctccga gcggtgccgc    1260
```
tatcccagaa gtccttcctc agggtctcgc tccattcctc tag    1303

<210> SEQ ID NO 8
<211> LENGTH: 429
<212> TYPE: PRT
<213> ORGANISM: BASIDIOMYCETE CBS 495.95

<400> SEQUENCE: 8

Met Val Lys Phe Ala Leu Val Ala Thr Val Gly Ala Ile Leu Ser Ala
1               5                   10                  15

Ser Ala Asn Ala Ala Ser Ile Tyr Gln Gln Cys Gly Gly Ile Gly
            20                  25                  30

Trp Ser Gly Ser Thr Val Cys Asp Ala Gly Leu Ala Cys Val Ile Leu
        35                  40                  45

Asn Ala Tyr Tyr Phe Gln Cys Leu Thr Pro Ala Ala Gly Gln Thr Thr
    50                  55                  60

Thr Gly Ser Gly Ala Pro Ala Ser Thr Ser Thr Ser His Ser Thr Val
65                  70                  75                  80

Thr Thr Gly Ser Ser His Ser Thr Thr Gly Thr Thr Ala Thr Lys Thr
                85                  90                  95

Thr Thr Thr Pro Ser Thr Thr Thr Leu Pro Ala Ile Ser Val Ser
                100                 105                 110

Gly Arg Val Cys Ser Gly Ser Arg Thr Lys Phe Lys Phe Phe Gly Val
            115                 120                 125

Asn Glu Ser Gly Ala Glu Phe Gly Asn Thr Ala Trp Pro Gly Gln Leu
    130                 135                 140

Gly Lys Asp Tyr Thr Trp Pro Ser Pro Ser Ser Val Asp Tyr Phe Met
145                 150                 155                 160

Gly Ala Gly Phe Asn Thr Phe Arg Ile Thr Phe Leu Met Glu Arg Met
                165                 170                 175

Ser Pro Pro Ala Thr Gly Leu Thr Gly Pro Phe Asn Gln Thr Tyr Leu
            180                 185                 190

Ser Gly Leu Thr Thr Ile Val Asp Tyr Ile Thr Asn Lys Gly Gly Tyr
        195                 200                 205

Ala Leu Ile Asp Pro His Asn Phe Met Arg Tyr Asn Asn Gly Ile Ile
    210                 215                 220

Ser Ser Thr Ser Asp Phe Ala Thr Trp Trp Ser Asn Leu Ala Thr Val
225                 230                 235                 240

Phe Lys Ser Thr Lys Asn Ala Ile Phe Asp Ile Gln Asn Glu Pro Tyr
                245                 250                 255

Gly Ile Asp Ala Gln Thr Val Tyr Glu Leu Asn Gln Ala Ala Ile Asn
            260                 265                 270

Ser Ile Arg Ala Ala Gly Ala Thr Ser Gln Leu Ile Leu Val Glu Gly
        275                 280                 285

Thr Ser Tyr Thr Gly Ala Trp Thr Trp Val Ser Ser Gly Asn Gly Ala
    290                 295                 300

Ala Phe Ala Ala Val Thr Asp Pro Tyr Asn Asn Thr Ala Ile Glu Met
305                 310                 315                 320

His Gln Tyr Leu Asp Ser Asp Gly Ser Gly Thr Asn Glu Asp Cys Val
                325                 330                 335

Ser Ser Thr Ile Gly Ser Gln Arg Leu Gln Ala Ala Thr Ala Trp Leu
            340                 345                 350

Gln Gln Thr Gly Leu Lys Gly Phe Leu Gly Glu Thr Gly Ala Gly Ser
        355                 360                 365

Asn Ser Gln Cys Ile Asp Ala Val Phe Asp Glu Leu Cys Tyr Met Gln
    370                 375                 380

Gln Gln Gly Gly Ser Trp Ile Gly Ala Leu Trp Trp Ala Ala Gly Pro
385                 390                 395                 400

Trp Trp Gly Thr Tyr Ile Tyr Ser Ile Glu Pro Pro Ser Gly Ala Ala
            405                 410                 415

Ile Pro Glu Val Leu Pro Gln Gly Leu Ala Pro Phe Leu
            420                 425

<210> SEQ ID NO 9
<211> LENGTH: 1580
<212> TYPE: DNA
<213> ORGANISM: Thielavia terrestris

<400> SEQUENCE: 9

```
agccccccgt tcaggcacac ttggcatcag atcagcttag cagcgcctgc acagcatgaa      60
gctctcgcag tcggccgcgc tggcggcact caccgcgacg gcgctcgccg ccccctcgcc     120
cacgacgccg caggcgccga ggcaggcttc agccggctgc tcgtctgcgg tcacgctcga     180
cgccagcacc aacgtttgga gaagtacacg ctgcacccc aacagctact accgcaagga     240
ggttgaggcc gcggtggcgc agatctcgga cccggacctc gccgccaagg ccaagaaggt     300
ggccgacgtc ggcaccttcc tgtggctcga ctcgatcgag aacatcggca agctggagcc     360
ggcgatccag gacgtgccct gcgagaacat cctgggcctg gtcatctacg acctgccggg     420
ccgcgactgc gcggccaagg cgtccaacgg cgagctcaag gtcggcgaga tcgaccgcta     480
caagaccgag tacatcgaca gtgagtgctg ccccccgggt tcgagaagag cgtgggggaa     540
agggaaaggg ttgactgact gacacggcgc actgcagaga tcgtgtcgat cctcaaggca     600
caccccaaca cggcgttcgc gctggtcatc gagccggact cgctgcccaa cctggtgacc     660
aacagcaact tggacacgtg ctcgagcagc gcgtcgggct accgcgaagg cgtggcttac     720
gccctcaaga acctcaacct gcccaacgtg atcatgtacc tcgacgccgg ccacggcggc     780
tggctcggct gggacgccaa cctgcagccc ggcgcgcagg agctagccaa ggcgtacaag     840
aacgccggct cgcccaagca gctccgcggc ttctcgacca cgtggccgg ctggaactcc     900
tggtgagctt ttttccattc catttcttct tcctcttctc tcttcgctcc cactctgcag     960
ccccccctcc cccaagcacc cactggcgtt ccggcttgct gactcggcct cccttttcccc    1020
gggcaccagg gatcaatcgc ccggcgaatt ctcccaggcg tccgacgcca agtacaacaa    1080
gtgccagaac gagaagatct acgtcagcac cttcggctcc gcgctccagt cggccggcat    1140
gcccaaccac gccatcgtcg acacgggccg caacggcgtc accggcctgc gcaaggagtg    1200
gggtgactgt gcaacgtca acggtgcagg ttcgttgtct tctttttctc ctcttttgtt    1260
tgcacgtcgt ggtcctttc aagcagccgt gtttggttgg gggagatgga ctccggctga    1320
tgttctgctt cctctctagg cttcggcgtg cgcccgacga gcaacacggg cctcgagctg    1380
gccgacgcgt tcgtgtgggt caagcccggc ggcgagtcgg acggcaccag cgacagctcg    1440
tcgccgcgct acgacagctt ctgcggcaag gacgacgcct tcaagccctc gcccgaggcc    1500
ggcacctgga acgaggccta cttcgagatg ctgctcaaga acgccgtgcc gtcgttctaa    1560
gacggtccag catcatccgg                                                1580
```

<210> SEQ ID NO 10
<211> LENGTH: 396
<212> TYPE: PRT

<213> ORGANISM: Thielavia terrestris

<400> SEQUENCE: 10

```
Met Lys Leu Ser Gln Ser Ala Ala Leu Ala Leu Thr Ala Thr Ala
1               5                   10                  15

Leu Ala Ala Pro Ser Pro Thr Thr Pro Gln Ala Pro Arg Gln Ala Ser
            20                  25                  30

Ala Gly Cys Ser Ser Ala Val Thr Leu Asp Ala Ser Thr Asn Val Trp
        35                  40                  45

Lys Lys Tyr Thr Leu His Pro Asn Ser Tyr Tyr Arg Lys Glu Val Glu
    50                  55                  60

Ala Ala Val Ala Gln Ile Ser Asp Pro Asp Leu Ala Ala Lys Ala Lys
65                  70                  75                  80

Lys Val Ala Asp Val Gly Thr Phe Leu Trp Leu Asp Ser Ile Glu Asn
                85                  90                  95

Ile Gly Lys Leu Glu Pro Ala Ile Gln Asp Val Pro Cys Glu Asn Ile
            100                 105                 110

Leu Gly Leu Val Ile Tyr Asp Leu Pro Gly Arg Asp Cys Ala Ala Lys
        115                 120                 125

Ala Ser Asn Gly Glu Leu Lys Val Gly Glu Ile Asp Arg Tyr Lys Thr
    130                 135                 140

Glu Tyr Ile Asp Lys Ile Val Ser Ile Leu Lys Ala His Pro Asn Thr
145                 150                 155                 160

Ala Phe Ala Leu Val Ile Glu Pro Asp Ser Leu Pro Asn Leu Val Thr
                165                 170                 175

Asn Ser Asn Leu Asp Thr Cys Ser Ser Ser Ala Ser Gly Tyr Arg Glu
            180                 185                 190

Gly Val Ala Tyr Ala Leu Lys Asn Leu Asn Leu Pro Asn Val Ile Met
        195                 200                 205

Tyr Leu Asp Ala Gly His Gly Gly Trp Leu Gly Trp Asp Ala Asn Leu
    210                 215                 220

Gln Pro Gly Ala Gln Glu Leu Ala Lys Ala Tyr Lys Asn Ala Gly Ser
225                 230                 235                 240

Pro Lys Gln Leu Arg Gly Phe Ser Thr Asn Val Ala Gly Trp Asn Ser
                245                 250                 255

Trp Asp Gln Ser Pro Gly Glu Phe Ser Gln Ala Ser Asp Ala Lys Tyr
            260                 265                 270

Asn Lys Cys Gln Asn Glu Lys Ile Tyr Val Ser Thr Phe Gly Ser Ala
        275                 280                 285

Leu Gln Ser Ala Gly Met Pro Asn His Ala Ile Val Asp Thr Gly Arg
    290                 295                 300

Asn Gly Val Thr Gly Leu Arg Lys Glu Trp Gly Asp Trp Cys Asn Val
305                 310                 315                 320

Asn Gly Ala Gly Phe Gly Val Arg Pro Thr Ser Asn Thr Gly Leu Glu
                325                 330                 335

Leu Ala Asp Ala Phe Val Trp Val Lys Pro Gly Gly Glu Ser Asp Gly
            340                 345                 350

Thr Ser Asp Ser Ser Ser Pro Arg Tyr Asp Ser Phe Cys Gly Lys Asp
        355                 360                 365

Asp Ala Phe Lys Pro Ser Pro Glu Ala Gly Thr Trp Asn Glu Ala Tyr
    370                 375                 380

Phe Glu Met Leu Leu Lys Asn Ala Val Pro Ser Phe
385                 390                 395
```

<210> SEQ ID NO 11
<211> LENGTH: 1203
<212> TYPE: DNA
<213> ORGANISM: Thielavia terrestris

<400> SEQUENCE: 11

| | | | |
|---|---|---|---|
| atgaagtacc tcaacctcct cgcagctctc ctcgccgtcg ctcctctctc cctcgctgca | 60 |
| cccagcatcg aggccagaca gtcgaacgtc aacccataca tcggcaagag cccgctcgtt | 120 |
| attaggtcgt acgcccaaaa gcttgaggag accgtcagga ccttccagca acgtggcgac | 180 |
| cagctcaacg ctgcgaggac acggacggtg cagaacgttg cgactttcgc ctggatctcg | 240 |
| gataccaatg gtattggagc cattcgacct ctcatccaag atgctctcgc ccagcaggct | 300 |
| cgcactggac agaaggtcat cgtccaaatc gtcgtctaca acctcccaga tcgcgactgc | 360 |
| tctgccaacg cctcgactgg agagttcacc gtaggaaacg acggtctcaa ccgatacaag | 420 |
| aactttgtca caccatcgc ccgcgagctc tcgactgctg acgctgacaa gctccacttt | 480 |
| gccctcctcc tcgaacccga cgcacttgcc aacctcgtca ccaacgcgaa tgccccagg | 540 |
| tgccgaatcg ccgctcccgc ttacaaggag ggtatcgcct acaccctcgc caccttgtcc | 600 |
| aagcccaacg tcgacgtcta catcgacgcc gccaacggtg gctggctcgg ctggaacgac | 660 |
| aacctccgcc ccttcgccga actcttcaag gaagtctacg acctcgcccg ccgcatcaac | 720 |
| cccaacgcca aggtccgcgg cgtccccgtc aacgtctcca actacaacca gtaccgcgct | 780 |
| gaagtccgcg agcccttcac cgagtggaag gacgcctggg acgagagccg ctacgtcaac | 840 |
| gtcctcaccc cgcacctcaa cgccgtcggc ttctccgcgc acttcatcgt tgaccaggga | 900 |
| cgcggtggca agggcggtat caggacggag tggggccagt ggtgcaacgt taggaacgct | 960 |
| gggttcggta tcaggcctac tgcggatcag ggcgtgctcc agaacccgaa tgtggatgcg | 1020 |
| attgtgtggg ttaagccggg tggagagtcg gatggcacga gtgatttgaa ctcgaacagg | 1080 |
| tatgatccta cgtgcaggag tccggtggcg catgttcccg ctcctgaggc tggccagtgg | 1140 |
| ttcaacgagt atgttgttaa cctcgttttg aacgctaacc cccctcttga gcctacctgg | 1200 |
| taa | 1203 |

<210> SEQ ID NO 12
<211> LENGTH: 400
<212> TYPE: PRT
<213> ORGANISM: Thielavia terrestris

<400> SEQUENCE: 12

Met Lys Tyr Leu Asn Leu Leu Ala Ala Leu Ala Val Ala Pro Leu
1               5                   10                  15

Ser Leu Ala Ala Pro Ser Ile Glu Ala Arg Gln Ser Asn Val Asn Pro
            20                  25                  30

Tyr Ile Gly Lys Ser Pro Leu Val Ile Arg Ser Tyr Ala Gln Lys Leu
        35                  40                  45

Glu Glu Thr Val Arg Thr Phe Gln Gln Arg Gly Asp Gln Leu Asn Ala
    50                  55                  60

Ala Arg Thr Arg Thr Val Gln Asn Val Ala Thr Phe Ala Trp Ile Ser
65                  70                  75                  80

Asp Thr Asn Gly Ile Gly Ala Ile Arg Pro Leu Ile Gln Asp Ala Leu
                85                  90                  95

Ala Gln Gln Ala Arg Thr Gly Gln Lys Val Ile Val Gln Ile Val Val
            100                 105                 110

```
Tyr Asn Leu Pro Asp Arg Asp Cys Ser Ala Asn Ala Ser Thr Gly Glu
        115                 120                 125

Phe Thr Val Gly Asn Asp Gly Leu Asn Arg Tyr Lys Asn Phe Val Asn
    130                 135                 140

Thr Ile Ala Arg Glu Leu Ser Thr Ala Asp Ala Asp Lys Leu His Phe
145                 150                 155                 160

Ala Leu Leu Leu Glu Pro Asp Ala Leu Ala Asn Leu Val Thr Asn Ala
                165                 170                 175

Asn Ala Pro Arg Cys Arg Ile Ala Ala Pro Ala Tyr Lys Glu Gly Ile
            180                 185                 190

Ala Tyr Thr Leu Ala Thr Leu Ser Lys Pro Asn Val Asp Val Tyr Ile
        195                 200                 205

Asp Ala Ala Asn Gly Gly Trp Leu Gly Trp Asn Asp Asn Leu Arg Pro
    210                 215                 220

Phe Ala Glu Leu Phe Lys Glu Val Tyr Asp Leu Ala Arg Arg Ile Asn
225                 230                 235                 240

Pro Asn Ala Lys Val Arg Gly Val Pro Val Asn Val Ser Asn Tyr Asn
                245                 250                 255

Gln Tyr Arg Ala Glu Val Arg Glu Pro Phe Thr Glu Trp Lys Asp Ala
            260                 265                 270

Trp Asp Glu Ser Arg Tyr Val Asn Val Leu Thr Pro His Leu Asn Ala
        275                 280                 285

Val Gly Phe Ser Ala His Phe Ile Val Asp Gln Gly Arg Gly Gly Lys
    290                 295                 300

Gly Gly Ile Arg Thr Glu Trp Gly Gln Trp Cys Asn Val Arg Asn Ala
305                 310                 315                 320

Gly Phe Gly Ile Arg Pro Thr Ala Asp Gln Gly Val Leu Gln Asn Pro
                325                 330                 335

Asn Val Asp Ala Ile Val Trp Val Lys Pro Gly Gly Glu Ser Asp Gly
            340                 345                 350

Thr Ser Asp Leu Asn Ser Asn Arg Tyr Asp Pro Thr Cys Arg Ser Pro
        355                 360                 365

Val Ala His Val Pro Ala Pro Glu Ala Gly Gln Trp Phe Asn Glu Tyr
    370                 375                 380

Val Val Asn Leu Val Leu Asn Ala Asn Pro Pro Leu Glu Pro Thr Trp
385                 390                 395                 400

<210> SEQ ID NO 13
<211> LENGTH: 1501
<212> TYPE: DNA
<213> ORGANISM: Thielavia terrestris

<400> SEQUENCE: 13
gccgttgtca agatgggcca agagacgctg cacggattcg ccgccacggc tttggccgtt      60 ctccccttg tgaaggctca gcagcccggc aacttcacgc cggaggtgca cccgcaactg     120
ccaacgtgga agtgcacgac cgccggcggc tgcgttcagc aggacacttc ggtggtgctc     180
gactggaact accgttggat ccacaatgcc gacggcaccg cctcgtgcac gacgtccagc     240
ggggtcgacc acacgctgtg tccagatgag gcgacctgcg cgaagaactg cttcgtggaa     300
ggcgtcaact acacgagcag cggtgtcacc acatccggca gttcgctgac gatgaggcag     360
tatttcaagg ggagcaacgg gcagaccaac agcgtttcgc ctcgtctcta cctgctcggc     420
tcggatggaa actacgtaat gctcaagctg ctcggccagg agctgagctt cgatgtcgat     480
ctctccacgc tccctgcgg cgagaacggc gcgctgtacc tgtccgagat ggacgcgacc     540
```

```
ggtggcagga accagtacaa caccggcggt gccaactacg gctcgggcta ctgtgacgcc      600
cagtgtcccg tgcagacgtg gatgaacggc acgctgaaca ccaacgggca gggctactgc      660
tgcaacgaga tggacatcct cgaggccaac tcccgcgcca acgcgatgac acctcacccc      720
tgcgccaacg gcagctgcga caagagcggg tgcggactca cccctacgc cgagggctac       780 aagagctact acggaccggg cctcacggtt gacacgtcga agcccttcac catcattacc      840
cgcttcatca ccgacgacgg cacgaccagc ggcaccctca accagatcca gcggatctat      900
gtgcagaatg caagacggt cgcgtcggct gcgtccggag gcgacatcat cacggcatcc       960
ggctgcacct cggcccaggc gttcggcggg ctggccaaca tgggcgcggc gcttggacgg      1020
ggcatggtgc tgaccttcag catctggaac gacgctgggg gctacatgaa ctggctcgac      1080
agcggcaaca acgcccgtg cagcagcacc gagggcaacc cgtccaacat cctgccaac       1140 tacccggaca cccacgtggt cttctccaac atccgctggg gagacatcgg ctcgacggtc      1200
caggtctcgg gaggcggcaa cggcggctcg accaccacca cgtcgaccac cacgctgagg     1260
acctcgacca cgaccaccac caccgccccg acggccactg ccacgcactg gggacaatgc     1320
ggcggaatcg gggtacgtca accgcctcct gcattctgtt gaggaagtta actaacgtgg     1380
cctacgcagt ggactggacc gaccgtctgc gaatcgccgt acgcatgcaa ggagctgaac      1440
ccctggtact accagtgcct ctaaagtatt gcagtgaagc catactccgt gctcggcatg     1500
g                                                                      1501
```

<210> SEQ ID NO 14
<211> LENGTH: 464
<212> TYPE: PRT
<213> ORGANISM: Thielavia terrestris

<400> SEQUENCE: 14

```
Met Gly Gln Lys Thr Leu His Gly Phe Ala Ala Thr Ala Leu Ala Val
1               5                   10                  15

Leu Pro Phe Val Lys Ala Gln Gln Pro Gly Asn Phe Thr Pro Glu Val
                20                  25                  30

His Pro Gln Leu Pro Thr Trp Lys Cys Thr Thr Ala Gly Gly Cys Val
            35                  40                  45

Gln Gln Asp Thr Ser Val Val Leu Asp Trp Asn Tyr Arg Trp Ile His
        50                  55                  60

Asn Ala Asp Gly Thr Ala Ser Cys Thr Thr Ser Gly Val Asp His
65                  70                  75                  80

Thr Leu Cys Pro Asp Glu Ala Thr Cys Ala Lys Asn Cys Phe Val Glu
                85                  90                  95

Gly Val Asn Tyr Thr Ser Ser Gly Val Thr Thr Ser Gly Ser Ser Leu
            100                 105                 110

Thr Met Arg Gln Tyr Phe Lys Gly Ser Asn Gly Gln Thr Asn Ser Val
        115                 120                 125

Ser Pro Arg Leu Tyr Leu Leu Gly Ser Asp Gly Asn Tyr Val Met Leu
    130                 135                 140

Lys Leu Leu Gly Gln Glu Leu Ser Phe Asp Val Asp Leu Ser Thr Leu
145                 150                 155                 160

Pro Cys Gly Glu Asn Gly Ala Leu Tyr Leu Ser Glu Met Asp Ala Thr
                165                 170                 175

Gly Gly Arg Asn Gln Tyr Asn Thr Gly Gly Ala Asn Tyr Gly Ser Gly
            180                 185                 190
```

Tyr Cys Asp Ala Gln Cys Pro Val Gln Thr Trp Met Asn Gly Thr Leu
            195                 200                 205

Asn Thr Asn Gly Gln Gly Tyr Cys Cys Asn Glu Met Asp Ile Leu Glu
        210                 215                 220

Ala Asn Ser Arg Ala Asn Ala Met Thr Pro His Pro Cys Ala Asn Gly
225                 230                 235                 240

Ser Cys Asp Lys Ser Gly Cys Gly Leu Asn Pro Tyr Ala Glu Gly Tyr
                245                 250                 255

Lys Ser Tyr Tyr Gly Pro Gly Leu Thr Val Asp Thr Ser Lys Pro Phe
            260                 265                 270

Thr Ile Ile Thr Arg Phe Ile Thr Asp Asp Gly Thr Thr Ser Gly Thr
        275                 280                 285

Leu Asn Gln Ile Gln Arg Ile Tyr Val Gln Asn Gly Lys Thr Val Ala
        290                 295                 300

Ser Ala Ala Ser Gly Gly Asp Ile Ile Thr Ala Ser Gly Cys Thr Ser
305                 310                 315                 320

Ala Gln Ala Phe Gly Gly Leu Ala Asn Met Gly Ala Ala Leu Gly Arg
                325                 330                 335

Gly Met Val Leu Thr Phe Ser Ile Trp Asn Asp Ala Gly Gly Tyr Met
            340                 345                 350

Asn Trp Leu Asp Ser Gly Asn Asn Gly Pro Cys Ser Ser Thr Glu Gly
        355                 360                 365

Asn Pro Ser Asn Ile Leu Ala Asn Tyr Pro Asp Thr His Val Val Phe
        370                 375                 380

Ser Asn Ile Arg Trp Gly Asp Ile Gly Ser Thr Val Gln Val Ser Gly
385                 390                 395                 400

Gly Gly Asn Gly Gly Ser Thr Thr Thr Thr Ser Thr Thr Thr Leu Arg
                405                 410                 415

Thr Ser Thr Thr Thr Thr Thr Thr Ala Pro Thr Ala Thr Ala Thr His
            420                 425                 430

Trp Gly Gln Cys Gly Gly Ile Gly Trp Thr Gly Pro Thr Val Cys Glu
        435                 440                 445

Ser Pro Tyr Ala Cys Lys Glu Leu Asn Pro Trp Tyr Tyr Gln Cys Leu
450                 455                 460

<210> SEQ ID NO 15
<211> LENGTH: 1368
<212> TYPE: DNA
<213> ORGANISM: Thielavia terrestris

<400> SEQUENCE: 15
accgatccgc tcgaagatgg cgcccaagtc tacagttctg gccgcctggc tgctctcctc    60
gctggccgcg gccagcagga tcggcaaagc cgtgcccgag gtccacccca aactgacaac   120
gcagaagtgc actctccgcg gcgggtgcaa gcctgtccgc acctcggtcg tgctcgactc   180
gtccgcgcgc tcgctgcaca aggtcgggga ccccaacacc agctgcagcg tcggcggcga   240
cctgtgctcg gacgcgaagt cgtgcggcaa gaactgcgcg ctcgagggcg tcgactacgc   300
ggcccacggc gtggcgacca agggcgacgc cctcacgctg caccagtggc tcaagggggc   360
cgacggcacc tacaggaccg tctcgccgcg cgtatacctc ctgggcgagg acgggaagaa   420
ctacgaggac ttcaagctgc tcaacgccga gctcagcttc gacgtcgacg tgtcccagct   480
cgtctgcggc atgaacggcg ccctgtactt ctccgagatg gagatggacg gcggccgcag   540
cccgctgaac ccggcggggcg ccacgtacgg cacgggctac tgcgacgcgc agtgccccaa   600

```
gttggacttt atcaacggcg aggtatttct tctctcttct gtttttcttt tccatcgctt    660
tttctgaccg gaatccgccc tcttagctca acaccaacca cacgtacggg gcgtgctgca    720
acgagatgga catctgggag ccaacgcgc tggcgcaggc gctcacgccg cacccgtgca    780
acgcgacgcg ggtgtacaag tgcgacacgg cggacgagtg cgggcagccg gtgggcgtgt    840
gcgacgaatg ggggtgctcg tacaacccgt ccaacttcgg ggtcaaggac tactacgggc    900
gcaacctgac ggtggacacg aaccgcaagt tcacggtgac gacgcagttc gtgacgtcca    960
acgggcgggc ggacggcgag ctgaccgaga tccggcggct gtacgtgcag gacggcgtgg   1020
tgatccagaa ccacgcggtc acggcgggcg gggcgacgta cgacagcatc acggacggct   1080
tctgcaacgc gacggccacc tggacgcagc agcggggcgg gctcgcgcgc atgggcgagg   1140
ccatcggccg cggcatggtg ctcatcttca gcctgtgggt tgacaacggc ggcttcatga   1200
actggctcga cagcggcaac gccgggccct gcaacgccac cgagggcgac ccggccctga   1260
tcctgcagca gcaccggac gccagcgtca ccttctccaa catccgatgg ggcgagatcg   1320
gcagcacgta caagagcgag tgcagccact agagtagagc ttgtaatt              1368
```

<210> SEQ ID NO 16
<211> LENGTH: 423
<212> TYPE: PRT
<213> ORGANISM: Thielavia terrestris

<400> SEQUENCE: 16

```
Met Ala Pro Lys Ser Thr Val Leu Ala Ala Trp Leu Leu Ser Ser Leu
1               5                   10                  15

Ala Ala Ala Gln Gln Ile Gly Lys Ala Val Pro Glu Val His Pro Lys
            20                  25                  30

Leu Thr Thr Gln Lys Cys Thr Leu Arg Gly Gly Cys Lys Pro Val Arg
        35                  40                  45

Thr Ser Val Val Leu Asp Ser Ser Ala Arg Ser Leu His Lys Val Gly
    50                  55                  60

Asp Pro Asn Thr Ser Cys Ser Val Gly Gly Asp Leu Cys Ser Asp Ala
65                  70                  75                  80

Lys Ser Cys Gly Lys Asn Cys Ala Leu Glu Gly Val Asp Tyr Ala Ala
                85                  90                  95

His Gly Val Ala Thr Lys Gly Asp Ala Leu Thr Leu His Gln Trp Leu
            100                 105                 110

Lys Gly Ala Asp Gly Thr Tyr Arg Thr Val Ser Pro Arg Val Tyr Leu
        115                 120                 125

Leu Gly Glu Asp Gly Lys Asn Tyr Glu Asp Phe Lys Leu Leu Asn Ala
    130                 135                 140

Glu Leu Ser Phe Asp Val Asp Val Ser Gln Leu Val Cys Gly Met Asn
145                 150                 155                 160

Gly Ala Leu Tyr Phe Ser Glu Met Glu Met Asp Gly Gly Arg Ser Pro
                165                 170                 175

Leu Asn Pro Ala Gly Ala Thr Tyr Gly Thr Gly Tyr Cys Asp Ala Gln
            180                 185                 190

Cys Pro Lys Leu Asp Phe Ile Asn Gly Glu Leu Asn Thr Asn His Thr
        195                 200                 205

Tyr Gly Ala Cys Cys Asn Glu Met Asp Ile Trp Glu Ala Asn Ala Leu
    210                 215                 220

Ala Gln Ala Leu Thr Pro His Pro Cys Asn Ala Thr Arg Val Tyr Lys
225                 230                 235                 240
```

```
Cys Asp Thr Ala Asp Glu Cys Gly Gln Pro Val Gly Val Cys Asp Glu
                245                 250                 255

Trp Gly Cys Ser Tyr Asn Pro Ser Asn Phe Gly Val Lys Asp Tyr Tyr
            260                 265                 270

Gly Arg Asn Leu Thr Val Asp Thr Asn Arg Lys Phe Thr Val Thr Thr
        275                 280                 285

Gln Phe Val Thr Ser Asn Gly Arg Ala Asp Gly Glu Leu Thr Glu Ile
    290                 295                 300

Arg Arg Leu Tyr Val Gln Asp Gly Val Val Ile Gln Asn His Ala Val
305                 310                 315                 320

Thr Ala Gly Gly Ala Thr Tyr Asp Ser Ile Thr Asp Gly Phe Cys Asn
                325                 330                 335

Ala Thr Ala Thr Trp Thr Gln Gln Arg Gly Gly Leu Ala Arg Met Gly
            340                 345                 350

Glu Ala Ile Gly Arg Gly Met Val Leu Ile Phe Ser Leu Trp Val Asp
        355                 360                 365

Asn Gly Gly Phe Met Asn Trp Leu Asp Ser Gly Asn Ala Gly Pro Cys
    370                 375                 380

Asn Ala Thr Glu Gly Asp Pro Ala Leu Ile Leu Gln Gln His Pro Asp
385                 390                 395                 400

Ala Ser Val Thr Phe Ser Asn Ile Arg Trp Gly Glu Ile Gly Ser Thr
                405                 410                 415

Tyr Lys Ser Glu Cys Ser His
            420

<210> SEQ ID NO 17
<211> LENGTH: 1011
<212> TYPE: DNA
<213> ORGANISM: Thielavia terrestris

<400> SEQUENCE: 17
atgaccctac ggctccctgt catcagcctg ctggcctcgc tggcagcagg cgccgtcgtc      60
gtcccacggg cggagtttca ccccctctc ccgacttgga aatgcacgac ctccggggcc     120
tgcgtgcagc agaacaccag cgtcgtcctg accgtgact cgaagtacgc cgcacacagc     180
gccggctcgc ggacggaatc ggattacgcg gcaatgggag tgtccacttc gggcaatgcc     240
gtgacgctgt accactacgt caagaccaac ggcaccctcg tccccgcttc gccgcgcatc     300
tacctcctgg gcgcggacgg caagtacgtg cttatggacc tcctcaacca ggagctgtcg     360
gtggacgtcg acttctcggc gctgccgtgc ggcgagaacg gggccttcta cctgtccgag     420
atggcggcgg acgggcgggg cgacgcgggg gcgggcgacg ggtactgcga cgcgcagtgc     480
cagggctact gctgcaacga gatggacatc ctcgaggcca actcgatggc gacggccatg     540
acgccgcacc cgtgcaaggg caacaactgc gaccgcagcg gctgcggcta caacccgtac     600
gccagcggcc agcgcggctt ctacgggccc ggcaagacgg tcgacacgag caagcccttc     660
accgtcgtca cgcagttcgc cgccagcggc ggcaagctga cccagatcac cgcaagtac      720 atccagaacg gccgggagat cggcggcggc ggcaccatct ccagctgcgg ctccgagtct     780
tcgacgggcg gcctgaccgg catgggcgag gcgctgggc gcggaatggt gctggccatg     840
agcatctgga cgacgcggc ccaggagatg gcatggctcg atgccggcaa caacggccct     900
tgcgccagtg gccagggcag cccgtccgtc attcagtcgc agcatcccga cacccacgtc     960
gtcttctcca acatcaggtg gggcgacatc gggtctacca cgaagaacta g            1011
```

<210> SEQ ID NO 18
<211> LENGTH: 336
<212> TYPE: PRT
<213> ORGANISM: Thielavia terrestris

<400> SEQUENCE: 18

```
Met Thr Leu Arg Leu Pro Val Ile Ser Leu Leu Ala Ser Leu Ala Ala
1               5                   10                  15

Gly Ala Val Val Pro Arg Ala Glu Phe His Pro Pro Leu Pro Thr
            20                  25                  30

Trp Lys Cys Thr Thr Ser Gly Gly Cys Val Gln Gln Asn Thr Ser Val
                35                  40                  45

Val Leu Asp Arg Asp Ser Lys Tyr Ala Ala His Ser Ala Gly Ser Arg
50                  55                  60

Thr Glu Ser Asp Tyr Ala Ala Met Gly Val Ser Thr Ser Gly Asn Ala
65                  70                  75                  80

Val Thr Leu Tyr His Tyr Val Lys Thr Asn Gly Thr Leu Val Pro Ala
                85                  90                  95

Ser Pro Arg Ile Tyr Leu Leu Gly Ala Asp Gly Lys Tyr Val Leu Met
                100                 105                 110

Asp Leu Leu Asn Gln Glu Leu Ser Val Asp Val Asp Phe Ser Ala Leu
            115                 120                 125

Pro Cys Gly Glu Asn Gly Ala Phe Tyr Leu Ser Glu Met Ala Ala Asp
130                 135                 140

Gly Arg Gly Asp Ala Gly Ala Gly Asp Gly Tyr Cys Asp Ala Gln Cys
145                 150                 155                 160

Gln Gly Tyr Cys Cys Asn Glu Met Asp Ile Leu Glu Ala Asn Ser Met
                165                 170                 175

Ala Thr Ala Met Thr Pro His Pro Cys Lys Gly Asn Asn Cys Asp Arg
            180                 185                 190

Ser Gly Cys Gly Tyr Asn Pro Tyr Ala Ser Gly Gln Arg Gly Phe Tyr
            195                 200                 205

Gly Pro Gly Lys Thr Val Asp Thr Ser Lys Pro Phe Thr Val Val Thr
210                 215                 220

Gln Phe Ala Ala Ser Gly Gly Lys Leu Thr Gln Ile Thr Arg Lys Tyr
225                 230                 235                 240

Ile Gln Asn Gly Arg Glu Ile Gly Gly Gly Thr Ile Ser Ser Cys
                245                 250                 255

Gly Ser Glu Ser Ser Thr Gly Gly Leu Thr Gly Met Gly Glu Ala Leu
            260                 265                 270

Gly Arg Gly Met Val Leu Ala Met Ser Ile Trp Asn Asp Ala Ala Gln
            275                 280                 285

Glu Met Ala Trp Leu Asp Ala Gly Asn Asn Gly Pro Cys Ala Ser Gly
290                 295                 300

Gln Gly Ser Pro Ser Val Ile Gln Ser Gln His Pro Asp Thr His Val
305                 310                 315                 320

Val Phe Ser Asn Ile Arg Trp Gly Asp Ile Gly Ser Thr Thr Lys Asn
                325                 330                 335
```

<210> SEQ ID NO 19
<211> LENGTH: 1480
<212> TYPE: DNA
<213> ORGANISM: Cladorrhinum foecundissimum

<400> SEQUENCE: 19
gatccgaatt cctcctctcg ttctttagtc acagaccaga catctgccca cgatggttca    60

```
caagttcgcc ctcctcaccg gcctcgccgc ctccctcgca tctgcccagc agatcggcac    120
cgtcgtcccc gagtctcacc ccaagcttcc caccaagcgc tgcactctcg ccggtggctg    180
ccagaccgtc gacacctcca tcgtcatcga cgccttccag cgtccccctcc acaagatcgg    240 cgacccttcc actccttgcg tcgtcggcgg ccctctctgc cccgacgcca agtcctgcgc    300
tgagaactgc gcgctcgagg gtgtcgacta tgcctcctgg ggcatcaaga ccgagggcga    360
cgccctaact ctcaaccagt ggatgcccga cccggcgaac cctggccagt acaagacgac    420
tactccccgt acttaccttg ttgctgagga cggcaagaac tacgaggatg tgaagctcct    480
ggctaaggag atctcgtttg atgccgatgt cagcaaccct ccctgcggca tgaacggtgc    540
tttctacttg tctgagatgt tgatggatgg tggacgtggc gaccctcaac ctgctggtgc    600
cgagtatggt accggttact gtgatgcgca gtgcttcaag ttggatttca tcaacgcgca    660
ggccaacatc gaccaaaagc acggcgcctg ctgcaacgaa atggacattt tcgaatccaa    720
ctcgcgcgcc aagaccttcg tcccccaccc ctgcaacatc acgcaggtct acaagtgcga    780
aggcgaagac gagtgcggcc agcccgtcgg cgtgtgcgac aagtgggggt gcggcttcaa    840
cgagtacaaa tggggcgtcg agtccttcta cggccgggc tcgcagttcg ccatcgactc    900
ctccaagaag ttcaccgtca ccacgcagtt cctgaccgac aacggcaagg aggacggcgt    960
cctcgtcgag atccgccgct gtgtggcacca ggatggcaag ctgatcaaga acaccgctat   1020
ccaggttgag gagaactaca gcacggactc ggtgagcacc gagttctgcg agaagactgc   1080
ttctttcacc atgcagcgcg gtggtctcaa ggcgatgggc gaggctatcg gtcgtggtat   1140
ggtgctggtt ttcagcatct gggcggatga ttcgggtttt atgaactggt tggatgcgga   1200
gggtaatggc ccttgcagcg cgactgaggg cgatccgaag gagattgtca agaataagcc   1260
ggatgctagg gttacgttct caaacattag gattggtgag gttggtagca cgtatgctcc   1320
gggtgggaag tgcggtgtta agagcagggt tgctagggg cttactgctt cttaagggg    1380 gtgtgaagag aggaggaggt gttgttgggg gttggagatg ataattgggc gagatggtgt   1440
agagcgggtt ggttggatat gaatacgttg aattggatgt                         1480
```

<210> SEQ ID NO 20
<211> LENGTH: 440
<212> TYPE: PRT
<213> ORGANISM: Cladorrhinum foecundissimum

<400> SEQUENCE: 20

```
Met Val His Lys Phe Ala Leu Leu Thr Gly Leu Ala Ala Ser Leu Ala
1               5                   10                  15

Ser Ala Gln Gln Ile Gly Thr Val Val Pro Glu Ser His Pro Lys Leu
            20                  25                  30

Pro Thr Lys Arg Cys Thr Leu Ala Gly Gly Cys Gln Thr Val Asp Thr
        35                  40                  45

Ser Ile Val Ile Asp Ala Phe Gln Arg Pro Leu His Lys Ile Gly Asp
    50                  55                  60

Pro Ser Thr Pro Cys Val Val Gly Gly Pro Leu Cys Pro Asp Ala Lys
65                  70                  75                  80

Ser Cys Ala Glu Asn Cys Ala Leu Glu Gly Val Asp Tyr Ala Ser Trp
                85                  90                  95

Gly Ile Lys Thr Glu Gly Asp Ala Leu Thr Leu Asn Gln Trp Met Pro
            100                 105                 110

Asp Pro Ala Asn Pro Gly Gln Tyr Lys Thr Thr Thr Pro Arg Thr Tyr
```

```
                    115                 120                 125
Leu Val Ala Glu Asp Gly Lys Asn Tyr Glu Asp Val Lys Leu Leu Ala
            130                 135                 140
Lys Glu Ile Ser Phe Asp Ala Asp Val Ser Asn Leu Pro Cys Gly Met
145                 150                 155                 160
Asn Gly Ala Phe Tyr Leu Ser Glu Met Leu Met Asp Gly Gly Arg Gly
                165                 170                 175
Asp Leu Asn Pro Ala Gly Ala Glu Tyr Gly Thr Gly Tyr Cys Asp Ala
            180                 185                 190
Gln Cys Phe Lys Leu Asp Phe Ile Asn Gly Glu Ala Asn Ile Asp Gln
        195                 200                 205
Lys His Gly Ala Cys Cys Asn Glu Met Asp Ile Phe Glu Ser Asn Ser
    210                 215                 220
Arg Ala Lys Thr Phe Val Pro His Pro Cys Asn Ile Thr Gln Val Tyr
225                 230                 235                 240
Lys Cys Glu Gly Glu Asp Glu Cys Gly Gln Pro Val Gly Val Cys Asp
                245                 250                 255
Lys Trp Gly Cys Gly Phe Asn Glu Tyr Lys Trp Gly Val Glu Ser Phe
            260                 265                 270
Tyr Gly Arg Gly Ser Gln Phe Ala Ile Asp Ser Ser Lys Lys Phe Thr
        275                 280                 285
Val Thr Thr Gln Phe Leu Thr Asp Asn Gly Lys Glu Asp Gly Val Leu
    290                 295                 300
Val Glu Ile Arg Arg Leu Trp His Gln Asp Gly Lys Leu Ile Lys Asn
305                 310                 315                 320
Thr Ala Ile Gln Val Glu Glu Asn Tyr Ser Thr Asp Ser Val Ser Thr
                325                 330                 335
Glu Phe Cys Glu Lys Thr Ala Ser Phe Thr Met Gln Arg Gly Gly Leu
            340                 345                 350
Lys Ala Met Gly Glu Ala Ile Gly Arg Gly Met Val Leu Val Phe Ser
        355                 360                 365
Ile Trp Ala Asp Asp Ser Gly Phe Met Asn Trp Leu Asp Ala Glu Gly
    370                 375                 380
Asn Gly Pro Cys Ser Ala Thr Glu Gly Asp Pro Lys Glu Ile Val Lys
385                 390                 395                 400
Asn Lys Pro Asp Ala Arg Val Thr Phe Ser Asn Ile Arg Ile Gly Glu
                405                 410                 415
Val Gly Ser Thr Tyr Ala Pro Gly Gly Lys Cys Gly Val Lys Ser Arg
            420                 425                 430
Val Ala Arg Gly Leu Thr Ala Ser
        435                 440

<210> SEQ ID NO 21
<211> LENGTH: 1380
<212> TYPE: DNA
<213> ORGANISM: Trichoderma reesei

<400> SEQUENCE: 21
atggcgccct cagttacact gccgttgacc acggccatcc tggccattgc ccggctcgtc     60
gccgcccagc aaccgggtac cagcaccccc gaggtccatc ccaagttgac aacctacaag    120
tgtacaaagt ccggggggtg cgtggcccag gacacctcgg tggtccttga ctggaactac    180
cgctggatgc acgacgcaaa ctacaactcg tgcaccgtca acggcggcgt caacaccacg    240
ctctgccctg acgaggcgac ctgtggcaag aactgcttca tcgagggcgt cgactacgcc    300
```

```
gcctcgggcg tcacgacctc gggcagcagc ctcaccatga accagtacat gcccagcagc    360
tctggcggct acagcagcgt ctctcctcgg ctgtatctcc tggactctga cggtgagtac    420
gtgatgctga agctcaacgg ccaggagctg agcttcgacg tcgacctctc tgctctgccg    480
tgtggagaga acggctcgct ctacctgtct cagatggacg agaacggggg cgccaaccag    540
tataacacgg ccggtgccaa ctacgggagc ggctactgcg atgctcagtg ccccgtccag    600
acatggagga acggcaccct caacactagc caccagggct ctgctgcaa cgagatggat     660 atcctggagg gcaactcgag ggcgaatgcc ttgacccctc actcttgcac ggccacggcc    720
tgcgactctg ccgttgcgg cttcaacccc tatggcagcg gctacaaaag ctactacggc     780
cccggagata ccgttgacac ctccaagacc ttcaccatca tcacccagtt caacacggac    840
aacggctcgc cctcgggcaa ccttgtgagc atcacccgca agtaccagca aaacggcgtc    900
gacatcccca gcgcccagcc cggcggcgac accatctcgt cctgcccgtc cgcctcagcc    960
tacgcgggcc tcgccaccat gggcaaggcc ctgagcagcg gcatggtgct cgtgttcagc   1020
atttggaacg acaacagcca gtacatgaac tggctcgaca gcggcaacgc cggcccctgc   1080
agcagcaccg agggcaaccc atccaacatc ctggccaaca ccccaacac gcacgtcgtc    1140 ttctccaaca tccgctgggg agacattggg tctactacga actcgactgc gcccccgccc   1200
ccgcctgcgt ccagcacgac gttttcgact acacggagga gctcgacgac ttcgagcagc   1260
ccgagctgca cgcagactca ctgggggcag tgcggtggca ttgggtacag cgggtgcaag   1320
acgtgcacgt cgggcactac cgtgccagtat agcaacgact actactcgca atgcctttag   1380
```

<210> SEQ ID NO 22
<211> LENGTH: 459
<212> TYPE: PRT
<213> ORGANISM: Trichoderma reesei

<400> SEQUENCE: 22

```
Met Ala Pro Ser Val Thr Leu Pro Leu Thr Thr Ala Ile Leu Ala Ile
1               5                   10                  15

Ala Arg Leu Val Ala Ala Gln Gln Pro Gly Thr Ser Thr Pro Glu Val
            20                  25                  30

His Pro Lys Leu Thr Thr Tyr Lys Cys Thr Lys Ser Gly Gly Cys Val
        35                  40                  45

Ala Gln Asp Thr Ser Val Val Leu Asp Trp Asn Tyr Arg Trp Met His
    50                  55                  60

Asp Ala Asn Tyr Asn Ser Cys Thr Val Asn Gly Gly Val Asn Thr Thr
65                  70                  75                  80

Leu Cys Pro Asp Glu Ala Thr Cys Gly Lys Asn Cys Phe Ile Glu Gly
                85                  90                  95

Val Asp Tyr Ala Ala Ser Gly Val Thr Thr Ser Gly Ser Ser Leu Thr
            100                 105                 110

Met Asn Gln Tyr Met Pro Ser Ser Gly Gly Tyr Ser Ser Val Ser
        115                 120                 125

Pro Arg Leu Tyr Leu Leu Asp Ser Asp Gly Glu Tyr Val Met Leu Lys
    130                 135                 140

Leu Asn Gly Gln Glu Leu Ser Phe Asp Val Asp Leu Ser Ala Leu Pro
145                 150                 155                 160

Cys Gly Glu Asn Gly Ser Leu Tyr Leu Ser Gln Met Asp Glu Asn Gly
                165                 170                 175

Gly Ala Asn Gln Tyr Asn Thr Ala Gly Ala Asn Tyr Gly Ser Gly Tyr
```

```
                180                 185                 190
Cys Asp Ala Gln Cys Pro Val Gln Thr Trp Arg Asn Gly Thr Leu Asn
            195                 200                 205

Thr Ser His Gln Gly Phe Cys Cys Asn Glu Met Asp Ile Leu Glu Gly
        210                 215                 220

Asn Ser Arg Ala Asn Ala Leu Thr Pro His Ser Cys Thr Ala Thr Ala
225                 230                 235                 240

Cys Asp Ser Ala Gly Cys Gly Phe Asn Pro Tyr Gly Ser Gly Tyr Lys
                245                 250                 255

Ser Tyr Tyr Gly Pro Gly Asp Thr Val Asp Thr Ser Lys Thr Phe Thr
            260                 265                 270

Ile Ile Thr Gln Phe Asn Thr Asp Asn Gly Ser Pro Ser Gly Asn Leu
        275                 280                 285

Val Ser Ile Thr Arg Lys Tyr Gln Gln Asn Gly Val Asp Ile Pro Ser
290                 295                 300

Ala Gln Pro Gly Gly Asp Thr Ile Ser Ser Cys Pro Ser Ala Ser Ala
305                 310                 315                 320

Tyr Gly Gly Leu Ala Thr Met Gly Lys Ala Leu Ser Ser Gly Met Val
                325                 330                 335

Leu Val Phe Ser Ile Trp Asn Asp Asn Ser Gln Tyr Met Asn Trp Leu
            340                 345                 350

Asp Ser Gly Asn Ala Gly Pro Cys Ser Ser Thr Glu Gly Asn Pro Ser
        355                 360                 365

Asn Ile Leu Ala Asn Asn Pro Asn Thr His Val Val Phe Ser Asn Ile
370                 375                 380

Arg Trp Gly Asp Ile Gly Ser Thr Thr Asn Ser Thr Ala Pro Pro Pro
385                 390                 395                 400

Pro Pro Ala Ser Ser Thr Thr Phe Ser Thr Thr Arg Arg Ser Ser Thr
                405                 410                 415

Thr Ser Ser Ser Pro Ser Cys Thr Gln Thr His Trp Gly Gln Cys Gly
            420                 425                 430

Gly Ile Gly Tyr Ser Gly Cys Lys Thr Cys Thr Ser Gly Thr Thr Cys
        435                 440                 445

Gln Tyr Ser Asn Asp Tyr Tyr Ser Gln Cys Leu
    450                 455
```

<210> SEQ ID NO 23
<211> LENGTH: 2586
<212> TYPE: DNA
<213> ORGANISM: Aspergillus oryzae

<400> SEQUENCE: 23

```
atgaagcttg gttggatcga ggtggccgca ttggcggctg cctcagtagt cagtgccaag      60
gatgatctcg cgtactcccc tcctttctac ccttccccat gggcagatgg tcagggtgaa     120
tgggcggaag tatacaaacg cgctgtagac atagtttccc agatgacgtt gacagagaaa     180
gtcaacttaa cgactggaac aggatggcaa ctagagaggt gtgttggaca aactggcagt     240
gttcccagac tcaacatccc cagcttgtgt ttgcaggata gtcctcttgg tattcgtttc     300
tcggactaca attcagcttt ccctgcgggt gttaatgtcg ctgccacctg ggacaagacg     360
ctcgcctacc ttcgtggtca ggcaatgggt gaggagttca gtgataaggg tattgacgtt     420
cagctgggtc ctgctgctgg ccctctcggt gctcatccgg atggcggtag aaactgggaa     480
ggtttctcac cagatccagc cctcaccggt gtacttttg cggagacgat taagggtatt     540
```

| | |
|---|---:|
| caagatgctg gtgtcattgc gacagctaag cattatatca tgaacgaaca agagcatttc | 600 |
| cgccaacaac ccgaggctgc gggttacgga ttcaacgtaa gcgacagttt gagttccaac | 660 |
| gttgatgaca agactatgca tgaattgtac ctctggccct tcgcggatgc agtacgcgct | 720 |
| ggagtcggtg ctgtcatgtg ctcttacaac caaatcaaca acagctacgg ttgcgagaat | 780 |
| agcgaaactc tgaacaagct tttgaaggcg agcttggtt tccaaggctt cgtcatgagt | 840 |
| gattggaccg ctcatcacag cggcgtaggc gctgctttag caggtctgga tatgtcgatg | 900 |
| cccggtgatg ttaccttcga tagtggtacg tctttctggg gtgcaaactt gacggtcggt | 960 |
| gtccttaacg gtacaatccc ccaatggcgt gttgatgaca tggctgtccg tatcatggcc | 1020 |
| gcttattaca aggttggccg cgacaccaaa tacacccctc ccaacttcag ctcgtggacc | 1080 |
| agggacgaat atggtttcgc gcataaccat gtttcggaag gtgcttacga gagggtcaac | 1140 |
| gaattcgtgg acgtgcaacg cgatcatgcc gacctaatcc gtcgcatcgg cgcgcagagc | 1200 |
| actgttctgc tgaagaacaa gggtgccttg cccttgagcc gcaaggaaaa gctggtcgcc | 1260 |
| cttctgggag aggatgcggg ttccaactcg tggggcgcta acggctgtga tgaccgtggt | 1320 |
| tgcgataacg gtaccttgc catggcctgg ggtagcggta ctgcgaattt cccatacctc | 1380 |
| gtgacaccag agcaggcgat tcagaacgaa gttcttcagg gccgtggtaa tgtcttcgcc | 1440 |
| gtgaccgaca gttgggcgct cgacaagatc gctgcggctg cccgccaggc cagcgtatct | 1500 |
| ctcgtgttcg tcaactccga ctcaggagaa ggctatctta gtgtggatgg aaatgagggc | 1560 |
| gatcgtaaca acatcactct gtggaagaac ggcgacaatg tggtcaagac cgcagcgaat | 1620 |
| aactgtaaca acaccgttgt catcatccac tccgtcggac cagttttgat cgatgaatgg | 1680 |
| tatgaccacc ccaatgtcac tggtattctc tgggctggtc tgccaggcca ggagtctggt | 1740 |
| aactccattg ccgatgtgct gtacggtcgt gtcaaccctg cgccaagtc tcctttcact | 1800 |
| tggggcaaga cccgggagtc gtatggttct cccttggtca aggatgccaa caatggcaac | 1860 |
| ggagcgcccc agtctgattt cacccagggt gttttcatcg attaccgcca tttcgataag | 1920 |
| ttcaatgaga cccctatcta cgagtttggc tacggcttga gctacaccac cttcgagctc | 1980 |
| tccgacctcc atgttcagcc cctgaacgcg tcccgataca ctcccaccag tggcatgact | 2040 |
| gaagctgcaa agaactttgg tgaaattggc gatgcgtcgg agtacgtgta tccggagggg | 2100 |
| ctggaaagga tccatgagtt tatctatccc tggatcaact ctaccgacct gaaggcatcg | 2160 |
| tctgacgatt ctaactacgg ctgggaagac tccaagtata ttcccgaagg cgccacggat | 2220 |
| gggtctgccc agccccgttt gcccgctagt ggtggtgccg gaggaaaccc cggtctgtac | 2280 |
| gaggatcttt tccgcgtctc tgtgaaggtc aagaacacgg gcaatgtcgc cggtgatgaa | 2340 |
| gttcctcagc tgtacgtttc cctaggcggc ccgaatgagc ccaaggtggt actgcgcaag | 2400 |
| tttgagcgta ttcacttggc cccttcgcag gaggccgtgt ggacaacgac ccttacccgt | 2460 |
| cgtgaccttg caaactggga cgtttcggct caggactgga ccgtcactcc ttaccccaag | 2520 |
| acgatctacg ttggaaactc ctcacggaaa ctgccgctcc aggcctcgct gcctaaggcc | 2580 |
| cagtaa | 2586 |

<210> SEQ ID NO 24
<211> LENGTH: 861
<212> TYPE: PRT
<213> ORGANISM: Aspergillus oryzae

<400> SEQUENCE: 24

Met Lys Leu Gly Trp Ile Glu Val Ala Ala Leu Ala Ala Ala Ser Val

-continued

```
1               5                   10                  15
Val Ser Ala Lys Asp Asp Leu Ala Tyr Ser Pro Pro Phe Tyr Pro Ser
                20                  25                  30

Pro Trp Ala Asp Gly Gln Gly Glu Trp Ala Glu Val Tyr Lys Arg Ala
            35                  40                  45

Val Asp Ile Val Ser Gln Met Thr Leu Thr Glu Lys Val Asn Leu Thr
    50                  55                  60

Thr Gly Thr Gly Trp Gln Leu Glu Arg Cys Val Gly Gln Thr Gly Ser
65                  70                  75                  80

Val Pro Arg Leu Asn Ile Pro Ser Leu Cys Leu Gln Asp Ser Pro Leu
                85                  90                  95

Gly Ile Arg Phe Ser Asp Tyr Asn Ser Ala Phe Pro Ala Gly Val Asn
            100                 105                 110

Val Ala Ala Thr Trp Asp Lys Thr Leu Ala Tyr Leu Arg Gly Gln Ala
            115                 120                 125

Met Gly Glu Glu Phe Ser Asp Lys Gly Ile Asp Val Gln Leu Gly Pro
    130                 135                 140

Ala Ala Gly Pro Leu Gly Ala His Pro Asp Gly Gly Arg Asn Trp Glu
145                 150                 155                 160

Gly Phe Ser Pro Asp Pro Ala Leu Thr Gly Val Leu Phe Ala Glu Thr
                165                 170                 175

Ile Lys Gly Ile Gln Asp Ala Gly Val Ile Ala Thr Ala Lys His Tyr
            180                 185                 190

Ile Met Asn Glu Gln Glu His Phe Arg Gln Pro Glu Ala Ala Gly
            195                 200                 205

Tyr Gly Phe Asn Val Ser Asp Ser Leu Ser Ser Asn Val Asp Asp Lys
    210                 215                 220

Thr Met His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
                245                 250                 255

Gly Cys Glu Asn Ser Glu Thr Leu Asn Lys Leu Leu Lys Ala Glu Leu
            260                 265                 270

Gly Phe Gln Gly Phe Val Met Ser Asp Trp Thr Ala His His Ser Gly
            275                 280                 285

Val Gly Ala Ala Leu Ala Gly Leu Asp Met Ser Met Pro Gly Asp Val
    290                 295                 300

Thr Phe Asp Ser Gly Thr Ser Phe Trp Gly Ala Asn Leu Thr Val Gly
305                 310                 315                 320

Val Leu Asn Gly Thr Ile Pro Gln Trp Arg Val Asp Asp Met Ala Val
                325                 330                 335

Arg Ile Met Ala Ala Tyr Tyr Lys Val Gly Arg Asp Thr Lys Tyr Thr
            340                 345                 350

Pro Pro Asn Phe Ser Ser Trp Thr Arg Asp Glu Tyr Gly Phe Ala His
            355                 360                 365

Asn His Val Ser Glu Gly Ala Tyr Glu Arg Val Asn Glu Phe Val Asp
    370                 375                 380

Val Gln Arg Asp His Ala Asp Leu Ile Arg Ile Gly Ala Gln Ser
385                 390                 395                 400

Thr Val Leu Leu Lys Asn Lys Gly Ala Leu Pro Leu Ser Arg Lys Glu
            405                 410                 415

Lys Leu Val Ala Leu Leu Gly Glu Asp Ala Gly Ser Asn Ser Trp Gly
            420                 425                 430
```

```
Ala Asn Gly Cys Asp Asp Arg Gly Cys Asp Asn Gly Thr Leu Ala Met
        435                 440                 445

Ala Trp Gly Ser Gly Thr Ala Asn Phe Pro Tyr Leu Val Thr Pro Glu
450                 455                 460

Gln Ala Ile Gln Asn Glu Val Leu Gln Gly Arg Gly Asn Val Phe Ala
465                 470                 475                 480

Val Thr Asp Ser Trp Ala Leu Asp Lys Ile Ala Ala Ala Arg Gln
                485                 490                 495

Ala Ser Val Ser Leu Val Phe Val Asn Ser Asp Ser Gly Glu Gly Tyr
                500                 505                 510

Leu Ser Val Asp Gly Asn Glu Gly Asp Arg Asn Asn Ile Thr Leu Trp
                515                 520                 525

Lys Asn Gly Asp Asn Val Val Lys Thr Ala Ala Asn Cys Asn Asn
530                 535                 540

Thr Val Val Ile Ile His Ser Val Gly Pro Val Leu Ile Asp Glu Trp
545                 550                 555                 560

Tyr Asp His Pro Asn Val Thr Gly Ile Leu Trp Ala Gly Leu Pro Gly
                565                 570                 575

Gln Glu Ser Gly Asn Ser Ile Ala Asp Val Leu Tyr Gly Arg Val Asn
                580                 585                 590

Pro Gly Ala Lys Ser Pro Phe Thr Trp Gly Lys Thr Arg Glu Ser Tyr
                595                 600                 605

Gly Ser Pro Leu Val Lys Asp Ala Asn Asn Gly Asn Gly Ala Pro Gln
                610                 615                 620

Ser Asp Phe Thr Gln Gly Val Phe Ile Asp Tyr Arg His Phe Asp Lys
625                 630                 635                 640

Phe Asn Glu Thr Pro Ile Tyr Glu Phe Gly Tyr Gly Leu Ser Tyr Thr
                645                 650                 655

Thr Phe Glu Leu Ser Asp Leu His Val Gln Pro Leu Asn Ala Ser Arg
                660                 665                 670

Tyr Thr Pro Thr Ser Gly Met Thr Glu Ala Ala Lys Asn Phe Gly Glu
                675                 680                 685

Ile Gly Asp Ala Ser Glu Tyr Val Tyr Pro Glu Gly Leu Glu Arg Ile
                690                 695                 700

His Glu Phe Ile Tyr Pro Trp Ile Asn Ser Thr Asp Leu Lys Ala Ser
705                 710                 715                 720

Ser Asp Asp Ser Asn Tyr Gly Trp Glu Asp Ser Lys Tyr Ile Pro Glu
                725                 730                 735

Gly Ala Thr Asp Gly Ser Ala Gln Pro Arg Leu Pro Ala Ser Gly Gly
                740                 745                 750

Ala Gly Gly Asn Pro Gly Leu Tyr Glu Asp Leu Phe Arg Val Ser Val
                755                 760                 765

Lys Val Lys Asn Thr Gly Asn Val Ala Gly Asp Glu Val Pro Gln Leu
770                 775                 780

Tyr Val Ser Leu Gly Gly Pro Asn Glu Pro Lys Val Val Leu Arg Lys
785                 790                 795                 800

Phe Glu Arg Ile His Leu Ala Pro Ser Gln Glu Ala Val Trp Thr Thr
                805                 810                 815

Thr Leu Thr Arg Arg Asp Leu Ala Asn Trp Asp Val Ser Ala Gln Asp
                820                 825                 830

Trp Thr Val Thr Pro Tyr Pro Lys Thr Ile Tyr Val Gly Asn Ser Ser
                835                 840                 845
```

Arg Lys Leu Pro Leu Gln Ala Ser Leu Pro Lys Ala Gln
    850                 855                 860

<210> SEQ ID NO 25
<211> LENGTH: 2586
<212> TYPE: DNA
<213> ORGANISM: Aspergillus oryzae

<400> SEQUENCE: 25

| | |
|---|---|
| atgaagcttg gttggatcga ggtggccgca ttggcggctg cctcagtagt cagtgccaag | 60 |
| gatgatctcg cgtactcccc tcctttctac ccttccccat gggcagatgg tcagggtgaa | 120 |
| tgggcggaag tatacaaacg cgctgtagac atagtttccc agatgacgtt gacagagaaa | 180 |
| gtcaacttaa cgactggaac aggatggcaa ctagagaggt gtgttggaca aactggcagt | 240 |
| gttcccagac tcaacatccc cagcttgtgt ttgcaggata gtcctcttgg tattcgtttc | 300 |
| tcggactaca attcagcttt ccctgcgggt gttaatgtcg ctgccacctg ggacaagacg | 360 |
| ctcgcctacc ttcgtggtca ggcaatgggg gaggagttca gtgataaggg tattgacgtt | 420 |
| cagctgggtc ctgctgctgg ccctctcggt gctcatccgg atggcggtag aaactgggaa | 480 |
| agtttctcac cagatccagc cctcaccggt gtactttttg cggagacgat taagggtatt | 540 |
| caagatgctg gtgtcattgc gacagctaag cattatatca tgaacgaaca agagcatttc | 600 |
| cgccaacaac ccgaggctgc gggttacgga ttcaacgtaa gcgacagttt gagttccaac | 660 |
| gttgatgaca agactatgca tgaattgtac ctctggccct tcgcggatgc agtacgcgct | 720 |
| ggagtcggtg ctgttatgtg ctcttacaac caaatcaaca acagctacgg ttgcgagaat | 780 |
| agcgaaactc tgaacaagct tttgaaggcg agcttggtt tccaaggctt cgtcatgagt | 840 |
| gattggaccg ctcaacacag cggcgtaggc gctgctttag caggtctgga tatgtcgatg | 900 |
| cccggtgatg ttaccttcga tagtggtacg tctttctggg gtgcaaactt gacggtcggt | 960 |
| gtccttaacg gtacaatccc ccaatggcgt gttgatgaca tggctgtccg tatcatggcc | 1020 |
| gcttattaca aggttggccg cgacaccaaa tacacccctc ccaacttcag ctcgtggacc | 1080 |
| agggacgaat atggttcgc gcataaccat gtttcggaag tgcttacga gagggtcaac | 1140 |
| gaattcgtgg acgtgcaacg cgatcatgcc gacctaatcc gtcgcatcgg cgcgcagagc | 1200 |
| actgttctgc tgaagaacaa gggtgccttg cccttgagcc gcaaggaaaa gctggtcgcc | 1260 |
| cttctgggag aggatgcggg ttccaactcg tgggcgcta acggctgtga tgaccgtggt | 1320 |
| tgcgataacg gtaccccttgc catggcctgg ggtagcggta ctgcgaattt cccatacctc | 1380 |
| gtgacaccag agcaggcgat tcagaacgaa gttcttcagg gccgtggtaa tgtcttcgcc | 1440 |
| gtgaccgaca gttgggcgct cgacaagatc gctgcggctg cccgccaggc cagcgtatct | 1500 |
| ctcgtgttcg tcaactccga ctcaggagaa ggctatctta gtgtggatgg aaatgagggc | 1560 |
| gatcgtaaca acatcactct gtggaagaac ggcgacaatg tggtcaagac cgcagcgaat | 1620 |
| aactgtaaca cgccgttgt catcatccac tccgtcggac cagttttgat cgatgaatgg | 1680 |
| tatgaccacc ccaatgtcac tggtattctc tgggctggtc tgccaggcca ggagtctggt | 1740 |
| aactccattg ccgatgtgct gtacggtcgt gtcaaccctg gcgccaagtc tccttcact | 1800 |
| tggggcaaga cccgggagtc gtatggttct cccttggtca aggatgccaa caatggcaac | 1860 |
| ggagcgcccc agtctgattt cacccagggt gttttcatcg attaccgcca tttcgataag | 1920 |
| ttcaatgaga cccctatcta cgagtttggc tacggcttga gctacaccac cttcgagctc | 1980 |
| tccgacctcc atgttcagcc cctgaacgcg tcccgataca ctcccaccag tggcatgact | 2040 |

-continued

```
gaagctgcaa agaactttgg tgaaattggc gatgcgtcgg agtacgtgta tccggagggg    2100
ctggaaagga tccatgagtt tatctatccc tggatcaact ctaccgacct gaaggcatcg    2160
tctgacgatt ctaactacgg ctgggaagac tccaagtata ttcccgaagg cgccacggat    2220
gggtctgccc agccccgttt gcccgctagt ggtggtgccg aggaaacccc cggtctgtac    2280
gaggatcttt tccgcgtctc tgtgaaggtc aagaacacgg gcaatgtcgc cggtgatgaa    2340
gttcctcagc tgtacgtttc cctaggcggc ccgaatgagc ccaaggtggt actgcgcaag    2400
tttgagcgta ttcacttggc cccttcgcag gaggccgtgt ggacaacgac ccttacccgt    2460
cgtgaccttg caaactggga cgtttcggct caggactgga ccgtcactcc ttaccccaag    2520
acgatctacg ttggaaactc ctcacggaaa ctgccgctcc aggcctcgct gcctaaggcc    2580
cagtaa                                                               2586
```

<210> SEQ ID NO 26
<211> LENGTH: 861
<212> TYPE: PRT
<213> ORGANISM: Aspergillus oryzae

<400> SEQUENCE: 26

```
Met Lys Leu Gly Trp Ile Glu Val Ala Ala Leu Ala Ala Ala Ser Val
1               5                   10                  15

Val Ser Ala Lys Asp Asp Leu Ala Tyr Ser Pro Pro Phe Tyr Pro Ser
            20                  25                  30

Pro Trp Ala Asp Gly Gln Gly Glu Trp Ala Glu Val Tyr Lys Arg Ala
        35                  40                  45

Val Asp Ile Val Ser Gln Met Thr Leu Thr Glu Lys Val Asn Leu Thr
    50                  55                  60

Thr Gly Thr Gly Trp Gln Leu Glu Arg Cys Val Gly Gln Thr Gly Ser
65                  70                  75                  80

Val Pro Arg Leu Asn Ile Pro Ser Leu Cys Leu Gln Asp Ser Pro Leu
                85                  90                  95

Gly Ile Arg Phe Ser Asp Tyr Asn Ser Ala Phe Pro Ala Gly Val Asn
            100                 105                 110

Val Ala Ala Thr Trp Asp Lys Thr Leu Ala Tyr Leu Arg Gly Gln Ala
        115                 120                 125

Met Gly Glu Glu Phe Ser Asp Lys Gly Ile Asp Val Gln Leu Gly Pro
    130                 135                 140

Ala Ala Gly Pro Leu Gly Ala His Pro Asp Gly Gly Arg Asn Trp Glu
145                 150                 155                 160

Ser Phe Ser Pro Asp Pro Ala Leu Thr Gly Val Leu Phe Ala Glu Thr
                165                 170                 175

Ile Lys Gly Ile Gln Asp Ala Gly Val Ile Ala Thr Ala Lys His Tyr
            180                 185                 190

Ile Met Asn Glu Gln Glu His Phe Arg Gln Pro Glu Ala Ala Gly
        195                 200                 205

Tyr Gly Phe Asn Val Ser Asp Ser Leu Ser Ser Asn Val Asp Asp Lys
    210                 215                 220

Thr Met His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
                245                 250                 255

Gly Cys Glu Asn Ser Glu Thr Leu Asn Lys Leu Leu Lys Ala Glu Leu
            260                 265                 270
```

```
Gly Phe Gln Gly Phe Val Met Ser Asp Trp Thr Ala Gln His Ser Gly
            275                 280                 285

Val Gly Ala Ala Leu Ala Gly Leu Asp Met Ser Met Pro Gly Asp Val
    290                 295                 300

Thr Phe Asp Ser Gly Thr Ser Phe Trp Gly Ala Asn Leu Thr Val Gly
305                 310                 315                 320

Val Leu Asn Gly Thr Ile Pro Gln Trp Arg Val Asp Met Ala Val
                325                 330                 335

Arg Ile Met Ala Ala Tyr Tyr Lys Val Gly Arg Asp Thr Lys Tyr Thr
            340                 345                 350

Pro Pro Asn Phe Ser Ser Trp Thr Arg Asp Glu Tyr Gly Phe Ala His
            355                 360                 365

Asn His Val Ser Glu Gly Ala Tyr Glu Arg Val Asn Glu Phe Val Asp
    370                 375                 380

Val Gln Arg Asp His Ala Asp Leu Ile Arg Arg Ile Gly Ala Gln Ser
385                 390                 395                 400

Thr Val Leu Leu Lys Asn Lys Gly Ala Leu Pro Leu Ser Arg Lys Glu
                405                 410                 415

Lys Leu Val Ala Leu Leu Gly Glu Asp Ala Gly Ser Asn Ser Trp Gly
            420                 425                 430

Ala Asn Gly Cys Asp Asp Arg Gly Cys Asp Asn Gly Thr Leu Ala Met
            435                 440                 445

Ala Trp Gly Ser Gly Thr Ala Asn Phe Pro Tyr Leu Val Thr Pro Glu
            450                 455                 460

Gln Ala Ile Gln Asn Glu Val Leu Gln Gly Arg Gly Asn Val Phe Ala
465                 470                 475                 480

Val Thr Asp Ser Trp Ala Leu Asp Lys Ile Ala Ala Ala Arg Gln
                485                 490                 495

Ala Ser Val Ser Leu Val Phe Val Asn Ser Asp Ser Gly Glu Gly Tyr
            500                 505                 510

Leu Ser Val Asp Gly Asn Glu Gly Asp Arg Asn Asn Ile Thr Leu Trp
            515                 520                 525

Lys Asn Gly Asp Asn Val Val Lys Thr Ala Ala Asn Cys Asn Asn
530                 535                 540

Thr Val Val Ile Ile His Ser Val Gly Pro Val Leu Ile Asp Glu Trp
545                 550                 555                 560

Tyr Asp His Pro Asn Val Thr Gly Ile Leu Trp Ala Gly Leu Pro Gly
                565                 570                 575

Gln Glu Ser Gly Asn Ser Ile Ala Asp Val Leu Tyr Gly Arg Val Asn
            580                 585                 590

Pro Gly Ala Lys Ser Pro Phe Thr Trp Gly Lys Thr Arg Glu Ser Tyr
            595                 600                 605

Gly Ser Pro Leu Val Lys Asp Ala Asn Asn Gly Asn Gly Ala Pro Gln
            610                 615                 620

Ser Asp Phe Thr Gln Gly Val Phe Ile Asp Tyr Arg His Phe Asp Lys
625                 630                 635                 640

Phe Asn Glu Thr Pro Ile Tyr Glu Phe Gly Tyr Gly Leu Ser Tyr Thr
                645                 650                 655

Thr Phe Glu Leu Ser Asp Leu His Val Gln Pro Leu Asn Ala Ser Arg
            660                 665                 670

Tyr Thr Pro Thr Ser Gly Met Thr Glu Ala Ala Lys Asn Phe Gly Glu
            675                 680                 685

Ile Gly Asp Ala Ser Glu Tyr Val Tyr Pro Glu Gly Leu Glu Arg Ile
```

His Glu Phe Ile Tyr Pro Trp Ile Asn Ser Thr Asp Leu Lys Ala Ser
705                 710                 715                 720

Ser Asp Ser Asn Tyr Gly Trp Glu Asp Ser Lys Tyr Ile Pro Glu
            725                 730                 735

Gly Ala Thr Asp Gly Ser Ala Gln Pro Arg Leu Pro Ala Ser Gly Gly
            740                 745                 750

Ala Gly Gly Asn Pro Gly Leu Tyr Glu Asp Leu Phe Arg Val Ser Val
            755                 760                 765

Lys Val Lys Asn Thr Gly Asn Val Ala Gly Asp Glu Val Pro Gln Leu
770                 775                 780

Tyr Val Ser Leu Gly Gly Pro Asn Glu Pro Lys Val Val Leu Arg Lys
785                 790                 795                 800

Phe Glu Arg Ile His Leu Ala Pro Ser Gln Glu Ala Val Trp Thr Thr
                805                 810                 815

Thr Leu Thr Arg Arg Asp Leu Ala Asn Trp Asp Val Ser Ala Gln Asp
            820                 825                 830

Trp Thr Val Thr Pro Tyr Pro Lys Thr Ile Tyr Val Gly Asn Ser Ser
            835                 840                 845

Arg Lys Leu Pro Leu Gln Ala Ser Leu Pro Lys Ala Gln
    850                 855                 860

<210> SEQ ID NO 27
<211> LENGTH: 3060
<212> TYPE: DNA
<213> ORGANISM: Aspergillus fumigatus

<400> SEQUENCE: 27

| | |
|---|---|
| atgagattcg gttggctcga ggtggccgct ctgacggccg cttctgtagc caatgcccag | 60 |
| gtttgtgatg cttttccgtc attgtttcgg atatagttga caatagtcat ggaaataatc | 120 |
| aggaattggc tttctctcca ccattctacc cttcgccttg ggctgatggc cagggagagt | 180 |
| gggcagatgc ccatcgacgc gccgtcgaga tcgtttctca gatgacactg gcggagaagg | 240 |
| ttaaccttac aacgggtact gggtgggttg cgactttttt gttgacagtg agctttcttc | 300 |
| actgaccatc tacacagatg ggaaatggac cgatgcgtcg gtcaaaccgg cagcgttccc | 360 |
| aggtaagctt gcaattctgc aacaacgtgc aagtgtagtt gctaaaacgc ggtggtgcag | 420 |
| acttggtatc aactggggtc tttgtggcca ggattcccct tgggtatccc gtttctgtga | 480 |
| gctatacccg cggagtcttt cagtccttgt attatgtgct gatgattgtc tctgtatagc | 540 |
| tgacctcaac tccgccttcc ctgctggtac taatgtcgcc gcgacatggg acaagacact | 600 |
| cgcctacctt cgtggcaagg ccatgggtga ggaattcaac gacaagggcg tggacatttt | 660 |
| gctggggcct gctgctggtc ctctcggcaa atacccggac ggcggcagaa tctgggaagg | 720 |
| cttctctcct gatccggttc tcactggtgt acttttcgcc gaaactatca agggtatcca | 780 |
| agacgcgggt gtgattgcta ctgccaagca ttacattctg aatgaacagg agcatttccg | 840 |
| acaggttggc gaggcccagg gatatggtta caacatcacg gagacgatca gctccaacgt | 900 |
| ggatgacaag accatgcacg agttgtacct tggtgagta gttgacactg caaatgagga | 960 |
| ccttgattga tttgactgac ctggaatgca ggcccttgc agatgctgtg cgcggtaaga | 1020 |
| ttttccgtag acttgacctc gcgacgaaga atcgctgac gaaccatcgt agctggcgtt | 1080 |
| ggcgctgtca tgtgttccta caatcaaatc aacaacagct acggttgtca aaacagtcaa | 1140 |
| actctcaaca agctcctcaa ggctgagctg ggcttccaag gcttcgtcat gagtgactgg | 1200 |

```
agcgctcacc acagcggtgt cggcgctgcc ctcgctgggt tggatatgtc gatgcctgga    1260
gacatttcct tcgacgacgg actctccttc tggggcacga acctaactgt cagtgttctt    1320
aacggcaccg ttccagcctg gcgtgtcgat gacatggctg ttcgtatcat gaccgcgtac    1380
tacaaggttg gtcgtgaccg tcttcgtatt cccctaact tcagctcctg acccgggat     1440
gagtacggct gggagcattc tgctgtctcc gagggagcct ggaccaaggt gaacgacttc    1500
gtcaatgtgc agcgcagtca ctctcagatc atccgtgaga ttggtgccgc tagtacagtg    1560
ctcttgaaga acacgggtgc tcttcctttg accggcaagg aggttaaagt gggtgttctc    1620
ggtgaagacc tggttccaa cccgtggggt gctaacggct gccccgaccg cggctgtgat    1680
aacggcactc ttgctatggc ctggggtagt ggtactgcca acttcccttta ccttgtcacc    1740
cccgagcagg ctatccagcg agaggtcatc agcaacggcg gcaatgtctt tgctgtgact    1800
gataacgggg ctctcagcca gatggcagat gttgcatctc aatccaggtg agtgcgggct    1860
cttagaaaaa gaacgttctc tgaatgaagt tttttaacca ttgcgaacag cgtgtctttg    1920
gtgtttgtca acgccgactc tggagagggt ttcatcagtg tcgacggcaa cgagggtgac    1980
cgcaaaaatc tcactctgtg gaagaacggc gaggccgtca ttgacactgt tgtcagccac    2040
tgcaacaaca cgattgtggt tattcacagt gttgggcccg tcttgatcga ccggtggtat    2100
gataacccca acgtcactgc catcatctgg gccggcttgc ccggtcagga gagtggcaac    2160
tccctggtcg acgtgctcta tggccgcgtc aaccccagcg ccaagacccc gttcacctgg    2220
ggcaagactc gggagtctta cggggctccc ttgctcaccg agcctaacaa tggcaatggt    2280
gctccccagg atgatttcaa cgagggcgtc ttcattgact accgtcactt tgacaagcgc    2340
aatgagaccc ccatttatga gtttggccat ggcttgagct acaccacctt tggttactct    2400
caccttcggg ttcaggccct caatagttcg agttcggcat atgtcccgac tagcggagag    2460
accaagcctg cgccaaccta tggtgagatc ggtagtgccg ccgactacct gtatcccgag    2520
ggtctcaaaa gaattaccaa gtttatttac ccttggctca actcgaccga cctcgaggat    2580
tcttctgacg acccgaacta cggctgggag gactcggagt acattcccga aggcgctagg    2640
gatgggtctc ctcaaccct cctgaaggct ggcggcgctc ctggtggtaa ccctaccctt    2700
tatcaggatc ttgttagggt gtcggccacc ataaccaaca ctggtaacgt cgccggttat    2760
gaagtccctc aattggtgag tgacccgcat gttccttgcg ttgcaatttg gctaactcgc    2820
ttctagtatg tttcactggg cggaccgaac gagcctcggg tcgttctgcg caagttcgac    2880
cgaatcttcc tggctcctgg ggagcaaaag gtttggacca cgactcttaa ccgtcgtgat    2940
ctcgccaatt gggatgtgga ggctcaggac tgggtcatca caaagtaccc caagaaagtg    3000
cacgtcggca gctcctcgcg taagctgcct ctgagagcgc tctgccccg tgtctactag    3060
```

<210> SEQ ID NO 28
<211> LENGTH: 863
<212> TYPE: PRT
<213> ORGANISM: Aspergillus fumigatus

<400> SEQUENCE: 28

Met Arg Phe Gly Trp Leu Glu Val Ala Ala Leu Thr Ala Ala Ser Val
1               5                   10                  15

Ala Asn Ala Gln Glu Leu Ala Phe Ser Pro Pro Phe Tyr Pro Ser Pro
            20                  25                  30

Trp Ala Asp Gly Gln Gly Glu Trp Ala Asp Ala His Arg Arg Ala Val
        35                  40                  45

```
Glu Ile Val Ser Gln Met Thr Leu Ala Glu Lys Val Asn Leu Thr Thr
 50                  55                  60
Gly Thr Gly Trp Glu Met Asp Arg Cys Val Gly Gln Thr Gly Ser Val
 65                  70                  75                  80
Pro Arg Leu Gly Ile Asn Trp Gly Leu Cys Gly Gln Asp Ser Pro Leu
                 85                  90                  95
Gly Ile Arg Phe Ser Asp Leu Asn Ser Ala Phe Pro Ala Gly Thr Asn
                100                 105                 110
Val Ala Ala Thr Trp Asp Lys Thr Leu Ala Tyr Leu Arg Gly Lys Ala
                115                 120                 125
Met Gly Glu Glu Phe Asn Asp Lys Gly Val Asp Ile Leu Leu Gly Pro
                130                 135                 140
Ala Ala Gly Pro Leu Gly Lys Tyr Pro Asp Gly Gly Arg Ile Trp Glu
145                 150                 155                 160
Gly Phe Ser Pro Asp Pro Val Leu Thr Gly Val Leu Phe Ala Glu Thr
                165                 170                 175
Ile Lys Gly Ile Gln Asp Ala Gly Val Ile Ala Thr Ala Lys His Tyr
                180                 185                 190
Ile Leu Asn Glu Gln Glu His Phe Arg Gln Val Gly Glu Ala Gln Gly
                195                 200                 205
Tyr Gly Tyr Asn Ile Thr Glu Thr Ile Ser Ser Asn Val Asp Asp Lys
                210                 215                 220
Thr Met His Glu Leu Tyr Leu Trp Pro Phe Ala Asp Ala Val Arg Ala
225                 230                 235                 240
Gly Val Gly Ala Val Met Cys Ser Tyr Asn Gln Ile Asn Asn Ser Tyr
                245                 250                 255
Gly Cys Gln Asn Ser Gln Thr Leu Asn Lys Leu Leu Lys Ala Glu Leu
                260                 265                 270
Gly Phe Gln Gly Phe Val Met Ser Asp Trp Ser Ala His His Ser Gly
                275                 280                 285
Val Gly Ala Ala Leu Ala Gly Leu Asp Met Ser Met Pro Gly Asp Ile
                290                 295                 300
Ser Phe Asp Asp Gly Leu Ser Phe Trp Gly Thr Asn Leu Thr Val Ser
305                 310                 315                 320
Val Leu Asn Gly Thr Val Pro Ala Trp Arg Val Asp Asp Met Ala Val
                325                 330                 335
Arg Ile Met Thr Ala Tyr Tyr Lys Val Gly Arg Asp Arg Leu Arg Ile
                340                 345                 350
Pro Pro Asn Phe Ser Ser Trp Thr Arg Asp Glu Tyr Gly Trp Glu His
                355                 360                 365
Ser Ala Val Ser Glu Gly Ala Trp Thr Lys Val Asn Asp Phe Val Asn
                370                 375                 380
Val Gln Arg Ser His Ser Gln Ile Ile Arg Glu Ile Gly Ala Ala Ser
385                 390                 395                 400
Thr Val Leu Leu Lys Asn Thr Gly Ala Leu Pro Leu Thr Gly Lys Glu
                405                 410                 415
Val Lys Val Gly Val Leu Gly Glu Asp Ala Gly Ser Asn Pro Trp Gly
                420                 425                 430
Ala Asn Gly Cys Pro Asp Arg Gly Cys Asp Asn Gly Thr Leu Ala Met
                435                 440                 445
Ala Trp Gly Ser Gly Thr Ala Asn Phe Pro Tyr Leu Val Thr Pro Glu
                450                 455                 460
```

```
Gln Ala Ile Gln Arg Glu Val Ile Ser Asn Gly Asn Val Phe Ala
465                 470                 475                 480

Val Thr Asp Asn Gly Ala Leu Ser Gln Met Ala Asp Val Ala Ser Gln
                485                 490                 495

Ser Ser Val Ser Leu Val Phe Val Asn Ala Asp Ser Gly Glu Gly Phe
            500                 505                 510

Ile Ser Val Asp Gly Asn Glu Gly Asp Arg Lys Asn Leu Thr Leu Trp
            515                 520                 525

Lys Asn Gly Glu Ala Val Ile Asp Thr Val Val Ser His Cys Asn Asn
        530                 535                 540

Thr Ile Val Val Ile His Ser Val Gly Pro Val Leu Ile Asp Arg Trp
545                 550                 555                 560

Tyr Asp Asn Pro Asn Val Thr Ala Ile Ile Trp Ala Gly Leu Pro Gly
                565                 570                 575

Gln Glu Ser Gly Asn Ser Leu Val Asp Val Leu Tyr Gly Arg Val Asn
            580                 585                 590

Pro Ser Ala Lys Thr Pro Phe Thr Trp Gly Lys Thr Arg Glu Ser Tyr
            595                 600                 605

Gly Ala Pro Leu Leu Thr Glu Pro Asn Asn Gly Asn Gly Ala Pro Gln
        610                 615                 620

Asp Asp Phe Asn Glu Gly Val Phe Ile Asp Tyr Arg His Phe Asp Lys
625                 630                 635                 640

Arg Asn Glu Thr Pro Ile Tyr Glu Phe Gly His Gly Leu Ser Tyr Thr
                645                 650                 655

Thr Phe Gly Tyr Ser His Leu Arg Val Gln Ala Leu Asn Ser Ser Ser
            660                 665                 670

Ser Ala Tyr Val Pro Thr Ser Gly Glu Thr Lys Pro Ala Pro Thr Tyr
            675                 680                 685

Gly Glu Ile Gly Ser Ala Ala Asp Tyr Leu Tyr Pro Glu Gly Leu Lys
        690                 695                 700

Arg Ile Thr Lys Phe Ile Tyr Pro Trp Leu Asn Ser Thr Asp Leu Glu
705                 710                 715                 720

Asp Ser Ser Asp Asp Pro Asn Tyr Gly Trp Glu Asp Ser Glu Tyr Ile
                725                 730                 735

Pro Glu Gly Ala Arg Asp Gly Ser Pro Gln Pro Leu Leu Lys Ala Gly
            740                 745                 750

Gly Ala Pro Gly Gly Asn Pro Thr Leu Tyr Gln Asp Leu Val Arg Val
            755                 760                 765

Ser Ala Thr Ile Thr Asn Thr Gly Asn Val Ala Gly Tyr Glu Val Pro
770                 775                 780

Gln Leu Tyr Val Ser Leu Gly Gly Pro Asn Glu Pro Arg Val Val Leu
785                 790                 795                 800

Arg Lys Phe Asp Arg Ile Phe Leu Ala Pro Gly Glu Gln Lys Val Trp
                805                 810                 815

Thr Thr Thr Leu Asn Arg Arg Asp Leu Ala Asn Trp Asp Val Glu Ala
            820                 825                 830

Gln Asp Trp Val Ile Thr Lys Tyr Pro Lys Lys Val His Val Gly Ser
            835                 840                 845

Ser Ser Arg Lys Leu Pro Leu Arg Ala Pro Leu Pro Arg Val Tyr
        850                 855                 860

<210> SEQ ID NO 29
<211> LENGTH: 2800
<212> TYPE: DNA
```

<213> ORGANISM: Penicillium brasilianum

<400> SEQUENCE: 29

```
tgaaaatgca gggttctaca atctttctgg ctttcgcctc atgggcgagc caggttgctg      60
ccattgcgca gcccatacag aagcacgagg tttgttttat cttgctcatg gacgtgcttt     120
gacttgacta attgttttac atacagcccg gatttctgca cgggcccaa gccatagaat      180
cgttctcaga accgttctac ccgtcgccct ggatgaatcc tcacgccgag ggctgggagg     240
ccgcatatca gaaagctcaa gattttgtct cgcaactcac tatcttggag aaaataaatc     300
tgaccaccgg tgttgggtaa gtctctccga ctgcttctgg gtcacggtgc gacgagccac     360
tgactttttg aagctgggaa atgggccgt gtgtaggaaa cactggatca attcctcgtc      420
tcggattcaa aggattttgt acccaggatt caccacaggg tgttcggttc gcagattatt     480
cctccgcttt cacatctagc caaatggccg ccgcaacatt tgaccgctca attctttatc     540
aacgaggcca agccatggca caggaacaca aggctaaggg tatcacaatt caattgggcc     600
ctgttgccgg ccctctcggt cgcatccccg agggcggccg caactgggaa ggattctccc     660
ctgatcctgt cttgactggt atagccatgg ctgagacaat aagggcatg caggatactg      720
gagtgattgc ttgcgctaaa cattatattg gaaacgagca ggagcactt cgtcaagtgg      780
gtgaagctgc gggtcacgga tacactattt ccgatactat ttcatctaat attgacgacc     840
gtgctatgca tgagctatac ttgtggccat ttgctgatgc cgttcgcgct ggtgtgggtt     900
ctttcatgtg ctcatactct cagatcaaca actcctacgg atgccaaaac agtcagaccc     960
tcaacaagct cctcaagagc gaattgggct tccaaggctt tgtcatgagc gattggggtg    1020
cccatcactc tggagtgtca tcggcgctag ctggacttga tatgagcatg ccgggtgata    1080
ccgaatttga ttctggcttg agcttctggg gctctaacct caccattgca attctgaacg    1140
gcacggttcc cgaatggcgc ctggatgaca tggcgatgcg aattatggct gcatacttca    1200
aagttggcct tactattgag gatcaaccag atgtcaactt caatgcctgg acccatgaca    1260
cctacggata taaatacgct tatagcaagg aagattacga gcaggtcaac tggcatgtcg    1320
atgttcgcag cgaccacaat aagctcattc gcgagactgc cgcgaagggt acagttctgc    1380
tgaagaacaa cttcatgct ctccctctga gcagcccag gttcgtggcc gtcgttggtc      1440
aggatgccgg gccaaacccc aagggcccta acggctgcgc agaccgagga tgcgaccaag    1500
gcactctcgc aatgggatgg ggctcagggt ctaccgaatt cccttacctg gtcactcctg    1560
acactgctat tcagtcaaag gtcctcgaat acggggtcg atacgagagt attttgata     1620
actatgacga caatgctatc ttgtcgcttg tctcacagcc tgatgcaacc tgtatcgttt    1680
ttgcaaatgc cgattccggt gaaggctaca tcactgtcga caacaactgg ggtgaccgca    1740
acaatctgac cctctggcaa aatgccgatc aagtgattag cactgtcagc tcgcgatgca    1800
acaacacaat cgttgttctc cactctgtcg gaccagtgtt gctaaatggt atatatgagc    1860
acccgaacat cacagctatt gtctgggcag ggatgccagg cgaagaatct ggcaatgctc    1920
tcgtggatat tctttgggc aatgttaacc ctgccggtcg cactccgttc acctgggcca     1980
aaagtcgaga ggactatggc actgatataa tgtacgagcc caacaacggc cagcgtgcgc    2040
ctcagcagga tttcaccgag agcatctacc tcgactaccg ccatttcgac aaagctggta    2100
tcgagccaat ttacgagttt ggattcggcc tctcctatac caccttcgaa tactctgacc    2160
tccgtgttgt gaagaagtat gttcaaccat acagtcccac gaccggcacc ggtgctcaag    2220
caccttccat cggacagcca cctagccaga acctggatac ctacaagttc cctgctacat    2280
```

```
acaagtacat caaaaccttc atttatccct acctgaacag cactgtctcc ctccgcgctg    2340
cttccaagga tcccgaatac ggtcgtacag actttatccc accccacgcg cgtgatggct    2400
cccctcaacc tctcaacccc gctggagacc cagtggccag tggtggaaac aacatgctct    2460
acgacgaact ttacgaggtc actgcacaga tcaaaaacac tggcgacgtg ccggcgacg    2520 aagtcgtcca gctttacgta gatctcgggg gtgacaaccc gcctcgtcag ttgagaaact    2580
ttgacaggtt ttatctgctg cccggtcaga gctcaacatt ccgggctaca ttgacgcgcc    2640
gtgatttgag caactgggat attgaggcgc agaactggcg agttacggaa tcgcctaaga    2700
gagtgtatgt tggacggtcg agtcgggatt tgccgctgag ctcacaattg gagtaatgat    2760
catgtctacc aatagatgtt gaatgtctgg tgtggatatt                          2800
```

<210> SEQ ID NO 30
<211> LENGTH: 878
<212> TYPE: PRT
<213> ORGANISM: Penicillium brasilianum

<400> SEQUENCE: 30

```
Met Gln Gly Ser Thr Ile Phe Leu Ala Phe Ala Ser Trp Ala Ser Gln
1               5                   10                  15

Val Ala Ala Ile Ala Gln Pro Ile Gln Lys His Glu Pro Gly Phe Leu
            20                  25                  30

His Gly Pro Gln Ala Ile Glu Ser Phe Ser Glu Pro Phe Tyr Pro Ser
        35                  40                  45

Pro Trp Met Asn Pro His Ala Glu Gly Trp Glu Ala Ala Tyr Gln Lys
    50                  55                  60

Ala Gln Asp Phe Val Ser Gln Leu Thr Ile Leu Glu Lys Ile Asn Leu
65                  70                  75                  80

Thr Thr Gly Val Gly Trp Glu Asn Gly Pro Cys Val Gly Asn Thr Gly
                85                  90                  95

Ser Ile Pro Arg Leu Gly Phe Lys Gly Phe Cys Thr Gln Asp Ser Pro
            100                 105                 110

Gln Gly Val Arg Phe Ala Asp Tyr Ser Ser Ala Phe Thr Ser Ser Gln
        115                 120                 125

Met Ala Ala Thr Phe Asp Arg Ser Ile Leu Tyr Gln Arg Gly Gln
    130                 135                 140

Ala Met Ala Gln Glu His Lys Ala Lys Gly Ile Thr Ile Gln Leu Gly
145                 150                 155                 160

Pro Val Ala Gly Pro Leu Gly Arg Ile Pro Glu Gly Gly Arg Asn Trp
                165                 170                 175

Glu Gly Phe Ser Pro Asp Pro Val Leu Thr Gly Ile Ala Met Ala Glu
            180                 185                 190

Thr Ile Lys Gly Met Gln Asp Thr Gly Val Ile Ala Cys Ala Lys His
        195                 200                 205

Tyr Ile Gly Asn Glu Gln Glu His Phe Arg Gln Val Gly Glu Ala Ala
    210                 215                 220

Gly His Gly Tyr Thr Ile Ser Asp Thr Ile Ser Ser Asn Ile Asp Asp
225                 230                 235                 240

Arg Ala Met His Glu Leu Tyr Leu Trp Pro Phe Ala Asp Ala Val Arg
                245                 250                 255

Ala Gly Val Gly Ser Phe Met Cys Ser Tyr Ser Gln Ile Asn Asn Ser
            260                 265                 270

Tyr Gly Cys Gln Asn Ser Gln Thr Leu Asn Lys Leu Leu Lys Ser Glu
```

```
            275                 280                 285
Leu Gly Phe Gln Gly Phe Val Met Ser Asp Trp Gly Ala His His Ser
290                 295                 300
Gly Val Ser Ser Ala Leu Ala Gly Leu Asp Met Ser Met Pro Gly Asp
305                 310                 315                 320
Thr Glu Phe Asp Ser Gly Leu Ser Phe Trp Gly Ser Asn Leu Thr Ile
                    325                 330                 335
Ala Ile Leu Asn Gly Thr Val Pro Glu Trp Arg Leu Asp Asp Met Ala
                340                 345                 350
Met Arg Ile Met Ala Ala Tyr Phe Lys Val Gly Leu Thr Ile Glu Asp
            355                 360                 365
Gln Pro Asp Val Asn Phe Asn Ala Trp Thr His Asp Thr Tyr Gly Tyr
        370                 375                 380
Lys Tyr Ala Tyr Ser Lys Glu Asp Tyr Glu Gln Val Asn Trp His Val
385                 390                 395                 400
Asp Val Arg Ser Asp His Asn Lys Leu Ile Arg Glu Thr Ala Ala Lys
                405                 410                 415
Gly Thr Val Leu Leu Lys Asn Asn Phe His Ala Leu Pro Leu Lys Gln
                420                 425                 430
Pro Arg Phe Val Ala Val Val Gly Gln Asp Ala Gly Pro Asn Pro Lys
            435                 440                 445
Gly Pro Asn Gly Cys Ala Asp Arg Gly Cys Asp Gln Gly Thr Leu Ala
        450                 455                 460
Met Gly Trp Gly Ser Gly Ser Thr Glu Phe Pro Tyr Leu Val Thr Pro
465                 470                 475                 480
Asp Thr Ala Ile Gln Ser Lys Val Leu Glu Tyr Gly Arg Tyr Glu
                485                 490                 495
Ser Ile Phe Asp Asn Tyr Asp Asp Asn Ala Ile Leu Ser Leu Val Ser
                500                 505                 510
Gln Pro Asp Ala Thr Cys Ile Val Phe Ala Asn Ala Asp Ser Gly Glu
            515                 520                 525
Gly Tyr Ile Thr Val Asp Asn Asn Trp Gly Asp Arg Asn Asn Leu Thr
        530                 535                 540
Leu Trp Gln Asn Ala Asp Gln Val Ile Ser Thr Val Ser Ser Arg Cys
545                 550                 555                 560
Asn Asn Thr Ile Val Val Leu His Ser Val Gly Pro Val Leu Leu Asn
                565                 570                 575
Gly Ile Tyr Glu His Pro Asn Ile Thr Ala Ile Val Trp Ala Gly Met
                580                 585                 590
Pro Gly Glu Glu Ser Gly Asn Ala Leu Val Asp Ile Leu Trp Gly Asn
            595                 600                 605
Val Asn Pro Ala Gly Arg Thr Pro Phe Thr Trp Ala Lys Ser Arg Glu
        610                 615                 620
Asp Tyr Gly Thr Asp Ile Met Tyr Glu Pro Asn Asn Gly Gln Arg Ala
625                 630                 635                 640
Pro Gln Gln Asp Phe Thr Glu Ser Ile Tyr Leu Asp Tyr Arg His Phe
                645                 650                 655
Asp Lys Ala Gly Ile Glu Pro Ile Tyr Glu Phe Gly Phe Gly Leu Ser
                660                 665                 670
Tyr Thr Thr Phe Glu Tyr Ser Asp Leu Arg Val Val Lys Lys Tyr Val
            675                 680                 685
Gln Pro Tyr Ser Pro Thr Thr Gly Thr Gly Ala Gln Ala Pro Ser Ile
        690                 695                 700
```

-continued

Gly Gln Pro Pro Ser Gln Asn Leu Asp Thr Tyr Lys Phe Pro Ala Thr
705                 710                 715                 720

Tyr Lys Tyr Ile Lys Thr Phe Ile Tyr Pro Tyr Leu Asn Ser Thr Val
            725                 730                 735

Ser Leu Arg Ala Ala Ser Lys Asp Pro Glu Tyr Gly Arg Thr Asp Phe
        740                 745                 750

Ile Pro Pro His Ala Arg Asp Gly Ser Pro Gln Pro Leu Asn Pro Ala
    755                 760                 765

Gly Asp Pro Val Ala Ser Gly Gly Asn Asn Met Leu Tyr Asp Glu Leu
770                 775                 780

Tyr Glu Val Thr Ala Gln Ile Lys Asn Thr Gly Asp Val Ala Gly Asp
785                 790                 795                 800

Glu Val Val Gln Leu Tyr Val Asp Leu Gly Gly Asp Asn Pro Pro Arg
                805                 810                 815

Gln Leu Arg Asn Phe Asp Arg Phe Tyr Leu Leu Pro Gly Gln Ser Ser
            820                 825                 830

Thr Phe Arg Ala Thr Leu Thr Arg Arg Asp Leu Ser Asn Trp Asp Ile
835                 840                 845

Glu Ala Gln Asn Trp Arg Val Thr Glu Ser Pro Lys Arg Val Tyr Val
    850                 855                 860

Gly Arg Ser Ser Arg Asp Leu Pro Leu Ser Ser Gln Leu Glu
865                 870                 875

<210> SEQ ID NO 31
<211> LENGTH: 2235
<212> TYPE: DNA
<213> ORGANISM: Trichoderma reesei

<400> SEQUENCE: 31
atgcgttacc gaacagcagc tgcgctggca cttgccactg ggccctttgc tagggcagac      60
agtcactcaa catcgggggc ctcggctgag gcagttgtac ctcctgcagg gactccatgg     120
ggaaccgcgt acgacaaggc gaaggccgca ttggcaaagc tcaatctcca agataaggtc     180
ggcatcgtga gcggtgtcgg ctggaacggc ggtccttgcg ttggaaacac atctccggcc     240
tccaagatca gctatccatc gctatgcctt caagacggac ccctcggtgt cgatactcg      300 acaggcagca cagcctttac gccgggcgtt caagcggcct cgacgtggga tgtcaatttg     360
atccgcgaac gtggacagtt catcggtgag gaggtgaagg cctcggggat tcatgtcata     420
cttggtcctg tggctgggcc gctgggaaag actccgcagg gcggtcgcaa ctgggagggc     480
ttcggtgtcg atccatatct cacgggcatt gccatgggtc aaaccatcaa cggcatccag     540
tcggtaggcg tgcaggcgac agcgaagcac tatatcctca cgagcagga gctcaatcga      600 gaaaccattt cgagcaaccc agatgaccga actctccatg agctgtatac ttggccattt     660
gccgacgcgg ttcaggccaa tgtcgcttct gtcatgtgct cgtacaacaa ggtcaatacc     720
acctgggcct gcgaggatca gtacacgctg cagactgtgc tgaaagacca gctggggttc     780
ccaggctatg tcatgacgga ctggaacgca cagcacacga ctgtccaaag cgcgaattct     840
gggcttgaca tgtcaatgcc tggcacagac ttcaacggta caatcggct ctggggtcca      900 gctctcacca atgcggtaaa tagcaatcag gtccccacga gcagagtcga cgatatggtg     960
actcgtatcc tcgccgcatg gtacttgaca ggccaggacc aggcaggcta tccgtcgttc    1020
aacatcagca gaaatgttca aggaaaccac aagaccaatg tcagggcaat tgccagggac    1080
ggcatcgttc tgctcaagaa tgacgccaac atcctgccgc tcaagaagcc cgctagcatt    1140

-continued

```
gccgtcgttg gatctgccgc aatcattggt aaccacgcca gaaactcgcc ctcgtgcaac    1200
gacaaaggct gcgacgacgg ggccttgggc atgggttggg gttccggcgc cgtcaactat    1260
ccgtacttcg tcgcgcccta cgatgccatc aataccagag cgtcttcgca gggcacccag    1320
gttaccttga gcaacaccga caacacgtcc tcaggcgcat ctgcagcaag aggaaaggac    1380
gtcgccatcg tcttcatcac cgccgactcg ggtgaaggct acatcaccgt ggagggcaac    1440
gcgggcgatc gcaacaacct ggatccgtgg cacaacggca atgccctggt ccaggcggtg    1500
gccggtgcca acagcaacgt cattgttgtt gtccactccg ttggcgccat cattctggag    1560
cagattcttg ctcttccgca ggtcaaggcc gttgtctggg cgggtcttcc ttctcaggag    1620
agcggcaatg cgctcgtcga cgtgctgtgg ggagatgtca gcccttctgg caagctggtg    1680
tacaccattg cgaagagccc caatgactat aacactcgca tcgtttccgg cggcagtgac    1740
agcttcagcg agggactgtt catcgactat aagcacttcg acgacgccaa tatcacgccg    1800
cggtacgagt tcggctatgg actgtcttac accaagttca actactcacg cctctccgtc    1860
ttgtcgaccg ccaagtctgg tcctgcgact ggggccgttg tgccgggagg cccgagtgat    1920
ctgttccaga atgtcgcgac agtcaccgtt gacatcgcaa actctggcca agtgactggt    1980
gccgaggtag cccagctgta catcacctac ccatcttcag cacccaggac ccctccgaag    2040
cagctgcgag gctttgccaa gctgaacctc acgcctggtc agagcggaac agcaacgttc    2100
aacatccgac gacgagatct cagctactgg gacacggctt cgcagaaatg ggtggtgccg    2160
tcggggtcgt ttggcatcag cgtgggagcg agcagccggg atatcaggct gacgagcact    2220
ctgtcggtag cgtag                                                     2235
```

<210> SEQ ID NO 32
<211> LENGTH: 744
<212> TYPE: PRT
<213> ORGANISM: Trichoderma reesei

<400> SEQUENCE: 32

```
Met Arg Tyr Arg Thr Ala Ala Leu Ala Leu Ala Thr Gly Pro Phe
1               5                   10                  15

Ala Arg Ala Asp Ser His Ser Thr Ser Gly Ala Ser Ala Glu Ala Val
                20                  25                  30

Val Pro Pro Ala Gly Thr Pro Trp Gly Thr Ala Tyr Asp Lys Ala Lys
            35                  40                  45

Ala Ala Leu Ala Lys Leu Asn Leu Gln Asp Lys Val Gly Ile Val Ser
        50                  55                  60

Gly Val Gly Trp Asn Gly Gly Pro Cys Val Gly Asn Thr Ser Pro Ala
65                  70                  75                  80

Ser Lys Ile Ser Tyr Pro Ser Leu Cys Leu Gln Asp Gly Pro Leu Gly
                85                  90                  95

Val Arg Tyr Ser Thr Gly Ser Thr Ala Phe Thr Pro Gly Val Gln Ala
            100                 105                 110

Ala Ser Thr Trp Asp Val Asn Leu Ile Arg Glu Arg Gly Gln Phe Ile
        115                 120                 125

Gly Glu Glu Val Lys Ala Ser Gly Ile His Val Ile Leu Gly Pro Val
    130                 135                 140

Ala Gly Pro Leu Gly Lys Thr Pro Gln Gly Gly Arg Asn Trp Glu Gly
145                 150                 155                 160

Phe Gly Val Asp Pro Tyr Leu Thr Gly Ile Ala Met Gly Gln Thr Ile
                165                 170                 175
```

```
Asn Gly Ile Gln Ser Val Gly Val Gln Ala Thr Ala Lys His Tyr Ile
            180                 185                 190

Leu Asn Glu Gln Glu Leu Asn Arg Glu Thr Ile Ser Ser Asn Pro Asp
            195                 200                 205

Asp Arg Thr Leu His Glu Leu Tyr Thr Trp Pro Phe Ala Asp Ala Val
210                 215                 220

Gln Ala Asn Val Ala Ser Val Met Cys Ser Tyr Asn Lys Val Asn Thr
225                 230                 235                 240

Thr Trp Ala Cys Glu Asp Gln Tyr Thr Leu Gln Thr Val Leu Lys Asp
            245                 250                 255

Gln Leu Gly Phe Pro Gly Tyr Val Met Thr Asp Trp Asn Ala Gln His
            260                 265                 270

Thr Thr Val Gln Ser Ala Asn Ser Gly Leu Asp Met Ser Met Pro Gly
            275                 280                 285

Thr Asp Phe Asn Gly Asn Asn Arg Leu Trp Gly Pro Ala Leu Thr Asn
            290                 295                 300

Ala Val Asn Ser Asn Gln Val Pro Thr Ser Arg Val Asp Asp Met Val
305                 310                 315                 320

Thr Arg Ile Leu Ala Ala Trp Tyr Leu Thr Gly Gln Asp Gln Ala Gly
            325                 330                 335

Tyr Pro Ser Phe Asn Ile Ser Arg Asn Val Gln Gly Asn His Lys Thr
            340                 345                 350

Asn Val Arg Ala Ile Ala Arg Asp Gly Ile Val Leu Leu Lys Asn Asp
            355                 360                 365

Ala Asn Ile Leu Pro Leu Lys Lys Pro Ala Ser Ile Ala Val Val Gly
            370                 375                 380

Ser Ala Ala Ile Ile Gly Asn His Ala Arg Asn Ser Pro Ser Cys Asn
385                 390                 395                 400

Asp Lys Gly Cys Asp Asp Gly Ala Leu Gly Met Gly Trp Gly Ser Gly
            405                 410                 415

Ala Val Asn Tyr Pro Tyr Phe Val Ala Pro Tyr Asp Ala Ile Asn Thr
            420                 425                 430

Arg Ala Ser Ser Gln Gly Thr Gln Val Thr Leu Ser Asn Thr Asp Asn
            435                 440                 445

Thr Ser Ser Gly Ala Ser Ala Ala Arg Gly Lys Asp Val Ala Ile Val
450                 455                 460

Phe Ile Thr Ala Asp Ser Gly Glu Gly Tyr Ile Thr Val Glu Gly Asn
465                 470                 475                 480

Ala Gly Asp Arg Asn Asn Leu Asp Pro Trp His Asn Gly Asn Ala Leu
            485                 490                 495

Val Gln Ala Val Ala Gly Ala Asn Ser Asn Val Ile Val Val His
            500                 505                 510

Ser Val Gly Ala Ile Ile Leu Glu Gln Ile Leu Ala Leu Pro Gln Val
            515                 520                 525

Lys Ala Val Val Trp Ala Gly Leu Pro Ser Gln Glu Ser Gly Asn Ala
            530                 535                 540

Leu Val Asp Val Leu Trp Gly Asp Val Ser Pro Ser Gly Lys Leu Val
545                 550                 555                 560

Tyr Thr Ile Ala Lys Ser Pro Asn Asp Tyr Asn Thr Arg Ile Val Ser
            565                 570                 575

Gly Gly Ser Asp Ser Phe Ser Glu Gly Leu Phe Ile Asp Tyr Lys His
            580                 585                 590
```

```
Phe Asp Asp Ala Asn Ile Thr Pro Arg Tyr Glu Phe Gly Tyr Gly Leu
            595                 600                 605
Ser Tyr Thr Lys Phe Asn Tyr Ser Arg Leu Ser Val Leu Ser Thr Ala
        610                 615                 620
Lys Ser Gly Pro Ala Thr Gly Ala Val Val Pro Gly Gly Pro Ser Asp
625                 630                 635                 640
Leu Phe Gln Asn Val Ala Thr Thr Val Asp Ile Ala Asn Ser Gly
            645                 650                 655
Gln Val Thr Gly Ala Glu Val Ala Gln Leu Tyr Ile Thr Tyr Pro Ser
            660                 665                 670
Ser Ala Pro Arg Thr Pro Pro Lys Gln Leu Arg Gly Phe Ala Lys Leu
        675                 680                 685
Asn Leu Thr Pro Gly Gln Ser Gly Thr Ala Thr Phe Asn Ile Arg Arg
        690                 695                 700
Arg Asp Leu Ser Tyr Trp Asp Thr Ala Ser Gln Lys Trp Val Val Pro
705                 710                 715                 720
Ser Gly Ser Phe Gly Ile Ser Val Gly Ala Ser Ser Arg Asp Ile Arg
            725                 730                 735
Leu Thr Ser Thr Leu Ser Val Ala
            740

<210> SEQ ID NO 33
<211> LENGTH: 29
<212> TYPE: DNA
<213> ORGANISM: Trichoderma reesei

<400> SEQUENCE: 33
aacgttaatt aaggaatcgt tttgtgttt                                    29

<210> SEQ ID NO 34
<211> LENGTH: 29
<212> TYPE: DNA
<213> ORGANISM: Trichoderma reesei

<400> SEQUENCE: 34
agtactagta gctccgtggc gaaagcctg                                    29

<210> SEQ ID NO 35
<211> LENGTH: 31
<212> TYPE: DNA
<213> ORGANISM: Saccharomyces cerevisiae

<400> SEQUENCE: 35
ttgaattgaa aatagattga tttaaaactt c                                 31

<210> SEQ ID NO 36
<211> LENGTH: 25
<212> TYPE: DNA
<213> ORGANISM: Saccharomyces cerevisiae

<400> SEQUENCE: 36
ttgcatgcgt aatcatggtc atagc                                        25

<210> SEQ ID NO 37
<211> LENGTH: 26
<212> TYPE: DNA
<213> ORGANISM: Saccharomyces cerevisiae

<400> SEQUENCE: 37
ttgaattcat gggtaataac tgatat                                       26
```

<210> SEQ ID NO 38
<211> LENGTH: 32
<212> TYPE: DNA
<213> ORGANISM: Saccharomyces cerevisiae

<400> SEQUENCE: 38
aaatcaatct attttcaatt caattcatca tt                          32

<210> SEQ ID NO 39
<211> LENGTH: 11
<212> TYPE: DNA
<213> ORGANISM: Aspergillus niger

<400> SEQUENCE: 39
gtactaaaac c                                                 11

<210> SEQ ID NO 40
<211> LENGTH: 11
<212> TYPE: DNA
<213> ORGANISM: Aspergillus niger

<400> SEQUENCE: 40
ccgttaaatt t                                                 11

<210> SEQ ID NO 41
<211> LENGTH: 45
<212> TYPE: DNA
<213> ORGANISM: Aspergillus niger

<400> SEQUENCE: 41
ggatgctgtt gactccggaa atttaacggt ttggtcttgc atccc            45

<210> SEQ ID NO 42
<211> LENGTH: 14
<212> TYPE: DNA
<213> ORGANISM: Aspergillus niger

<400> SEQUENCE: 42
atgcaattta aact                                              14

<210> SEQ ID NO 43
<211> LENGTH: 14
<212> TYPE: DNA
<213> ORGANISM: Aspergillus niger

<400> SEQUENCE: 43
cggcaattta acgg                                              14

<210> SEQ ID NO 44
<211> LENGTH: 44
<212> TYPE: DNA
<213> ORGANISM: Aspergillus niger

<400> SEQUENCE: 44
ggtattgtcc tgcagacggc aatttaacgg cttctgcgaa tcgc             44

<210> SEQ ID NO 45
<211> LENGTH: 29
<212> TYPE: DNA
<213> ORGANISM: Humicola insolens

<400> SEQUENCE: 45
aagcttaagc atgcgttcct ccccccctcc                29

<210> SEQ ID NO 46
<211> LENGTH: 32
<212> TYPE: DNA
<213> ORGANISM: Humicola insolens

<400> SEQUENCE: 46
ctgcagaatt ctacaggcac tgatggtacc ag              32

<210> SEQ ID NO 47
<211> LENGTH: 32
<212> TYPE: DNA
<213> ORGANISM: Trichoderma reesei

<400> SEQUENCE: 47
ctgcagaatt ctacaggcac tgatggtacc ag              32

<210> SEQ ID NO 48
<211> LENGTH: 36
<212> TYPE: DNA
<213> ORGANISM: Trichoderma reesei

<400> SEQUENCE: 48
accgcggact gcgcatcatg cgttcctccc ccctcc          36

<210> SEQ ID NO 49
<211> LENGTH: 29
<212> TYPE: DNA
<213> ORGANISM: Trichoderma reesei

<400> SEQUENCE: 49
aaacgtcgac cgaatgtagg attgttatc                  29

<210> SEQ ID NO 50
<211> LENGTH: 17
<212> TYPE: DNA
<213> ORGANISM: Trichoderma reesei

<400> SEQUENCE: 50
gatgcgcagt ccgcggt                               17

<210> SEQ ID NO 51
<211> LENGTH: 29
<212> TYPE: DNA
<213> ORGANISM: Trichoderma reesei

<400> SEQUENCE: 51
aaacgtcgac cgaatgtagg attgttatc                  29

<210> SEQ ID NO 52
<211> LENGTH: 36
<212> TYPE: DNA
<213> ORGANISM: Trichoderma reesei

<400> SEQUENCE: 52
ggagggggga ggaacgcatg atgcgcagtc cgcggt          36

<210> SEQ ID NO 53
<211> LENGTH: 29
<212> TYPE: DNA
<213> ORGANISM: Trichoderma reesei

<400> SEQUENCE: 53

-continued

```
aaacgtcgac cgaatgtagg attgttatc                                          29

<210> SEQ ID NO 54
<211> LENGTH: 32
<212> TYPE: DNA
<213> ORGANISM: Trichoderma reesei

<400> SEQUENCE: 54
ctgcagaatt ctacaggcac tgatggtacc ag                                      32

<210> SEQ ID NO 55
<211> LENGTH: 46
<212> TYPE: DNA
<213> ORGANISM: Aspergillus oryzae

<400> SEQUENCE: 55
atagtcaacc gcggactgcg catcatgaag cttggttgga tcgagg                       46

<210> SEQ ID NO 56
<211> LENGTH: 26
<212> TYPE: DNA
<213> ORGANISM: Aspergillus oryzae

<400> SEQUENCE: 56
actagtttac tgggccttag gcagcg                                             26

<210> SEQ ID NO 57
<211> LENGTH: 26
<212> TYPE: DNA
<213> ORGANISM: Trichoderma reesei

<400> SEQUENCE: 57
gtcgactcga agcccgaatg taggat                                             26

<210> SEQ ID NO 58
<211> LENGTH: 45
<212> TYPE: DNA
<213> ORGANISM: Trichoderma reesei

<400> SEQUENCE: 58
cctcgatcca accaagcttc atgatgcgca gtccgcggtt gacta                        45

<210> SEQ ID NO 59
<211> LENGTH: 57
<212> TYPE: DNA
<213> ORGANISM: Aspergillus oryzae

<400> SEQUENCE: 59
atgaagcttg gttggatcga ggtggccgca ttggcggctg cctcagtagt cagtgcc           57

<210> SEQ ID NO 60
<211> LENGTH: 19
<212> TYPE: PRT
<213> ORGANISM: Aspergillus oryzae

<400> SEQUENCE: 60

Met Lys Leu Gly Trp Ile Glu Val Ala Ala Leu Ala Ala Ala Ser Val
1               5                   10                  15

Val Ser Ala

<210> SEQ ID NO 61
<211> LENGTH: 42
```

```
<212> TYPE: DNA
<213> ORGANISM: Aspergillus oryzae

<400> SEQUENCE: 61
tgccggtgtt ggcccttgcc aaggatgatc tcgcgtactc cc                          42

<210> SEQ ID NO 62
<211> LENGTH: 28
<212> TYPE: DNA
<213> ORGANISM: Aspergillus oryzae

<400> SEQUENCE: 62
gactagtctt actgggcctt aggcagcg                                          28

<210> SEQ ID NO 63
<211> LENGTH: 63
<212> TYPE: DNA
<213> ORGANISM: Humicola insolens

<400> SEQUENCE: 63
atgcgttcct cccccctcct ccgctccgcc gttgtggccg ccctgccggt gttggccctt       60
gcc                                                                     63

<210> SEQ ID NO 64
<211> LENGTH: 21
<212> TYPE: PRT
<213> ORGANISM: Humicola insolens

<400> SEQUENCE: 64

Met Arg Ser Ser Pro Leu Leu Arg Ser Ala Val Val Ala Ala Leu Pro
1               5                   10                  15

Val Leu Ala Leu Ala
            20

<210> SEQ ID NO 65
<211> LENGTH: 30
<212> TYPE: DNA
<213> ORGANISM: Trichoderma reesei

<400> SEQUENCE: 65
acgcgtcgac cgaatgtagg attgttatcc                                        30

<210> SEQ ID NO 66
<211> LENGTH: 42
<212> TYPE: DNA
<213> ORGANISM: Trichoderma reesei

<400> SEQUENCE: 66
gggagtacgc gagatcatcc ttggcaaggg ccaacaccgg ca                          42

<210> SEQ ID NO 67
<211> LENGTH: 20
<212> TYPE: DNA
<213> ORGANISM: Trichoderma reesei

<400> SEQUENCE: 67
cccaagctta gccaagaaca                                                   20

<210> SEQ ID NO 68
<211> LENGTH: 29
<212> TYPE: DNA
<213> ORGANISM: Trichoderma reesei
```

```
<400> SEQUENCE: 68
gggggaggaa cgcatgggat ctggacggc                                          29

<210> SEQ ID NO 69
<211> LENGTH: 30
<212> TYPE: DNA
<213> ORGANISM: Aspergillus oryzae

<400> SEQUENCE: 69
gccgtccaga tccccatgcg ttcctccccc                                         30

<210> SEQ ID NO 70
<211> LENGTH: 20
<212> TYPE: DNA
<213> ORGANISM: Aspergillus oryzae

<400> SEQUENCE: 70
ccaagcttgt tcagagtttc                                                    20

<210> SEQ ID NO 71
<211> LENGTH: 20
<212> TYPE: DNA
<213> ORGANISM: Aspergillus oryzae

<400> SEQUENCE: 71
ggactgcgca gcatgcgttc                                                    20

<210> SEQ ID NO 72
<211> LENGTH: 30
<212> TYPE: DNA
<213> ORGANISM: Aspergillus oryzae

<400> SEQUENCE: 72
agttaattaa ttactgggcc ttaggcagcg                                         30

<210> SEQ ID NO 73
<211> LENGTH: 3294
<212> TYPE: DNA
<213> ORGANISM: Aspergillus oryzae

<400> SEQUENCE: 73
atgcgttcct ccccctcct  ccgctccgcc gttgtggccg ccctgccggt gttggccctt         60
gccgctgatg gcaggtccac ccgctactgg gactgctgca agccttcgtg cggctgggcc        120
aagaaggctc ccgtgaacca gcctgtcttt tcctgcaacg ccaacttcca gcgtatcacg        180
gacttcgacg ccaagtccgg ctgcgagccg ggcggtgtcg cctactcgtg cgccgaccag        240
acccatgggg ctgtgaacga cgacttcgcg ctcggttttg ctgccacctc tattgccggc        300
agcaatgagg cgggctggtg ctgcgcctgc tacgagctca ccttcacatc cggtcctgtt        360
gctggcaaga agatggtcgt ccagtccacc agcactggcg tgatcttgg  cagcaaccac        420 ttcgatctca acatccccgg cggcggcgtc ggcatcttcg acggatgcac tccccagttc        480
ggtggtctgc ccggccagcg ctacggcggc atctcgtccc gcaacgagtg cgatcggttc        540
cccgacgccc tcaagcccgg ctgctactgg cgcttcgact ggttcaagaa cgccgacaat        600
ccgagcttca gcttccgtca ggtccagtgc ccagccgagc tcgtcgctcg caccggatgc        660
cgccgcaacg acgacggcaa cttccctgcc gtccagatcc ccatgcgttc ctcccccctc        720
ctccgctccg ccgttgtggc cgccctgccg gtgttggccc ttgccaagga tgatctcgcg        780
tactccccct ctttctaccc ttccccatgg gcagatggtc agggtgaatg ggcggaagta        840
```

-continued

| | |
|---|---|
| tacaaacgcg ctgtagacat agtttcccag atgacgttga cagagaaagt caacttaacg | 900 |
| actggaacag gatggcaact agagaggtgt gttggacaaa ctggcagtgt tcccagactc | 960 |
| aacatcccca gcttgtgttt gcaggatagt cctcttggta ttcgtttctc ggactacaat | 1020 |
| tcagctttcc ctgcgggtgt taatgtcgct gccacctggg acaagacgct cgcctacctt | 1080 |
| cgtggtcagg caatgggtga ggagttcagt gataagggta ttgacgttca gctgggtcct | 1140 |
| gctgctggcc ctctcggtgc tcatccggat ggcggtagaa actgggaagg tttctcacca | 1200 |
| gatccagccc tcaccggtgt acttttgcg gagacgatta agggtattca agatgctggt | 1260 |
| gtcattgcga cagctaagca ttatatcatg aacgaacaag agcatttccg ccaacaaccc | 1320 |
| gaggctgcgg gttacggatt caacgtaagc gacagtttga gttccaacgt tgatgacaag | 1380 |
| actatgcatg aattgtacct ctggcccttc gcggatgcag tacgcgctgg agtcggtgct | 1440 |
| gtcatgtgct cttacaacca aatcaacaac agctacggtt gcgagaatag cgaaactctg | 1500 |
| aacaagcttt tgaaggcgga gcttggtttc caaggcttcg tcatgagtga ttggaccgct | 1560 |
| catcacagcg gcgtaggcgc tgctttagca ggtctggata tgtcgatgcc cggtgatgtt | 1620 |
| accttcgata gtggtacgtc tttctgggggt gcaaacttga cggtcggtgt ccttaacggt | 1680 |
| acaatccccc aatggcgtgt tgatgacatg gctgtccgta tcatggccgc ttattacaag | 1740 |
| gttggccgcg acaccaaata caccccctccc aacttcagct cgtggaccag ggacgaatat | 1800 |
| ggtttcgcgc ataaccatgt ttcggaaggt gcttacgaga gggtcaacga attcgtggac | 1860 |
| gtgcaacgcg atcatgccga cctaatccgt cgcatcggcg cgcagagcac tgttctgctg | 1920 |
| aagaacaagg gtgccttgcc cttgagccgc aaggaaaagc tggtcgccct tctgggagag | 1980 |
| gatgcgggtt ccaactcgtg gggcgctaac ggctgtgatg accgtggttg cgataacggt | 2040 |
| acccttgcca tggcctgggg tagcggtact gcgaatttcc cataccctcgt gacaccagag | 2100 |
| caggcgattc agaacgaagt tcttcagggc cgtggtaatg tcttcgccgt gaccgacagt | 2160 |
| tgggcgctcg acaagatcgc tgcggctgcc cgccaggcca gcgtatctct cgtgttcgtc | 2220 |
| aactccgact caggagaagg ctatcttagt gtggatggaa atgagggcga tcgtaacaac | 2280 |
| atcactctgt ggaagaacgg cgacaatgtg gtcaagaccg cagcgaataa ctgtaacaac | 2340 |
| accgttgtca tcatccactc cgtcggacca gttttgatcg atgaatggta tgaccacccc | 2400 |
| aatgtcactg gtattctctg ggctggtctg ccaggccagg agtctggtaa ctccattgcc | 2460 |
| gatgtgctgt acgtcgtgt caaccctggc gccaagtctc ctttcacttg gggcaagacc | 2520 |
| cgggagtcgt atggttctcc cttggtcaag gatgccaaca atggcaacgg agcgccccag | 2580 |
| tctgatttca cccagggtgt tttcatcgat taccgccatt tcgataagtt caatgagacc | 2640 |
| cctatctacg agtttggcta cggcttgagc tacaccacct tcgagctctc cgacctccat | 2700 |
| gttcagcccc tgaacgcgtc ccgatacact cccaccagtg gcatgactga agctgcaaag | 2760 |
| aactttggtg aaattggcga tcgtcggag tacgtgtatc cggaggggct ggaaaggatc | 2820 |
| catgagttta tctatccctg gatcaactct accgacctga aggcatcgtc tgacgattct | 2880 |
| aactacggct gggaagactc caagtatatt cccgaaggcg ccacggatgg gtctgcccag | 2940 |
| ccccgtttgc ccgctagtgg tggtgccgga ggaaaccccg gtctgtacga ggatcttttc | 3000 |
| cgcgtctctg tgaaggtcaa gaacacgggc aatgtcgccg gtgatgaagt tcctcagctg | 3060 |
| tacgttttccc taggcggccc gaatgagccc aaggtggtac tgcgcaagtt tgagcgtatt | 3120 |
| cacttggccc cttcgcagga ggccgtgtgg acaacgaccc ttacccgtcg tgaccttgca | 3180 |

```
aactgggacg tttcggctca ggactggacc gtcactcctt accccaagac gatctacgtt    3240
ggaaactcct cacggaaact gccgctccag gcctcgctgc ctaaggccca gtaa          3294
```

<210> SEQ ID NO 74
<211> LENGTH: 1097
<212> TYPE: PRT
<213> ORGANISM: Aspergillus oryzae

<400> SEQUENCE: 74

```
Met Arg Ser Ser Pro Leu Leu Arg Ser Ala Val Ala Ala Leu Pro
1               5                   10                  15

Val Leu Ala Leu Ala Ala Asp Gly Arg Ser Thr Arg Tyr Trp Asp Cys
            20                  25                  30

Cys Lys Pro Ser Cys Gly Trp Ala Lys Lys Ala Pro Val Asn Gln Pro
        35                  40                  45

Val Phe Ser Cys Asn Ala Asn Phe Gln Arg Ile Thr Asp Phe Asp Ala
    50                  55                  60

Lys Ser Gly Cys Glu Pro Gly Gly Val Ala Tyr Ser Cys Ala Asp Gln
65                  70                  75                  80

Thr Pro Trp Ala Val Asn Asp Asp Phe Ala Leu Gly Phe Ala Ala Thr
                85                  90                  95

Ser Ile Ala Gly Ser Asn Glu Ala Gly Trp Cys Cys Ala Cys Tyr Glu
            100                 105                 110

Leu Thr Phe Thr Ser Gly Pro Val Ala Gly Lys Lys Met Val Val Gln
        115                 120                 125

Ser Thr Ser Thr Gly Gly Asp Leu Gly Ser Asn His Phe Asp Leu Asn
    130                 135                 140

Ile Pro Gly Gly Gly Val Gly Ile Phe Asp Gly Cys Thr Pro Gln Phe
145                 150                 155                 160

Gly Gly Leu Pro Gly Gln Arg Tyr Gly Gly Ile Ser Ser Arg Asn Glu
                165                 170                 175

Cys Asp Arg Phe Pro Asp Ala Leu Lys Pro Gly Cys Tyr Trp Arg Phe
            180                 185                 190

Asp Trp Phe Lys Asn Ala Asp Asn Pro Ser Phe Ser Phe Arg Gln Val
        195                 200                 205

Gln Cys Pro Ala Glu Leu Val Ala Arg Thr Gly Cys Arg Arg Asn Asp
    210                 215                 220

Asp Gly Asn Phe Pro Ala Val Gln Ile Pro Met Arg Ser Ser Pro Leu
225                 230                 235                 240

Leu Arg Ser Ala Val Val Ala Ala Leu Pro Val Leu Ala Leu Ala Lys
                245                 250                 255

Asp Asp Leu Ala Tyr Ser Pro Pro Phe Tyr Pro Ser Pro Trp Ala Asp
            260                 265                 270

Gly Gln Gly Glu Trp Ala Glu Val Tyr Lys Arg Ala Val Asp Ile Val
        275                 280                 285

Ser Gln Met Thr Leu Thr Glu Lys Val Asn Leu Thr Thr Gly Thr Gly
    290                 295                 300

Trp Gln Leu Glu Arg Cys Val Gly Gln Thr Gly Ser Val Pro Arg Leu
305                 310                 315                 320

Asn Ile Pro Ser Leu Cys Leu Gln Asp Ser Pro Leu Gly Ile Arg Phe
                325                 330                 335

Ser Asp Tyr Asn Ser Ala Phe Pro Ala Gly Val Asn Val Ala Ala Thr
            340                 345                 350

Trp Asp Lys Thr Leu Ala Tyr Leu Arg Gly Gln Ala Met Gly Glu Glu
```

```
                355                 360                 365
Phe Ser Asp Lys Gly Ile Asp Val Gln Leu Gly Pro Ala Ala Gly Pro
    370                 375                 380
Leu Gly Ala His Pro Asp Gly Arg Asn Trp Glu Gly Phe Ser Pro
385                 390                 395                 400
Asp Pro Ala Leu Thr Gly Val Leu Phe Ala Glu Thr Ile Lys Gly Ile
                405                 410                 415
Gln Asp Ala Gly Val Ile Ala Thr Ala Lys His Tyr Ile Met Asn Glu
                420                 425                 430
Gln Glu His Phe Arg Gln Gln Pro Glu Ala Ala Gly Tyr Gly Phe Asn
            435                 440                 445
Val Ser Asp Ser Leu Ser Ser Asn Val Asp Asp Lys Thr Met His Glu
            450                 455                 460
Leu Tyr Leu Trp Pro Phe Ala Asp Ala Val Arg Ala Gly Val Gly Ala
465                 470                 475                 480
Val Met Cys Ser Tyr Asn Gln Ile Asn Asn Ser Tyr Gly Cys Glu Asn
                485                 490                 495
Ser Glu Thr Leu Asn Lys Leu Leu Lys Ala Glu Leu Gly Phe Gln Gly
            500                 505                 510
Phe Val Met Ser Asp Trp Thr Ala His His Ser Gly Val Gly Ala Ala
            515                 520                 525
Leu Ala Gly Leu Asp Met Ser Met Pro Gly Asp Val Thr Phe Asp Ser
530                 535                 540
Gly Thr Ser Phe Trp Gly Ala Asn Leu Thr Val Gly Val Leu Asn Gly
545                 550                 555                 560
Thr Ile Pro Gln Trp Arg Val Asp Asp Met Ala Val Arg Ile Met Ala
                565                 570                 575
Ala Tyr Tyr Lys Val Gly Arg Asp Thr Lys Tyr Thr Pro Pro Asn Phe
            580                 585                 590
Ser Ser Trp Thr Arg Asp Glu Tyr Gly Phe Ala His Asn His Val Ser
            595                 600                 605
Glu Gly Ala Tyr Glu Arg Val Asn Glu Phe Val Asp Val Gln Arg Asp
610                 615                 620
His Ala Asp Leu Ile Arg Arg Ile Gly Ala Gln Ser Thr Val Leu Leu
625                 630                 635                 640
Lys Asn Lys Gly Ala Leu Pro Leu Ser Arg Lys Glu Lys Leu Val Ala
                645                 650                 655
Leu Leu Gly Glu Asp Ala Gly Ser Asn Ser Trp Gly Ala Asn Gly Cys
            660                 665                 670
Asp Asp Arg Gly Cys Asp Asn Gly Thr Leu Ala Met Ala Trp Gly Ser
        675                 680                 685
Gly Thr Ala Asn Phe Pro Tyr Leu Val Thr Pro Glu Gln Ala Ile Gln
        690                 695                 700
Asn Glu Val Leu Gln Gly Arg Gly Asn Val Phe Ala Val Thr Asp Ser
705                 710                 715                 720
Trp Ala Leu Asp Lys Ile Ala Ala Ala Arg Gln Ala Ser Val Ser
                725                 730                 735
Leu Val Phe Val Asn Ser Asp Ser Gly Glu Gly Tyr Leu Ser Val Asp
            740                 745                 750
Gly Asn Glu Gly Asp Arg Asn Asn Ile Thr Leu Trp Lys Asn Gly Asp
            755                 760                 765
Asn Val Val Lys Thr Ala Ala Asn Asn Cys Asn Asn Thr Val Val Ile
            770                 775                 780
```

Ile His Ser Val Gly Pro Val Leu Ile Asp Glu Trp Tyr Asp His Pro
785                 790                 795                 800

Asn Val Thr Gly Ile Leu Trp Ala Gly Leu Pro Gly Gln Glu Ser Gly
            805                 810                 815

Asn Ser Ile Ala Asp Val Leu Tyr Gly Arg Val Asn Pro Gly Ala Lys
        820                 825                 830

Ser Pro Phe Thr Trp Gly Lys Thr Arg Glu Ser Tyr Gly Ser Pro Leu
    835                 840                 845

Val Lys Asp Ala Asn Asn Gly Asn Gly Ala Pro Gln Ser Asp Phe Thr
850                 855                 860

Gln Gly Val Phe Ile Asp Tyr Arg His Phe Asp Lys Phe Asn Glu Thr
865                 870                 875                 880

Pro Ile Tyr Glu Phe Gly Tyr Gly Leu Ser Tyr Thr Thr Phe Glu Leu
            885                 890                 895

Ser Asp Leu His Val Gln Pro Leu Asn Ala Ser Arg Tyr Thr Pro Thr
        900                 905                 910

Ser Gly Met Thr Glu Ala Ala Lys Asn Phe Gly Glu Ile Gly Asp Ala
    915                 920                 925

Ser Glu Tyr Val Tyr Pro Glu Gly Leu Glu Arg Ile His Glu Phe Ile
930                 935                 940

Tyr Pro Trp Ile Asn Ser Thr Asp Leu Lys Ala Ser Ser Asp Ser
945                 950                 955                 960

Asn Tyr Gly Trp Glu Asp Ser Lys Tyr Ile Pro Glu Gly Ala Thr Asp
            965                 970                 975

Gly Ser Ala Gln Pro Arg Leu Pro Ala Ser Gly Gly Ala Gly Gly Asn
        980                 985                 990

Pro Gly Leu Tyr Glu Asp Leu Phe Arg Val Ser Val Lys Val Lys Asn
    995                 1000                1005

Thr Gly Asn Val Ala Gly Asp Glu Val Pro Gln Leu Tyr Val Ser
    1010                1015                1020

Leu Gly Gly Pro Asn Glu Pro Lys Val Val Leu Arg Lys Phe Glu
    1025                1030                1035

Arg Ile His Leu Ala Pro Ser Gln Glu Ala Val Trp Thr Thr Thr
    1040                1045                1050

Leu Thr Arg Arg Asp Leu Ala Asn Trp Asp Val Ser Ala Gln Asp
    1055                1060                1065

Trp Thr Val Thr Pro Tyr Pro Lys Thr Ile Tyr Val Gly Asn Ser
    1070                1075                1080

Ser Arg Lys Leu Pro Leu Gln Ala Ser Leu Pro Lys Ala Gln
    1085                1090                1095

<210> SEQ ID NO 75
<211> LENGTH: 3294
<212> TYPE: DNA
<213> ORGANISM: Aspergillus oryzae

<400> SEQUENCE: 75
atgcgttcct ccccctcct ccgctccgcc gttgtggccg ccctgccggt gttggccctt      60
gccgctgatg caggtccac ccgctactgg gactgctgca agccttcgtg cggctgggcc     120
aagaaggctc ccgtgaacca gcctgtcttt tcctgcaacg ccaacttcca gcgtatcacg     180
gacttcgacg ccaagtccgg ctgcgagccg ggcggtgtcg cctactcgtg cgccgaccag     240
accccatggg ctgtgaacga cgacttcgcg ctcggttttg ctgccaccct tattgccggc     300

```
agcaatgagg cgggctggtg ctgcgcctgc tacgagctca ccttcacatc cggtcctgtt    360
gctggcaaga agatggtcgt ccagtccacc agcactggcg gtgatcttgg cagcaaccac    420
ttcgatctca acatccccgg cggcggcgtc ggcatcttcg acggatgcac tccccagttc    480
ggtggtctgc ccggccagcg ctacggcggc atctcgtccc gcaacgagtg cgatcggttc    540
cccgacgccc tcaagcccgg ctgctactgg cgcttcgact ggttcaagaa cgccgacaat    600
ccgagcttca gcttccgtca ggtccagtgc ccagccgagc tcgtcgctcg caccggatgc    660
cgccgcaacg acgacggcaa cttccctgcc gtccagatcc ccatgcgttc ctcccccctc    720
ctccgctccg ccgttgtggc cgccctgccg gtgttgggcc ttgccaagga tgatctcgcg    780
tactcccctc ctttctaccc ttccccatgg gcagatggtc agggtgaatg ggcggaagta    840
tacaaacgcg ctgtagacat agtttcccag atgacgttga cagagaaagt caacttaacg    900
actggaacag gatggcaact agagaggtgt gttggacaaa ctggcagtgt tcccagactc    960
aacatcccca gcttgtgttt gcaggatagt cctcttggta ttcgtttctc ggactacaat   1020
tcagctttcc ctgcgggtgt taatgtcgct gccacctggg acaagacgct cgcctacctt   1080
cgtggtcagg caatgggtga ggagttcagt gataagggta ttgacgttca gctgggtcct   1140
gctgctggcc ctctcggtgc tcatccggat ggcggtagaa actgggaaag tttctcacca   1200
gatccagccc tcaccggtgt acttttttgcg gagacgatta agggtattca agatgctggt   1260
gtcattgcga cagctaagca ttatatcatg aacgaacaag agcatttccg ccaacaaccc   1320
gaggctgcgg gttacggatt caacgtaagc gacagtttga gttccaacgt tgatgacaag   1380
actatgcatg aattgtacct ctggcccttc gcggatgcag tacgcgctgg agtcggtgct   1440
gttatgtgct cttacaacca aatcaacaac agctacggtt gcgagaatag cgaaactctg   1500
aacaagcttt tgaaggcgga gcttggtttc caaggcttcg tcatgagtga ttggaccgct   1560
caacacagcg gcgtaggcgc tgctttagca ggtctggata tgtcgatgcc cggtgatgtt   1620
accttcgata gtggtacgtc tttctggggt gcaaacttga cggtcggtgt ccttaacggt   1680
acaatccccc aatggcgtgt tgatgacatg gctgtccgta tcatggccgc ttattacaag   1740 gttgccgcg acaccaaata cacccctccc aacttcagct cgtggaccag ggacgaatat   1800
ggtttcgcgc ataaccatgt ttcggaaggt gcttacgaga gggtcaacga attcgtggac   1860
gtgcaacgcg atcatgccga cctaatccgt cgcatcggcg cgcagagcac tgttctgctg   1920
aagaacaagg gtgccttgcc cttgagccgc aaggaaaagc tggtcgccct tctgggagag   1980
gatgcgggtt ccaactcgtg gggcgctaac ggctgtgatg accgtggttg cgataacggt   2040
acccttgcca tggcctgggg tagcggtact gcgaatttcc cataccctcgt gacaccagag   2100 caggcgattc agaacgaagt tcttcagggc cgtggtaatg tcttcgccgt gaccgacagt   2160
tgggcgctcg acaagatcgc tgcggctgcc cgccaggcca gcgtatctct cgtgttcgtc   2220
aactccgact caggagaagg ctatcttagt gtggatggaa atgagggcga tcgtaacaac   2280
atcactctgt ggaagaacgg cgacaatgtg gtcaagaccg cagcgaataa ctgtaacaac   2340
accgttgtca tcatccactc cgtcggacca gttttgatcg atgaatggta tgaccacccc   2400
aatgtcactg gtattctctg ggctggtctg ccaggccagg agtctggtaa ctccattgcc   2460
gatgtgctgt acggtcgtgt caaccctggc gccaagtctc ctttcacttg ggcaagacc   2520 cgggagtcgt atggttctcc cttggtcaag gatgccaaca atggcaacgg agcgccccag   2580
tctgatttca cccagggtgt tttcatcgat taccgccatt tcgataagtt caatgagacc   2640
cctatctacg agtttggcta cggcttgagc tacaccacct tcgagctctc cgacctccat   2700
```

-continued

```
gttcagcccc tgaacgcgtc ccgatacact cccaccagtg gcatgactga agctgcaaag    2760
aactttggtg aaattggcga tgcgtcggag tacgtgtatc cggaggggct ggaaaggatc    2820
catgagttta tctatccctg gatcaactct accgacctga aggcatcgtc tgacgattct    2880
aactacggct gggaagactc caagtatatt cccgaaggcg ccacggatgg gtctgcccag    2940
ccccgtttgc ccgctagtgg tggtgccgga ggaaaccccg gtctgtacga ggatcttttc    3000
cgcgtctctg tgaaggtcaa gaacacgggc aatgtcgccg tgatgaagt tcctcagctg     3060 tacgtttccc taggcggccc gaatgagccc aaggtggtac tgcgcaagtt tgagcgtatt    3120
cacttggccc cttcgcagga ggccgtgtgg acaacgaccc ttacccgtcg tgaccttgca    3180
aactgggacg tttcggctca ggactggacc gtcactcctt accccaagac gatctacgtt    3240
ggaaactcct cacggaaact gccgctccag gcctcgctgc ctaaggccca gtaa           3294
```

<210> SEQ ID NO 76
<211> LENGTH: 1097
<212> TYPE: PRT
<213> ORGANISM: Aspergillus oryzae

<400> SEQUENCE: 76

```
Met Arg Ser Ser Pro Leu Leu Arg Ser Ala Val Val Ala Ala Leu Pro
1               5                   10                  15

Val Leu Ala Leu Ala Ala Asp Gly Arg Ser Thr Arg Tyr Trp Asp Cys
            20                  25                  30

Cys Lys Pro Ser Cys Gly Trp Ala Lys Lys Ala Pro Val Asn Gln Pro
        35                  40                  45

Val Phe Ser Cys Asn Ala Asn Phe Gln Arg Ile Thr Asp Phe Asp Ala
    50                  55                  60

Lys Ser Gly Cys Glu Pro Gly Gly Val Ala Tyr Ser Cys Ala Asp Gln
65                  70                  75                  80

Thr Pro Trp Ala Val Asn Asp Asp Phe Ala Leu Gly Phe Ala Ala Thr
                85                  90                  95

Ser Ile Ala Gly Ser Asn Glu Ala Gly Trp Cys Cys Ala Cys Tyr Glu
            100                 105                 110

Leu Thr Phe Thr Ser Gly Pro Val Ala Gly Lys Lys Met Val Val Gln
        115                 120                 125

Ser Thr Ser Thr Gly Gly Asp Leu Gly Ser Asn His Phe Asp Leu Asn
    130                 135                 140

Ile Pro Gly Gly Gly Val Gly Ile Phe Asp Gly Cys Thr Pro Gln Phe
145                 150                 155                 160

Gly Gly Leu Pro Gly Gln Arg Tyr Gly Gly Ile Ser Ser Arg Asn Glu
                165                 170                 175

Cys Asp Arg Phe Pro Asp Ala Leu Lys Pro Gly Cys Tyr Trp Arg Phe
            180                 185                 190

Asp Trp Phe Lys Asn Ala Asp Asn Pro Ser Phe Ser Phe Arg Gln Val
        195                 200                 205

Gln Cys Pro Ala Glu Leu Val Ala Arg Thr Gly Cys Arg Arg Asn Asp
    210                 215                 220

Asp Gly Asn Phe Pro Ala Val Gln Ile Pro Met Arg Ser Ser Pro Leu
225                 230                 235                 240

Leu Arg Ser Ala Val Val Ala Ala Leu Pro Val Leu Ala Leu Ala Lys
                245                 250                 255

Asp Asp Leu Ala Tyr Ser Pro Pro Phe Tyr Pro Ser Trp Ala Asp
            260                 265                 270
```

```
Gly Gln Gly Glu Trp Ala Glu Val Tyr Lys Arg Ala Val Asp Ile Val
        275                 280                 285

Ser Gln Met Thr Leu Thr Glu Lys Val Asn Leu Thr Thr Gly Thr Gly
    290                 295                 300

Trp Gln Leu Glu Arg Cys Val Gly Gln Thr Gly Ser Val Pro Arg Leu
305                 310                 315                 320

Asn Ile Pro Ser Leu Cys Leu Gln Asp Ser Pro Leu Gly Ile Arg Phe
                325                 330                 335

Ser Asp Tyr Asn Ser Ala Phe Pro Ala Gly Val Asn Val Ala Ala Thr
            340                 345                 350

Trp Asp Lys Thr Leu Ala Tyr Leu Arg Gly Gln Ala Met Gly Glu Glu
        355                 360                 365

Phe Ser Asp Lys Gly Ile Asp Val Gln Leu Gly Pro Ala Ala Gly Pro
    370                 375                 380

Leu Gly Ala His Pro Asp Gly Arg Asn Trp Glu Ser Phe Ser Pro
385                 390                 395                 400

Asp Pro Ala Leu Thr Gly Val Leu Phe Ala Glu Thr Ile Lys Gly Ile
                405                 410                 415

Gln Asp Ala Gly Val Ile Ala Thr Ala Lys His Tyr Ile Met Asn Glu
            420                 425                 430

Gln Glu His Phe Arg Gln Gln Pro Glu Ala Ala Gly Tyr Gly Phe Asn
        435                 440                 445

Val Ser Asp Ser Leu Ser Ser Asn Val Asp Asp Lys Thr Met His Glu
    450                 455                 460

Leu Tyr Leu Trp Pro Phe Ala Asp Ala Val Arg Ala Gly Val Gly Ala
465                 470                 475                 480

Val Met Cys Ser Tyr Asn Gln Ile Asn Asn Ser Tyr Gly Cys Glu Asn
                485                 490                 495

Ser Glu Thr Leu Asn Lys Leu Leu Lys Ala Glu Leu Gly Phe Gln Gly
            500                 505                 510

Phe Val Met Ser Asp Trp Thr Ala Gln His Ser Gly Val Gly Ala Ala
        515                 520                 525

Leu Ala Gly Leu Asp Met Ser Met Pro Gly Asp Val Thr Phe Asp Ser
    530                 535                 540

Gly Thr Ser Phe Trp Gly Ala Asn Leu Thr Val Gly Val Leu Asn Gly
545                 550                 555                 560

Thr Ile Pro Gln Trp Arg Val Asp Asp Met Ala Val Arg Ile Met Ala
                565                 570                 575

Ala Tyr Tyr Lys Val Gly Arg Asp Thr Lys Tyr Thr Pro Pro Asn Phe
            580                 585                 590

Ser Ser Trp Thr Arg Asp Glu Tyr Gly Phe Ala His Asn His Val Ser
        595                 600                 605

Glu Gly Ala Tyr Glu Arg Val Asn Glu Phe Val Asp Val Gln Arg Asp
    610                 615                 620

His Ala Asp Leu Ile Arg Arg Ile Gly Ala Gln Ser Thr Val Leu Leu
625                 630                 635                 640

Lys Asn Lys Gly Ala Leu Pro Leu Ser Arg Lys Glu Lys Leu Val Ala
                645                 650                 655

Leu Leu Gly Glu Asp Ala Gly Ser Asn Ser Trp Gly Ala Asn Gly Cys
            660                 665                 670

Asp Asp Arg Gly Cys Asp Asn Gly Thr Leu Ala Met Ala Trp Gly Ser
        675                 680                 685
```

-continued

```
Gly Thr Ala Asn Phe Pro Tyr Leu Val Thr Pro Glu Gln Ala Ile Gln
    690                 695                 700
Asn Glu Val Leu Gln Gly Arg Gly Asn Val Phe Ala Val Thr Asp Ser
705                 710                 715                 720
Trp Ala Leu Asp Lys Ile Ala Ala Ala Arg Gln Ala Ser Val Ser
                725                 730                 735
Leu Val Phe Val Asn Ser Asp Ser Gly Glu Gly Tyr Leu Ser Val Asp
                740                 745                 750
Gly Asn Glu Gly Asp Arg Asn Asn Ile Thr Leu Trp Lys Asn Gly Asp
                755                 760                 765
Asn Val Val Lys Thr Ala Ala Asn Asn Cys Asn Asn Thr Val Val Ile
770                 775                 780
Ile His Ser Val Gly Pro Val Leu Ile Asp Glu Trp Tyr Asp His Pro
785                 790                 795                 800
Asn Val Thr Gly Ile Leu Trp Ala Gly Leu Pro Gly Gln Glu Ser Gly
                805                 810                 815
Asn Ser Ile Ala Asp Val Leu Tyr Gly Arg Val Asn Pro Gly Ala Lys
                820                 825                 830
Ser Pro Phe Thr Trp Gly Lys Thr Arg Glu Ser Tyr Gly Ser Pro Leu
                835                 840                 845
Val Lys Asp Ala Asn Asn Gly Asn Gly Ala Pro Gln Ser Asp Phe Thr
850                 855                 860
Gln Gly Val Phe Ile Asp Tyr Arg His Phe Asp Lys Phe Asn Glu Thr
865                 870                 875                 880
Pro Ile Tyr Glu Phe Gly Tyr Gly Leu Ser Tyr Thr Thr Phe Glu Leu
                885                 890                 895
Ser Asp Leu His Val Gln Pro Leu Asn Ala Ser Arg Tyr Thr Pro Thr
                900                 905                 910
Ser Gly Met Thr Glu Ala Ala Lys Asn Phe Gly Glu Ile Gly Asp Ala
                915                 920                 925
Ser Glu Tyr Val Tyr Pro Glu Gly Leu Glu Arg Ile His Glu Phe Ile
                930                 935                 940
Tyr Pro Trp Ile Asn Ser Thr Asp Leu Lys Ala Ser Ser Asp Asp Ser
945                 950                 955                 960
Asn Tyr Gly Trp Glu Asp Ser Lys Tyr Ile Pro Glu Gly Ala Thr Asp
                965                 970                 975
Gly Ser Ala Gln Pro Arg Leu Pro Ala Ser Gly Gly Ala Gly Gly Asn
                980                 985                 990
Pro Gly Leu Tyr Glu Asp Leu Phe Arg Val Ser Val Lys Val Lys Asn
                995                 1000                1005
Thr Gly Asn Val Ala Gly Asp Glu Val Pro Gln Leu Tyr Val Ser
    1010                1015                1020
Leu Gly Gly Pro Asn Glu Pro Lys Val Val Leu Arg Lys Phe Glu
    1025                1030                1035
Arg Ile His Leu Ala Pro Ser Gln Glu Ala Val Trp Thr Thr Thr
    1040                1045                1050
Leu Thr Arg Arg Asp Leu Ala Asn Trp Asp Val Ser Ala Gln Asp
    1055                1060                1065
Trp Thr Val Thr Pro Tyr Pro Lys Thr Ile Tyr Val Gly Asn Ser
    1070                1075                1080
Ser Arg Lys Leu Pro Leu Gln Ala Ser Leu Pro Lys Ala Gln
    1085                1090                1095
```